(12) United States Patent
Ramharter et al.

(10) Patent No.: US 11,814,380 B2
(45) Date of Patent: *Nov. 14, 2023

(54) BENZYLAMINO SUBSTITUTED PYRIDOPYRIMIDINONES AND DERIVATIVES AS SOS1 INHIBITORS

(71) Applicant: Boehringer Ingelheim International GmbH, Ingelheim am Rhein (DE)

(72) Inventors: Juergen Ramharter, Vienna (AT); Christiane Kofink, Perchtoldsdorf (AT); Heinz Stadtmueller, Vienna (AT); Tobias Wunberg, Hinterbruehl (AT); Marco Hans Hofmann, Vienna (AT); Anke Baum, Moedling (AT); Michael Gmachl, Vienna (AT); Dorothea Ingrid Rudolph, Vienna (AT); Fabio Savarese, Maria Enzersdorf (AT); Markus Ostermeier, Biberach an der Riss (DE); Markus Frank, Ulm (DE); Annika Gille, Ulm (DE); Stefan Goepper, Biberach an der Riss (DE); Marco Santagostino, Mittelbiberach (DE); Julian Wippich, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/030,603

(22) Filed: Sep. 24, 2020

(65) Prior Publication Data

US 2021/0009588 A1 Jan. 14, 2021

Related U.S. Application Data

(63) Continuation of application No. 16/226,824, filed on Dec. 20, 2018, now Pat. No. 10,829,487.

(30) Foreign Application Priority Data

Dec. 21, 2017 (EP) .................................. 17209865

(51) Int. Cl.
| | |
|---|---|
| *C07D 471/04* | (2006.01) |
| *A61P 35/00* | (2006.01) |
| *C07D 471/08* | (2006.01) |
| *C07D 519/00* | (2006.01) |
| *C07D 453/02* | (2006.01) |
| *A61K 45/06* | (2006.01) |

(52) U.S. Cl.
CPC ............ *C07D 471/04* (2013.01); *A61P 35/00* (2018.01); *C07D 453/02* (2013.01); *C07D 471/08* (2013.01); *C07D 519/00* (2013.01); *A61K 45/06* (2013.01)

(58) Field of Classification Search
CPC ............... C07D 471/04; A61K 31/519

USPC ....................... 544/279; 514/264.11
See application file for complete search history.

(56) References Cited

U.S. PATENT DOCUMENTS

| | | | |
|---|---|---|---|
| 5,654,307 A | 8/1997 | Bridges et al. | |
| 6,174,899 B1 | 1/2001 | Shulman | |
| 10,829,487 B2 * | 11/2020 | Ramharter | C07D 471/08 |
| 2011/0136838 A1 | 6/2011 | Atkinson et al. | |
| 2022/0249492 A1 | 8/2022 | Gmachl et al. | |

FOREIGN PATENT DOCUMENTS

| | | |
|---|---|---|
| WO | 2008116742 A1 | 10/2008 |
| WO | 2008150118 A2 | 12/2008 |
| WO | 2010019637 A1 | 2/2010 |
| WO | 2010060940 A2 | 6/2010 |
| WO | 2011053861 A1 | 5/2011 |
| WO | 2012078677 A2 | 6/2012 |
| WO | 2013016197 A1 | 1/2013 |
| WO | 2013136254 A1 | 9/2013 |
| WO | 2016077793 A1 | 5/2016 |

(Continued)

OTHER PUBLICATIONS

Baltanás et al., "Functional Redundancy of Sos1 and Sos2 for Lymphopoiesis and Organismal Homeostasis and Survival", Mol. Cell. Biol., 2013, 33(22), pp. 4562-4578.

(Continued)

*Primary Examiner* — Jeffrey H Murray
(74) *Attorney, Agent, or Firm* — Philip I. Datlow

(57) ABSTRACT

The present invention encompasses compounds of formula (1)

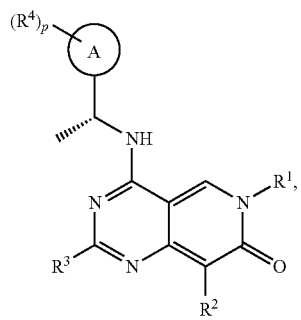

wherein the groups $R^1$ to $R^4$, A and p have the meanings given in the claims and specification, their use as inhibitors of SOS1, pharmaceutical compositions which contain compounds of this kind and their use as medicaments/medical uses, especially as agents for treatment and/or prevention of oncological diseases.

14 Claims, No Drawings

(56) References Cited

FOREIGN PATENT DOCUMENTS

| WO | 2018115380 A1 | 6/2018 |
| WO | 2018172250 A1 | 9/2018 |
| WO | 2020254451 A1 | 12/2020 |

OTHER PUBLICATIONS

Bid et al., "RAC1: an emerging therapeutic option for targeting cancer angiogenesis and metastasis", Mol. Cancer Ther. 2013, 12(10), pp. 1925-1934.
Buday et al., "Many faces of Ras activation", Biochim. Biophys. Acta., 2008, 1786(2), pp. 178-187.
Burns et al., "Approach for targeting Ras with small molecules that activate SOS-mediated nucleotide exchange", Proc. Natl. Acad. Sci. 2014, 111(9), pp. 3401-3406.
Cancer Genome Atlas Research Network., "Comprehensive molecular profiling of lung adenocarcinoma", Nature, 2014, 511(7511), pp. 543-550.
Chardin et al., "Chromosomal localization of two genes encoding human ras exchange factors: SOS1 maps to the 2p22→p16 region and SOS2 to the 14q21→q22 region of the human genome",Science, 1993, 260(5112), pp. 1338-1343.
Chardin et al., "Human Sos1: a guanine nucleotide exchange factor for Ras that binds to GRB2", Cytogenet. Cell. Genet., 1994, 66(1), pp. 68-69.
Cox et al., "Drugging the undruggable RAS: Mission possible", Nat. Rev. Drug Discov., 2014, 13(11), pp. 828-851.
Denayer et al., "Tumor spectrum in children with Noonan syndrome and SOS1 or RAF1 mutations", Genes Chromosomes Cancer, 2010, 49(3), pp. 242-252.
Eberlein et al., "Acquired Resistance to the Mutant-Selective EGFR Inhibitor AZD9291 Is Associated with Increased Dependence on RAS Signaling in Preclinical Models", Cancer Res., 2015, 75(12), pp. 2489-2500.
Esteban et al., "Ras-guanine nucleotide exchange factor sos2 is dispensable for mouse growth and development", Mol. Cell. Biol., 2000, 20(17), pp. 6410-6413.
Evelyn et al., "Rational design of small molecule inhibitors targeting the Ras GEF, SOS1", Chem. Biol. 2014, 21(12), pp. 1618-1628.
Evelyn et al., "Rational design of small molecule inhibitors targeting the Ras GEF, SOS1", J. Biol. Chem. 2015, 290(20), pp. 12879-12898.
Freedman et al., "A Ras-induced conformational switch in the Ras activator Son of sevenless", Proc. Natl. Acad. Sci. U S A., 2006, 103(45), pp. 16692-16697.
Hou Ju et al., "Design, synthesis,anti-tumor activity, and molecular modeling of quinazoline and pyrido[2,3-d]pyrimidine derivatives targeting epidermal growth factor receptor", European Journal of Medicinal Chemistry, Editions Scientifique Elsevier, Paris, FR, vol. 118, Apr. 20, 2016 (Apr. 20, 2016), pp. 276-289.

Hunter et al., "Biochemical and Structural Analysis of Common Cancer-Associated KRAS Mutations", Mol. Cancer Res., 2015, 13(9), pp. 1325-1335.
Innocenti et al., "Mechanisms through which Sos-1 coordinates the activation of Ras and Rac", J. Cell Biol., 2002, 156(1), pp. 125-136.
International Search Report and Written Opinion for corresponding application, PCT/EP2017/084265, dated Apr. 23, 2018.
International Search Report and Written Opinion for corresponding application, PCT/EP2018/086197, dated Feb. 12, 2019.
Jeng et al., "Sos-mediated cross-activation of wild-type Ras by oncogenic Ras is essential for tumorigenesis", Nat. Commun., 2012, 3, pp. 1168.
Kardinal et al., "Chronic myelogenous leukemia blast cell proliferation is inhibited by peptides that disrupt Grb2-SoS complexes". Blood, 2001, 98, pp. 1773-1781.
Leto et al., "Primary and acquired resistance to EGFR-targeted therapies in colorectal cancer: impact on future treatment strategies", J. Mol. Med. (Berl). Jul. 2014;92(7), pp. 709-722.
Lu et al., "Inhibitors of Ras-SOS Interactions", ChemMedChem. 2016, 11(8), pp. 814-821.
McCormick et al., "K-Ras protein as a drug target", J. Mol. Med. (Berl)., 2016, 94(3), pp. 253-258.
McCormick et al., "The potential of targeting Ras proteins in lung cancer", Expert Opin. Ther. Targets., 2015, 19(4), pp. 451-454.
Nimnual et al., "The two hats of SOS", Sci. STKE., 2002, 2002(145), p. 36.
Ortiz-Cuaran et al., "Heterogeneous Mechanisms of Primary and Acquired Resistance to Third-Generation EGFR Inhibitors", Clin. Cancer Res., 2016, 22(19), pp. 4837-4847.
Pierre et al., "Understanding SOS (Son of Sevenless)", Biochem. Pharmacol., 2011, 82(9), pp. 1049-1056.
Qian et al., "The Sos1 and Sos2 Ras-specific exchange factors: differences in placental expression and signaling properties.", EMBO J., 2000, 19(4), pp. 642-654.
Rodriguez-Viciana et al., "RalGDS comes of age", Cancer Cell. 2005, 7(3), pp. 205-206.
Salojin et al., "ZAP-70 is essential for the T cell antigen receptor-induced plasma membrane targeting of SOS and Vav in T cells", J. Biol. Chem. 2000, 275(8), pp. 5966-5975.
Sini et al., "Abl-dependent tyrosine phosphorylation of Sos-1 mediates growth-factor-induced Rac activation", Nat. Cell Biol., 2004, 6(3), pp. 268-274.
Timofeeva et al., "Enhanced expression of SOS1 is detected in prostate cancer epithelial cells from African-American men", Int. J. Oncol., 2009, 35(4), pp. 751-760.
Watanabe et al., "Significance of the Grb2 and son of sevenless (Sos) proteins in human bladder cancer cell lines", IUBMB Life., 2000, 49(4), pp. 317-320.
Winter et al., "Small molecule binding sites on the Ras:SOS complex can be exploited for inhibition of Ras activation", J. Med. Chem. 2015, 58(5), pp. 2265-2274.
Young et al., "Ras signaling and therapies", Adv. Cancer Res., 2009, 102, pp. 1-17.

\* cited by examiner

BENZYLAMINO SUBSTITUTED PYRIDOPYRIMIDINONES AND DERIVATIVES AS SOS1 INHIBITORS

FIELD OF THE INVENTION

The present invention relates to new benzylamino substituted pyridopyrimidinones and derivatives of formula (I)

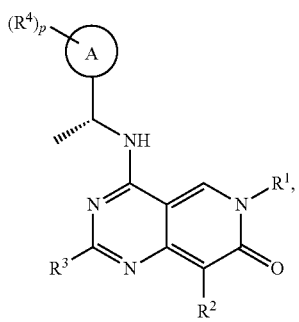

wherein the groups $R^1$ to $R^4$, A and p have the meanings given in the claims and specification, their use as inhibitors of SOS1, pharmaceutical compositions which contain compounds of this kind and their use as medicaments/medical uses, especially as agents for treatment and/or prevention of oncological diseases.

BACKGROUND OF THE INVENTION

RAS-family proteins including KRAS (V-Ki-ras2 Kirsten rat sarcoma viral oncogene homolog), NRAS (neuroblastoma RAS viral oncogene homolog) and HRAS (Harvey murine sarcoma virus oncogene) and any mutants thereof are small GTPases that exist in cells in either GTP-bound or GDP-bound states (McCormick et al., J. Mol. Med. (Berl)., 2016, 94(3):253-8; Nimnual et al., Sci. STKE., 2002, 2002 (145):pe36). The RAS-family proteins have a weak intrinsic GTPase activity and slow nucleotide exchange rates (Hunter et al., Mol. Cancer Res., 2015, 13(9):1325-35). Binding of GTPase activating proteins (GAPs) such as NF1 increases the GTPase activity of RAS-family proteins. The binding of guanine nucleotide exchange factors (GEFs) such as SOS1 (Son of Sevenless 1) promote release GDP from RAS-family proteins, enabling GTP binding (Chardin et al., Science, 1993, 260(5112):1338-43). When in the GTP-bound state, RAS-family proteins are active and engage effector proteins including C-RAF and phosphoinositide 3-kinase (PI3K) to promote the RAF/mitogen or extracellular signal-regulated kinases (MEK/ERK) pathway, PI3K/AKT/mammalian target of rapamycin (mTOR) pathway and RalGDS (Ral guanine nucleotide dissociation stimulator) pathway (McCormick et al., J. Mol. Med. (Berl)., 2016, 94(3):253-8; Rodriguez-Viciana et al., Cancer Cell. 2005, 7(3):205-6). These pathways affect diverse cellular processes such as proliferation, survival, metabolism, motility, angiogenesis, immunity and growth (Young et al., Adv. Cancer Res., 2009, 102:1-17; Rodriguez-Viciana et al., Cancer Cell. 2005, 7(3): 205-6).

Cancer-associated mutations in RAS-family proteins suppress their intrinsic and GAP-induced GTPase activity leading to an increased population of GTP-bound/active RAS-family proteins (McCormick et al., Expert Opin. Ther. Targets., 2015, 19(4):451-4; Hunter et al., Mol. Cancer Res., 2015, 13(9):1325-35). This in turn leads to persistent activation of effector pathways (e.g. MEK/ERK, PI3K/AKT/mTOR, RalGDS pathways) downstream of RAS-family proteins. KRAS mutations (e.g. amino acids G12, G13, Q61, A146) are found in a variety of human cancers including lung cancer, colorectal cancer and pancreatic cancer (Cox et al., Nat. Rev. Drug Discov., 2014, 13(11):828-51). Mutations in HRAS (e.g. amino acids G12, G13, Q61) and NRAS (e.g. amino acids G12, G13, Q61, A146) are also found in a variety of human cancer types however typically at a lower frequency compared to KRAS mutations (Cox et al., Nat. Rev. Drug Discov., 2014, 13(11):828-51). Alterations (e.g. mutation, over-expression, gene amplification) in RAS-family proteins have also been described as a resistance mechanism against cancer drugs such as the EGFR antibodies cetuximab and panitumumab (Leto et al., J. Mol. Med. (Berl). 2014 July; 92(7):709-22) and the EGFR tyrosine kinase inhibitor osimertinib/AZD9291 (Ortiz-Cuaran et al., Clin. Cancer Res., 2016, 22(19):4837-47; Eberlein et al., Cancer Res., 2015, 75(12):2489-500).

Son of Sevenless 1 (SOS1) is a human homologue of the originally identified Drosophila protein Son of Sevenless (Pierre et al., Biochem. Pharmacol., 2011, 82(9):1049-56; Chardin et al., Cytogenet. Cell. Genet., 1994, 66(1):68-9). The SOS1 protein consists of 1333 amino acids (150 kDa). SOS1 is a multi-domain protein with two tandem N-terminal histone domains (HD) followed by the Dbl homology domain (DH), a Pleckstrin homology domain (PH), a helical linker (HL), RAS exchanger motif (REM), CDC25 homology domain and a C-terminal proline rich domain (PR). SOS1 has two binding sites for RAS-family proteins; a catalytic site that binds GDP-bound RAS-family proteins to promote guanine nucleotide exchange and an allosteric site that binds GTP-bound RAS-family proteins which causes a further increase in the catalytic GEF function of SOS1 (Freedman et al., Proc. Natl. Acad. Sci. USA., 2006, 103 (45):16692-7; Pierre et al., Biochem. Pharmacol., 2011, 82(9):1049-56). Published data indicate a critical involvement of SOS1 in mutant KRAS activation and oncogenic signaling in cancer (Jeng et al., Nat. Commun., 2012, 3:1168). Depleting SOS1 levels decreased the proliferation rate and survival of tumor cells carrying a KRAS mutation whereas no effect was observed in KRAS wild type cell lines. The effect of loss of SOS1 could not be rescued by introduction of a catalytic site mutated SOS1, demonstrating the essential role of SOS1 GEF activity in KRAS mutant cancer cells.

SOS1 is critically involved in the activation of RAS-family protein signaling in cancer via mechanisms other than mutations in RAS-family proteins. SOS1 interacts with the adaptor protein Grb2 and the resulting SOS1/Grb2 complex binds to activated/phosphorylated Receptor Tyrosine Kinases (e.g. EGFR, ErbB2, ErbB3, ErbB4, PDGFR-A/B, FGFR1/2/3, IGF1R, INSR, ALK, ROS, TrkA, TrkB, TrkC, RET, c-MET, VEGFR1/2/3, AXL) (Pierre et al., Biochem. Pharmacol., 2011, 82(9):1049-56). SOS1 is also recruited to other phosphorylated cell surface receptors such as the T cell Receptor (TCR), B cell Receptor (BCR) and monocyte colony-stimulating factor receptor (Salojin et al., J. Biol. Chem. 2000, 275(8):5966-75). This localization of SOS1 to the plasma membrane, proximal to RAS-family proteins, enables SOS1 to promote RAS-family protein activation. SOS1-activation of RAS-family proteins can also be mediated by the interaction of SOS1/Grb2 with the BCR-ABL oncoprotein commonly found in chronic myelogenous leukemia (Kardinal et al., 2001, Blood, 98:1773-81; Sini et al., Nat. Cell Biol., 2004, 6(3):268-74).

Furthermore, alterations in SOS1 have been implicated in cancer. SOS1 mutations are found in embryonal rhabdomyosarcomas, sertoli cell testis tumors, granular cell tumors of the skin (Denayer et al., Genes Chromosomes Cancer, 2010, 49(3):242-52) and lung adenocarcinoma (Cancer Genome Atlas Research Network., Nature. 2014, 511(7511):543-50). Meanwhile over-expression of SOS1 has been described in bladder cancer (Watanabe et al., IUBMB Life., 2000, 49(4): 317-20) and prostate cancer (Timofeeva et al., Int. J. Oncol., 2009, 35(4):751-60). In addition to cancer, hereditary SOS1 mutations are implicated in the pathogenesis of RASopathies like e.g. Noonan syndrome (NS), cardio-facio-cutaneous syndrome (CFC) and hereditary gingival fibromatosis type 1 (Pierre et al., Biochem. Pharmacol., 2011, 82(9): 1049-56).

SOS1 is also a GEF for the activation of the GTPases RAC1 (Ras-related C3 botulinum toxin substrate 1) (Innocenti et al., J. Cell Biol., 2002, 156(1):125-36). RAC1, like RAS-family proteins, is implicated in the pathogenesis of a variety of human cancers and other diseases (Bid et al., Mol. Cancer Ther. 2013, 12(10):1925-34).

Son of Sevenless 2 (SOS2), a homolog of SOS1 in mammalian cells, also acts as a GEF for the activation of RAS-family proteins (Pierre et al., Biochem. Pharmacol., 2011, 82(9):1049-56; Buday et al., Biochim. Biophys. Acta., 2008, 1786(2):178-87). Published data from mouse knockout models suggests a redundant role for SOS1 and SOS2 in homeostasis in the adult mouse. Whilst germline knockout of SOS1 in mice results in lethality during mid-embryonic gestation (Qian et al., EMBO J., 2000, 19(4):642-54), systemic conditional SOS1 knockout adult mice are viable (Baltanns et al., Mol. Cell. Biol., 2013, 33(22):4562-78). SOS2 gene targeting did not result in any overt phenotype in mice (Esteban et al., Mol. Cell. Biol., 2000, 20(17):6410-3). In contrast, double SOS1 and SOS2 knockout leads to rapid lethality in adult mice (Baltanns et al., Mol. Cell. Biol., 2013, 33(22):4562-78). These published data suggest that selective targeting of individual SOS isoforms (e.g. selective SOS1 targeting) may be adequately tolerated to achieve a therapeutic index between SOS1/RAS-family protein driven cancers (or other SOS1/RAS-family protein pathologies) and normal cells and tissues.

Selective pharmacological inhibition of the binding of the catalytic site of SOS1 to RAS-family proteins is expected to prevent SOS1-mediated activation of RAS-family proteins to the GTP-bound form. Such SOS1 inhibitor compounds are expected to consequently inhibit signaling in cells downstream of RAS-family proteins (e.g. ERK phosphorylation). In cancer cells associated with dependence on RAS-family proteins (e.g. KRAS mutant cancer cell lines), SOS1 inhibitor compounds are expected to deliver anti-cancer efficacy (e.g. inhibition of proliferation, survival, metastasis etc.). High potency towards inhibition of SOS1:RAS-family protein binding (nanomolar level $IC_{50}$ values) and ERK phosphorylation in cells (nanomolar level $IC_{50}$ values) are desirable characteristics for a SOS1 inhibitor compound. Furthermore, a desirable characteristic of SOS1 inhibitor compound would be the selective inhibition of SOS1 over SOS2. This conclusion is based on the viable phenotype of SOS1 knockout mice and lethality of SOS1/SOS2 double knockout mice, as described above.

These characteristics have not been fully achieved in previously described SOS1 inhibitor compounds. In the last decades the RAS family proteins-SOS1 protein interaction has gained increasing recognition. Until today several efforts to identify and optimize binders, which target either the effector binding site of RAS or the catalytic binding site of SOS1 (for a selected review see: Lu et al., Chem Med Chem. 2016, 11(8):814-21), have been made with limited success.

Recently, small activating molecules have been identified, which bind to a lipophilic pocket of SOS1 in close proximity to the RAS binding site (Burns et al., Proc. Natl. Acad. Sci. 2014, 111(9):3401-6). However, binding of these molecules seems to lead to increased nucleotide exchange and thereby activation of RAS instead of deactivation.

In an effort to stabilize the protein-protein-interaction of RAS-family proteins with SOS1 and to prevent reloading of RAS-family proteins with GTP, several different fragments were subsequently identified (Winter et al., J. Med. Chem. 2015, 58(5):2265-74). However, reversible binding of fragments to SOS1 did not translate into a measurable effect on the nucleotide exchange and only a weak effect was observed for fragments covalently bound to RAS.

Also recently, studies have been conducted to combine rational design and screening platforms to identify small molecule inhibitors of SOS1 (Evelyn et al., Chem. Biol. 2014, 21(12):1618-28; Evelyn et al., J. Biol. Chem. 2015, 290(20):12879-98; Zheng et al., WO 2016/077793), i.e. compounds which bind to SOS1 and inhibit protein-protein interaction with RAS-family proteins. Although compounds with a slight inhibitory effect on SOS1 have been identified, the effects on guanine nucleotide exchange and cellular signal transduction modulation (e.g. ERK phosphorylation) are weak.

WO 2018/115380 and WO 2018/172250 disclose quinazoline-based SOS inhibitors.

Herein we describe novel SOS1 inhibitor compounds, which bind to the SOS1 catalytic site (confirmed by means of crystallography) and simultaneously prevent interactions with and activation of RAS-family proteins. This results in a pronounced inhibitory effect on the interaction of SOS1 with RAS-family proteins, in particular KRAS (with low single digit nanomolar $IC_{50}$ activity) and consequently a significant reduction of ERK phosphorylation in KRAS mutant cancer cell lines.

The selective SOS1 inhibitor compounds described herein are expected to deliver a pharmacological benefit to patients with cancers that are associated with dependence on RAS-family protein signaling. Such cancers expected to be targeted by a SOS1 inhibitor compound include those exhibiting alterations (mutations, gene amplification, over-expression) of components (proteins, genes) in the RAS-family protein pathway such as KRAS, NRAS, HRAS, receptor tyrosine kinases (e.g. EGFR, ErbB2, ErbB3, ErbB4, PDGFR-A/B, FGFR1/2/3, IGF1R, INSR, ALK, ROS, TrkA, TrkB, TrkC, RET, c-MET, VEGFR1/2/3, AXL), GAPs (e.g. NF1) and SOS1. Additionally, given the role of SOS1 in RAC1 activation, cancers demonstrating dependence on RAC1 are expected to be targeted by SOS1 inhibitor compounds. Furthermore, in other diseases associated with RAS-family protein pathway dysregulation such as the neurofibromatosis, Noonan syndrome (NS), cardio-facio-cutaneous syndrome (CFC) and hereditary gingival fibromatosis type 1, SOS1 inhibitor compounds would also be expected to deliver a pharmacological benefit.

In addition to the inhibitory effect and potency, compounds disclosed herein show good solubility, fine-tuned DMPK properties and good selectivity over kinases of the human kinome. Furthermore, these structurally and synthetically novel pyridopyrimidinone based compounds show a good metabolic stability, a decreased risk of time dependent inhibition of cytochromes and, presumably, a decreased general off target liability.

DETAILED DESCRIPTION OF THE INVENTION

Compounds

It has now been found that, surprisingly, compounds of formula (I) wherein the groups $R^1$ to $R^4$, A and p have the meanings given hereinafter act as inhibitors of the interaction of the catalytic site of SOS1 with RAS-family proteins which is involved in controlling cell proliferation. Thus, the compounds according to the invention may be used for example for the treatment of diseases characterised by excessive or abnormal cell proliferation.

The present invention therefore relates to a compound of formula (I)

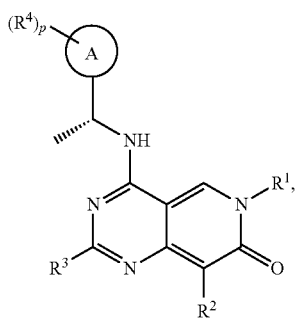

wherein

[A0]

$R^1$ is $R^{a1}$;

$R^{a1}$ is selected from the group consisting of $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-10 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-10 membered heterocyclyl, $C_{6-10}$aryl and 5-10 membered heteroaryl are all optionally substituted by one or more, identical or different $R^{b1}$ and/or $R^{c1}$;

each $R^{b1}$ is independently selected from the group consisting of —$OR^{c1}$, —$NR^{c1}R^{c1}$, halogen, —CN, —$C(O)R^{c1}$, —$C(O)OR^{c1}$, —$C(O)NR^{c1}R^{c1}$, —$S(O)_2R^{c1}$, —$S(O)_2NR^{c1}R^{c1}$, —$NHC(O)R^{c1}$, —$N(C_{1-4}alkyl)C(O)R^{c1}$, —$NHC(O)OR^{c1}$ and —$N(C_{1-4}alkyl)C(O)OR^{c1}$;

each $R^{c1}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-10 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-10 membered heterocyclyl, $C_{6-10}$aryl and 5-10 membered heteroaryl are all optionally substituted by one or more, identical or different $R^{d1}$ and/or $R^{e1}$;

each $R^{d1}$ is independently selected from the group consisting of —$OR^{e1}$, —$NR^{e1}R^{e1}$, halogen, —CN, —$C(O)R^{e1}$, —$C(O)OR^{e1}$, —$C(O)NR^{e1}R^{e1}$, —$S(O)_2R^{e1}$, —$S(O)_2NR^{e1}R^{e1}$, —$NHC(O)R^{e1}$, —$N(C_{1-4}alkyl)C(O)R^{e1}$, —$NHC(O)OR^{e1}$ and —$N(C_{1-4}alkyl)C(O)OR^{e1}$; each $R^{e1}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-10 membered heterocyclyl, $C_{6-10}$aryl and 5-10 membered heteroaryl;

[B0]

$R^2$ is selected from the group consisting of hydrogen, $C_{1-4}$alkyl, $C_{3-6}$cycloalkyl, 3-6 membered heterocyclyl and halogen;

[C0]

$R^3$ is selected from the group consisting of hydrogen, $C_{1-4}$alkyl and $C_{1-4}$haloalkyl;

[D0]

ring system A is selected from the group consisting of $C_{6-10}$aryl, 5-10 membered heteroaryl and 9-10 membered bicyclic heterocyclyl;

p denotes 1, 2 or 3;

each $R^4$ is independently selected from the group consisting of $C_{1-4}$alkyl, $C_{2-4}$alkenyl, $C_{2-4}$alkinyl, $C_{1-4}$haloalkyl, hydroxy-$C_{1-4}$alkyl, hydroxy-$C_{1-4}$haloalkyl, $C_{3-6}$cycloalkyl, 3-6 membered heterocyclyl, hydroxy-$C_{3-6}$cycloalkyl, $C_{1-4}$haloalkyl substituted with a 3-6 membered heterocyclyl, 3-6 membered heterocyclyl substituted with hydroxy, halogen, —$NH_2$, —$SO_2$—$C_{1-4}$alkyl and the bivalent substituent =O, while =O may only be a substituent in a non-aromatic ring;

or a salt thereof.

In one aspect [A1] the invention relates to a compound of formula (I) or a salt thereof, wherein $R^1$ is $R^{a1}$;

$R^{a1}$ is selected from the group consisting of $C_{1-6}$alkyl, $C_{1-6}$haloalkyl, $C_{3-10}$cycloalkyl, $C_{4-10}$cycloalkenyl, 3-10 membered heterocyclyl, $C_{6-10}$aryl and 5-10 membered heteroaryl, wherein the $C_{1-6}$alkyl, $C_{1-6}$haloalkyl, $C_{3-10}$cycloalkyl, $C_{4-10}$cycloalkenyl, 3-10 membered heterocyclyl, $C_{6-10}$aryl and 5-10 membered heteroaryl are all optionally substituted by one or more, identical or different $R^{b1}$ and/or $R^{c1}$;

each $R^{b1}$ is independently selected from the group consisting of —$OR^{c1}$, —$NR^{c1}R^{c1}$, halogen, —CN, —$C(O)R^{c1}$, —$C(O)OR^{c1}$ and —$C(O)NR^{c1}R^{c1}$;

each $R^{c1}$ is independently selected from the group consisting of hydrogen, $C_{1-6}$alkyl, $C_{1-6}$haloalkyl, $C_{3-10}$cycloalkyl, $C_{4-10}$cycloalkenyl, 3-10 membered heterocyclyl, $C_{6-10}$aryl and 5-10 membered heteroaryl, wherein the $C_{1-6}$alkyl, $C_{1-6}$haloalkyl, $C_{3-10}$cycloalkyl, $C_{4-10}$cycloalkenyl, 3-10 membered heterocyclyl, $C_{6-10}$aryl and 5-10 membered heteroaryl are all optionally substituted by one or more, identical or different $R^{d1}$ and/or $R^{e1}$;

each $R^{d1}$ is independently selected from the group consisting of —$OR^{e1}$, —$NR^{e1}R^{e1}$, halogen, —CN, —$C(O)R^{e1}$, —$C(O)OR^{e1}$ and —$C(O)NR^{e1}R^{e1}$;

each $R^{e1}$ is independently selected from the group consisting of hydrogen, $C_{1-6}$alkyl, $C_{1-6}$haloalkyl, $C_{3-10}$cycloalkyl, $C_{4-10}$cycloalkenyl, 3-10 membered heterocyclyl, $C_{6-10}$aryl and 5-10 membered heteroaryl.

In another aspect [A2] the invention relates to a compound of formula (I) or a salt thereof, wherein $R^1$ is $R^{a1}$;

$R^{a1}$ is selected from the group consisting of $C_{1-6}$alkyl, $C_{1-6}$haloalkyl, $C_{3-10}$cycloalkyl, $C_{4-10}$cycloalkenyl, 3-10 membered heterocyclyl and 5-10 membered heteroaryl, wherein the $C_{1-6}$alkyl, $C_{1-6}$haloalkyl, $C_{3-10}$cycloalkyl, $C_{4-10}$cycloalkenyl, 3-10 membered heterocyclyl and 5-10 membered heteroaryl are all optionally substituted by one or more, identical or different $R^{b1}$ and/or $R^1$;

each $R^{b1}$ is independently selected from the group consisting of —$OR^{c1}$, halogen and —$C(O)NR^{c1}R^{c1}$;

each $R^{c1}$ is independently selected from the group consisting of hydrogen, $C_{1-6}$alkyl, $C_{1-6}$haloalkyl, 3-10 membered heterocyclyl, $C_{6-10}$aryl and 5-10 membered heteroaryl, wherein the $C_{1-6}$alkyl, $C_{1-6}$haloalkyl, 3-10 membered heterocyclyl, $C_{6-10}$aryl and 5-10 membered heteroaryl are all optionally substituted by one or more, identical or different $R^{d1}$ and/or $R^{e1}$;

each $R^{d1}$ is independently selected from the group consisting of —$OR^{e1}$ and halogen;

each $R^{e1}$ is independently selected from the group consisting of hydrogen and $C_{1-6}$alkyl.

In another aspect [A3] the invention relates to a compound of formula (I) or a salt thereof, wherein $R^1$ is $R^{a1}$;

$R^{a1}$ is selected from the group consisting of $C_{3-10}$cycloalkyl and $C_{4-10}$cycloalkenyl, wherein the $C_{3-10}$cycloalkyl and $C_{4-10}$cycloalkenyl are both optionally substituted by one or more, identical or different $R^{b1}$ and/or $R^{c1}$;

each $R^{b1}$ is independently selected from the group consisting of —$OR^{c1}$, —$NR^{c1}R^{c1}$, halogen, —CN, —$C(O)R^{c1}$, —$C(O)OR^{c1}$ and —$C(O)NR^{c1}R^{c1}$;

each $R^{c1}$ is independently selected from the group consisting of hydrogen, $C_{1-6}$alkyl, $C_{1-6}$haloalkyl, $C_{3-10}$cycloalkyl, $C_{4-10}$cycloalkenyl, 3-10 membered heterocyclyl, $C_{6-10}$aryl and 5-10 membered heteroaryl, wherein the $C_{1-6}$alkyl, $C_{1-6}$haloalkyl, $C_{3-10}$cycloalkyl, $C_{4-10}$cycloalkenyl, 3-10 membered heterocyclyl, $C_{6-10}$aryl and 5-10 membered heteroaryl are all optionally substituted by one or more, identical or different $R^{d1}$ and/or $R^{e1}$;

each $R^{d1}$ is independently selected from the group consisting of —$OR^{e1}$, —$NR^{e1}R^{e1}$, halogen, —CN, —$C(O)R^{e1}$, —$C(O)OR^{e1}$, —$C(O)NR^{e1}R^{e1}$;

each $R^{e1}$ is independently selected from the group consisting of hydrogen, $C_{1-6}$alkyl, $C_{1-6}$haloalkyl, $C_{3-10}$cycloalkyl, $C_{4-10}$cycloalkenyl, 3-10 membered heterocyclyl, $C_{6-10}$aryl and 5-10 membered heteroaryl.

In another aspect [A4] the invention relates to a compound of formula (I) or a salt thereof, wherein $R^1$ is $C_{3-6}$cycloalkyl optionally substituted by one or more, identical or different $R^{b1}$ and/or $R^{c1}$;

each $R^{b1}$ is independently selected from the group consisting of —$OR^{c1}$, halogen and —$C(O)NR^{c1}R^{c1}$;

each $R^{c1}$ is independently selected from the group consisting of hydrogen, $C_{1-6}$alkyl, $C_{1-6}$haloalkyl, 3-8 membered heterocyclyl, phenyl and 5-6 membered heteroaryl, wherein the $C_{1-6}$alkyl, $C_{1-6}$haloalkyl, 3-8 membered heterocyclyl, phenyl and 5-6 membered heteroaryl are all optionally substituted by one or more, identical or different $R^{d1}$ and/or $R^{e1}$;

each $R^{d1}$ is independently selected from the group consisting of —$OR^{e1}$ and halogen;

each $R^{e1}$ is independently selected from the group consisting of hydrogen and $C_{1-6}$alkyl.

In another aspect [A5] the invention relates to a compound of formula (I) or a salt thereof, wherein $R^1$ is $C_{3-6}$cycloalkyl optionally substituted by one or more, identical or different substituent(s) selected from the group consisting of $C_{1-4}$alkyl, $C_{1-4}$haloalkyl, $C_{1-4}$alkoxy-$C_{1-4}$alkyl, 5-6 membered heteroaryl, phenyl, halophenyl, halogen, 3-6 membered heterocyclyl, —$C(O)N(C_{1-4}alkyl)_2$ and hydroxy.

In another aspect [A6] the invention relates to a compound of formula (I) or a salt thereof, wherein $R^1$ is selected from among

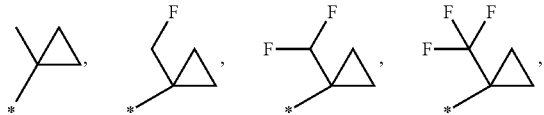

-continued

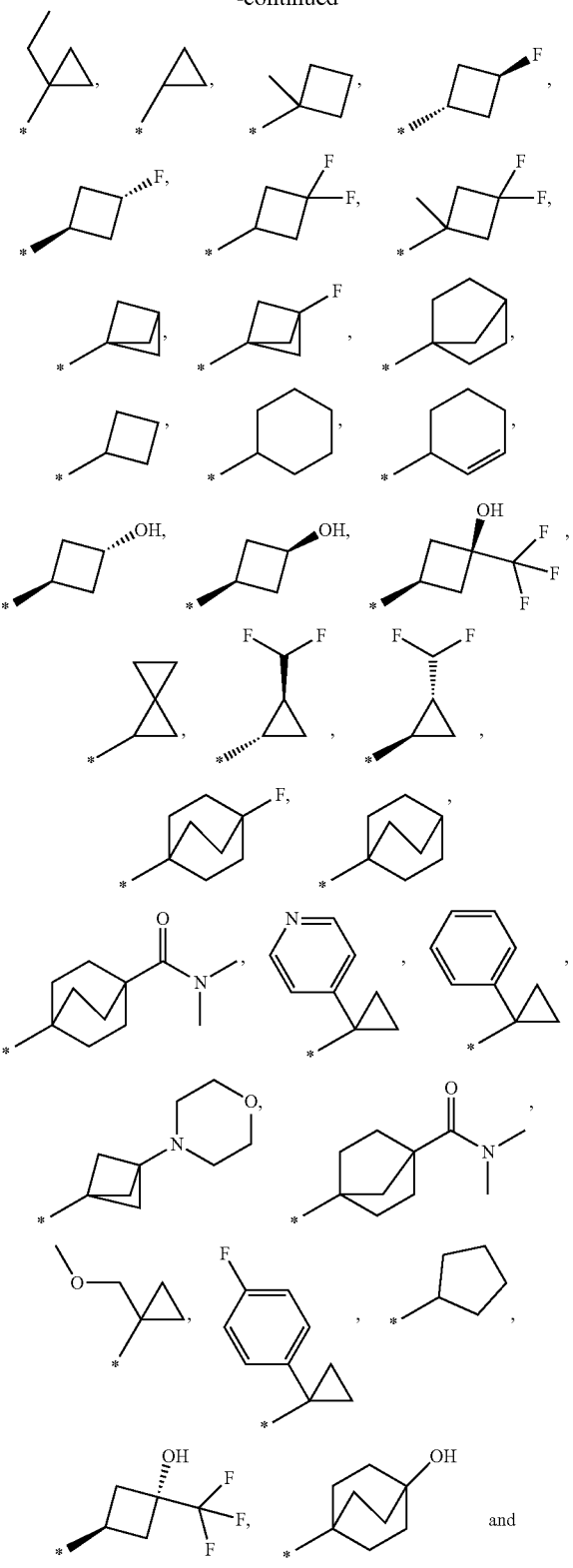

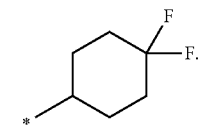

In another aspect [A7] the invention relates to a compound of formula (I) or a salt thereof, wherein $R^1$ is selected from the group consisting of $C_{1-6}$alkyl and $C_{1-6}$haloalkyl.

In another aspect [A8] the invention relates to a compound of formula (I) or a salt thereof, wherein $R^1$ is selected from the group consisting of $C_{1-4}$alkyl and $C_{1-4}$haloalkyl.

In another aspect [A9] the invention relates to a compound of formula (I) or a salt thereof, wherein $R^1$ is 3-10 membered heterocyclyl optionally substituted by one or more, identical or different $R^{b1}$ and/or $R^{c1}$;

each $R^{b1}$ is independently selected from the group consisting of —$OR^{c1}$, —$NR^{c1}R^{c1}$, halogen, —CN, —$C(O)R^{c1}$, —$C(O)OR^{c1}$ and —$C(O)NR^{c1}R^{c1}$;

each $R^{c1}$ is independently selected from the group consisting of hydrogen, $C_{1-6}$alkyl, $C_{1-6}$haloalkyl, $C_{3-10}$cycloalkyl, $C_{4-10}$cycloalkenyl, 3-10 membered heterocyclyl, $C_{6-10}$aryl and 5-10 membered heteroaryl, wherein the $C_{1-6}$alkyl, $C_{1-6}$haloalkyl, $C_{3-10}$cycloalkyl, $C_{4-10}$cycloalkenyl, 3-10 membered heterocyclyl, $C_{6-10}$aryl and 5-10 membered heteroaryl are all optionally substituted by one or more, identical or different $R^{d1}$ and/or $R^{e1}$;

each $R^{d1}$ is independently selected from the group consisting of —$OR^{e1}$, —$NR^{e1}R^{e1}$, halogen, —CN, —$C(O)R^{e1}$, —$C(O)OR^{e1}$ and —$C(O)NR^{e1}R^{e1}$;

each $R^{e1}$ is independently selected from the group consisting of hydrogen, $C_{1-6}$alkyl, $C_{1-6}$haloalkyl, $C_{3-10}$cycloalkyl, $C_{4-10}$cycloalkenyl, 3-10 membered heterocyclyl, $C_{6-10}$aryl and 5-10 membered heteroaryl.

In another aspect [A10] the invention relates to a compound of formula (I) or a salt thereof, wherein $R^1$ is 3-10 membered heterocyclyl optionally substituted by one or more, identical or different substituent(s) selected from the group consisting of $C_{1-6}$alkyl, $C_{1-6}$haloalkyl and $C_{6-10}$aryl.

In another aspect [A11] the invention relates to a compound of formula (I) or a salt thereof, wherein $R^1$ is 3-8 membered heterocyclyl optionally substituted by one substituent selected from the group consisting of $C_{1-6}$alkyl, $C_{1-6}$haloalkyl and $C_{6-10}$aryl.

In another aspect [A12] the invention relates to a compound of formula (I) or a salt thereof, wherein $R^1$ is selected from among

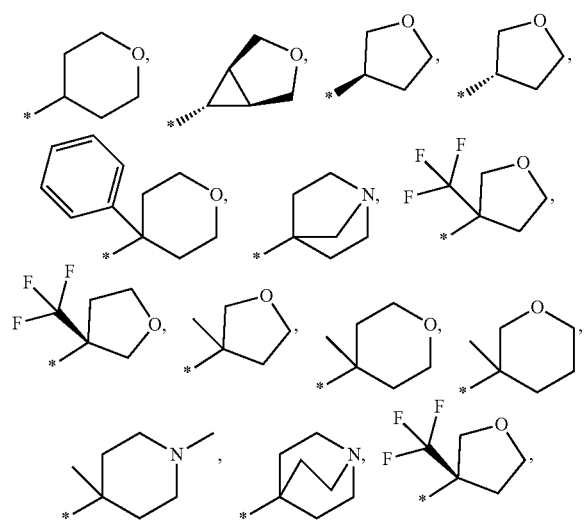

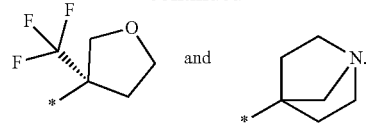

In another aspect [A13] the invention relates to a compound of formula (I) or a salt thereof, wherein $R^1$ is 5-6 membered heteroaryl optionally substituted with $C_{1-4}$alkyl.

In another aspect [B1] the invention relates to a compound of formula (I) or a salt thereof, wherein $R^2$ is hydrogen.

In another aspect [B2] the invention relates to a compound of formula (I) or a salt thereof, wherein $R^2$ is $C_{1-4}$alkyl.

In another aspect [B3] the invention relates to a compound of formula (I) or a salt thereof, wherein $R^2$ is methyl.

In another aspect [B4] the invention relates to a compound of formula (I) or a salt thereof, wherein $R^2$ is halogen.

In another aspect [B5] the invention relates to a compound of formula (I) or a salt thereof, wherein $R^2$ is selected from the group consisting of fluorine and bromine.

In another aspect [B6] the invention relates to a compound of formula (I) or a salt thereof, wherein $R^2$ is fluorine.

In another aspect [B7] the invention relates to a compound of formula (I) or a salt thereof, wherein $R^2$ is $C_{3-5}$cycloalkyl.

In another aspect [B8] the invention relates to a compound of formula (I) or a salt thereof, wherein $R^2$ is cyclopropyl.

In another aspect [$C_1$] the invention relates to a compound of formula (I) or a salt thereof, wherein $R^3$ is hydrogen.

In another aspect [$C_2$] the invention relates to a compound of formula (I) or a salt thereof, wherein $R^3$ is $C_{1-4}$alkyl.

In another aspect [$C_3$] the invention relates to a compound of formula (I) or a salt thereof, wherein $R^3$ is methyl.

In another aspect [D1] the invention relates to a compound of formula (I) or a salt thereof, wherein ring system A is selected from the group consisting of $C_{6-10}$aryl, 5-10 membered heteroaryl and 9-10 membered bicyclic heterocyclyl;

p denotes 1 or 2;

each $R^4$ is independently selected from the group consisting of $C_{1-4}$alkyl, $C_{2-4}$alkinyl, $C_{1-4}$haloalkyl, hydroxy-$C_{1-4}$haloalkyl, $C_{1-4}$haloalkyl substituted with a 3-6 membered heterocyclyl, halogen and the bivalent substituent =O, while =O may only be a substituent in a non-aromatic ring.

In another aspect [D2] the invention relates to a compound of formula (I) or a salt thereof, wherein ring system A is selected from the group consisting of $C_{6-10}$aryl and 9-10 membered bicyclic heterocyclyl;

p denotes 1 or 2;

each $R^4$ is independently selected from the group consisting of $C_{1-4}$alkyl, $C_{2-4}$alkinyl, $C_{1-4}$haloalkyl, hydroxy-$C_{1-4}$haloalkyl, $C_{1-4}$haloalkyl substituted with a 3-6 membered heterocyclyl, halogen and the bivalent substituent =O, while =O may only be a substituent in a non-aromatic ring.

In another aspect [D3] the invention relates to a compound of formula (I) or a salt thereof, wherein A together with the p substituents $R^4$ has substructure

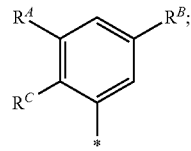

$R^A$ is selected from the group consisting of $C_{1-4}$alkyl, $C_{1-4}$haloalkyl, hydroxy-$C_{1-4}$alkyl, hydroxy-$C_{1-4}$haloalkyl, $C_{1-4}$haloalkyl substituted with a 3-6 membered heterocyclyl, $C_{3-6}$cycloalkyl, hydroxy-$C_{3-6}$cycloalkyl, 3-6 membered heterocyclyl, 3-6 membered hydroxy-heterocyclyl, halogen and —SO$_2$—C$_{1-4}$alkyl;

$R^B$ is selected from the group consisting of hydrogen and —NH$_2$;

$R^C$ is selected from the group consisting of hydrogen, $C_{1-4}$alkyl and halogen; or $R^A$ and $R^C$ together with the carbon atoms they are attached form a 5-6 membered non-aromatic carbocycle, a 5-6 membered non-aromatic heterocycle or a 5-6 membered heteroaryl, wherein the 5-6 membered non-aromatic carbocycle, 5-6 membered non-aromatic heterocycle and 5-6 membered heteroaryl are all optionally substituted by one or more halogen or by an oxo group.

In another aspect [D4] the invention relates to a compound of formula (I) or a salt thereof, wherein A together with the p substituents $R^4$ has substructure

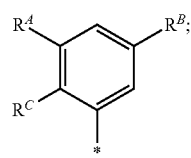

$R^A$ is selected from the group consisting of $C_{1-4}$alkyl, $C_{1-4}$haloalkyl, hydroxy-$C_{1-4}$alkyl, hydroxy-$C_{1-4}$haloalkyl, $C_{1-4}$haloalkyl substituted with a 3-6 membered heterocyclyl, $C_{3-6}$cycloalkyl, hydroxy-$C_{3-6}$cycloalkyl, 3-6 membered heterocyclyl, 3-6 membered hydroxy-heterocyclyl, halogen and —SO$_2$—C$_{1-4}$alkyl;

$R^B$ is selected from the group consisting of hydrogen and —NH$_2$;

$R^C$ is selected from the group consisting of hydrogen, $C_{1-4}$alkyl and halogen; or $R^A$ and $R^C$ together with the carbon atoms they are attached form a 5-6 membered non-aromatic carbocycle or a 5-6 membered non-aromatic heterocycle, wherein the 5-6 membered non-aromatic carbocycle and the 5-6 membered non-aromatic heterocycle are both optionally substituted by one or more halogen or by an oxo group.

In another aspect [D5] the invention relates to a compound of formula (I) or a salt thereof, wherein A together with the p substituents $R^4$ has substructure

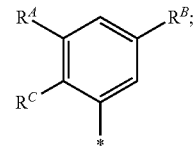

$R^A$ is selected from the group consisting of $C_{1-4}$haloalkyl, hydroxy-$C_{1-4}$haloalkyl and $C_{1-4}$haloalkyl substituted with a 3-6 membered heterocyclyl;

$R^B$ is hydrogen;

$R^C$ is selected from the group consisting of hydrogen, $C_{1-4}$alkyl and fluorine; or $R^A$ and $R^C$ together with the carbon atoms they are attached form a 5-6 membered non-aromatic carbocycle, a 5-6 membered non-aromatic heterocycle or a 5-6 membered heteroaryl, wherein the 5-6 membered non-aromatic carbocycle, 5-6 membered non-aromatic heterocycle and 5-6 membered heteroaryl are all optionally substituted by one or more fluorine or by an oxo group.

In another aspect [D6] the invention relates to a compound of formula (I) or a salt thereof, wherein A together with the p substituents $R^4$ has substructure

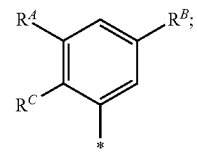

$R^A$ is selected from the group consisting of $C_{1-4}$haloalkyl, hydroxy-$C_{1-4}$haloalkyl and $C_{1-4}$haloalkyl substituted with a 3-6 membered heterocyclyl;

$R^B$ is hydrogen;

$R^C$ is selected from the group consisting of hydrogen, $C_{1-4}$alkyl and fluorine; or $R^A$ and $R^C$ together with the carbon atoms they are attached form a 5-6 membered non-aromatic carbocycle or a 5-6 membered non-aromatic heterocycle, wherein the 5-6 membered non-aromatic carbocycle and the 5-6 membered non-aromatic heterocycle are both optionally substituted by one or more fluorine or by an oxo group.

In another aspect [D7] the invention relates to a compound of formula (I) or a salt thereof, wherein A together with the p substituents $R^4$ are selected from among

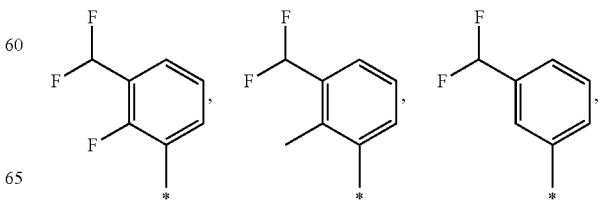

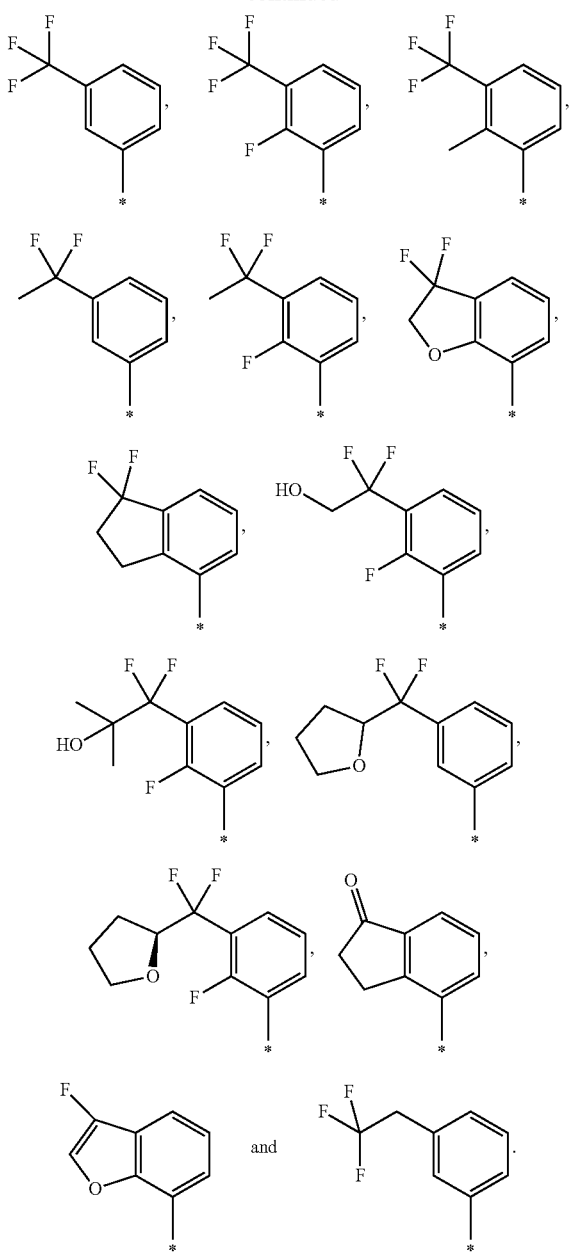

In another aspect [D8] the invention relates to a compound of formula (I) or a salt thereof, wherein A together with the p substituents R⁴ are selected from among

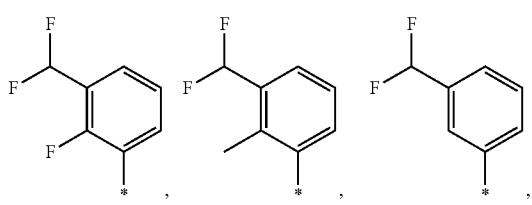

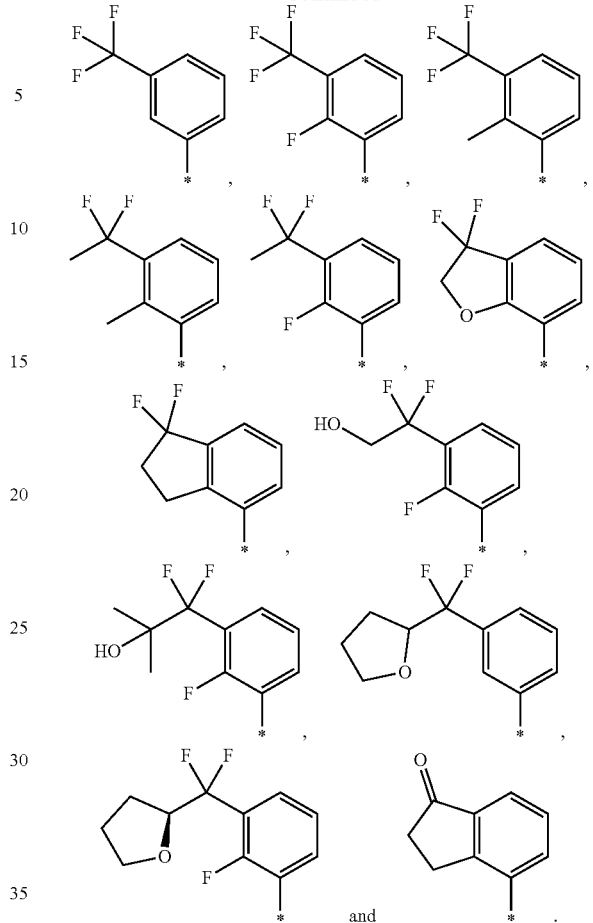

All the above-mentioned structural aspects [A1] to [A13], [B1] to [B8], [C1] to [C₃] and [D1] to [D8] are preferred embodiments of the corresponding aspects [A0], [B0], [C0] and [D0], respectively. The structural aspects [A0] to [A13], [B0] to [B8], [C0] to [C₃] and [D0] to [D8] relating to different molecular parts of the compounds (I) according to the invention may be combined with one another as desired in combinations [A][B][C][D] to obtain preferred compounds (I). Each combination [A][B][C][D] represents and defines individual embodiments or generic subsets of compounds (I) according to the invention.

Preferred embodiments of the invention with structure (I) are example compounds I-1 to I-179 and any subset thereof.

All synthetic intermediates generically defined as well as specifically disclosed herein and their salts are also part of the invention.

All individual synthetic reaction steps as well as reaction sequences comprising these individual synthetic reaction steps, both generically defined or specifically disclosed herein, are also part of the invention.

The present invention further relates to hydrates, solvates, polymorphs, metabolites, derivatives, isomers and prodrugs of a compound of formula (I) (including all its embodiments).

The present invention further relates to a hydrate of a compound of formula (I) (including all its embodiments).

The present invention further relates to a solvate of a compound of formula (I) (including all its embodiments).

Compounds of formula (I) (including all its embodiments) which e.g. bear ester groups are potential prodrugs the ester being cleaved under physiological conditions and are also part of the invention.

The present invention further relates to a pharmaceutically acceptable salt of a compound of formula (I) (including all its embodiments).

The present invention further relates to a pharmaceutically acceptable salt of a compound of formula (I) (including all its embodiments) with anorganic or organic acids or bases.

Medical Uses—Methods of Treatment

The present invention is directed to SOS1 inhibitor compounds, in particular compounds of formula (I) (including all its embodiments), which are useful in the treatment and/or prevention of a disease and/or condition associated with or modulated by SOS1, especially wherein the inhibition of the interaction of SOS1 and a RAS-family protein and/or RAC1 is of therapeutic benefit, including but not limited to the treatment and/or prevention of cancer.

In another aspect the invention relates to a compound of formula (I)—or a pharmaceutically acceptable salt thereof—for use as a medicament.

In another aspect the invention relates to a compound of formula (I)—or a pharmaceutically acceptable salt thereof—for use in a method of treatment of the human or animal body.

In another aspect the invention relates to a SOS1 inhibitor compound, in particular a compound of formula (I),—or a pharmaceutically acceptable salt thereof—for use in the treatment and/or prevention of a disease and/or condition wherein the inhibition of the interaction of SOS1 and a RAS-family protein and/or RAC1 is of therapeutic benefit, including but not limited to the treatment and/or prevention of cancer.

In another aspect the invention relates to a SOS1 inhibitor compound, in particular a compound of formula (I),—or a pharmaceutically acceptable salt thereof—for use in the treatment and/or prevention of cancer.

In another aspect the invention relates to a SOS1 inhibitor compound, in particular a compound of formula (I),—or a pharmaceutically acceptable salt thereof—for use in a method of treatment and/or prevention of cancer in the human or animal body.

In another aspect the invention relates to a SOS1 inhibitor compound, in particular a compound of formula (I),—or a pharmaceutically acceptable salt thereof—for use in a method of treatment and/or prevention of cancer in the human or animal body.

In another aspect the invention relates to a SOS1 inhibitor compound—or a pharmaceutically acceptable salt thereof—for use as hereinbefore defined wherein said SOS1 inhibitor compound is administered before, after or together with at least one other pharmacologically active substance.

In another aspect the invention relates to a compound of formula (I)—or a pharmaceutically acceptable salt thereof—for use as hereinbefore defined wherein said compound is administered before, after or together with at least one other pharmacologically active substance.

In another aspect the invention relates to a SOS1 inhibitor compound—or a pharmaceutically acceptable salt thereof—for use as hereinbefore defined, wherein said SOS1 inhibitor compound is administered in combination with at least one other pharmacologically active substance.

In another aspect the invention relates to a compound of formula (I)—or a pharmaceutically acceptable salt thereof—for use as hereinbefore defined, wherein said compound is administered in combination with at least one other pharmacologically active substance.

In another aspect the invention relates to a pharmacologically active substance prepared for being administered before, after or together with a SOS1 inhibitor compound—or a pharmaceutically acceptable salt thereof—for use as hereinbefore defined for the use of the compound of formula (I).

In another aspect the invention relates to a pharmacologically active substance prepared for being administered before, after or together with a compound of formula (I)—or a pharmaceutically acceptable salt thereof—for use as hereinbefore defined for the use of the compound of formula (I).

In another aspect the invention relates to a SOS1 inhibitor compound, in particular a compound of formula (I),—or a pharmaceutically acceptable salt thereof—for use in the treatment or in a method of treatment as hereinbefore defined.

In another aspect the invention relates to the use of a SOS1 inhibitor compound, in particular a compound of formula (I),—or a pharmaceutically acceptable salt thereof—for preparing a pharmaceutical composition for the treatment and/or prevention of cancer.

In another aspect the invention relates to the use of a SOS1 inhibitor compound—or a pharmaceutically acceptable salt thereof—as hereinbefore defined wherein said SOS1 inhibitor compound is administered before, after or together with at least one other pharmacologically active substance.

In another aspect the invention relates to the use of a compound of formula (I)—or a pharmaceutically acceptable salt thereof—as hereinbefore defined wherein said compound is administered before, after or together with at least one other pharmacologically active substance.

In another aspect the invention relates to the use of a SOS1 inhibitor compound, in particular a compound of formula (I),—or a pharmaceutically acceptable salt thereof—as hereinbefore defined for the treatment.

In another aspect the invention relates to a method for the treatment and/or prevention of a disease and/or condition wherein the inhibition of the interaction of SOS1 and a RAS-family protein or RAC1 is of therapeutic benefit comprising administering a therapeutically effective amount of a SOS1 inhibitor compound, in particular a compound of formula (I),—or a pharmaceutically acceptable salt thereof—to a human being.

In another aspect the invention relates to a method for the treatment and/or prevention of cancer comprising administering a therapeutically effective amount of a SOS1 inhibitor compound, in particular a compound of formula (I),—or a pharmaceutically acceptable salt thereof—to a human being.

In another aspect the invention relates to a method as hereinbefore defined wherein the SOS1 inhibitor compound—or a pharmaceutically acceptable salt thereof—is administered before, after or together with at least one other pharmacologically active substance.

In another aspect the invention relates to a method as hereinbefore defined wherein the compound of formula (I)—or a pharmaceutically acceptable salt thereof—is administered before, after or together with at least one other pharmacologically active substance.

In another aspect the invention relates to a method as hereinbefore defined wherein the SOS1 inhibitor compound—or a pharmaceutically acceptable salt thereof—is administered in combination with a therapeutically effective amount of at least one other pharmacologically active substance.

In another aspect the invention relates to a method as hereinbefore defined wherein the compound of formula (I)—or a pharmaceutically acceptable salt thereof—is administered in combination with a therapeutically effective amount of at least one other pharmacologically active substance.

In another aspect the invention relates to a method for the treatment as hereinbefore defined.

In another aspect the invention relates to a kit comprising
- a first pharmaceutical composition or dosage form comprising a SOS1 inhibitor compound and, optionally, one or more pharmaceutically acceptable carriers, excipients and/or vehicles, and
- at least a second pharmaceutical composition or dosage form comprising another pharmacologically active substance and, optionally, one or more pharmaceutically acceptable carriers, excipients and/or vehicles.

In another aspect the invention relates to a kit comprising
- a first pharmaceutical composition or dosage form comprising a compound of formula (I) and, optionally, one or more pharmaceutically acceptable carriers, excipients and/or vehicles, and
- at least a second pharmaceutical composition or dosage form comprising another pharmacologically active substance and, optionally, one or more pharmaceutically acceptable carriers, excipients and/or vehicles.

In another aspect the invention relates to a pharmaceutical composition comprising at least one (preferably one) compound of formula (I)—or a pharmaceutically acceptable salt thereof—and one or more pharmaceutically acceptable excipient(s).

In another aspect the invention relates to a pharmaceutical preparation comprising a compound of formula (I)—or a pharmaceutically acceptable salt thereof—and at least one (preferably one) other pharmacologically active substance.

In another aspect the pharmacologically active substance to be used together/in combination with the SOS1 inhibitor compound, in particular compound of formula (I) (including all individual embodiments or generic subsets of compounds (I)), or in the medical uses, uses, methods of treatment and/or prevention as herein (above and below) defined can be selected from any one or more of the following (preferably there is only one additional pharmacologically active substance used in all these embodiments):

1. an inhibitor of EGFR and/or of mutants thereof
   a. e.g. afatinib, erlotinib, gefitinib, lapatinib, cetuximab, panitumumab, osimertinib, olmutinib, EGF-816;
   b. preferred are afatinib, osimertinib and cetuximab;
   c. most preferred is afatinib
2. an inhibitor of ErbB2 (Her2) and/or of mutants thereof
   a. e.g. afatinib, lapatinib, trastuzumab, pertuzumab;
   b. preferred are afatinib and trastuzumab;
   c. most preferred is trastuzumab;
3. an inhibitor of ALK and/or of mutants thereof
   a. e.g. crizotinib, alectinib, entrectinib, brigatinib;
   b. preferred are crizotinib and alectinib;
   c. most preferred is crizotinib;
4. an inhibitor of MEK and/or of mutants thereof
   a. e.g. trametinib, cobimetinib, binimetinib, selumetinib, refametinib;
   b. preferred are trametinib and cobimetinib;
   c. most preferred is trametinib;
5. an inhibitor of GDP-bound KRAS and/or of mutants thereof
   a. an irreversible inhibitor of KRAS G12C
      i. e.g. ARS-853 (compound V-64 in WO 2014/152588), example I-272 in WO 2016/044772;
   b. a reversible inhibitor of GDP-bound KRAS and/or of mutants thereof;
6. an inhibitor of BCR-ABL and/or of mutants thereof
   a. e.g. imatinib, dasatinib, nilotinib;
   b. preferred are imatinib and nilotinib;
   c. most preferred is imatinib;
7. an inhibitor of FGFR1 and/or FGFR2 and/or FGFR3 and/or of mutants thereof
   a. e.g. nintedanib;
8. an inhibitor of ROS1 and/or of mutants thereof
   a. e.g. crizotinib, entrectinib, lorlatinib, ceritinib, merestinib;
   b. preferred are crizotinib and entrectinib;
   c. most preferred is crizotinib;
9. an inhibitor of c-MET and/or of mutants thereof
10. an inhibitor of AXL and/or of mutants thereof
11. an inhibitor of NTRK1 and/or of mutants thereof
12. an inhibitor of RET and/or of mutants thereof
13. a taxane
    a. e.g. paclitaxel, nab-paclitaxel, docetaxel;
    b. preferred is paclitaxel;
14. a platinum-containing compound
    a. e.g. cisplatin, carboplatin, oxaliplatin;
15. an anti-metabolite
    a. e.g. 5-fluorouracil, capecitabine, floxuridine, cytarabine, gemcitabine, combination of trifluridine and tipiracil (=TAS102);
    b. preferred is gemcitabine;
16. mitotic kinase inhibitor
    a. e.g. CDK4/6 inhibitor
       i. e.g. palbociclib, ribociclib, abemaciclib;
       ii. preferred are palbociclib and abemaciclib;
       iii. most preferred is abemaciclib;
17. an immunotherapeutic agent
    a. e.g. an immune checkpoint inhibitor
       i. e.g. an anti-CTLA4 mAb, anti-PD1 mAb, anti-PD-L1 mAb, anti-PD-L2 mAb, anti-LAG3 mAb, anti-TIM3 mAb;
       ii. preferred is an anti-PD1 mAb;
       iii. e.g. ipilimumab, nivolumab, pembrolizumab, atezolizumab, avelumab, durvalumab, pidilizumab, PDR-001 (=spartalizumab);
       iv. preferred are nivolumab, pembrolizumab and PDR-001 (=spartalizumab);
       v. most preferred is pembrolizumab;
18. an anti-angiogenic drug
    a. e.g. bevacizumab, nintedanib;
    b. most preferred is bevacizumab;
19. a topoisomerase inhibitor
    a. e.g. irinotecan, liposomal irinotecan, topotecan;
    b. most preferred is irinotecan;
20. an inhibitor of A-Raf and/or B-Raf and/or C-Raf and/or of mutants thereof
    a. e.g. RAF-709 (=example 131 in WO 2014/151616), LY-3009120 (=example 1 in WO 2013/134243);
21. an inhibitor of ERK and/or of mutants thereof
    a. e.g. ulixertinib;
22. an apoptose regulator
    a. e.g. an inhibitor of the interaction between p53 (preferably functional p53, most preferably wt p53) and MDM2 (a "MDM2 inhibitor");
       i. e.g. HDM-201, NVP-CGM097, RG-7112, MK-8242, RG-7388, SAR405838, AMG-232, DS-3032, RG-7775, APG-115;
       ii. preferred are HDM-201, RG-7388 and AMG-232
    b. e.g. a PARP inhibitor;
    c. e.g. a MCL-1 inhibitor;

23. an inhibitor of mTOR
   a. e.g. rapamycin, temsirolimus, everolimus, ridaforolimus;
24. an epigenetic regulator
   a. e.g. a BET inhibitor
      i. e.g. JQ-1, GSK 525762, OTX 015 (=MK8628), CPI 0610, TEN-010 (=RO6870810);
   b. e.g. a CDK9 inhibitor;
25. an inhibitor of IGF1/2 and/or of IGF1-R
   a. e.g. xentuzumab (antibody 60833 in WO 2010/066868), MEDI-573 (=dusigitumab);
26. an inhibitor of RAS GEFs and/or of mutants thereof
   a. e.g. an inhibitor of SOS2 and/or of mutants thereof
27. an inhibitor of PI3K and/or of mutants thereof Within this invention it is to be understood that the combinations, compositions, kits, methods, uses or compounds for use according to this invention may envisage the simultaneous, concurrent, sequential, successive, alternate or separate administration of the active ingredients or components. It will be appreciated that the SOS1 inhibitor compound (e.g. compound of formula (I)) and the at least one other pharmacologically active substance can be administered formulated either dependently or independently, such as e.g. the SOS1 inhibitor compound (e.g. compound of formula (I)) and the at least one other pharmacologically active substance may be administered either as part of the same pharmaceutical composition/dosage form or, preferably, in separate pharmaceutical compositions/dosage forms.

In this context, "combination" or "combined" within the meaning of this invention includes, without being limited, a product that results from the mixing or combining of more than one active ingredient and includes both fixed and non-fixed (e.g. free) combinations (including kits) and uses, such as e.g. the simultaneous, concurrent, sequential, successive, alternate or separate use of the components or ingredients. The term "fixed combination" means that the active ingredients are both administered to a patient simultaneously in the form of a single entity or dosage. The term "non-fixed combination" means that the active ingredients are both administered to a patient as separate entities either simultaneously, concurrently or sequentially with no specific time limits, wherein such administration provides therapeutically effective levels of the two compounds in the body of the patient.

The administration of the SOS1 inhibitor compound (e.g. compound of formula (I)) and the at least one other pharmacologically active substance may take place by co-administering the active components or ingredients, such as e.g. by administering them simultaneously or concurrently in one single or in two or more separate formulations or dosage forms. Alternatively, the administration of the SOS1 inhibitor compound (e.g. compound of formula (I)) and the at least one other pharmacologically active substance may take place by administering the active components or ingredients sequentially or in alternation, such as e.g. in two or more separate formulations or dosage forms.

For example, simultaneous administration includes administration at substantially the same time. This form of administration may also be referred to as "concomitant" administration. Concurrent administration includes administering the active agents within the same general time period, for example on the same day(s) but not necessarily at the same time. Alternate administration includes administration of one agent during a time period, for example over the course of a few days or a week, followed by administration of the other agent(s) during a subsequent period of time, for example over the course of a few days or a week, and then repeating the pattern for one or more cycles. Sequential or successive administration includes administration of one agent during a first time period (for example over the course of a few days or a week) using one or more doses, followed by administration of the other agent(s) during a second and/or additional time period (for example over the course of a few days or a week) using one or more doses. An overlapping schedule may also be employed, which includes administration of the active agents on different days over the treatment period, not necessarily according to a regular sequence. Variations on these general guidelines may also be employed, e.g. according to the agents used and the condition of the subject.

The elements of the combinations of this invention may be administered (whether dependently or independently) by methods customary to the skilled person, e.g. by oral, enterical, parenteral (e.g., intramuscular, intraperitoneal, intravenous, transdermal or subcutaneous injection, or implant), nasal, vaginal, rectal, or topical routes of administration and may be formulated, alone or together, in suitable dosage unit formulations containing conventional non-toxic pharmaceutically acceptable carriers, excipients and/or vehicles appropriate for each route of administration.

Accordingly, in one aspect of the invention the invention provides a method for the treatment and/or prevention of cancer comprising administering to a patient in need thereof a therapeutically effective amount of a SOS1 inhibitor compound (e.g. a compound of formula (I)) and a therapeutically effective amount of at least one other pharmacologically active substance, wherein the SOS1 inhibitor compound (e.g. a compound of formula (I)) is administered simultaneously, concurrently, sequentially, successively, alternately or separately with the at least one other pharmacologically active substance.

In another aspect the invention provides a SOS1 inhibitor compound (e.g. a compound of formula (I)) for use in the treatment and/or prevention of cancer, wherein the SOS1 inhibitor compound (e.g. a compound of formula (I)) is administered simultaneously, concurrently, sequentially, successively, alternately or separately with the at least one other pharmacologically active substance.

In another aspect the invention provides a kit comprising
   a first pharmaceutical composition or dosage form comprising a SOS1 inhibitor compound (e.g. a compound of formula (I)), and, optionally, one or more pharmaceutically acceptable carriers, excipients and/or vehicles, and
   at least a second pharmaceutical composition or dosage form comprising another pharmacologically active substance, and, optionally, one or more pharmaceutically acceptable carriers, excipients and/or vehicles,
for use in the treatment and/or prevention of cancer, wherein the first pharmaceutical composition is to be administered simultaneously, concurrently, sequentially, successively, alternately or separately with the second and/or additional pharmaceutical composition or dosage form.

In a further embodiment of the invention the components (i.e. the combination partners) of the combinations, kits, uses, methods and compounds for use according to the invention (including all embodiments) are administered simultaneously.

In a further embodiment of the invention the components (i.e. the combination partners) of the combinations, kits, uses, methods and compounds for use according to the invention (including all embodiments) are administered concurrently.

In a further embodiment of the invention the components (i.e. the combination partners) of the combinations, kits, uses, methods and compounds for use according to the invention (including all embodiments) are administered sequentially.

In a further embodiment of the invention the components (i.e. the combination partners) of the combinations, kits, uses, methods and compounds for use according to the invention (including all embodiments) are administered successively.

In a further embodiment of the invention the components (i.e. the combination partners) of the combinations, kits, uses, methods and compounds for use according to the invention (including all embodiments) are administered alternately.

In a further embodiment of the invention the components (i.e. the combination partners) of the combinations, kits, uses, methods and compounds for use according to the invention (including all embodiments) are administered separately.

The "therapeutically effective amount" of the active compound(s) to be administered is the minimum amount necessary to prevent, ameliorate, or treat a disease or disorder.

The combinations of this invention may be administered at therapeutically effective single or divided daily doses. The active components of the combination may be administered in such doses which are therapeutically effective in monotherapy, or in such doses which are lower than the doses used in monotherapy, but when combined result in a desired (joint) therapeutically effective amount.

In another aspect the disease/condition/cancer to be treated/prevented with the SOS1 inhibitor compound, SOS1 inhibitor compound for use, compound of formula (I), compound of formula (I) for use, use for preparing and method for the treatment and/or prevention as herein (above and below) defined is selected from the group consisting of pancreatic cancer, lung cancer, colorectal cancer, cholangiocarcinoma, multiple myeloma, melanoma, uterine cancer, endometrial cancer, thyroid cancer, acute myeloid leukaemia, bladder cancer, urothelial cancer, gastric cancer, cervical cancer, head and neck squamous cell carcinoma, diffuse large B cell lymphoma, oesophageal cancer, chronic lymphocytic leukaemia, hepatocellular cancer, breast cancer, ovarian cancer, prostate cancer, glioblastoma, renal cancer and sarcomas.

In another aspect the disease/condition/cancer to be treated/prevented with the SOS1 inhibitor compound, SOS1 inhibitor compound for use, compound of formula (I), compound of formula (I) for use, use for preparing and method for the treatment and/or prevention as herein (above and below) defined is selected from the group consisting of pancreatic cancer, lung cancer (preferably non-small cell lung cancer (NSCLC)), cholangiocarcinoma and colorectal cancer.

In another aspect the disease/condition to be treated/prevented with the SOS1 inhibitor compound, SOS1 inhibitor compound for use, compound of formula (I), compound of formula (I) for use, use for preparing and method for the treatment and/or prevention as herein (above and below) defined is a RASopathy, preferably selected from the group consisting of Neurofibromatosis type 1 (NF1), Noonan Syndrome (NS), Noonan Syndrome with Multiple Lentigines (NSML) (also referred to as LEOPARD syndrome), Capillary Malformation-Arteriovenous Malformation Syndrome (CM-AVM), Costello Syndrome (CS), Cardio-Facio-Cutaneous Syndrome (CFC), Legius Syndrome (also known as NF1-like Syndrome) and Hereditary gingival fibromatosis.

In another aspect the disease/condition/cancer to be treated/prevented with the SOS1 inhibitor compound, SOS1 inhibitor compound for use, compound of formula (I), compound of formula (I) for use, use for preparing and method for the treatment and/or prevention as herein (above and below) defined is a disease/condition/cancer defined as exhibiting one or more of the following molecular features:

1. KRAS alterations:
   a. KRAS amplification (wt or mutant);
   b. KRAS overexpression (wt or mutant);
   c. KRAS mutation(s):
      i. G12 mutations (e.g. G12C, G12V, G12S, G12A, G12V, G12R, G12F, G12D);
      ii. G13 mutations (e.g. G13C, G13D, G13R, G13V, G13S, G13A)
      iii. T35 mutation (e.g. T35);
      iv. I36 mutation (e.g. I36L, I36M);
      v. E49 mutation (e.g. E49K);
      vi. Q61 mutation (e.g. Q61H, Q61R, Q61P, Q61E, Q61K, Q61L, Q61K);
      vii. K117 mutation (e.g. K117N);
      viii. A146 mutation (e.g. A146T, A146V);
2. NRAS alterations:
   a. NRAS amplification (wt or mutant);
   b. NRAS overexpression (wt or mutant);
   c. NRAS mutation(s):
      i. G12 mutations (e.g. G12A, G12V, G12D, G12C, G12S, G12R);
      ii. G13 mutation (e.g. G13V, G13D, G13R, G13S, G13C, G13A);
      iii. Q61 mutation (e.g. Q61K, Q61L, Q61H, Q61P, Q61R);
      iv. A146 mutation (e.g. A146T, A146V);
3. HRAS alterations:
   a. HRAS amplification (wt or mutant);
   b. HRAS overexpression (wt or mutant);
   c. HRAS mutation(s);
      i. G12 mutation (e.g. G12C, G12V, G12S, G12A, G12V, G12R, G12F, G12D); ii. G13 mutation (e.g. G13C, G13D, G13R, G13V, G13S, G13A);
      iii. Q61 mutation (e.g. Q61K, Q61L, Q61H, Q61P, Q61R);
4. EGFR alterations:
   a. EGFR amplification (wt or mutant);
   b. EGFR overexpression (wt or mutant);
   c. EGFR mutation(s)
      i. e.g. exon 20 insertion, exon 19 deletion (Del19), G719X (e.g. G719A, G719C, G719S), T790M, C797S, T854A, L858R, L861Q, or any combination thereof;
5. ErbB2 (Her2) alterations:
   a. ErbB2 amplification;
   b. ErbB2 overexpression;
   c. ErbB2 mutation(s)
      i. e.g. R678, G309, L755, D769, D769, V777, P780, V842, R896, c.2264_2278del (L755_T759del), c.2339_2340ins (G778_P780dup), S310;
6. c-MET alterations:
   a. c-MET amplification;
   b. c-MET overexpression;
   c. c-MET mutation(s)
      i. e.g. E168, N375, Q648, A887, E908, T1010, V1088, H1112, R1166, R1188, Y1248, Y1253, M1268, D1304, A1357, P1382;

7. AXL alterations:
a. AXL amplification;
b. AXL overexpression;
8. BCR-ABL alterations:
a. chromosomal rearrangements involving the ABL gene;
9. ALK alterations:
a. ALK amplification;
b. ALK overexpression;
c. ALK mutation(s)
  i. e.g. 1151Tins, L1152R, C1156Y, F1174L, L1196M, L1198F, G1202R, S1206Y, G1269A;
d. chromosomal rearrangements involving the ALK gene;
10. FGFR1 alterations:
a. FGFR1 amplification;
b. FGFR1 overexpression;
11. FGFR2 alterations:
a. FGFR2 amplification;
b. FGFR2 overexpression;
12. FGFR3 alterations:
a. FGFR3 amplification;
b. FGFR3 overexpression;
c. chromosomal rearrangement involving the FGFR3 gene;
13. NTRK1 alterations:
a. chromosomal rearrangements involving the NTRK1 gene;
14. NF1 alterations:
a. NF1 mutation(s);
15. RET alterations:
a. RET amplification;
b. RET overexpression;
c. chromosomal rearrangements involving the RET gene
16. ROS1 alterations:
a. ROS1 amplification;
b. ROS1 overexpression;
c. ROS1 mutation(s)
  i. e.g. G2032R, D2033N, L2155S;
d. chromosomal rearrangements involving the ROS1 gene;
17. SOS1 alterations
a. SOS1 amplification;
b. SOS1 overexpression;
c. SOS1 mutation(s);
18. RAC1 alterations
a. RAC1 amplification;
b. RAC1 overexpression;
c. RAC1 mutation(s);
19. MDM2 alterations
a. MDM2 amplification
b. MDM2 overexpression
c. MDM2 amplification in combination with functional p53
d. MDM2 amplification in combination with wild-type p53
20. RAS wild-type
a. KRAS wild-type
b. HRAS wild-type
c. NRAS wild-type
21. B-Raf mutation(s) other than V600E Particularly preferred, the cancer to be treated/prevented with the SOS1 inhibitor compound, SOS1 inhibitor compound for use, compound of formula (I), compound of formula (I) for use, use for preparing and method for the treatment and/or prevention as herein (above and below) defined is selected from the group consisting of:

lung adenocarcinoma harboring a KRAS mutation selected from the group consisting of G12C, G12V, G12D and G12R;

colorectal adenocarcinoma harboring a KRAS mutation selected from the group consisting of G12D, G12V, G12C, G12R and G13D; and pancreatic adenocarcinoma harboring a KRAS mutation selected from the group consisting of G12D, G12V, G12R, G12C and Q61H.

Any disease/condition/cancer, medical use, use, method of treatment and/or prevention as disclosed or defined herein (including molecular/genetic features) may be treated/performed with any compound of formula (I) as disclosed or defined herein (including all individual embodiments or generic subsets of compounds (I)).

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to:

The use of the prefix $C_{x-y}$, wherein x and y each represent a positive integer (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroaryl, heteroarylalkyl, heterocyclyl, heterocycylalkyl) relates to the total number of atoms of all the ring members or the total of all the ring and carbon chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocycylalkyl, cycloalkylalkyl, arylalkyl) the last named subgroup is the radical attachment point, for example, the substituent aryl-$C_1$-alkyl means an aryl group which is bound to a $C_{1-6}$alkyl group, the latter of which is bound to the core or to the group to which the substituent is attached.

In groups like HO, $H_2N$, (O)S, $(O)_2S$, NC (cyano), HOOC, $F_3C$ or the like, the skilled artisan can see the radical attachment point(s) to the molecule from the free valences of the group itself.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

Further examples of alkyl are methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl (n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH (CH$_3$)$_2$), 2,2-dimethyl-1-propyl (neo-pentyl; —CH$_2$C (CH$_3$)$_3$), 2-methyl-1-butyl (—CH$_2$CH(CH$_3$)CH$_2$CH$_3$), 1-hexyl (n-hexyl; —CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$) (CH$_2$CH$_2$CH$_3$)), 2-methyl-2-pentyl (—C (CH$_3$)$_2$CH$_2$CH$_2$CH$_3$), 3-methyl-2-pentyl (—CH(CH$_3$)CH (CH$_3$)CH$_2$CH$_3$), 4-methyl-2-pentyl (—CH(CH$_3$)CH$_2$CH (CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 2,3-dimethyl-1-butyl (—CH$_2$CH (CH$_3$)CH(CH$_3$)CH$_3$), 2,2-dimethyl-1-butyl (—CH$_2$C (CH$_3$)$_2$CH$_2$CH$_3$), 3,3-dimethyl-1-butyl (—CH$_2$CH$_2$C (CH$_3$)$_3$), 2-methyl-1-pentyl (—CH$_2$CH(CH$_3$)CH$_2$CH$_2$CH$_3$), 3-methyl-1-pentyl (—CH$_2$CH$_2$CH(CH$_3$)CH$_2$CH$_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —CH$_3$ and —CH$_2$—, —CH$_2$CH$_3$ and —CH$_2$CH$_2$— or >CHCH$_3$ etc.

The term "$C_{1-4}$alkylene" includes for example —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CH(CH(CH$_3$))$_2$)— and —C(CH$_3$)(CH$_2$CH$_3$)—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another (combined) group such as for example in HO—$C_{x-y}$alkyleneamino or H$_2$N—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x-y}$alkenyleneamino or H$_2$N—$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x-y}$alkynyleneamino or $H_2N$—$C_{x-y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —$CH_2F$ and —CHF—, —$CHFCH_2F$ and —CHFCHF— or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms in common. In spiro-hydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x-y}$cycloalkylamino, $C_{x-y}$cycloalkyloxy or $C_{x-y}$cycloalkylalkyl.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:

cyclohexyl and

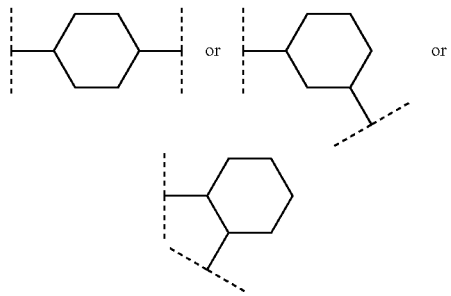

(cyclohexylene).

The above definition for cycloalkylene also applies if cycloalkylene is part of another (combined) group as for example in HO—$C_{x-y}$cycloalkyleneamino or $H_2N$—$C_{x-y}$cycloalkyleneoxy.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicyclic group is obtained.

The term cycloalkenyiene can thus be derived from the previously defined cycloalkenyl. Cycloalkenylene, unlike cycloalkenyl, is bivalent and requires two binding partners. Formally, the second valency is obtained by removing a hydrogen atom from a cycloalkenyl. Corresponding groups are for example: cyclopentenyl and

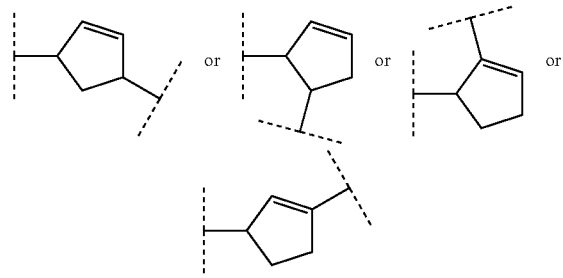

(cyclopentenylene) etc.

The above definition for cycloalkenylene also applies if cycloalkenylene is part of another (combined) group as for example in HO—$C_{x-y}$cycloalkenyleneamino or $H_2N$—$C_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc. Most preferred is phenyl.

The above definition of aryl also applies if aryl is part of another (combined) group as for example in arylamino, aryloxy or arylalkyl.

If the free valency of an aryl is saturated, then an aromatic aroup is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:

phenyl and

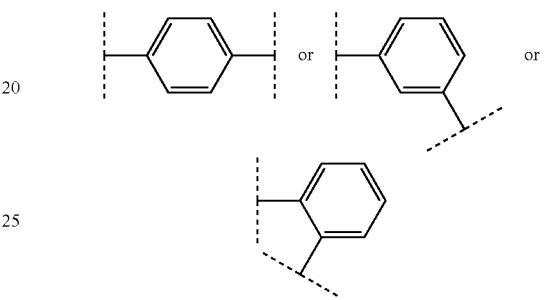

(o, m, p-phenylene), naphthyl and

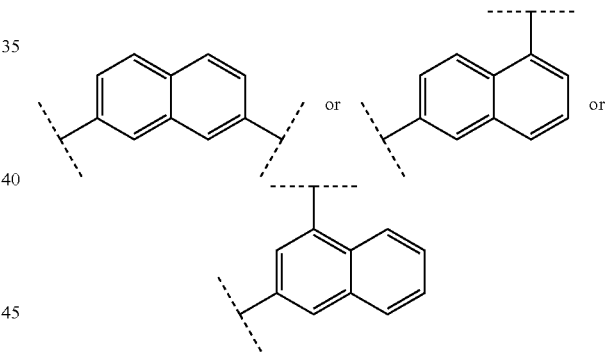

etc.

The above definition for arylene also applies if arylene is part of another (combined) group as for example in HO-aryleneamino or $H_2N$-aryleneoxy.

Heterocyclyl denotes ring systems, which are derived from the previously defined cycloalkyl, cycloalkenyl and aryl by replacing one or more of the groups —CH$_2$— independently of one another in the hydrocarbon rings by the groups —O—, —S— or —NH— or by replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (sulphur→sulphoxide —SO—, sulphone —SO$_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. Substituents on heterocyclyl do not count for the number of members of a heterocyclyl.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydro-pyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4,5]decyl etc.

Further examples are the structures illustrated below, which may be attached via each hydrogen-carrying atom (exchanged for hydrogen):

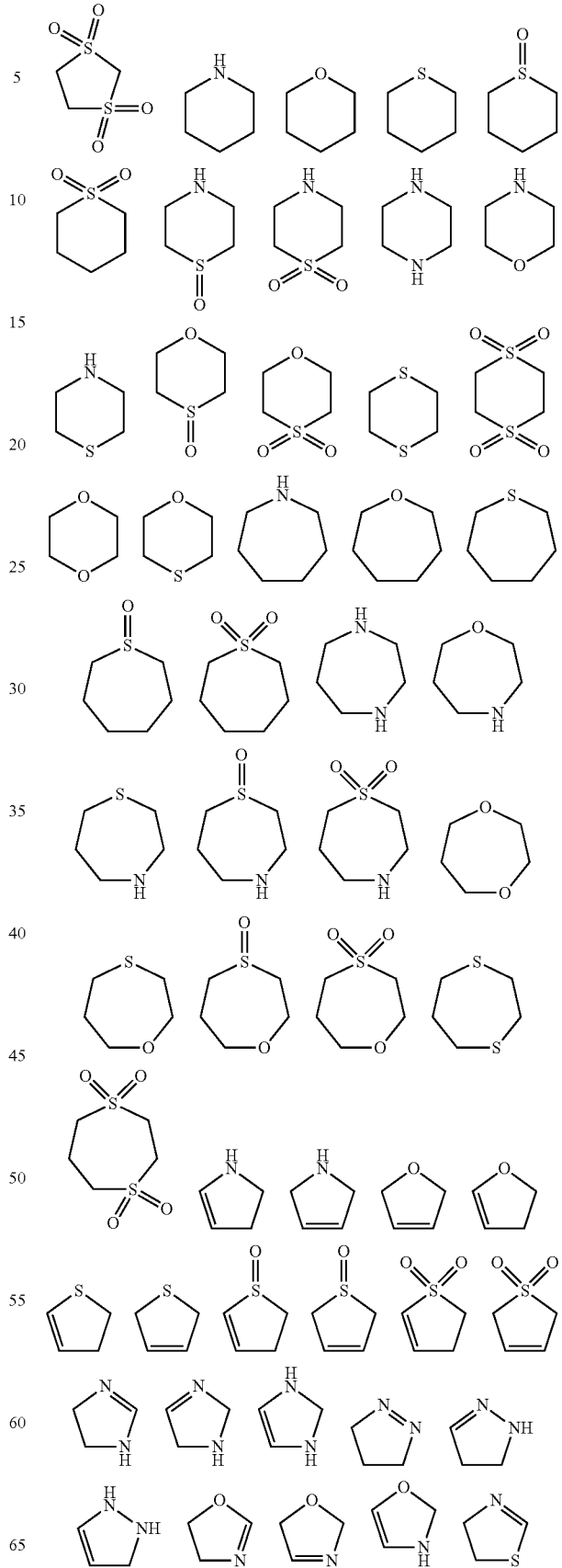

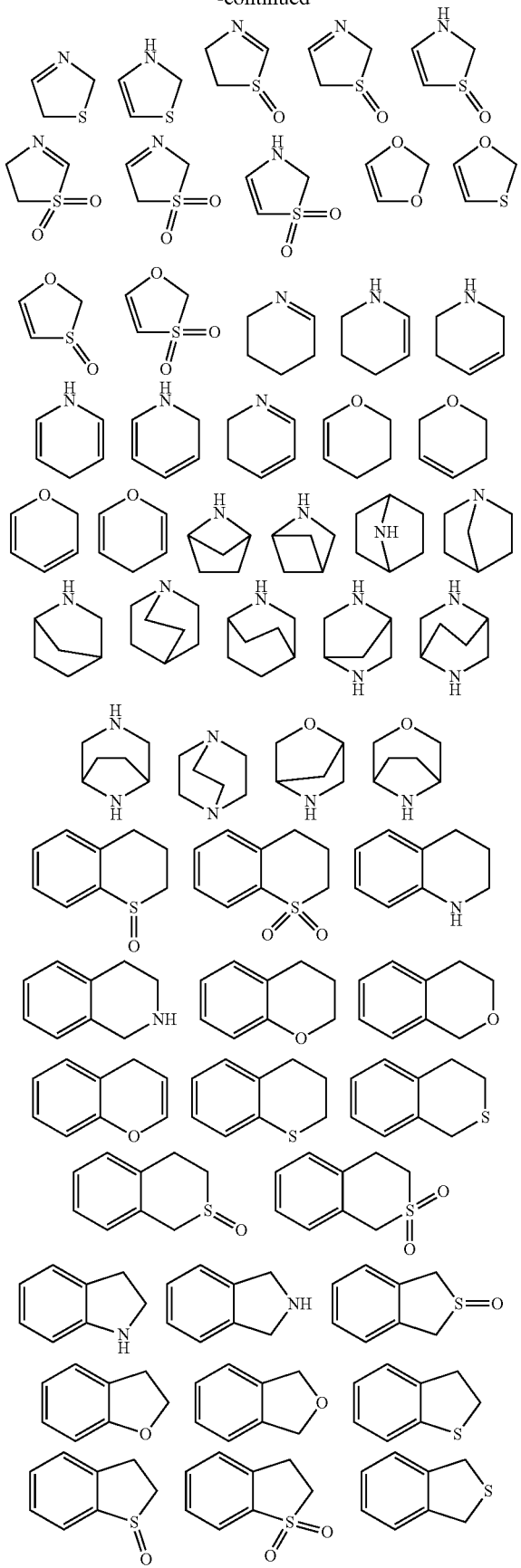
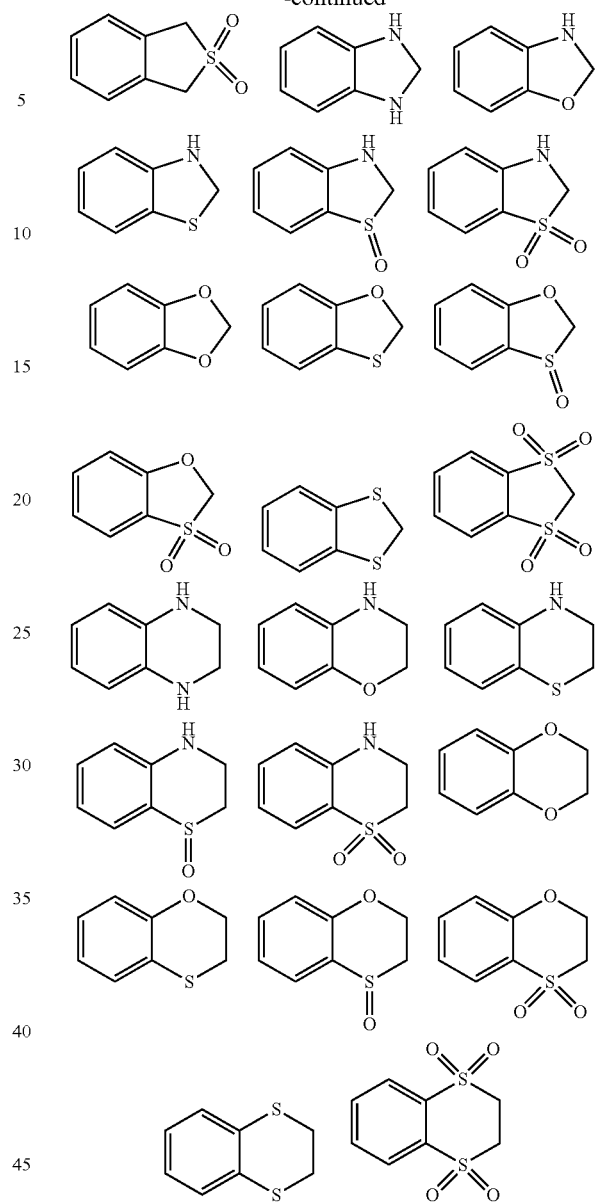

Preferably, heterocyclyls are 4 to 8 membered, monocyclic and have one or two heteroatoms independently selected from oxygen, nitrogen and sulfur.

Preferred heterocyclyls are: piperazinyl, piperidinyl, morpholinyl, pyrrolidinyl, azetidinyl, tetrahydropyranyl, tetrahydrofuranyl.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

piperidinyl and

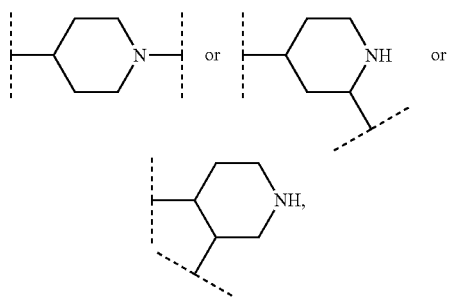

2,3-dihydro-1H-pyrrolyl and

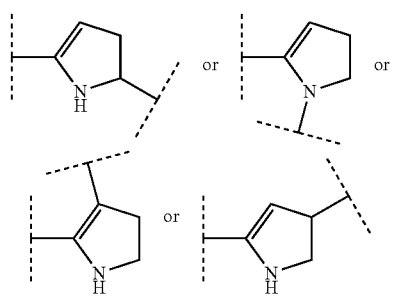

etc.

The above definition of heterocyclylene also applies if heterocyclylene is part of another (combined) group as for example in HO-heterocyclyleneamino or H₂N-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen. Substituents on heteroaryl do not count for the number of members of a heteroaryl.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

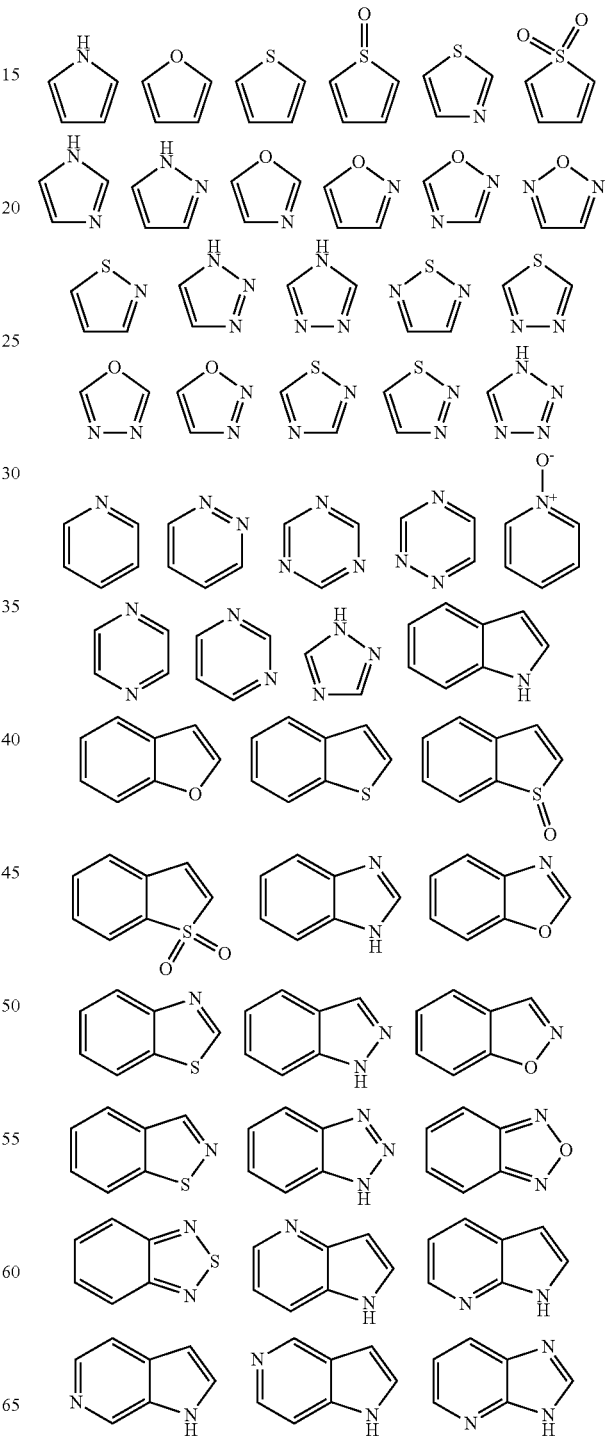

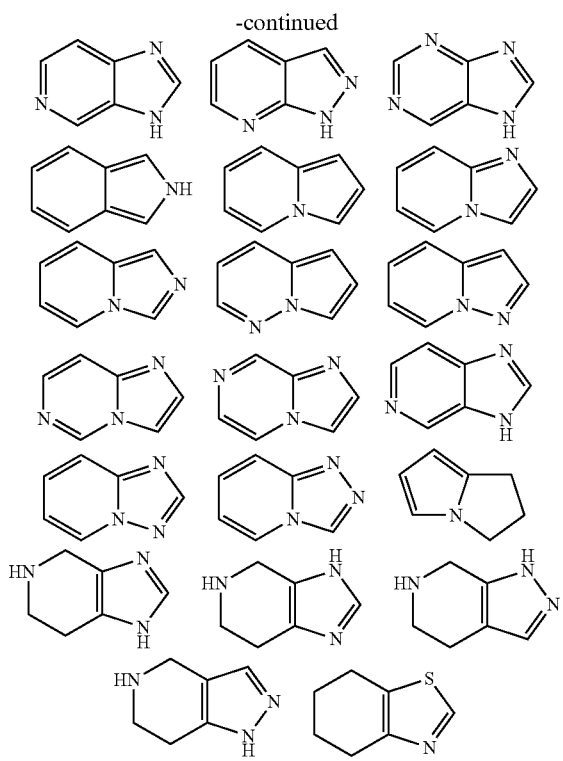

Preferably, heteroaryls are 5-6 membered monocyclic or 9-10 membered bicyclic, each with 1 to 4 heteroatoms independently selected from oxygen, nitrogen and sulfur.

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl. Heteroarylene, unlike heteroaryl, is bivalent and requires two binding partners. Formally, the second valency is obtained by removing a hydrogen atom from a heteroaryl. Corresponding groups are for example:

pyrrolyl and

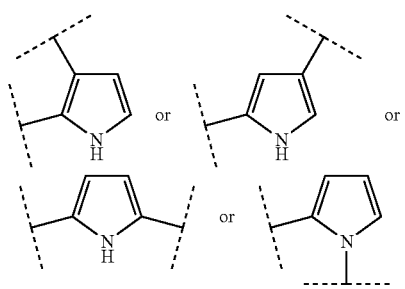

etc.

The above definition of heteroarylene also applies if heteroarylene is part of another (combined) group as for example in HO-heteroaryleneamino or $H_2N$-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents on carbon atoms, whereas the bivalent substituents =O and =NR may also be a substituent on sulphur. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group —CH$_2$— or sulphur atoms (=O group or =NR group only, one or two =O groups possible or, e.g., one =O group and one =NR group, each group replacing a free electron pair) of a ring system.

Stereochemistry/Solvates/Hydrates:

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates and hydrates of the free compound or solvates and hydrates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases, or by resolution of a racemic mixture using an appropriate resolving agent, e.g. by means of diastereomeric salt formation of the racemic compound with optically active acids or bases, subsequent resolution of the salts and release of the desired compound from the salt, or by derivatization of the corresponding racemic compounds with optically active chiral auxiliary reagents, subsequent diastereomer separation and removal of the chiral auxiliary group, or by kinetic resolution of a racemate (e.g. by enzymatic resolution); by enantioselective crystallization from a conglomerate of enantiomorphous crystals under suitable conditions, or by (fractional) crystallization from a suitable solvent in the presence of an optically active chiral auxiliary.

Salts:

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

In a representation such as for example

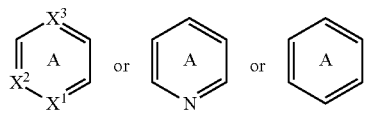

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

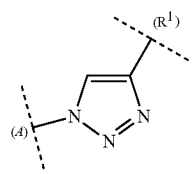

or (R²)—C(O)NH— or (R²)—NHC(O)—;

In a representation such as for example

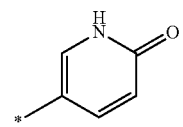

the asterisk designates the point of attachment of the respective group as a substituent.

Groups or substituents are frequently selected from among a number of alternative groups/substituents with a corresponding group designation (e.g. $R^a$, $R^b$ etc). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

RAS-family proteins are meant to include KRAS (V-Ki-ras2 Kirsten rat sarcoma viral oncogene homolog), NRAS (neuroblastoma RAS viral oncogene homolog) and HRAS (Harvey murine sarcoma virus oncogene) and any mutants thereof.

A SOS1 inhibitor compound is a compound, which binds to SOS1 and thereby prevents the SOS1 mediated nucleotide exchange and subsequently reduces the levels of RAS in its GTP bound form. More specifically, a SOS1 inhibitor compound shows a pharmacological inhibition of the binding of the catalytic site of SOS1 to RAS-family proteins. Thus, such a compound interacts with SOS1, e.g. the catalytic site on SOS1, and reduces the level of binding to the RAS-family protein in relation to said binding without addition of a SOS1 inhibitor compound. Accordingly, it is envisaged that a SOS1 inhibitor compound at least reduces the level of binding to the RAS-family protein about 5%, 10%, 20%, 30%, 40%, 50%, 60%, 70%, 80%, 90% or even 100% when compared to the binding that is achieved without the addition of said inhibitor compound. Suitable test systems to measure the binding to the catalytic site of SOS1 are disclosed herein. Said compound may be chemically synthesized (e.g. a small molecule) or microbiologically produced (e.g. a monoclonal antibody) and/or comprised in, for example, samples, e.g., cell extracts from, e.g., plants, animals or microorganisms. Preferably, the SOS1 inhibitor compound is a small molecule.

LIST OF ABBREVIATIONS

| | |
|---|---|
| Ac | acetyl |
| ACN | acetonitrile |
| amphos | bis(di-tert-butyl(4-dimethylaminophenyl)phosphine) |
| aq. | aquatic, aqueous |
| ATP | adenosine triphosphate |
| Bn | benzyl |
| Boc | tert-butyloxycarbonyl |
| Bu | butyl |
| c | concentration |
| Cbz | carboxybenzyl |
| $CH_2Cl_2$ | dichloro methane |
| d | day(s) |
| dba | dibenzylideneacetone |
| TLC | thin layer chromatography |
| DAST | diethylamino sulfurtrifluoride |
| Davephos | 2-dimethylamino-2'-dicyclohexylaminophosphinobiphenyl |
| DBA | dibenzylidene acetone |
| DBU | 1,8-Diazabicyclo(5.4.0)undec-7-ene |
| DCE | dichloro ethane |
| DCM | dichloro methane |
| DEA | diethyl amine |
| DEAD | diethyl azodicarboxylate |
| DIPEA | N-ethyl-N,N-diisopropylamine (Hünig's base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1.1'-bis(diphenylphosphino)ferrocene |
| EDTA | ethylenediaminetetraacetic acid |
| EGTA | ethyleneglycoltetraacetic acid |
| eq | equivalent(s) |
| equiv. | equivalent(s) |
| ESI | electron spray ionization |
| Et | ethyl |
| $Et_2O$ | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| IBX | 2-iodoxy benzoic acid |
| i | iso |
| conc. | concentrated |
| LC | liquid chromatography |
| LiHMDS | lithium bis(trimethylsilyl)amide |
| sln. | solution |
| Me | methyl |
| MeOH | methanol |
| min | minutes |
| MPLC | medium pressure liquid chromatography |
| MS | mass spectrometry |
| MTBE | methyl tert-butyl ether |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | phenyl |
| Pr | propyl |
| PTSA | p-toluenesulfonic acid |
| Py | pyridine |
| rac | racemic |
| red. | reduction |
| Rf ($R_f$) | retention factor |
| RP | reversed phase |
| RRLC | Rapid resolution liquid chromatography |
| rt | ambient temperature |
| SFC | supercritical fluid chromatography |
| $S_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethyl amine |
| temp. | temperature |
| tert | tertiary |
| Tf | triflate |
| TFA | trifluoroacetic acid |
| THF | tetrahydrofuran |
| TMS | trimethylsilyl |
| $t_{Ret.}$ | retention time (HPLC) |
| TRIS | tris(hydroxymethyl)-aminomethane |
| TsOH | p-toluenesulphonic acid |
| UPLC | ultra performance liquid chromatography |
| UV | ultraviolet |
| wt | weight |

Features and advantages of the present invention will become apparent from the following detailed examples which illustrate the principles of the invention by way of example without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom (Beilstein). If a compound is to be represented both by a structural formula and by its nomenclature, in the event of a conflict the structural formula is decisive.

Microwave reactions are carried out in an initiator/reactor made by Biotage or in an Explorer made by CEM or in Synthos 3000 or Monowave 3000 made by Anton Paar in sealed containers (preferably 2, 5 or 20 mL), preferably with stirring.

Chromatography

The thin layer chromatography is carried out on ready-made silica gel 60 TLC plates on glass (with fluorescence indicator F-254) made by Merck.

The preparative high pressure chromatography (RP HPLC) of the example compounds according to the invention is carried out on Agilent or Gilson systems with columns made by Waters (names: SunFire™ Prep C18, OBD™ 10 µm, 50×150 mm or SunFire™ Prep C18 OBD™ 5 µm, 30×50 mm or XBridge™ Prep C18, OBD™ 10 µm, 50×150 mm or XBridge™ Prep C18, OBD™ 5 µm, 30×150 mm or XBridge™ Prep C18, OBD™ 5 µm, 30×50 mm) and YMC (names: Actus-Triart Prep C18, 5 µm, 30×50 mm).

Different gradients of $H_2O$/acetonitrile are used to elute the compounds, while for Agilent systems 5% acidic modifier (20 mL HCOOH to 1 L $H_2O$/acetonitrile (1/1)) is added to the water (acidic conditions). For Gilson systems the water is added 0.1% HCOOH.

For the chromatography under basic conditions for Agilent systems $H_2O$/acetonitrile gradients are used as well, while the water is made alkaline by addition of 5% basic modifier (50 g $NH_4HCO_3$+50 mL $NH_3$ (25% in $H_2O$) to 1 L with $H_2O$). For Gilson systems the water is made alkaline as follows: 5 mL $NH_4HCO_3$ solution (158 g in 1 L $H_2O$) and 2 mL $NH_3$ (28% in $H_2O$) are replenished to 1 L with $H_2O$.

The supercritical fluid chromatography (SFC) of the intermediates and example compounds according to the invention is carried out on a JASCO SFC-system with the following colums: Chiralcel OJ (250×20 mm, 5 µm), Chiralpak AD (250×20 mm, 5 µm), Chiralpak AS (250×20 mm, 5 µm), Chiralpak IC (250×20 mm, 5 µm), Chiralpak IA (250×20 mm, 5 µm), Chiralcel OJ (250×20 mm, 5 µm), Chiralcel OD (250×20 mm, 5 µm), Phenomenex Lux $C_2$ (250×20 mm, 5 µm).

The analytical HPLC (reaction control) of intermediate and final compounds is carried out using columns made by Waters (names: XBridge™ C18, 2.5 µm, 2.1×20 mm or XBridge™ C18, 2.5 µm, 2.1×30 mm or Aquity UPLC BEH C18, 1.7 µm, 2.1×50 mm) and YMC (names: Triart C18, 3.0 µm, 2.0×30 mm) and Phenomenex (names: Luna C18, 5.0 µm, 2.0×30 mm). The analytical equipment is also equipped with a mass detector in each case.

HPLC-Mass Spectroscopy/UV-Spectrometry

The retention times/MS-ESI+ for characterizing the example compounds according to the invention are produced using an HPLC-MS apparatus (high performance liquid chromatography with mass detector). Compounds that elute at the injection peak are given the retention time $t_{Ret.}=0.00$.

HPLC-Methods (Preparative)
prep. HPLC1
HPLC: 333 and 334 Pumps
Column: Waters X-Bridge C18 OBD, 10 µm, 30×100 mm, Part.No. 186003930
Solvent: A: 10 mM $NH_4HCO_3$ in $H_2O$; B: Acetonitrile (HPLC grade)
Detection: UV/Vis-155
Flow: 50 mL/min
Gradient: 0.00-1.50 min: 1.5% B
1.50-7.50 min: varying
7.50-9.00 min: 100% B
prep. HPLC2
HPLC: 333 and 334 Pumps
Column: Waters Sunfire C18 OBD, 10 µm, 30×100 mm, Part.No. 186003971
Solvent: A: $H_2O$+0.2% HCOOH; B: Acetonitrile (HPLC grade)+0.2% HCOOH
Detection: UV/Vis-155
Flow: 50 mL/min
Gradient: 0.00-1.50 min: 1.5% B
1.50-7.50 min: varying
7.50-9.00 min: 100% B
HPLC-Methods (Analytic)
LCMSBAS1
HPLC: Agilent 1100 Series
MS: Agilent LC/MSD SL
Column: Phenomenex Mercury Gemini C18, 3 µm, 2×20 mm, Part.No. 00M-4439-BO-CE
Solvent: A: 5 mM $NH_4HCO_3$/20 mM $NH_3$ in $H_2O$; B: acetonitrile (HPLC grade)
Detection: MS: positive and negative mode
Mass range: 120-900 m/z
Flow: 1.00 mL/min
Column temperature: 40° C.
Gradient: 0.00-2.50 min: 5% B→95% B
2.50-2.80 min: 95% B
2.81-3.10 min: 95% B→5% B
VAB
HPLC: Agilent 1100/1200 Series
MS: Agilent LC/MSD SL
Column: Waters X-Bridge BEH C18, 2.5 µm, 2.1×30 mm XP
Solvent: A: 5 mM $NH_4HCO_3$/19 mM $NH_3$ in $H_2O$; B: acetonitrile (HPLC grade)
Detection: MS: positive and negative mode
Mass range: 100-1200 m/z
Flow: 1.40 mL/min
Column temperature: 45° C.
Gradient: 0.00-1.00 min: 5% B→100% B
1.00-1.37 min: 100% B
1.37-1.40 min: 100% B→5% B
RND-FA-3.5
HPLC: Agilent Infinity-1290 Series
MS: Agilent SQD-6150 (API-ES+/−3000 V)
MSD signal settings: Scan pos 100-1000, Scan neg 100-1000
Column: Aquity BEH C18, 2.1×50 mm, 1.7 µm
Eluent: A: 0.1% formic acid in water; B: 0.1% formic acid in acetonitrile
Detection signal: UV 215 nm (bandwidth 4, reference off)
Spectrum: range: 200-400 nm; step: 2 nm
Peak width: >0.025 min (0.5 S)
Injection: 0.5 µL injection with needle wash at flush port
Flow rate: 0.8 mL/min
Column temperature: 45° C.
Gradient: 0.0-0.2 min: 2% B
0.2-1.5 min: 2% B→98% B
1.5-2.6 min: 98% B
2.6-2.61 min: 98% B→2% B
2.61-3.2 min: 2% B
GVK_LCMS_18
HPLC: Agilent Infinity-1290 Series
MS: Agilent SQD-6130 (API-ES+3500 V/−3000 V)
MSD signal settings: Scan pos 100-1200, Scan neg 100-1200
Column: Aquity BEH C18, 2.1×50 mm, 1.7 µm
Eluent: A: 0.1% formic acid in acetonitrile; B: 0.1% formic acid in water
Detection signal: UV 215/254 nm (bandwidth 4, reference off)
Spectrum: range: 200-400 nm; step: 2 nm
Peak width: >0.025 min (0.5 S)
Injection: 0.5 µL injection with needle wash at flush port.
Flow rate: 0.8 mL/min
Column temperature: 60° C.
Gradient: 0.0-0.4 min: 97% B
0.4-2.2 min: 97% B→2% B
2.2-2.6 min: 2% B
2.6-2.61 min: 2% B497% B
2.61-3.0 min: 97% B
GVK_LCMS_02
UPLC: Waters UPLC
MS: Micromass Triple quad (ESI)
Capillary Voltage: 3500
Cone voltage: 25 to 50V
Disolvation gas: 600 L/h
Disolvation temp.: 350° C.
MSD signal settings: Scan pos 100-1000, Scan neg 100-1000
Column: Aquity BEH C18, 2.1×50 mm, 1.7 µm
Eluent: A: 0.1% formic acid in water; B: 0.1% formic acid in acetonitrile
Detection signal: UV-diode array
Spectrum: range: 200-400 nm; resolution: 1.2 nm
Sampling rate: 10 points/sec
Injection: 0.5 µL injection with needle wash
Flow rate: 0.4 mL/min
Column temperature: 35° C.
Gradient: 0.0-0.5 min: 5% B 0.5-2.0 min: 50% B
2.0-3.5 min: 100% B
3.5-5.0 min: 100% B→5% B
5.0-5.50 min: 5% B GVK_LCMS_31
HPLC: Agilent Infinity-1290 Series
MS: Agilent-6130 quadrupole LCMS (ESI/APCI, multi-mode+3500 V/−3000 V)
Charging Voltage: 2000
Fragmenter: 50 to 70
Corona voltage: 4μ amp
Disolvation temp.: 300° C.
Disolvation gas: 600 L/h
MSD signal settings: Scan pos 100-1200, Scan neg 100-1200
Column: Aquity BEH C18, 2.1×50 mm, 1.7 μm
Eluent: A: 0.1% formic acid in acetonitrile; B: 0.1% formic acid in water
Detection signal: UV 215 nm (bandwidth 4, reference off); UV 254 nm (bandwidth 4, reference off)
Spectrum: range: 200-400 nm; step: 2 nm
Peak width: >0.025 min (0.5 S)
Injection: 0.5 μL injection with needle wash at flush port
Flow rate: 0.8 mL/min
Column temperature: 50° C.
Gradient: 0.0-0.2 min: 2% A
0.2-2.3 min: 98% A
2.3-3.4 min: 98% A→2% A
3.4-3.41 min: 2% A
3.41-3.5 min: 2% A GVK_LCMS_34
HPLC: Agilent Infinity-1290 Series
MS: Agilent-6130 quadrupole LCMS (APCI-ES+3500 V/−3500 V)
Cone voltage: 25 to 50 V
Disolvation gas: 600 L/h
Disolvation temp.: 350° C.
MSD signal settings: Scan pos 100-1000, Scan neg 100-1000
Column: Aquity BEH C18, 2.1×50 mm, 1.7 μm
Eluent: A: 0.1% formic acid in water; B: 0.1% formic acid in acetonitrile
Detection signal: UV 215 nm (bandwidth 4, reference off); UV 254 nm (bandwidth 16, reference off)
Spectrum: range: 190-400 nm; step: 2 nm
Peak width: >0.05 min (0.5 S)
Injection: 0.5 μL injection with needle wash at flush port
Flow rate: 0.8 mL/min
Column temperature: 60° C.
Gradient: 0.0-0.4 min: 2% B
0.4-2.2 min: 2% B→98% B
2.2-2.6 min: 98% B
2.6-2.61 min: 98% B→2% B
2.61-3.0 min: 2% B GVK_LCMS_35
UPLC: Waters Acquity UPLC H-Class System
MS: Waters SQ Detector 2 (ESI);
Capillary voltage: 3.50 kV
Cone voltage: 50 V
Disolvation gas: 750 L/h
Disolvation temp.: 350° C.
MSD signal settings: Scan pos 100-1200, Scan neg 100-1200
Column: Aquity BEH C18, 2.1×50 mm, 1.7 μm
Eluent: A: 0.05% formic acid in acetonitrile; B: 0.05% formic acid in water
Detection signal: UV-diode array
Spectrum: range: 200-400 nm; resolution: 1.2 nm
Sampling rate: 10 Points/sec
Injection: 0.5 μL injection with pre-inject wash 15 sec & post-inject wash 20 sec
Flow rate: 0.6 mL/min
Column temperature: 35° C.
Gradient: 0.0-0.3 min: 97% B
0.3-2.2 min: 97% B→2% B
2.2-3.30 min: 2% B
3.30-4.50 min: 2% B→97% B
4.51-5.50 min: 97% B GVK_LCMS_21
LC: Agilent Infinity 1290 series
MS: Agilent 6130 Quadruple lcms(SQ)
MSD signal settings: Scan pos/neg 80-1200
Column: Aquity BEH C18 2.1×50 mm, 1.7 μm
Eluent: A: water+0.1% formic acid; B: acetonitrile (HPLC grade)+0.1% formic acid
Detection signal: UV 215/254 nm (bandwidth 4, reference off)
Spectrum: range: 200-400 nm; step: 2.0 nm
Peak width: >0.01 min (0.2 s)
Injection: 0.5 μL standard injection
Flow: 0.8 mL/min
Column temperature: 60° C.
Gradient: 0.0-0.2 min: 3% B
0.2-1.5 min: 3% B→95% B
1.5-2.5 min: 95% B
2.5-2.6 min: 95% B→3% B
2.6-3.2 min: 3% B GVK_LCMS_22
HPLC: Agilent Infinity-1290 Series
MS: Agilent SQD-6150 (API-ES+/−3000 V)
MSD signal settings: Scan pos 100-1000, Scan neg 100-1000
Column: Aquity BEH C18, 2.1×50 mm, 1.7 μm
Eluent: A: 0.1% formic acid in water; B: 0.1% formic acid in acetonitrile
Detection signal: UV 215 nm (bandwidth 4, reference off)
Spectrum: range: 200-400 nm; step: 2 nm
Peak width: >0.025 min (0.5 S)
Injection: 0.5 μL injection with needle wash at flush port
Flow rate: 0.8 mL/min
Column temperature: 45° C.
Gradient: 0.0-0.2 min: 2% B
0.2-1.5 min: 2% B→98% B
1.5-2.6 min: 98% B
2.6-2.61 min: 98% B→2% B
2.61-3.2 min: 2% B D_LC_SSTD
HPLC: Agilent 1100/1200 (binary Pump 1)
Column: (Waters) XBridge BEH C18, 30×3.0 mm; 2.5 μm
Eluent: A: 0.2% formic acid in water; B: acetonitrile
Detection signal: UV 254 nm (bandwidth 4, reference 550 nm, bandwidth 100)
Spectrum: range: 190-400 nm; step: 2 nm
Peak width: >0.01 min
Injection: 1.0 μL
Flow rate: 2.30 mL/min
Column temperature: 50° C.
Gradient: 0.1-1.4 min: 97% A→100% B
1.4-1.6 min: 100% B
1.6-1.8 min: 100% B→97% A D_LC_BSTD
HPLC: Agilent 1100/1200 (binary Pump 1)

Column: (Waters) XBridge BEH C18, 30×3.0 mm; 2.5 µm
Eluent: A: 0.2% ammonia (25%) in water; B: acetonitrile
Detection signal: UV 254 nm (bandwidth 4, reference 550 nm, bandwidth 100)
Spectrum: range: 190-400 nm; step: 2 nm
Peak width: >0.01 min
Injection: 1.0 µL
Flow rate: 2.00 mL/min
Column temperature: 50° C.
Gradient: 0.1-1.4 min: 97% A→100% B
1.4-1.6 min: 100% B
1.6-1.8 min: 100% B→97% A
GVK_LCMS_19
RRLC: Agilent RRLC
MS: Agilent SQD
Capillary voltage: 3.50 kV
Cone voltage: 25 to 50 V
Disolvation gas: 600 L/h
Disolvation temp.: 350° C.
Column: XBridge C18, 4.6×75 mm, 3.5 µm
Eluent: A: 10 mM ammonium acetate; B: acetonitrile
Flow rate: 2.0 mL/min
Column temperature: 35° C.
Gradient: [Time in min/% of B]: 0/10, 0.2/10, 2.5/75, 3.0/100, 4.8/100, 5.0/10
GVK_LCMS_41
UPLC: Waters Acquity-UPLC
MS: SQ Detector-2
Capillary voltage: 3.50 kV
Cone voltage: 50 V
Disolvation gas: 750 L/h
Disolvation temp.: 350° C.
Column: AQUITY UPLC BEH C18 1.7 µm, 2.1×50 mm
Eluent: A: 0.07% in acetonitrile; B: 0.07% formic acid in water
Flow rate: 0.6 mL/min
Column temperature: 35° C.
Gradient: [Time in min/% of B]: 0/97, 0.3/97, 2.2/2, 3.3/2, 4.5/2, 4.51/97

The compounds according to the invention and intermediates are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or their synthesis is described in the prior art or they may be prepared analogously to known prior art compounds or methods described herein, i.e. it is within the skills of an organic chemist to synthesize these compounds. Substances described in the literature can be prepared according to the published methods of synthesis.

General Reaction Scheme and Summary of the Syntheses Routes Towards Compounds (I) According to the Invention

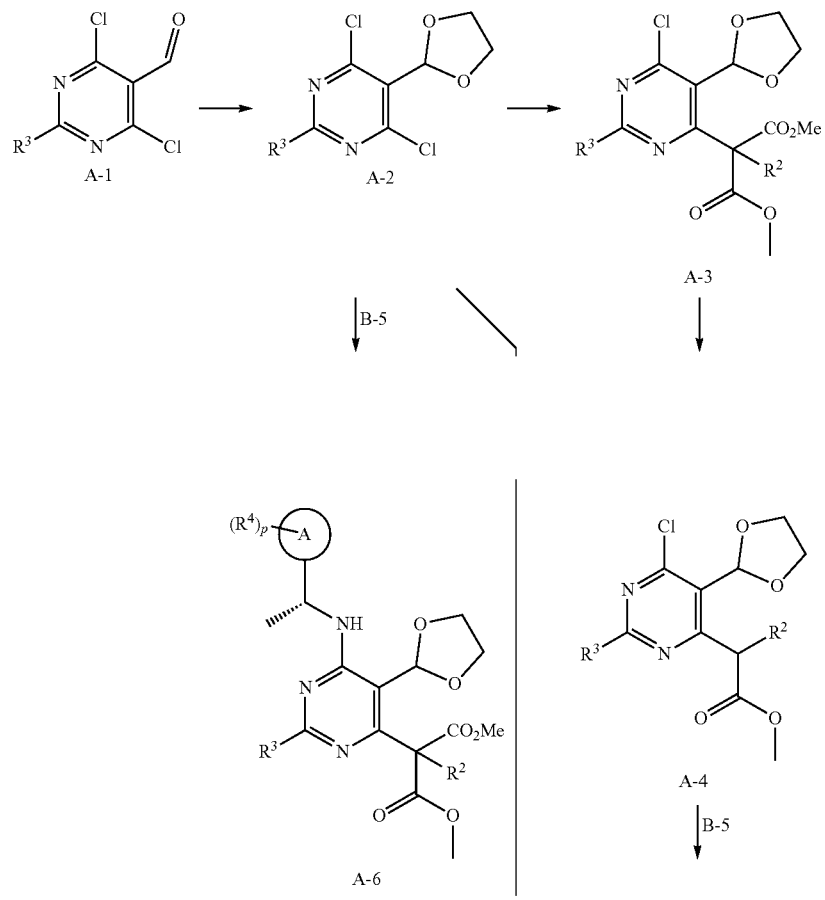

Scheme 1

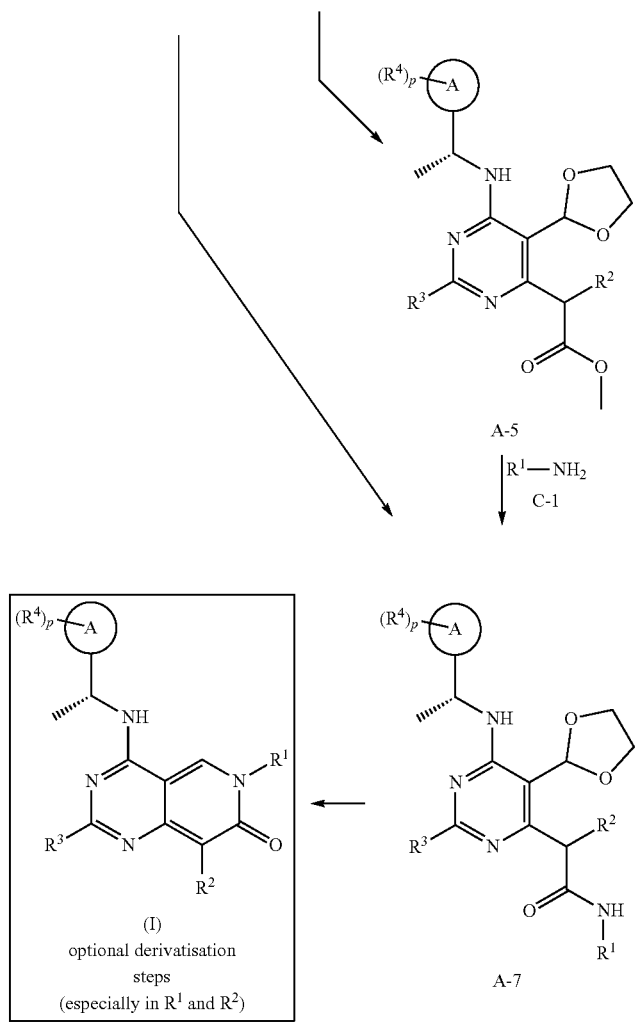

Compounds (I) according to the invention can be prepared stepwise with syntheses routes depicted in scheme 1.

Acetal A-2 can be prepared via acetalization of the corresponding aldehyde A-1.

A-7 can be prepared via different routes:

One approach starts with nucleophilic aromatic substitution of A-2 with a substituted or unsubstituted malonic ester to provide intermediate A-3 (introduction of $R^2$). Decarboxylation of intermediate A-3 leads to A-4, which is converted with building block B-5 (see below) in a nucleophilic aromatic substitution. Saponification of the resulting ester A-5 and subsequent amidation with building block C-1 (introduction of $R^1$) provides intermediate A-7 in a single step.

In an alternative approach compound A-2 is converted with a substituted or unsubstituted malonic ester (introduction of $R^2$) and then treated with building block B-5 (see below) to furnish compound A-5 in a single step. Saponification of the resulting ester A-5 and subsequent amidation with building block C-1 (introduction of $R^1$) provides intermediate A-7. Another route begins with nucleophilic aromatic substitution of A-2 with a substituted or unsubstituted malonic ester (introduction of $R^2$) followed by nucleophilic aromatic substitution with building block B-5 (see below) to provide compound A-6 in a single step.

Direct conversion of A-6 into A-7 can be achieved by saponification of diester A-6, in situ decarboxylation and subsequent amidation with building block C-1 (introduction of $R^1$) in a single step.

Final compounds (I) can be prepared by deprotection of acetal A-7 and cyclization. Compounds (I) can be further derivatized in optional steps (especially in $R^1$ and $R^2$) not depicted in scheme 1 to obtain further/additional compounds (I).

Thus, one aspect of the invention is the manufacture of a compound (1) as herein defined comprising ring closure of a compound A-7 as herein defined; optionally further comprising reacting a compound A-5 as herein defined with an amine C-1 as herein defined; optionally further comprising reacting a compound A-4 as herein defined with a compound B-5 as herein defined; optionally further comprising reacting a compound A-3 as herein defined to obtain the compound A-4 as herein defined; optionally further comprising reacting a compound A-2 as herein defined to obtain the compound A-3 as herein defined, optionally further comprising reacting a compound A-1 as herein defined to obtain the compound A-2 as herein defined.

Scheme 2
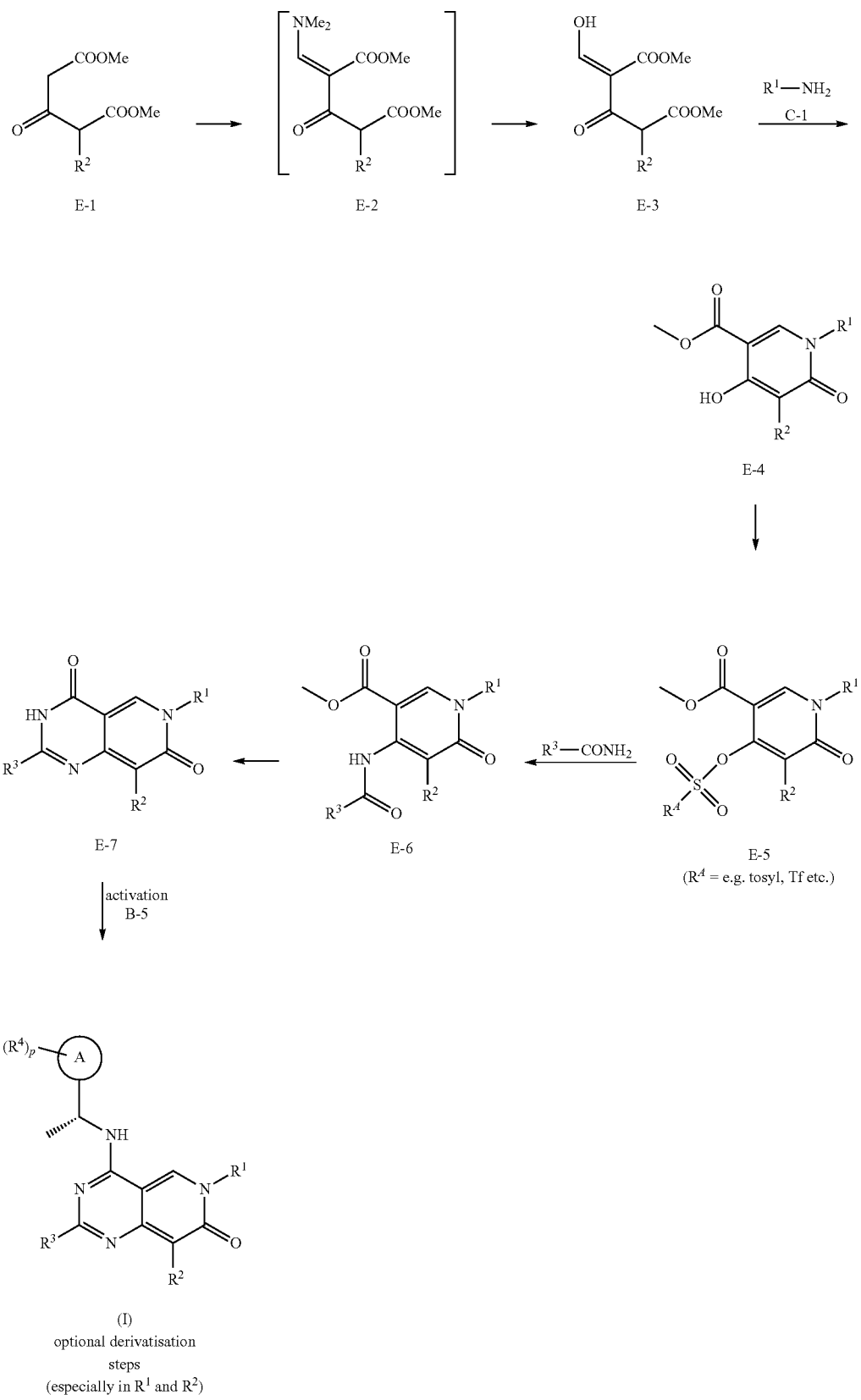

Alternatively, compounds (I) according to the invention may be prepared stepwise with the synthetic route depicted in scheme 2.

Starting from p-oxo diesters E-1 the corresponding α,β-dioxo esters E-3 can be prepared via intermediates E-2 obtained by reaction with DMF-acetale. Ring closure with amines C-1 leads to the hydroxy pyridon ring E-4. Palladium catalyzed cross coupling after transfer of the hydroxy group to the corresponding sulfonate (e.g. tosylate, triflate etc., E-5) with amides yields pyridon amides E-6, which allow for second ring closure to obtain the desired bicyclic pyridopyrimidine-dione scaffold (E-7). E-7 thus obtained can be activated (with e.g. hexachlorocyclotriphosphazene, $SOCl_2$, $POCl_3$ or the like) to be reacted with building block B-5 to reach final compounds (I) according to the invention (which can also be derivatized in additional steps).

Thus, one aspect of the invention is the manufacture of a compound (1) as herein defined comprising activating a compound E-7 as herein defined with an agent selected from hexachlorocyclotriphosphazene, $SOCl_2$ and $POCl_3$ and reacting activated E-7 with a compound B-5 as herein defined; optionally further comprising reacting a compound E-6 as herein defined to obtain the compound E-7 as herein defined; optionally further comprising reacting a compound E-5 as herein defined with an amide $R^3$—$CONH_2$ as herein defined; optionally further comprising reacting a compound E-4 as herein defined to obtain the compound E-5 as herein defined; optionally further comprising reacting a compound E-3 as herein defined with an amine C-1 as herein defined; optionally further comprising reacting a compound E-2 as herein defined to obtain the compound E-3 as herein defined; optionally further comprising reacting a compound E-1 as herein defined to obtain the compound E-2 as herein defined.

Scheme 3

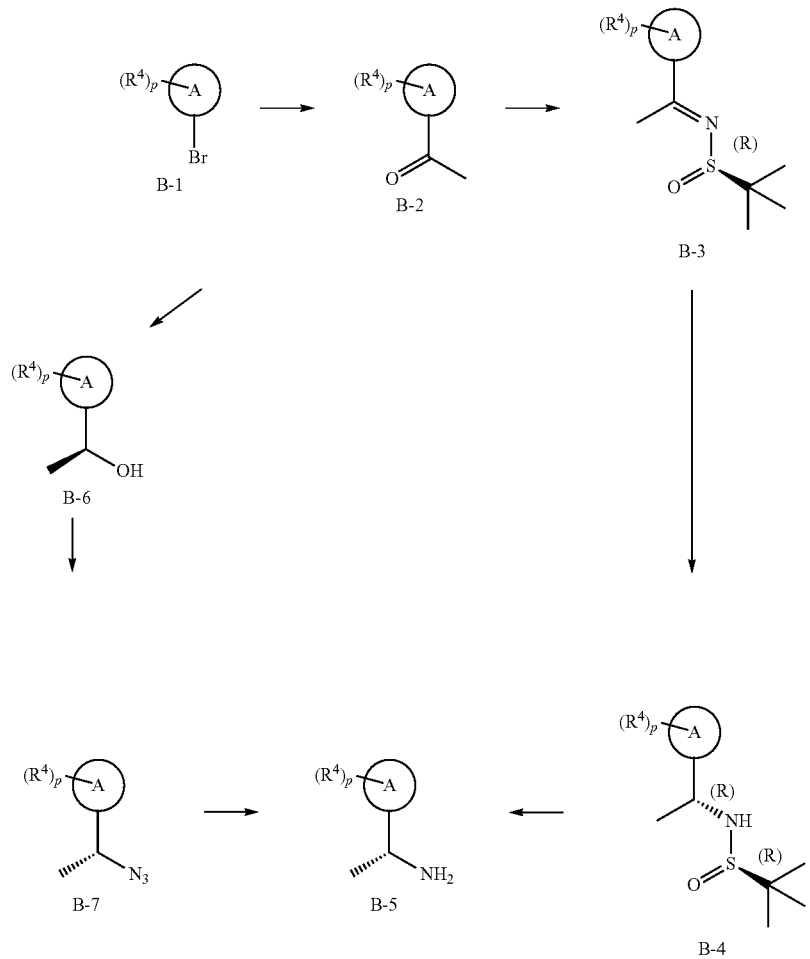

Building blocks B-5 can be prepared stepwise, starting with a synthesis depicted in scheme 3.

(Hetero)aryl ethylamine systems B-5 can be prepared from (hetero)arylbromides B-1, which are converted via a metal catalyzed cross coupling into the corresponding acetyl (hetero)aryls B-2. The formation of chiral sulfinamides B-3 is followed by stereoselective reduction to provide B-4. Finally cleavage of the sulfinamide provides the desired chiral (hetero)aryl ethylamine B-5.

Alternatively, acetyl (hetero)aryls B-2 can be reduced enantioselectively to the corresponding alcohols B-6 which are then transformed to azides B-7 and can in turn be hydrogenated to obtain chiral building blocks B-5.

Thus, one aspect of the invention is the manufacture of a compound B-5 as herein defined comprising reducing a compound B-7 as herein defined; optionally further comprising reacting a compound B-6 as herein defined to obtain the compound B-7 as herein defined; optionally further comprising reducing a compound B-2 as herein defined to obtain the compound B-6 as herein defined.

Synthesis of Intermediates A-2
Experimental Procedure for the Synthesis of A-2a

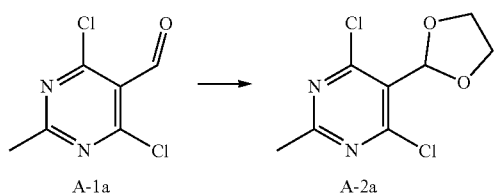

To a stirred solution of A-1a (150.00 g, 785.28 mmol, 1.0 equiv.) in benzene (1500 mL) ethylene glycol (48.69 g, 785.28 mmol, 1.0 equiv.) and a catalytic amount of p-toluenesulphonic acid (13.51 g, 78.53 mmol, 0.1 equiv.) are added. The reaction mixture is refluxed until full conversion of the starting material is observed. The solvent is evaporated under reduced pressure, the residue diluted with DCM and washed with an aqueous sodiumbicarbonate solution. Organic layers are combined, dried ($Na_2SO_4$) and concentrated under reduced pressure. Further purification by flash column chromatography (eluent: 10% ethyl acetate in hexane) yields the desired product A-2a.

The following intermediates A-2 (table 1) are available in an analogous manner starting from different pyrimidines A-1. The crude product A-2 is purified by chromatography if necessary.

TABLE 1

| # | structure | $t_{ret}$ [min] | [M + H]$^+$ | HPLC method |
|---|---|---|---|---|
| A-2a | 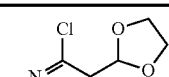 | 1.719 | 235 | GVK_LCMS_22 |
| A-2b | 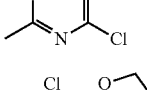 | n.a. | n.a. | — |

Synthesis of Intermediates A-3
Experimental Procedure for the Synthesis of A-3a

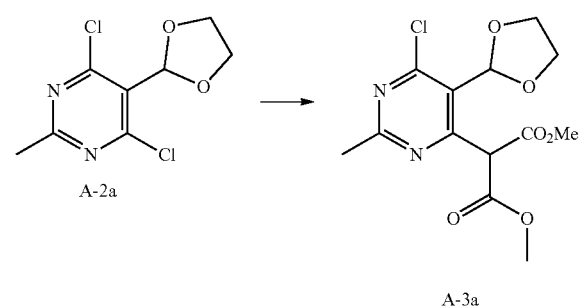 [SMILES: Cc1nc(Cl)c(C2OCCO2)c(Cl)n1 ; COC(=O)C(C(=O)OC)c1nc(C)nc(Cl)c1C1OCCO1]

A-2a (80.00 g, 340.33 mmol, 1.0 equiv.) is dissolved in DMSO (400 mL) and treated with cesium carbonate (220.53 g, 680.66 mmol, 2.0 equiv.) and dimethyl malonate (49.42 g, 374.36 mmol, 1.1 equiv.). The resulting mixture is heated to 80° C. for 10 h. After full conversion of the starting material the reaction mixture is diluted with ethyl acetate and poured on ice cold water. The aqueous layer is extracted with ethyl acetate. The organic layers are combined and washed with an aqueous solution of 0.1 N formic acid. The organic layer is dried ($Na_2SO_4$) and concentrated under reduced pressure. Further purification by flash column chromatography (eluent: 30% ethyl acetate in hexane) yields the desired product A-3a.

The following intermediates A-3 (table 2) are available in an analogous manner starting from different pyrimidines A-2. The crude product A-3 is purified by chromatography if necessary.

TABLE 2

| # | structure | $t_{ret}$ [min] | [M + H]$^+$ | HPLC method |
|---|---|---|---|---|
| A-3a | 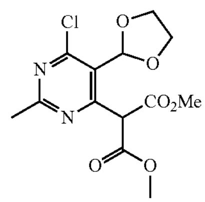 [SMILES: COC(=O)C(C(=O)OC)c1nc(C)nc(Cl)c1C1OCCO1] | 2.133 | 331 | GVK_LCMS_34 |
| A-3b | 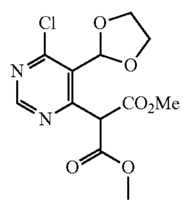 [SMILES: COC(=O)C(C(=O)OC)c1ncnc(Cl)c1C1OCCO1] | 1.537 | 317 | GVK_LCMS_34 |

Experimental Procedure for the Synthesis of A-3c

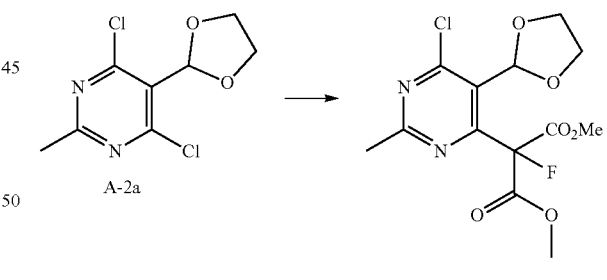

A stirred solution of 2-fluoro-malonic acid dimethyl ester (72.30 g, 481.99 mmol, 1.1 equiv.) in anhydrous DMF (300 mL) is cooled to 5° C. and treated portionwise with sodium hydride (20.16 g, 876.35 mmol, 2.0 equiv.). After stirring at room temperature for 10 minutes A-2a (103.00 g, 438.17 mmol, 1.0 equiv.) dissolved in DMF (50 mL) is added and the resulting mixture stirred for additional 2 h. After full conversion the reaction mixture is poured on ice cold water and the aqueous layer extracted with ethylacetate. The organic layers are combined, dried ($Na_2SO_4$) and concentrated under reduced pressure. Further purification by flash column chromatography (eluent: 15% ethyl acetate in hexane) yields the desired product A-3c (HPLC method: GVK_LCMS_31; $t_{ret}$=1.756 min; [M+H]$^+$=350).

Synthesis of Intermediates A-4

Experimental Procedure for the Synthesis of A-4a

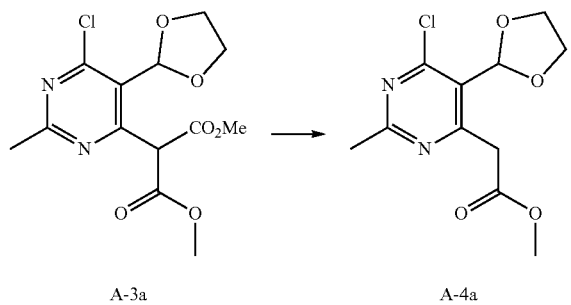 [SMILES: COC(=O)C(C(=O)OC)c1nc(C)nc(Cl)c1C1OCCO1 ; COC(=O)Cc1nc(C)nc(Cl)c1C1OCCO1]

A-3a → A-4a

A stirred solution of A-3a (40.00 g, 120.95 mmol, 1.0 equiv.) in DMSO (120 mL) is treated with lithium chloride (20.32 g, 483.79 mmol, 4.0 equiv.) and heated to 120° C. for 2 h. After complete conversion of the starting material the resulting reaction mixture is diluted with diethyl ether and poured on ice cold water. The aqueous layer is extracted with diethyl ether, the organic layers are combined, dried (Na$_2$SO$_4$) and concentrated under reduced pressure. Further purification by basic reversed phase chromatography (eluent: 20% acetonitrile in water) and normal phase (18% ethyl acetate in hexane) yields the desired product A-4a.

The following intermediates A-4 (table 3) are available in an analogous manner starting from different pyrimidines A-3. The crude product A-4 is purified by chromatography if necessary.

TABLE 3

| # | structure | $t_{ret}$ [min] | [M + H]$^+$ | HPLC method |
|---|---|---|---|---|
| A-4a | 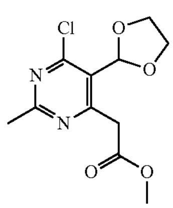 [SMILES: COC(=O)Cc1nc(C)nc(Cl)c1C1OCCO1] | 1.67 | 273.0 | RND-FA-3.5 |
| A-4b | 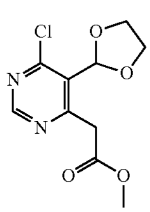 [SMILES: COC(=O)Cc1ncnc(Cl)c1C1OCCO1] | 1.55 | 258.9 | RND-FA-3.5 |

TABLE 3-continued

| # | structure | $t_{ret}$ [min] | [M + H]$^+$ | HPLC method |
|---|---|---|---|---|
| A-4c | 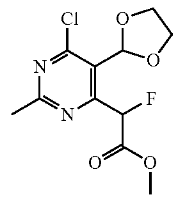 [SMILES: COC(=O)C(F)c1nc(C)nc(Cl)c1C1OCCO1] | 1.76 | 291.0 | RND-FA-3.5 |

Synthesis of Intermediates A-5

Experimental Procedure for the Synthesis of A-5a

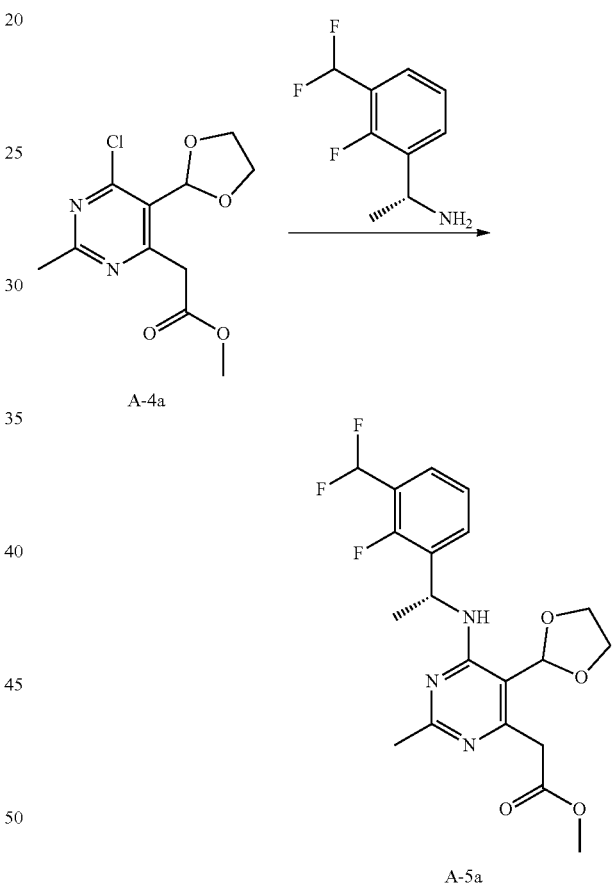

A-4a

A-5a

A-4a (3135 mg, 11.50 mmol, 1.5 equiv.) and B-5a (1450 mg, 7.67 mmol, 1.0 equiv.) are dissolved in anhydrous DMSO (10 mL) and DIPEA is added (2670 μL, 15.33 mmol, 2.0 equiv.). The reaction mixture is stirred at 80° C. for 6 h until complete conversion of B-5a is achieved. The reaction mixture is filtered and the filtrate purified by basic reversed phase chromatography (gradient elution: 25% to 65% acetonitrile in water) to furnish the desired product A-5a.

The following intermediates A-5 (table 4) are available in an analogous manner starting from different pyrimidines A-4 and amines B-5. The crude product A-5 is purified by chromatography if necessary.

TABLE 4

| # | structure | $t_{ret}$ [min] | $[M + H]^+$ | HPLC method |
|---|-----------|-----------------|-------------|-------------|
| A-5a | 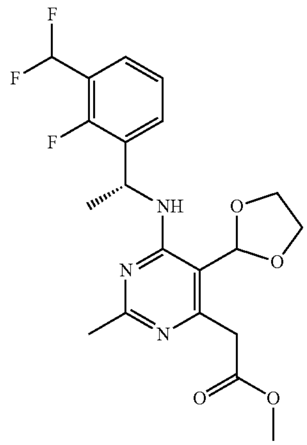 [SMILES: COC(=O)Cc1nc(C)nc(N[C@H](C)c2cccc(C(F)F)c2F)c1C1OCCO1] | 0.949 | 426.2 | VAB |
| A-5b | 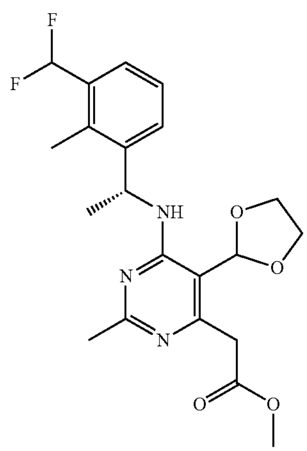 [SMILES: COC(=O)Cc1nc(C)nc(N[C@H](C)c2cccc(C(F)F)c2C)c1C1OCCO1] | 0.973 | 422.1 | VAB |
| A-5c | 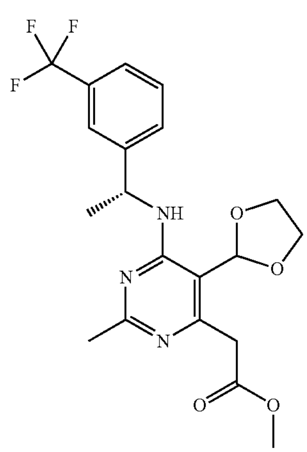 [SMILES: COC(=O)Cc1nc(C)nc(N[C@H](C)c2cccc(C(F)(F)F)c2)c1C1OCCO1] | 1.002 | 426.2 | VAB |

TABLE 4-continued
| # | structure | $t_{ret}$ [min] | $[M + H]^+$ | HPLC method |
|---|---|---|---|---|
| A-5d | 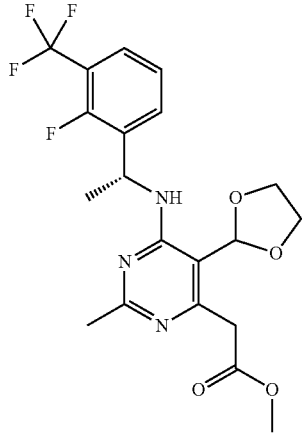 [SMILES: COC(=O)Cc1nc(C)nc(N[C@H](C)c2cccc(C(F)(F)F)c2F)c1C1OCCO1] | 1.014 | 444.2 | VAB |
| A-5e | 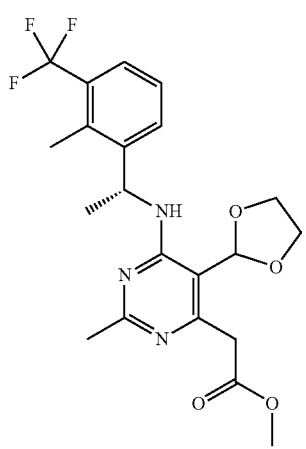 [SMILES: COC(=O)Cc1nc(C)nc(N[C@H](C)c2cccc(C(F)(F)F)c2C)c1C1OCCO1] | 1.143 | 440.3 | VAB |
| A-5f | 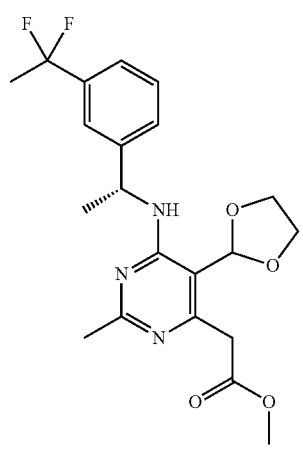 [SMILES: COC(=O)Cc1nc(C)nc(N[C@H](C)c2cccc(C(C)(F)F)c2)c1C1OCCO1] | 0.966 | 422.3 | VAB |

TABLE 4-continued
| # | structure | $t_{ret}$ [min] | $[M + H]^+$ | HPLC method |
|---|---|---|---|---|
| A-5g | 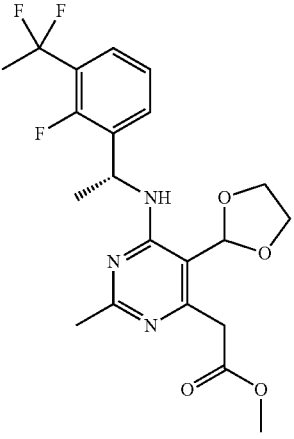 [SMILES: COC(=O)Cc1nc(C)nc(N[C@H](C)c2cccc(C(C)(F)F)c2F)c1C1OCCO1] | 1.027 | 440.3 | VAB |
| A-5h | 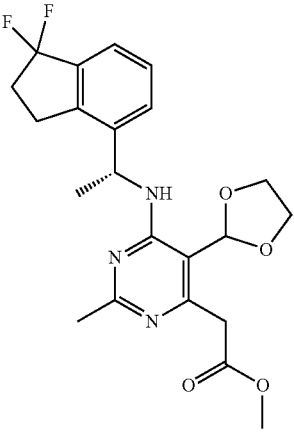 [SMILES: COC(=O)Cc1nc(C)nc(N[C@H](C)c2cccc3c2CCC3(F)F)c1C1OCCO1] | 0.992 | 434.3 | VAB |
| A-5i | 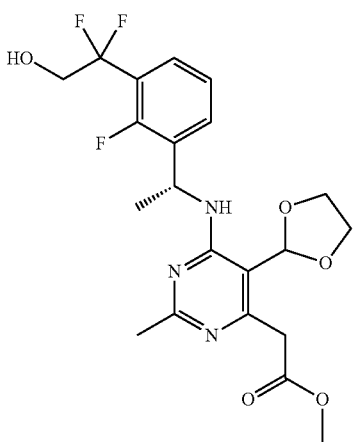 [SMILES: COC(=O)Cc1nc(C)nc(N[C@H](C)c2cccc(C(F)(F)CO)c2F)c1C1OCCO1] | 0.863 | 456.2 | VAB |

TABLE 4-continued

| # | structure | $t_{ret}$ [min] | [M + H]$^+$ | HPLC method |
|---|---|---|---|---|
| A-5j | 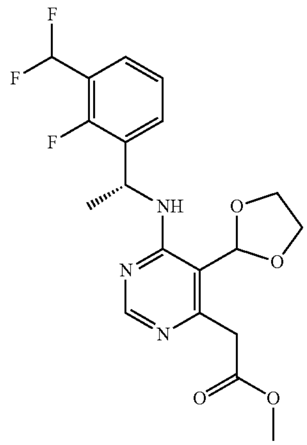 [SMILES: COC(=O)Cc1ncnc(N[C@H](C)c2cccc(C(F)F)c2F)c1C1OCCO1] | 0.903 | 412 | VAB |
| A-5k | 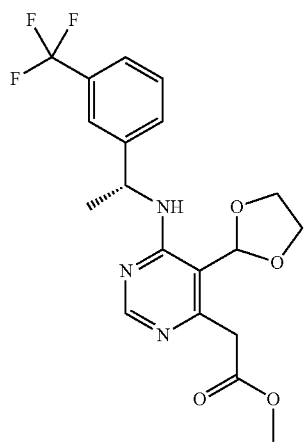 [SMILES: COC(=O)Cc1ncnc(N[C@H](C)c2cccc(C(F)(F)F)c2)c1C1OCCO1] | 0.967 | 412 | VAB |
| A-5l | 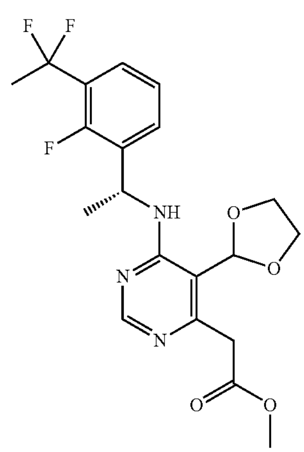 [SMILES: COC(=O)Cc1ncnc(N[C@H](C)c2cccc(C(C)(F)F)c2F)c1C1OCCO1] | 0.944 | 426.0 | VAB |

TABLE 4-continued
| # | structure | $t_{ret}$ [min] | [M + H]⁺ | HPLC method |
|---|---|---|---|---|
| A-5m | 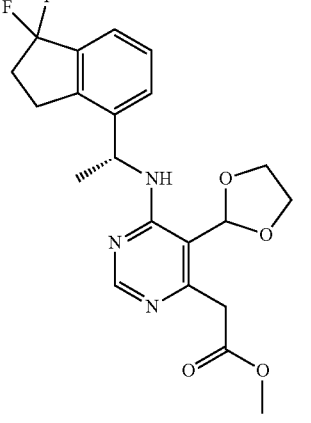 | 0.936 | 420.2 | VAB |
| A-5n | 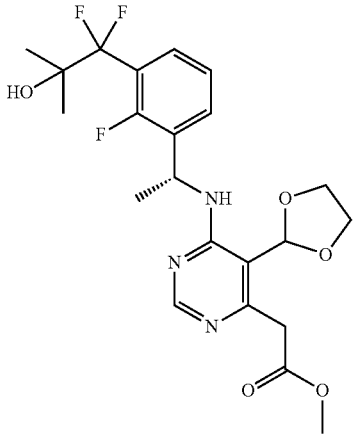 [SMILES: COC(=O)Cc1ncnc(N[C@H](C)c2cccc(C(F)(F)C(C)(C)O)c2F)c1C1OCCO1] | 0.874 | 470.1 | VAB |
| A-5o | 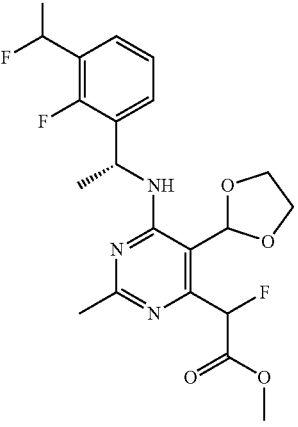 | 0.991 | 444.2 | VAB |

TABLE 4-continued
| # | structure | $t_{ret}$ [min] | $[M + H]^+$ | HPLC method |
|---|---|---|---|---|
| A-5p | 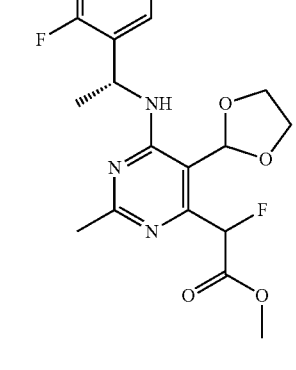 | 1.028 | 458.1 | VAB |
| A-5q | 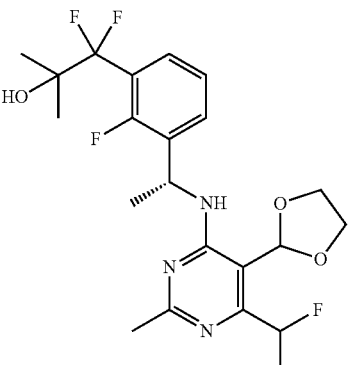 | 0.953 | 502.3 | VAB |
| A-5r | 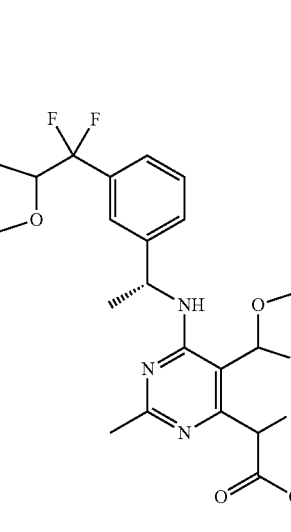 | 1.017 | 496.3 | VAB |

TABLE 4-continued
| # | structure | $t_{ret}$ [min] | $[M + H]^+$ | HPLC method |
|---|---|---|---|---|
| A-5s | 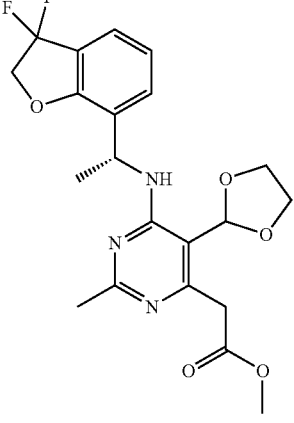 | 0.944 | 436.3 | VAB |
| A-5t | 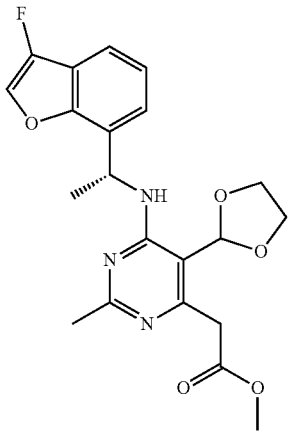 [SMILES: COC(=O)Cc1nc(C)nc(N[C@H](C)c2cccc3c(F)coc23)c1C1OCCO1] | 0.971 | 416.1 | VAB |
| A-5u | 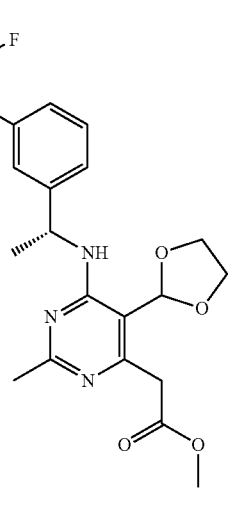 | n.a. | n.a. | — |

Experimental Procedure for the Synthesis of A-5v

Synthesis of Intermediates A-6

Experimental Procedure for the Synthesis of A-6a

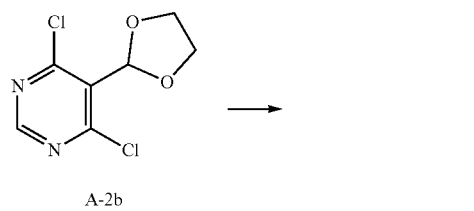

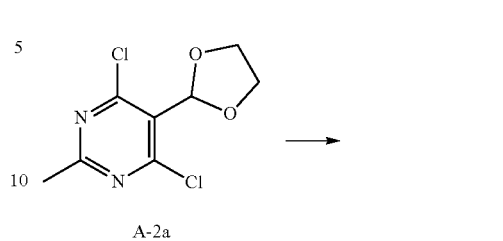

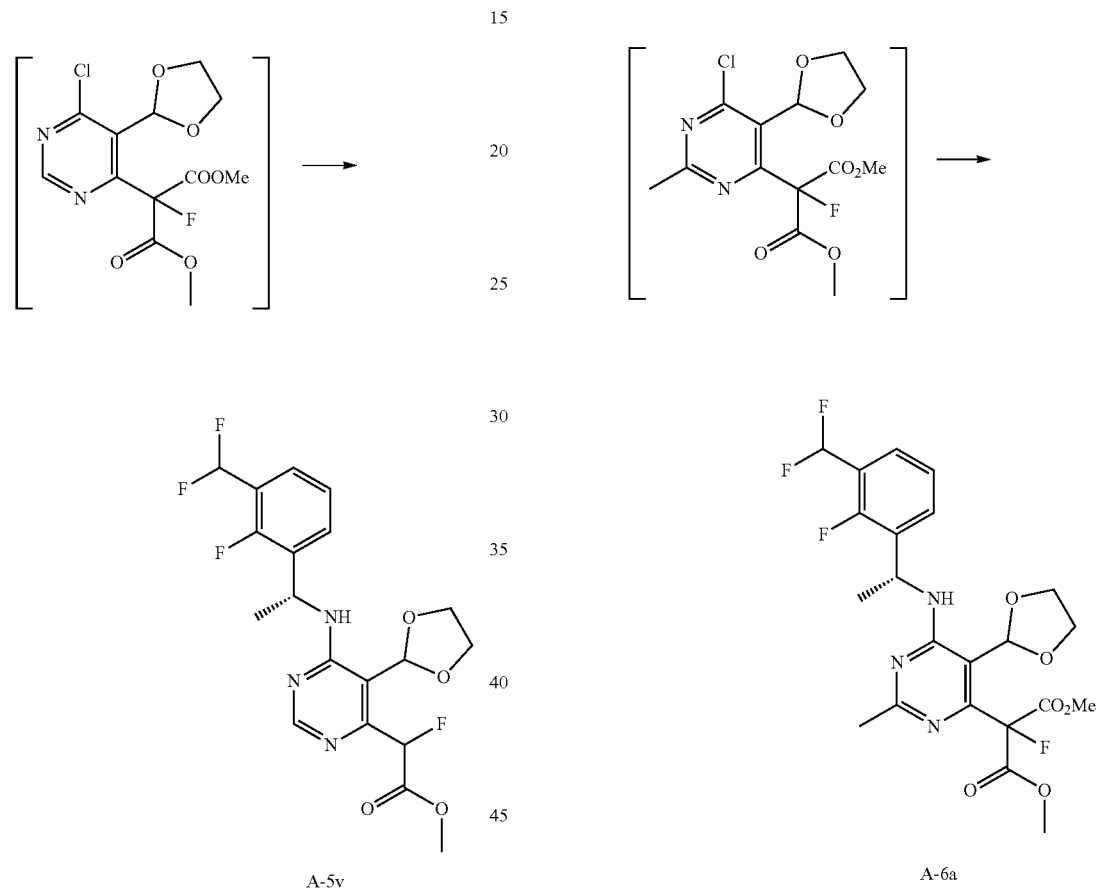

A solution of A-2b (500 mg, 2.262 mmol, 1.0 equiv.) in anhydrous DMSO (4.0 mL) is treated with 2-fluoro-malonic acid dimethyl ester (281 µL, 2.262 mmol, 1.0 equiv.) and sodium carbonate (360 mg, 3.393 mmol, 1.5 equiv.). The resulting mixture is stirred at room temperature for 4 d until full conversion of the starting material is observed. Triethylamine (627 µL, 4.524 mmol, 2.0 equiv.) and B-5a (642 mg, 3.393 mmol, 1.5 equiv.) are added and the reaction mixture stirred at 80° C. for additional 16 h. After complete conversion the reaction is quenched with an aqueous $NaHCO_3$ solution and the aqueous layer extracted with DCM. The organic layers are combined, dried ($Na_2SO_4$) and concentrated under reduced pressure. Further purification by basic reversed phase chromatography (gradient elution: 15% to 85% acetonitrile in water) yields the desired product A-5v (HPLC method: VAB, $t_{ret}$=0.945 min; $[M+H]^+$=430.3).

A-2a (50 mg, 0.213 mmol, 1.0 equiv.) is dissolved in DMSO (0.5 mL) and treated with 2-fluoro-malonic acid dimethyl ester (27 µL, 0.221 mmol, 1.0 equiv.) and potassium carbonate (58.8 mg, 0.425 mmol, 2.0 equiv.). The resulting mixture is stirred at 100° C. for 5 min until full conversion of the starting material is observed. Triethylamine (89 µL, 0.639 mmol, 3.0 equiv.) and B-5a (60.2 mg, 0.318 mmol, 1.5 equiv.) are added and the reaction mixture stirred at 60° C. for additional 3 h. The reaction mixture is filtered and the filtrate purified by basic reversed phase chromatography (gradient elution: 35% to 75% acetonitrile in water) to furnish the desired product A-6a.

The following intermediates A-6 (table 5) are available in an analogous manner starting from different pyrimidines A-5. The crude product A-6 is purified by chromatography if necessary.

TABLE 5
| # | structure | $t_{ret}$ [min] | $[M + H]^+$ | HPLC method |
|---|---|---|---|---|
| A-6a | 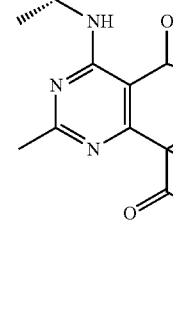 | 1.109 | 530.2 | VAB |
| A-6b | 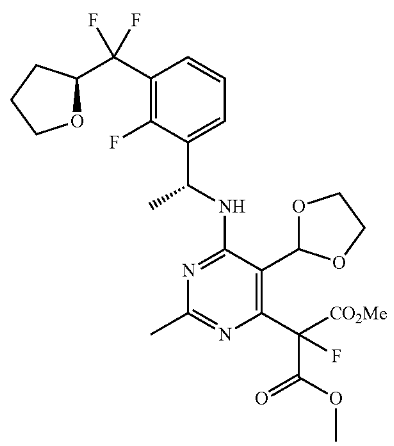 [SMILES: COC(=O)C(F)(C(=O)OC)c1nc(C)nc(N[C@H](C)c2cccc(C(F)(F)[C@@H]3CCCO3)c2F)c1C1OCCO1] | 1.087 | 572.2 | VAB |
Synthesis of Intermediates A-7
Experimental Procedure for the Synthesis of A-7a
-continued
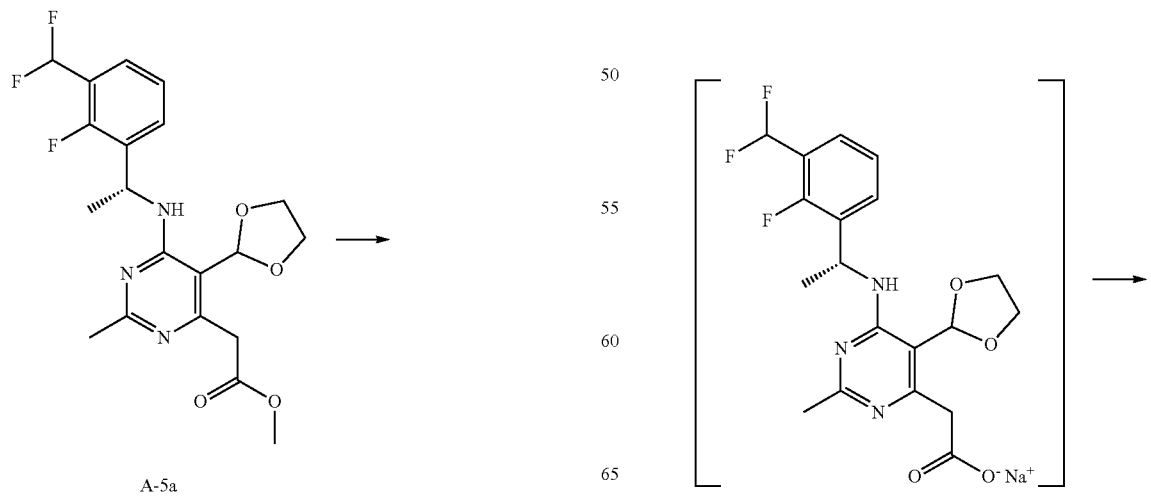

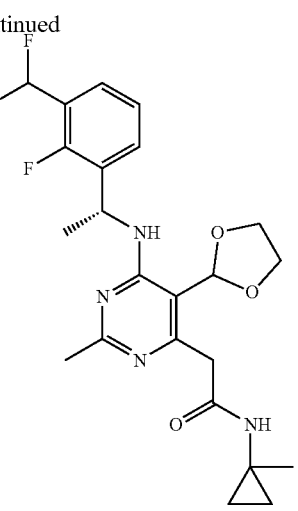

A-7a

A-5a (200.0 mg, 0.470 mmol, 1.0 equiv.) is dissolved in DMSO (2 mL) and ACN (1 mL). An aqueous sodium hydroxide solution (20%, 313 µL, 1.881 mmol, 4 equiv.) is added and the resulting mixture stirred for 30 min until complete conversion of the starting material is observed. Triethylamine (130 µL, 0.933 mmol, 2.0 equiv.), 1-methyl-cyclopropylamine hydrochloride (62.8 mg, 0.583 mmol, 1.3 equiv.) and HATU (266.3 mg, 0.700 mmol, 1.5 equiv.) are added and the resulting mixture stirred for 20 min until complete conversion is observed. Water is added and the mixture diluted with DCM. The aqueous layer is extracted with DCM, the organic layers are combined and dried with magnesium sulfate. The resulting crude product A-7a can be used without further purification in the next step.

The following intermediates A-7 (table 6) are available in an analogous manner starting from different pyrimidines A-5 and coupling with various amines C-1 or their corresponding salts. The crude product A-7 is purified by chromatography if necessary.

TABLE 6

| # | structure | $t_{ret}$ [min] | $[M + H]^+$ | HPLC method |
|---|---|---|---|---|
| A-7a | 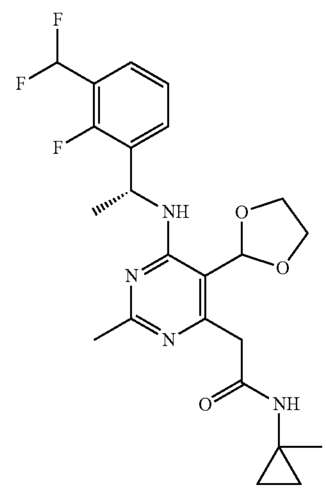 [SMILES: Cc1nc(CC(=O)NC2(C)CC2)c(C2OCCO2)c(N[C@H](C)c2cccc(C(F)F)c2F)n1] | 0.957 | 465.2 | VAB |
| A-7b | 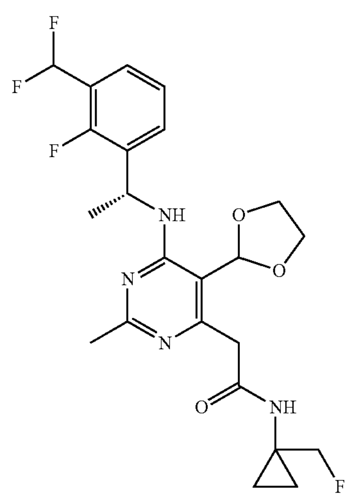 [SMILES: Cc1nc(CC(=O)NC2(CF)CC2)c(C2OCCO2)c(N[C@H](C)c2cccc(C(F)F)c2F)n1] | 0.903 | 483.2 | VAB |

TABLE 6-continued
| # | structure | $t_{ret}$ [min] | $[M + H]^+$ | HPLC method |
|---|---|---|---|---|
| A-7c | 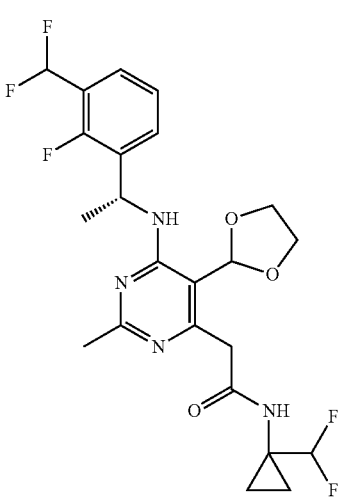 | 0.968 | 501.2 | VAB |
| A-7d | 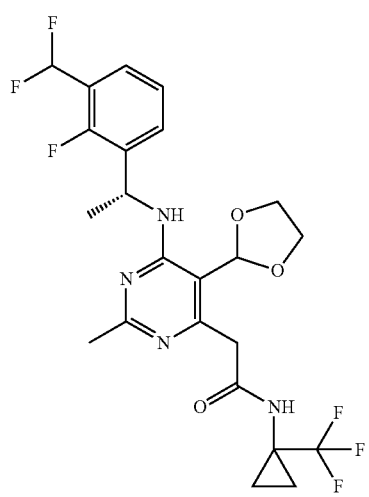 [SMILES: Cc1nc(CC(=O)NC2(C(F)(F)F)CC2)c(C2OCCO2)c(N[C@H](C)c2cccc(C(F)F)c2F)n1] | 0.983 | 519.2 | VAB |
| A-7e | 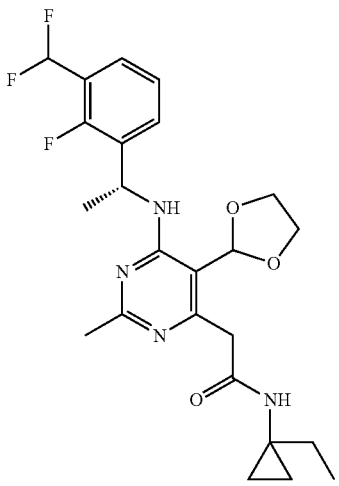 [SMILES: CCC1(NC(=O)Cc2nc(C)nc(N[C@H](C)c3cccc(C(F)F)c3F)c2C2OCCO2)CC1] | 0.992 | 479.3 | VAB |

TABLE 6-continued
| # | structure | $t_{ret}$ [min] | $[M + H]^+$ | HPLC method |
|---|---|---|---|---|
| A-7f | 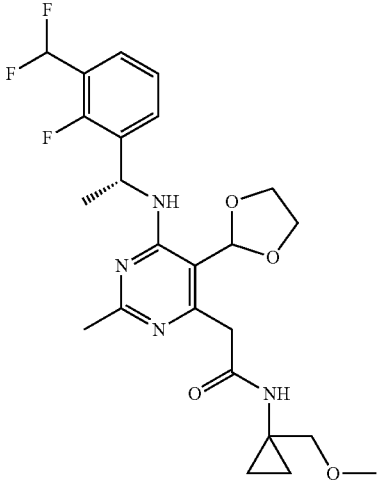 [SMILES: COCC1(NC(=O)Cc2nc(C)nc(N[C@H](C)c3cccc(C(F)F)c3F)c2C2OCCO2)CC1] | 0.911 | 495.2 | VAB |
| A-7g | 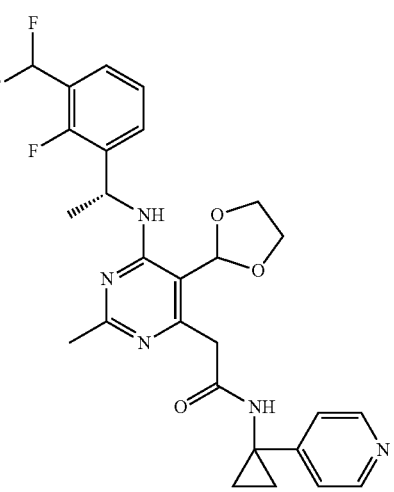 | 0.896 | 528.2 | VAB |
| A-7h | 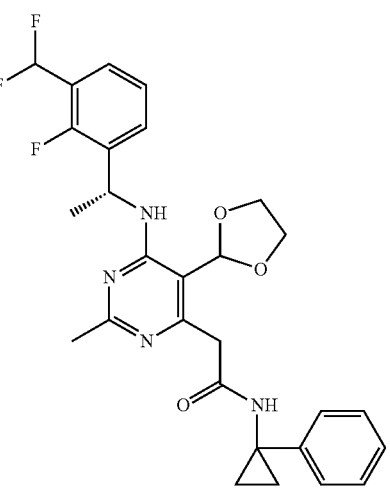 | 1.011 | 527.2 | VAB |

TABLE 6-continued

| # | structure | $t_{ret}$ [min] | $[M + H]^+$ | HPLC method |
|---|---|---|---|---|
| A-7i | 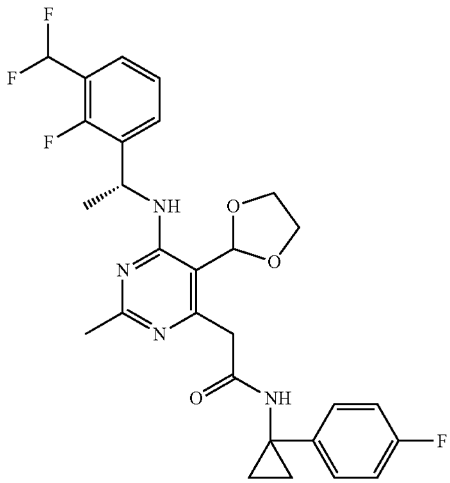 [SMILES: Cc1nc(CC(=O)NC2(c3ccc(F)cc3)CC2)c(C2OCCO2)c(N[C@H](C)c2cccc(C(F)F)c2F)n1] | 1.022 | 545.3 | VAB |
| A-7j | 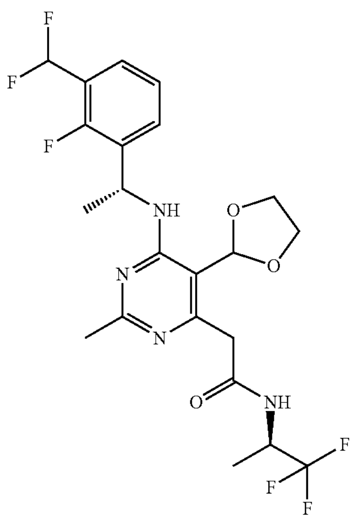 [SMILES: Cc1nc(CC(=O)N[C@H](C)C(F)(F)F)c(C2OCCO2)c(N[C@H](C)c2cccc(C(F)F)c2F)n1] | 1.002 | 507.2 | VAB |
| A-7k | 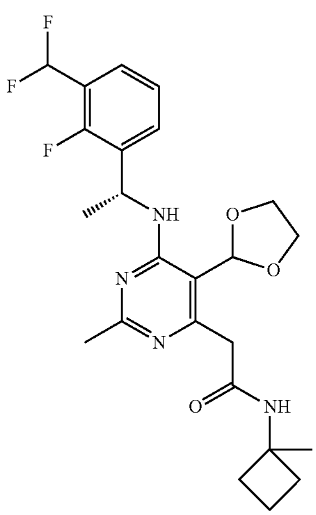 [SMILES: Cc1nc(CC(=O)NC2(C)CCC2)c(C2OCCO2)c(N[C@H](C)c2cccc(C(F)F)c2F)n1] | 1.004 | 479.1 | VAB |

TABLE 6-continued
| # | structure | $t_{ret}$ [min] | $[M + H]^+$ | HPLC method |
|---|---|---|---|---|
| A-7l | 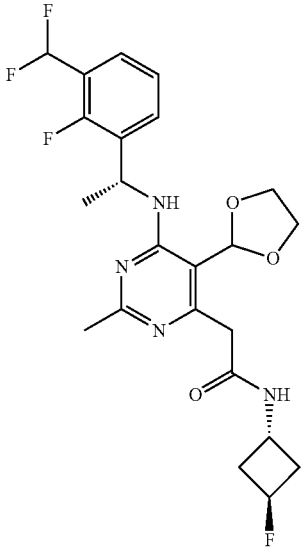 [SMILES: Cc1nc(CC(=O)N[C@H]2C[C@H](F)C2)c(C2OCCO2)c(N[C@H](C)c2cccc(C(F)F)c2F)n1] | 0.937 | 483.2 | VAB |
| A-7m | 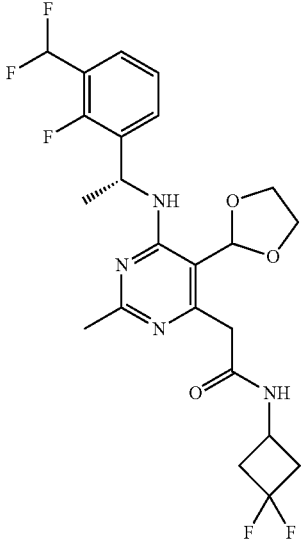 [SMILES: Cc1nc(CC(=O)NC2CC(F)(F)C2)c(C2OCCO2)c(N[C@H](C)c2cccc(C(F)F)c2F)n1] | 0.962 | 501.2 | VAB |

TABLE 6-continued
| # | structure | $t_{ret}$ [min] | $[M + H]^+$ | HPLC method |
|---|---|---|---|---|
| A-7n | 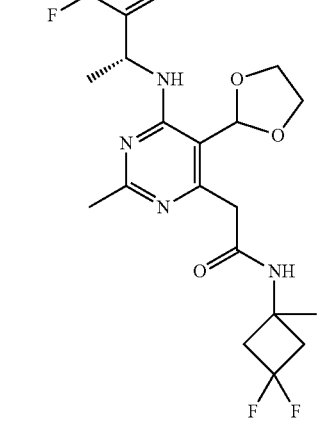 | 0.986 | 515.2 | VAB |
| A-7o | 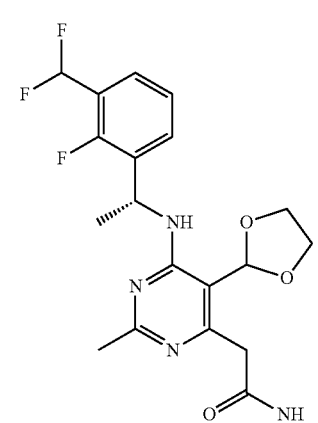 | 0.991 | 477.2 | VAB |
| A-7p | 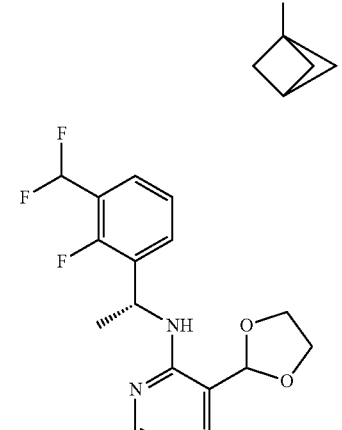 | 0.988 | 495.2 | VAB |

TABLE 6-continued
| # | structure | t_ret [min] | [M + H]+ | HPLC method |
|---|---|---|---|---|
| A-7q | 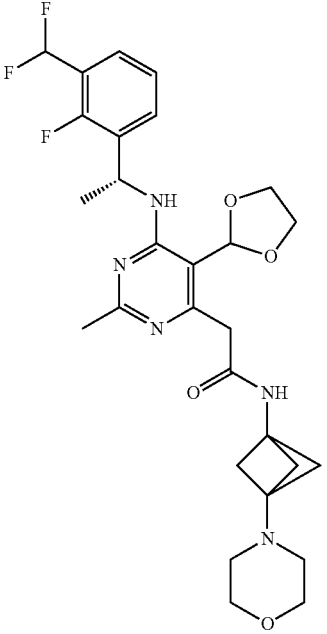 [SMILES: Cc1nc(CC(=O)NC23CC(N4CCOCC4)(C2)C3)c(C2OCCO2)c(N[C@H](C)c2cccc(C(F)F)c2F)n1] | 0.907 | 562.3 | VAB |
| A-7r | 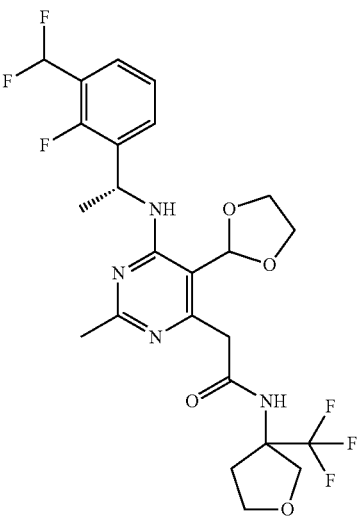 [SMILES: Cc1nc(CC(=O)NC2(C(F)(F)F)CCOC2)c(C2OCCO2)c(N[C@H](C)c2cccc(C(F)F)c2F)n1] | 0.978 | 549.2 | VAB |

TABLE 6-continued

| # | structure | t_ret [min] | [M + H]+ | HPLC method |
|---|---|---|---|---|
| A-7s | 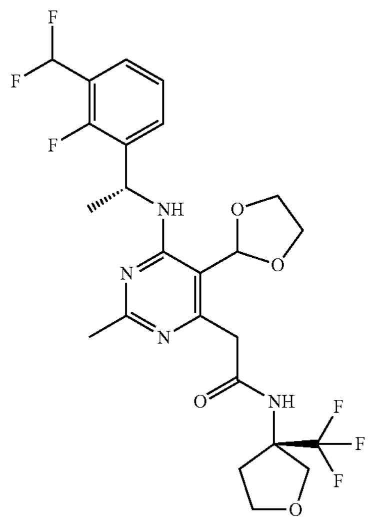 [SMILES: Cc1nc(CC(=O)N[C@@]2(C(F)(F)F)CCOC2)c(C2OCCO2)c(N[C@H](C)c2cccc(C(F)F)c2F)n1] | 0.978 | 549.2 | VAB |
| A-7t | 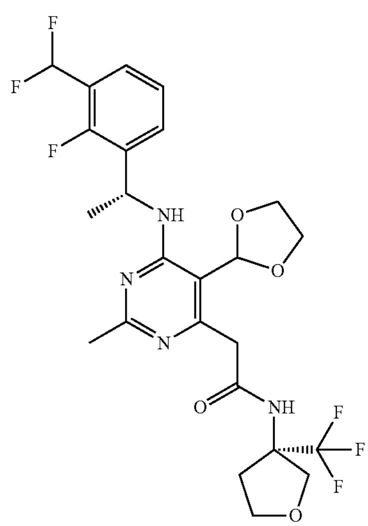 [SMILES: Cc1nc(CC(=O)N[C@]2(C(F)(F)F)CCOC2)c(C2OCCO2)c(N[C@H](C)c2cccc(C(F)F)c2F)n1] | 0.978 | 549.2 | VAB |
| A-7u | 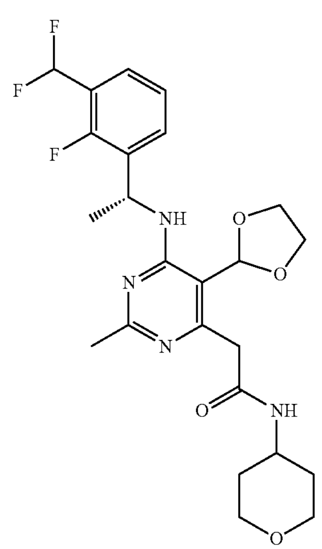 [SMILES: Cc1nc(CC(=O)NC2CCOCC2)c(C2OCCO2)c(N[C@H](C)c2cccc(C(F)F)c2F)n1] | 0.942 | 495.2 | VAB |

TABLE 6-continued

| # | structure | $t_{ret}$ [min] | [M + H]⁺ | HPLC method |
|---|---|---|---|---|
| A-7v | 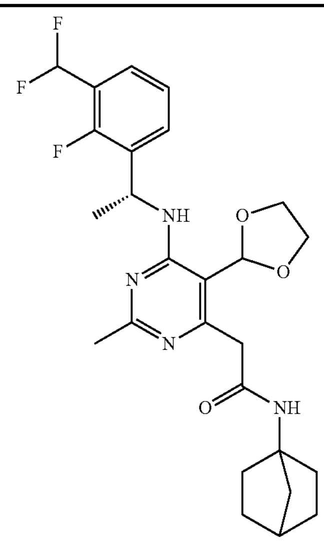 | 1.059 | 505.3 | VAB |
| A-7w | 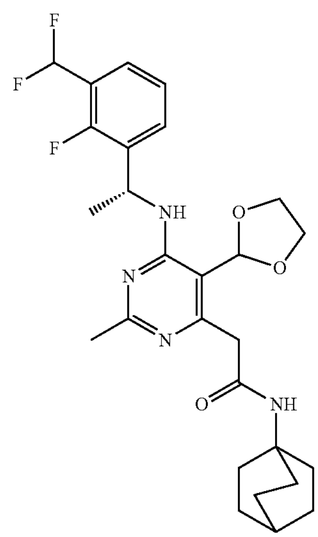 [SMILES: Cc1nc(CC(=O)NC23CCC(CC2)CC3)c(C2OCCO2)c(N[C@H](C)c2cccc(C(F)F)c2F)n1] | 1.080 | 519.2 | VAB |
| A-7x | 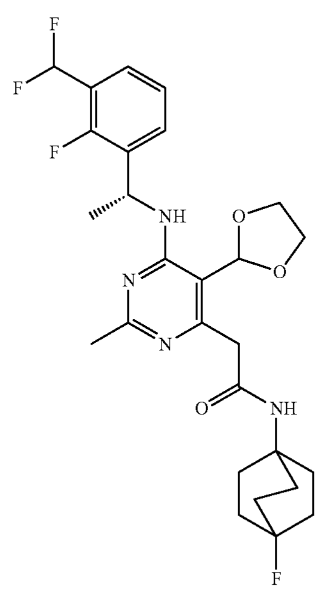 [SMILES: Cc1nc(CC(=O)NC23CCC(F)(CC2)CC3)c(C2OCCO2)c(N[C@H](C)c2cccc(C(F)F)c2F)n1] | 1.024 | 537.3 | VAB |

TABLE 6-continued

| # | structure | t_ret [min] | [M + H]+ | HPLC method |
|---|---|---|---|---|
| A-7y | 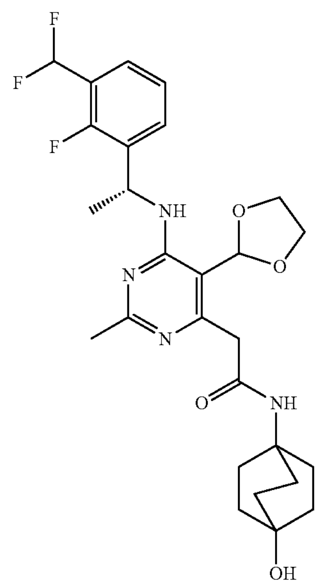 [SMILES: Cc1nc(CC(=O)NC23CCC(O)(CC2)CC3)c(C2OCCO2)c(N[C@H](C)c2cccc(C(F)F)c2F)n1] | 0.911 | 535.3 | VAB |
| A-7z | 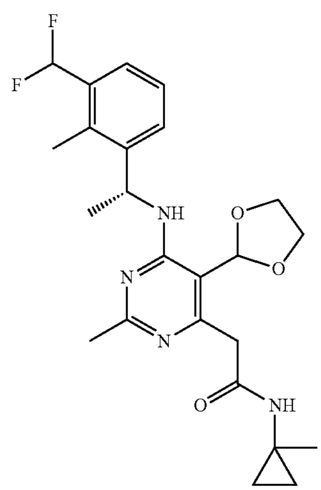 [SMILES: Cc1nc(CC(=O)NC2(C)CC2)c(C2OCCO2)c(N[C@H](C)c2cccc(C(F)F)c2C)n1] | 0.963 | 461.3 | VAB |
| A-7aa | 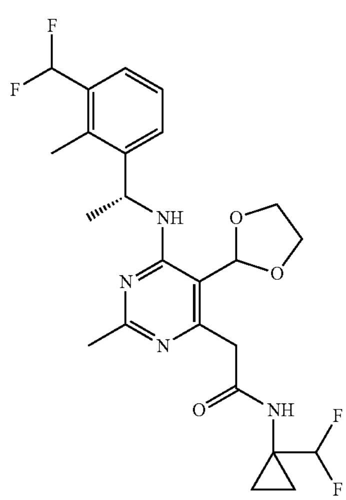 [SMILES: Cc1nc(CC(=O)NC2(C(F)F)CC2)c(C2OCCO2)c(N[C@H](C)c2cccc(C(F)F)c2C)n1] | 0.975 | 497.1 | VAB |

TABLE 6-continued

| # | structure | $t_{ret}$ [min] | [M + H]⁺ | HPLC method |
|---|---|---|---|---|
| A-7ab | 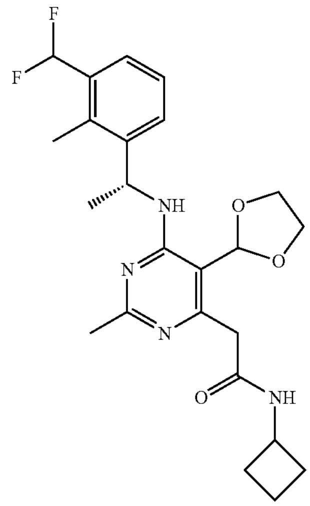 [SMILES: Cc1nc(CC(=O)NC2CCC2)c(C2OCCO2)c(N[C@H](C)c2cccc(C(F)F)c2C)n1] | 0.983 | 461.3 | VAB |
| A-7ac | 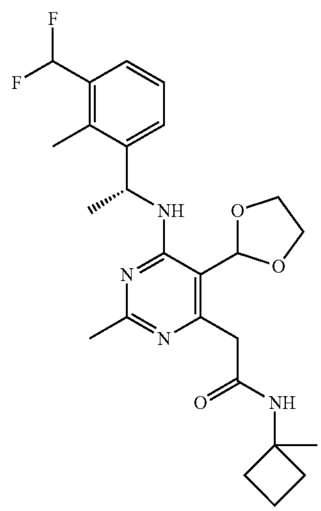 [SMILES: Cc1nc(CC(=O)NC2(C)CCC2)c(C2OCCO2)c(N[C@H](C)c2cccc(C(F)F)c2C)n1] | 1.013 | 475.4 | VAB |
| A-7ad | 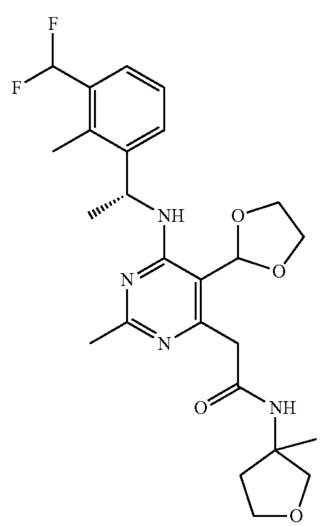 [SMILES: Cc1nc(CC(=O)NC2(C)CCOC2)c(C2OCCO2)c(N[C@H](C)c2cccc(C(F)F)c2C)n1] | 0.936 | 491.1 | VAB |

TABLE 6-continued
| # | structure | $t_{ret}$ [min] | $[M + H]^+$ | HPLC method |
|---|---|---|---|---|
| A-7ae | 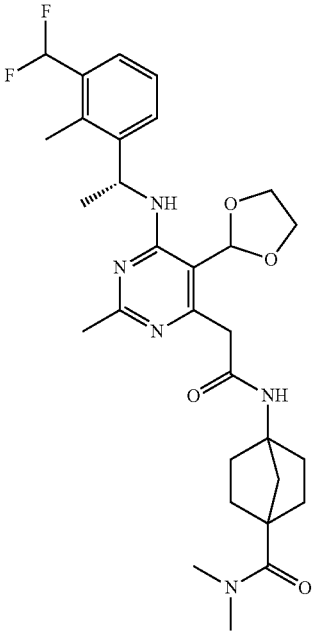 [SMILES: Cc1nc(CC(=O)NC23CCC(C(=O)N(C)C)(CC2)C3)c(C2OCCO2)c(N[C@H](C)c2cccc(C(F)F)c2C)n1] | 0.950 | 572.3 | VAB |
| A-7af | 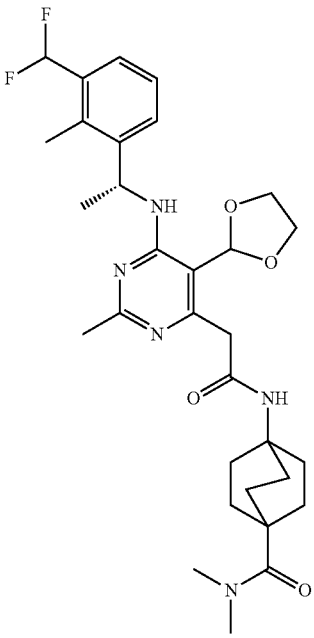 [SMILES: Cc1nc(CC(=O)NC23CCC(C(=O)N(C)C)(CC2)CC3)c(C2OCCO2)c(N[C@H](C)c2cccc(C(F)F)c2C)n1] | 0.962 | 586.3 | VAB |

TABLE 6-continued

| # | structure | $t_{ret}$ [min] | [M + H]⁺ | HPLC method |
|---|---|---|---|---|
| A-7ag | 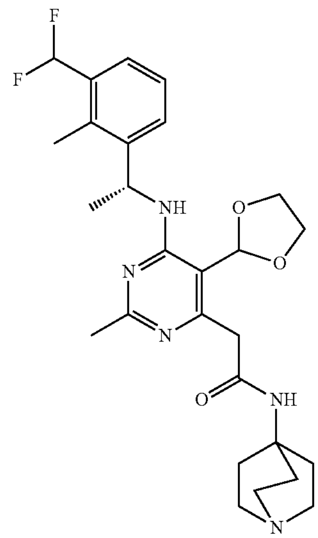 [SMILES: Cc1nc(CC(=O)NC23CCN(CC2)CC3)c(C2OCCO2)c(N[C@H](C)c2cccc(C(F)F)c2C)n1] | 0.906 | 516.2 | VAB |
| A-7ah | 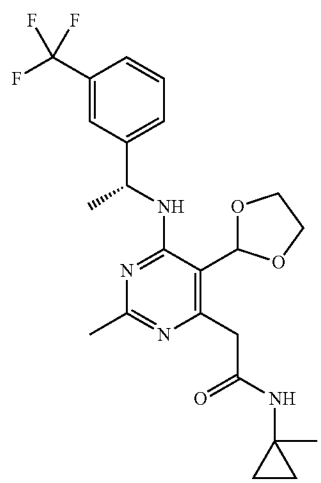 [SMILES: Cc1nc(CC(=O)NC2(C)CC2)c(C2OCCO2)c(N[C@H](C)c2cccc(C(F)(F)F)c2)n1] | 0.988 | 465.2 | VAB |
| A-7ai | 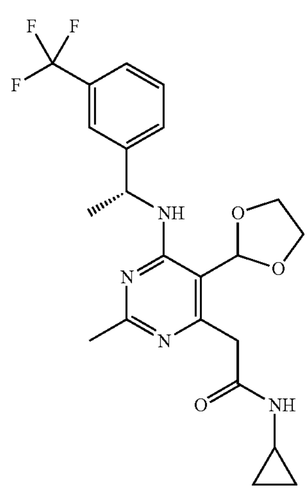 [SMILES: Cc1nc(CC(=O)NC2CC2)c(C2OCCO2)c(N[C@H](C)c2cccc(C(F)(F)F)c2)n1] | 0.864 | 451.3 | VAB |

TABLE 6-continued
| # | structure | $t_{ret}$ [min] | $[M + H]^+$ | HPLC method |
|---|---|---|---|---|
| A-7aj | 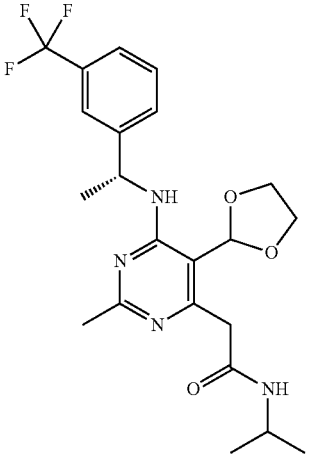 [SMILES: Cc1nc(CC(=O)NC(C)C)c(C2OCCO2)c(N[C@H](C)c2cccc(C(F)(F)F)c2)n1] | 1.171 | 453.2 | VAB |
| A-7ak | 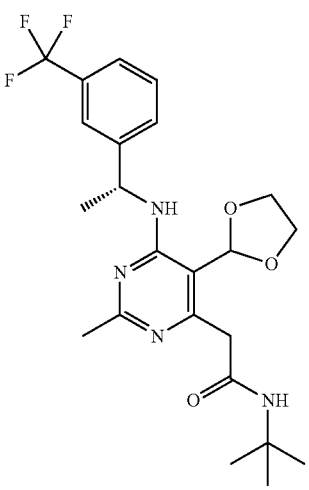 [SMILES: Cc1nc(CC(=O)NC(C)(C)C)c(C2OCCO2)c(N[C@H](C)c2cccc(C(F)(F)F)c2)n1] | 1.059 | 467.3 | VAB |
| A-7al | 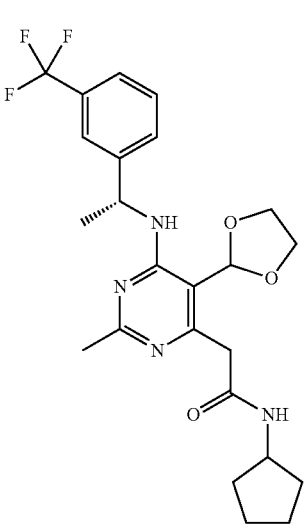 [SMILES: Cc1nc(CC(=O)NC2CCCC2)c(C2OCCO2)c(N[C@H](C)c2cccc(C(F)(F)F)c2)n1] | 1.061 | 479.1 | VAB |

TABLE 6-continued

| # | structure | $t_{ret}$ [min] | $[M + H]^+$ | HPLC method |
|---|---|---|---|---|
| A-7am | 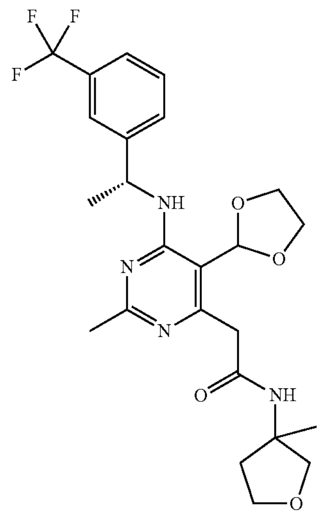 [SMILES: Cc1nc(CC(=O)NC2(C)CCOC2)c(C2OCCO2)c(N[C@H](C)c2cccc(C(F)(F)F)c2)n1] | 1.036 | 495.0 | VAB |
| A-7an | 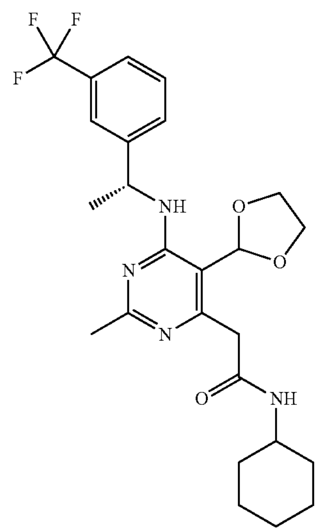 [SMILES: Cc1nc(CC(=O)NC2CCCCC2)c(C2OCCO2)c(N[C@H](C)c2cccc(C(F)(F)F)c2)n1] | 1.098 | 493.3 | VAB |
| A-7ao | 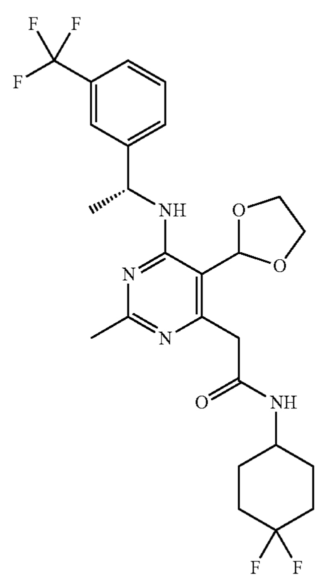 [SMILES: Cc1nc(CC(=O)NC2CCC(F)(F)CC2)c(C2OCCO2)c(N[C@H](C)c2cccc(C(F)(F)F)c2)n1] | 1.051 | 529.3 | VAB |

TABLE 6-continued

| # | structure | $t_{ret}$ [min] | $[M + H]^+$ | HPLC method |
|---|---|---|---|---|
| A-7ap | 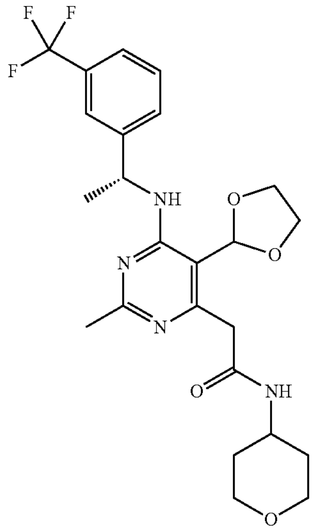 [SMILES: Cc1nc(CC(=O)NC2CCOCC2)c(C2OCCO2)c(N[C@H](C)c2cccc(C(F)(F)F)c2)n1] | 0.996 | 495.2 | VAB |
| A-7aq | 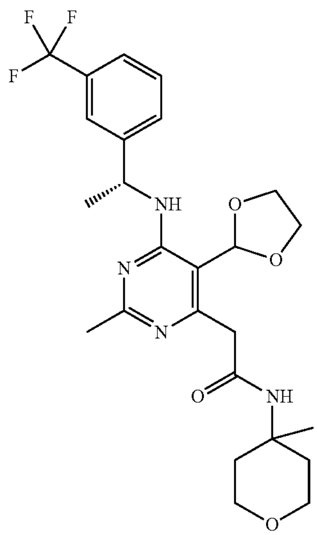 [SMILES: Cc1nc(CC(=O)NC2(C)CCOCC2)c(C2OCCO2)c(N[C@H](C)c2cccc(C(F)(F)F)c2)n1] | 1.334 | 509.1 | VAB |
| A-7ar | 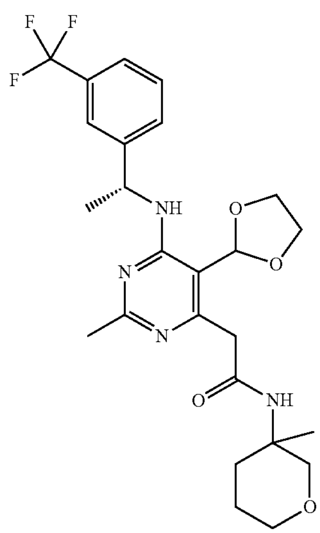 [SMILES: Cc1nc(CC(=O)NC2(C)CCCOC2)c(C2OCCO2)c(N[C@H](C)c2cccc(C(F)(F)F)c2)n1] | 1.309 | 509.1 | VAB |

TABLE 6-continued
| # | structure | $t_{ret}$ [min] | $[M + H]^+$ | HPLC method |
|---|---|---|---|---|
| A-7as | 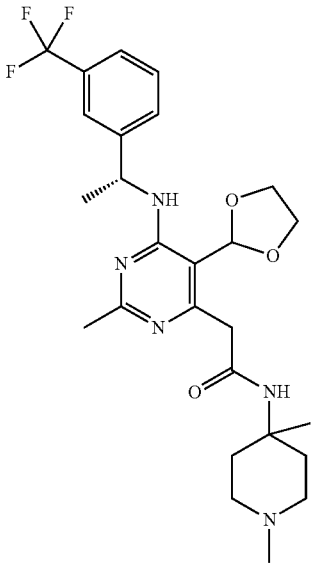 [SMILES: Cc1nc(CC(=O)NC2(C)CCN(C)CC2)c(C2OCCO2)c(N[C@H](C)c2cccc(C(F)(F)F)c2)n1] | 0.966 | 522.2 | VAB |
| A-7at | 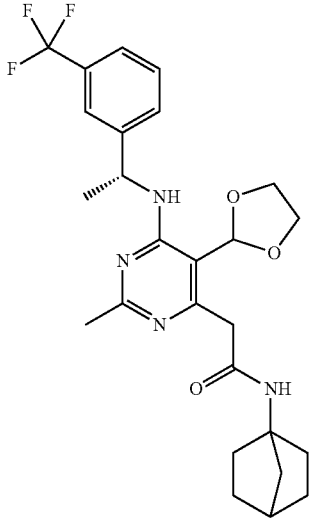 [SMILES: Cc1nc(CC(=O)NC23CCC(CC2)C3)c(C2OCCO2)c(N[C@H](C)c2cccc(C(F)(F)F)c2)n1] | 1.154 | 505.1 | VAB |
| A-7au | 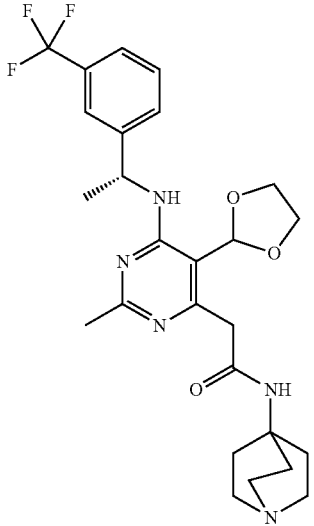 [SMILES: Cc1nc(CC(=O)NC23CCN(CC2)CC3)c(C2OCCO2)c(N[C@H](C)c2cccc(C(F)(F)F)c2)n1] | 0.935 | 520.3 | VAB |

TABLE 6-continued
| # | structure | $t_{ret}$ [min] | $[M + H]^+$ | HPLC method |
|---|---|---|---|---|
| A-7av | 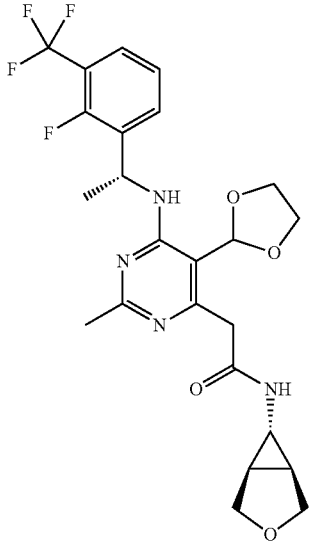 [SMILES: Cc1nc(CC(=O)N[C@H]2[C@@H]3COC[C@@H]32)c(C2OCCO2)c(N[C@H](C)c2cccc(C(F)(F)F)c2F)n1] | 1.003 | 493.3 | VAB |
| A-7aw | 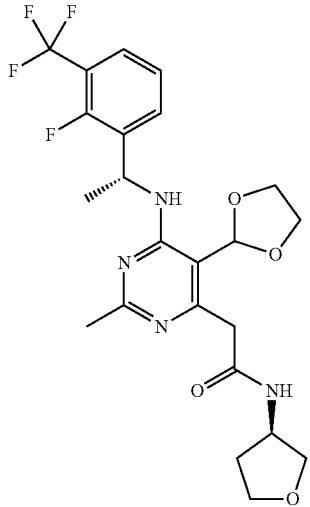 [SMILES: Cc1nc(CC(=O)N[C@@H]2CCOC2)c(C2OCCO2)c(N[C@H](C)c2cccc(C(F)(F)F)c2F)n1] | 1.023 | 499.3 | VAB |
| A-7ax | 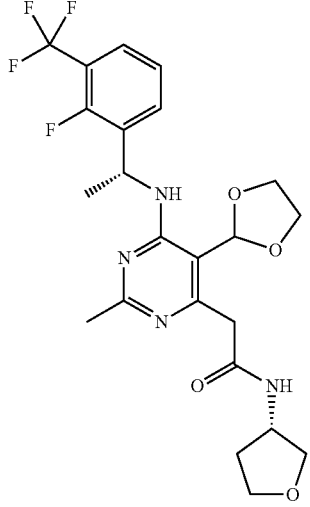 [SMILES: Cc1nc(CC(=O)N[C@H]2CCOC2)c(C2OCCO2)c(N[C@H](C)c2cccc(C(F)(F)F)c2F)n1] | 1.090 | 499.3 | VAB |

TABLE 6-continued
| # | structure | $t_{ret}$ [min] | $[M + H]^+$ | HPLC method |
|---|---|---|---|---|
| A-7ay | 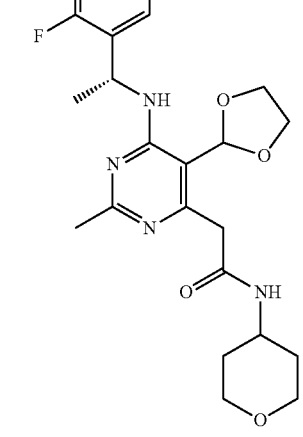 | 1.062 | 513.2 | VAB |
| A-7az | 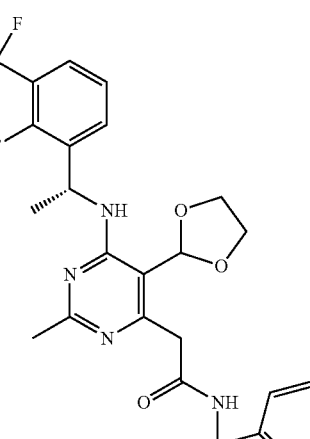 | 1.190 | 589.3 | VAB |
| A-7ba | 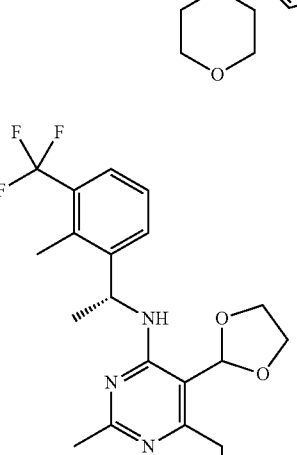 | 1.026 | 479.1 | VAB |

TABLE 6-continued
| # | structure | $t_{ret}$ [min] | $[M + H]^+$ | HPLC method |
|---|---|---|---|---|
| A-7bb | 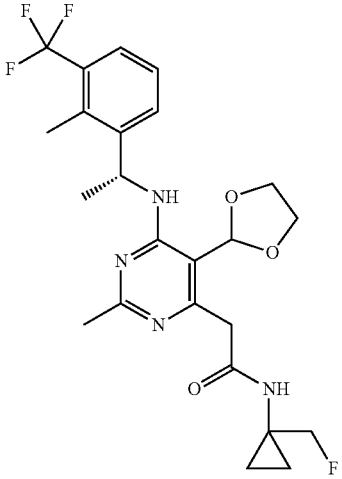 [SMILES: Cc1nc(CC(=O)NC2(CF)CC2)c(C2OCCO2)c(N[C@H](C)c2cccc(C(F)(F)F)c2C)n1] | 1.010 | 497.3 | VAB |
| A-7bc | 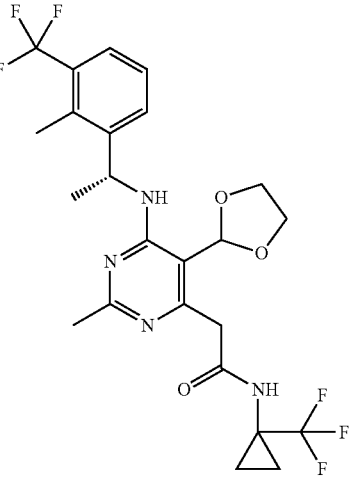 | 1.053 | 533.3 | VAB |
| A-7bd | 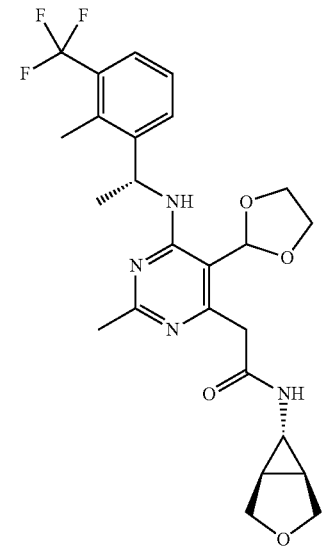 [SMILES: Cc1nc(CC(=O)N[C@H]2[C@@H]3COC[C@@H]32)c(C2OCCO2)c(N[C@H](C)c2cccc(C(F)(F)F)c2C)n1] | 1.157 | 507.4 | VAB |

TABLE 6-continued
| # | structure | $t_{ret}$ [min] | $[M + H]^+$ | HPLC method |
|---|---|---|---|---|
| A-7be | 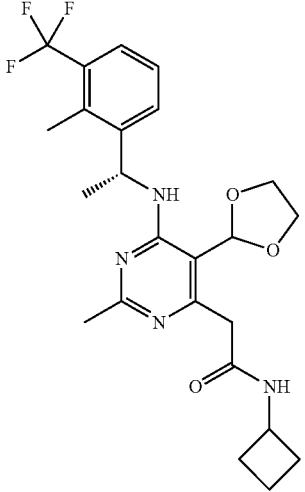 [SMILES: Cc1nc(CC(=O)NC2CCC2)c(C2OCCO2)c(N[C@H](C)c2cccc(C(F)(F)F)c2C)n1] | 1.044 | 479.3 | VAB |
| A-7bf | 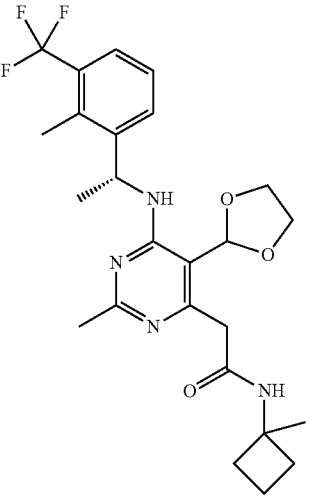 [SMILES: Cc1nc(CC(=O)NC2(C)CCC2)c(C2OCCO2)c(N[C@H](C)c2cccc(C(F)(F)F)c2C)n1] | 1.069 | 493.3 | VAB |
| A-7bg | 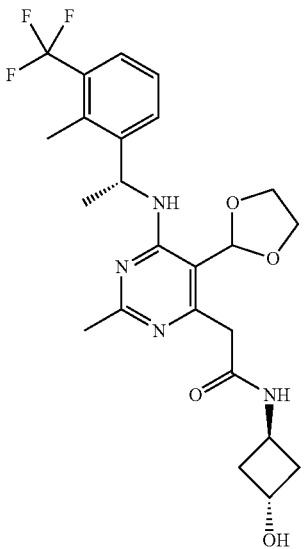 [SMILES: Cc1nc(CC(=O)N[C@H]2C[C@H](O)C2)c(C2OCCO2)c(N[C@H](C)c2cccc(C(F)(F)F)c2C)n1] | 0.919 | 495.2 | VAB |

TABLE 6-continued
| # | structure | $t_{ret}$ [min] | $[M + H]^+$ | HPLC method |
|---|---|---|---|---|
| A-7bh | 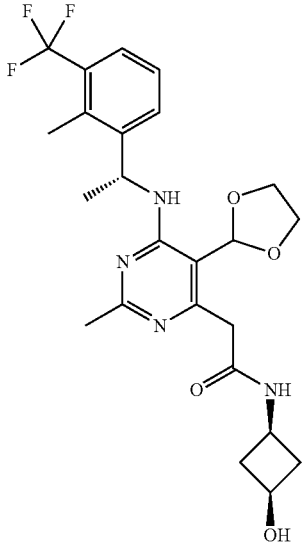 [SMILES: Cc1nc(CC(=O)N[C@H]2C[C@@H](O)C2)c(C2OCCO2)c(N[C@H](C)c2cccc(C(F)(F)F)c2C)n1] | 0.932 | 495.2 | VAB |
| A-7bi | 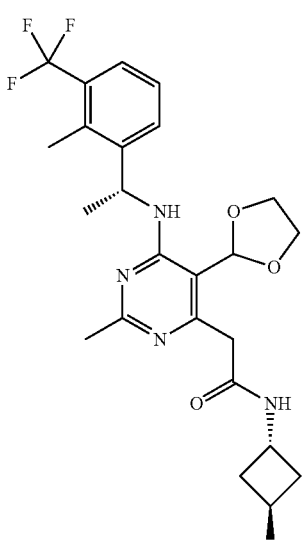 | 1.010 | 497.3 | VAB |

TABLE 6-continued

| # | structure | $t_{ret}$ [min] | $[M + H]^+$ | HPLC method |
|---|---|---|---|---|
| A-7bj | 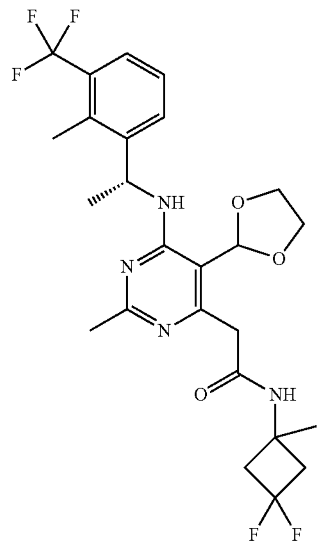 [SMILES: Cc1nc(CC(=O)NC2(C)CC(F)(F)C2)c(C2OCCO2)c(N[C@H](C)c2cccc(C(F)(F)F)c2C)n1] | 1.061 | 529.3 | VAB |
| A-7bk | 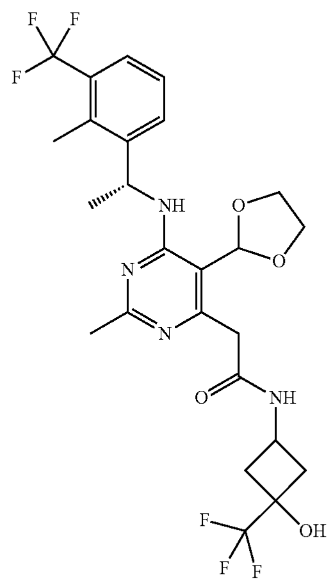 [SMILES: Cc1nc(CC(=O)NC2CC(O)(C(F)(F)F)C2)c(C2OCCO2)c(N[C@H](C)c2cccc(C(F)(F)F)c2C)n1] | 1.007 | 563.2 | VAB |
| A-7bl | 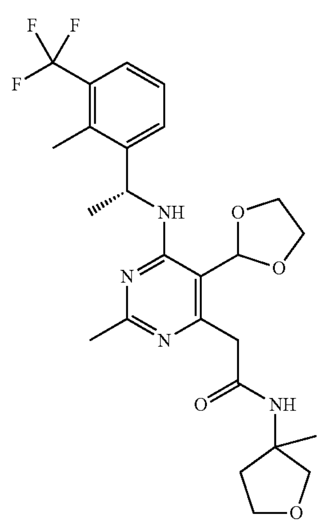 [SMILES: Cc1nc(CC(=O)NC2(C)CCOC2)c(C2OCCO2)c(N[C@H](C)c2cccc(C(F)(F)F)c2C)n1] | 1.001 | 509.1 | VAB |

TABLE 6-continued
| # | structure | $t_{ret}$ [min] | [M + H]+ | HPLC method |
|---|---|---|---|---|
| A-7bm | 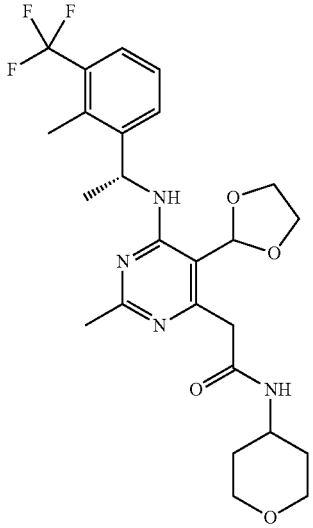 | 1.198 | 509.3 | VAB |
| A-7bn | 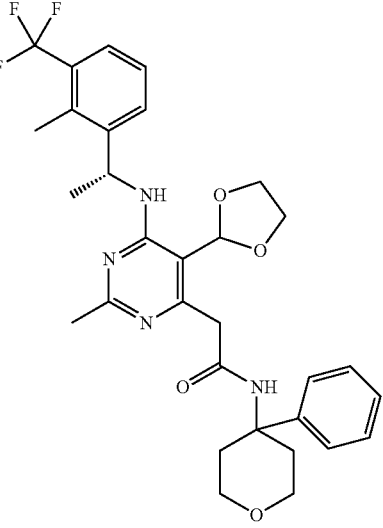 | 1.127 | 585.3 | VAB |
| A-7bo | 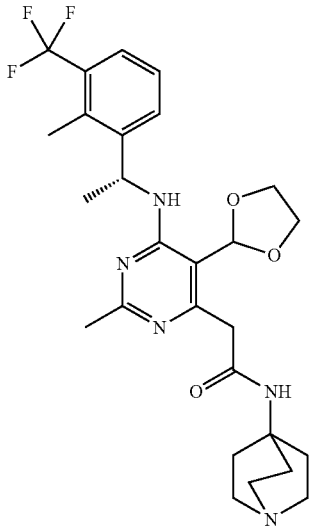 [SMILES: Cc1nc(CC(=O)NC23CCN(CC2)CC3)c(C2OCCO2)c(N[C@H](C)c2cccc(C(F)(F)F)c2C)n1] | 0.978 | 534.2 | VAB |

TABLE 6-continued

| # | structure | t_ret [min] | [M + H]+ | HPLC method |
|---|---|---|---|---|
| A-7bp | 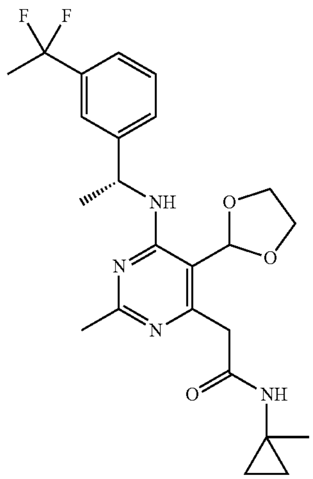 [SMILES: Cc1nc(CC(=O)NC2(C)CC2)c(C2OCCO2)c(N[C@H](C)c2cccc(C(C)(F)F)c2)n1] | 0.954 | 461.3 | VAB |
| A-7bq | 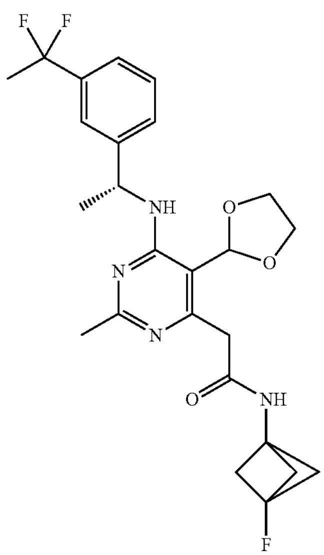 [SMILES: Cc1nc(CC(=O)NC23CC(F)(C2)C3)c(C2OCCO2)c(N[C@H](C)c2cccc(C(C)(F)F)c2)n1] | 0.995 | 491.3 | VAB |
| A-7br | 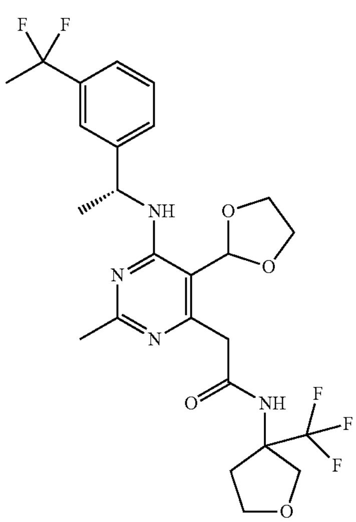 [SMILES: Cc1nc(CC(=O)NC2(C(F)(F)F)CCOC2)c(C2OCCO2)c(N[C@H](C)c2cccc(C(C)(F)F)c2)n1] | 0.986 | 545.3 | VAB |

TABLE 6-continued
| # | structure | $t_{ret}$ [min] | $[M + H]^+$ | HPLC method |
|---|---|---|---|---|
| A-7bs | 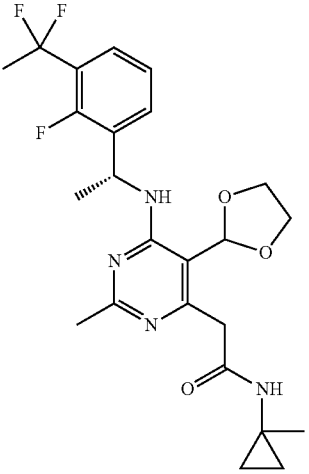 [SMILES: Cc1nc(CC(=O)NC2(C)CC2)c(C2OCCO2)c(N[C@H](C)c2cccc(C(C)(F)F)c2F)n1] | 0.974 | 479.1 | VAB |
| A-7bt | 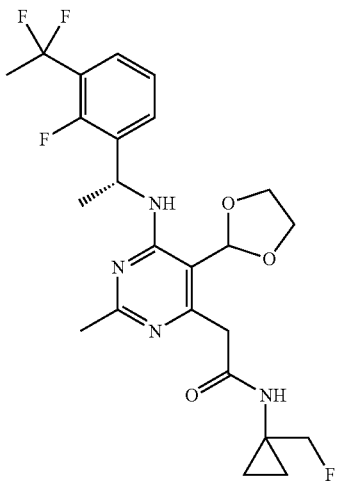 [SMILES: Cc1nc(CC(=O)NC2(CF)CC2)c(C2OCCO2)c(N[C@H](C)c2cccc(C(C)(F)F)c2F)n1] | 0.964 | 497.3 | VAB |
| A-7bu | 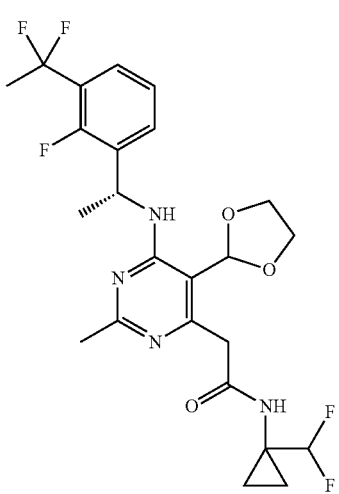 [SMILES: Cc1nc(CC(=O)NC2(C(F)F)CC2)c(C2OCCO2)c(N[C@H](C)c2cccc(C(C)(F)F)c2F)n1] | 0.982 | 515.2 | VAB |

TABLE 6-continued
| # | structure | t_ret [min] | [M + H]+ | HPLC method |
|---|---|---|---|---|
| A-7bv | 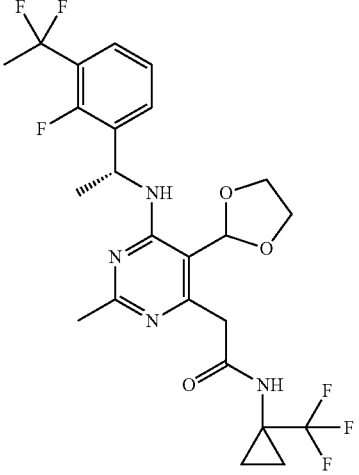 [SMILES: Cc1nc(CC(=O)NC2(C(F)(F)F)CC2)c(C2OCCO2)c(N[C@H](C)c2cccc(C(C)(F)F)c2F)n1] | 1.014 | 533.2 | VAB |
| A-7bw | 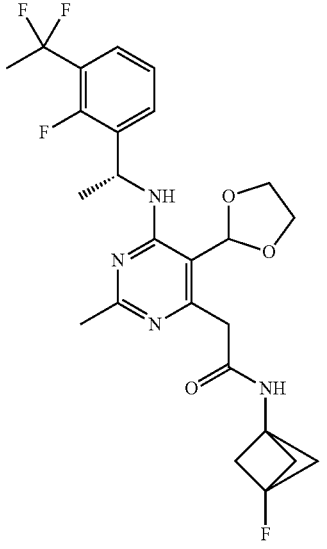 [SMILES: Cc1nc(CC(=O)NC23CC(F)(C2)C3)c(C2OCCO2)c(N[C@H](C)c2cccc(C(C)(F)F)c2F)n1] | 1.003 | 509.1 | VAB |
| A-7bx | 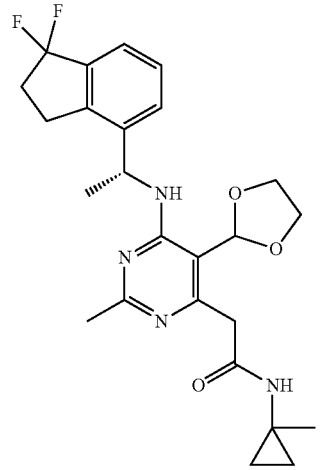 [SMILES: Cc1nc(CC(=O)NC2(C)CC2)c(C2OCCO2)c(N[C@H](C)c2cccc3c2CCC3(F)F)n1] | 0.964 | 473.3 | VAB |

TABLE 6-continued
| # | structure | $t_{ret}$ [min] | $[M + H]^+$ | HPLC method |
|---|---|---|---|---|
| A-7by | 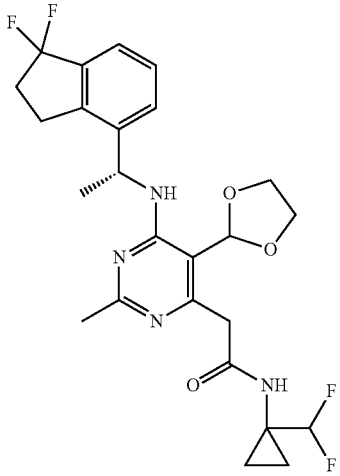 [SMILES: Cc1nc(CC(=O)NC2(C(F)F)CC2)c(C2OCCO2)c(N[C@H](C)c2cccc3c2CCC3(F)F)n1] | 0.990 | 509.3 | VAB |
| A-7bz | 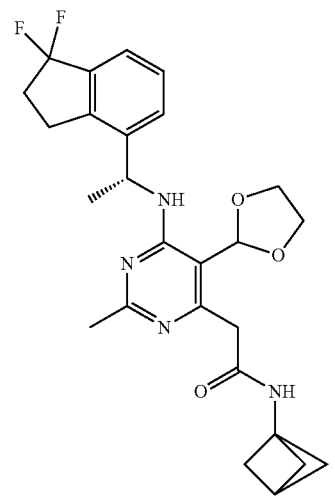 [SMILES: Cc1nc(CC(=O)NC23CC(C2)C3)c(C2OCCO2)c(N[C@H](C)c2cccc3c2CCC3(F)F)n1] | 1.007 | 485.3 | VAB |
| A-7ca | 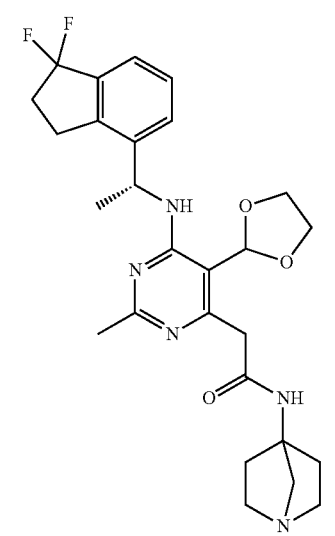 [SMILES: Cc1nc(CC(=O)NC23CCN(CC2)C3)c(C2OCCO2)c(N[C@H](C)c2cccc3c2CCC3(F)F)n1] | 0.904 | 514.3 | VAB |

TABLE 6-continued
| # | structure | t_ret [min] | [M + H]+ | HPLC method |
|---|---|---|---|---|
| A-7cb | 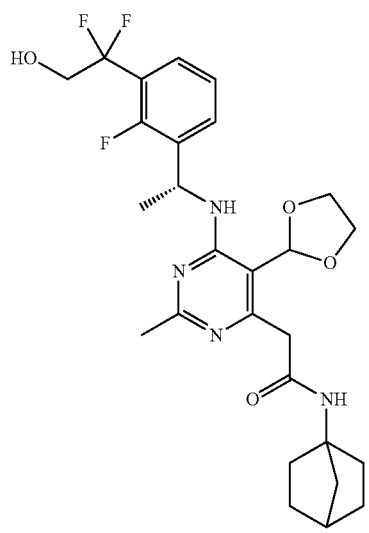 [SMILES: Cc1nc(CC(=O)NC23CCC(CC2)C3)c(C2OCCO2)c(N[C@H](C)c2cccc(C(F)(F)CO)c2F)n1] | 0.973 | 535.3 | VAB |
| A-7cc | 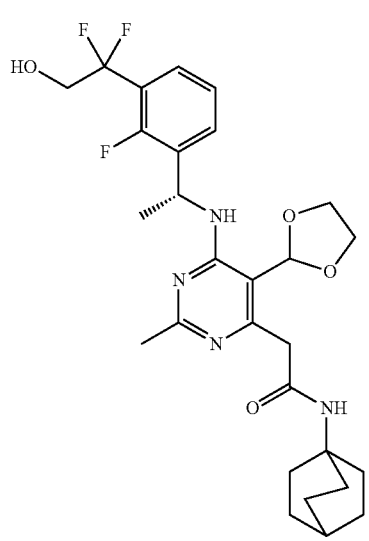 [SMILES: Cc1nc(CC(=O)NC23CCC(CC2)CC3)c(C2OCCO2)c(N[C@H](C)c2cccc(C(F)(F)CO)c2F)n1] | 0.991 | 549.2 | VAB |
| A-7cd | 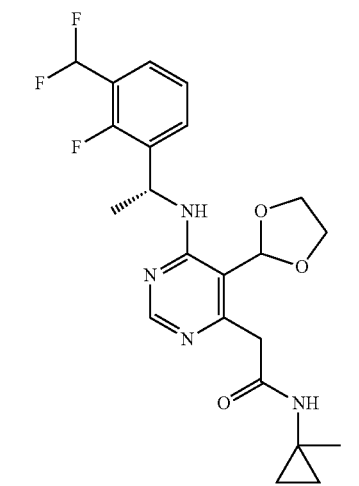 [SMILES: C[C@@H](Nc1ncnc(CC(=O)NC2(C)CC2)c1C1OCCO1)c1cccc(C(F)F)c1F] | 0.906 | 451.3 | VAB |

TABLE 6-continued

| # | structure | $t_{ret}$ [min] | [M + H]⁺ | HPLC method |
|---|---|---|---|---|
| A-7ce | 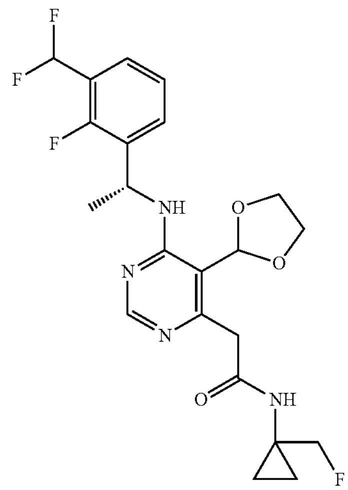 [SMILES: C[C@@H](Nc1ncnc(CC(=O)NC2(CF)CC2)c1C1OCCO1)c1cccc(C(F)F)c1F] | 0.896 | 469.3 | VAB |
| A-7cf | 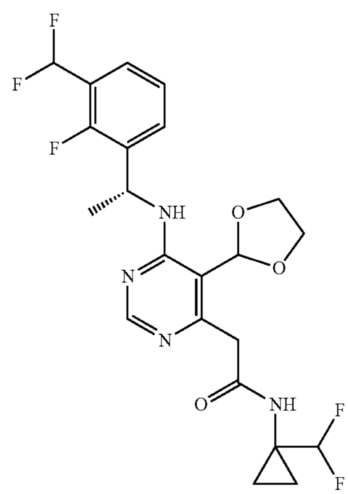 [SMILES: C[C@@H](Nc1ncnc(CC(=O)NC2(C(F)F)CC2)c1C1OCCO1)c1cccc(C(F)F)c1F] | 0.909 | 487.3 | VAB |
| A-7cg | 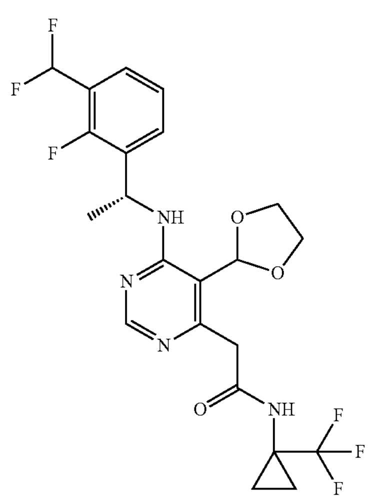 [SMILES: C[C@@H](Nc1ncnc(CC(=O)NC2(C(F)(F)F)CC2)c1C1OCCO1)c1cccc(C(F)F)c1F] | 0.952 | 505.3 | VAB |

TABLE 6-continued

| # | structure | $t_{ret}$ [min] | [M + H]$^+$ | HPLC method |
|---|---|---|---|---|
| A-7ch | 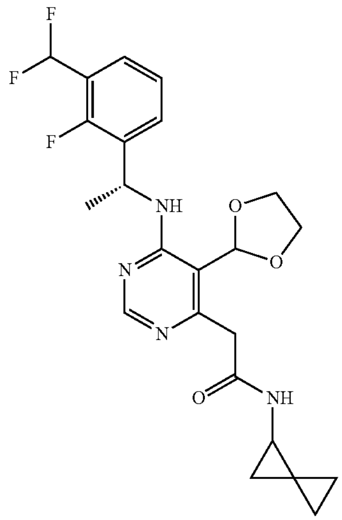 [SMILES: C[C@@H](Nc1ncnc(CC(=O)NC2CC23CC3)c1C1OCCO1)c1cccc(C(F)F)c1F] | 0.936 | 463.3 | VAB |
| A-7ci | 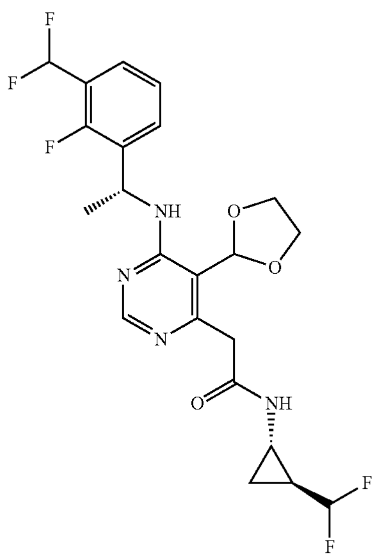 [SMILES: C[C@@H](Nc1ncnc(CC(=O)N[C@H]2C[C@@H]2C(F)F)c1C1OCCO1)c1cccc(C(F)F)c1F] | 0.906 | 487 | VAB |
| A-7cj | 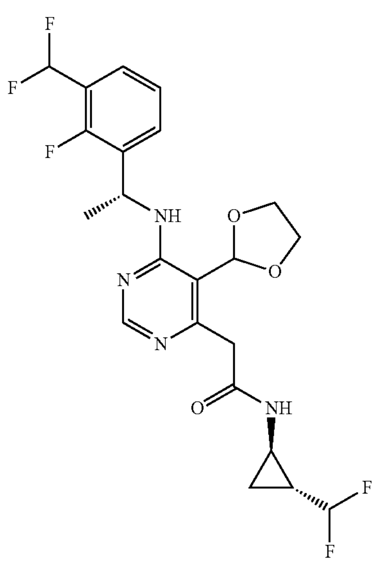 [SMILES: C[C@@H](Nc1ncnc(CC(=O)N[C@@H]2C[C@H]2C(F)F)c1C1OCCO1)c1cccc(C(F)F)c1F] | 0.906 | 487 | VAB |

TABLE 6-continued
| # | structure | $t_{ret}$ [min] | [M + H]+ | HPLC method |
|---|---|---|---|---|
| A-7ck | 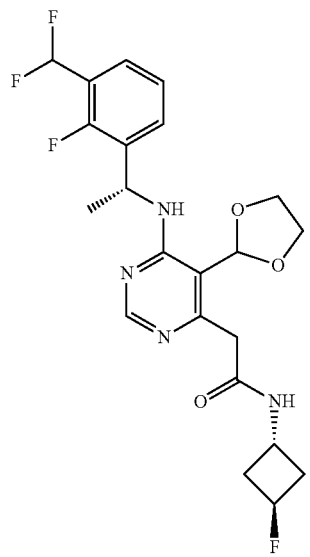 [SMILES: C[C@@H](Nc1ncnc(CC(=O)N[C@H]2C[C@H](F)C2)c1C1OCCO1)c1cccc(C(F)F)c1F] | 0.889 | 469.3 | VAB |
| A-7cl | 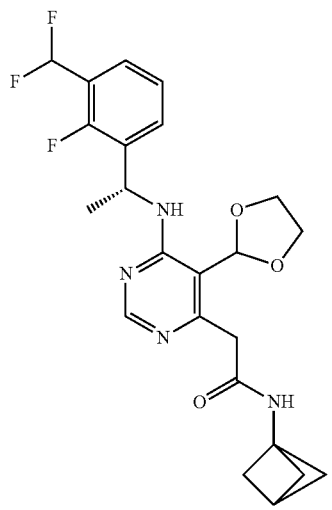 | 0.956 | 463.3 | VAB |

TABLE 6-continued
| # | structure | $t_{ret}$ [min] | [M + H]$^+$ | HPLC method |
|---|---|---|---|---|
| A-7cm | 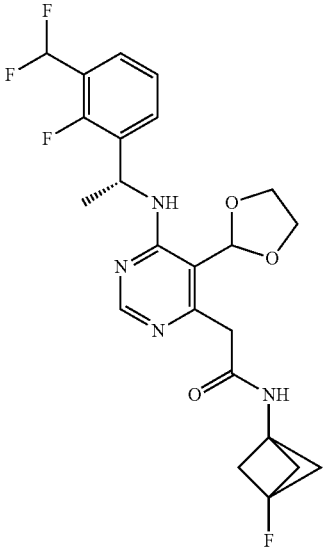 | 0.940 | 481.1 | VAB |
| A-7cn | 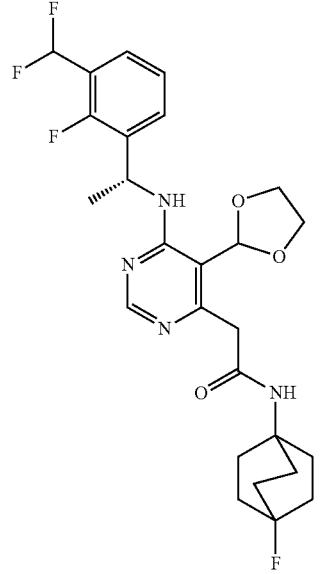 | 0.990 | 523.3 | VAB |

TABLE 6-continued

| # | structure | $t_{ret}$ [min] | $[M + H]^+$ | HPLC method |
|---|---|---|---|---|
| A-7co | 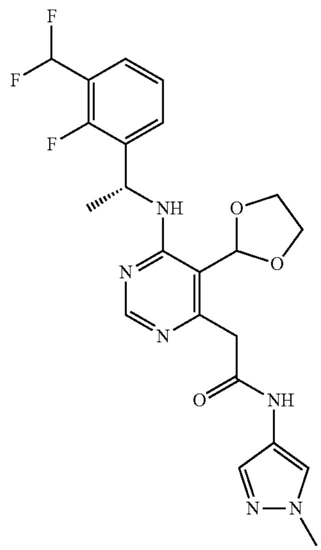 [SMILES: C[C@@H](Nc1ncnc(CC(=O)Nc2cnn(C)c2)c1C1OCCO1)c1cccc(C(F)F)c1F] | 0.845 | 477.2 | VAB |
| A-7cp | 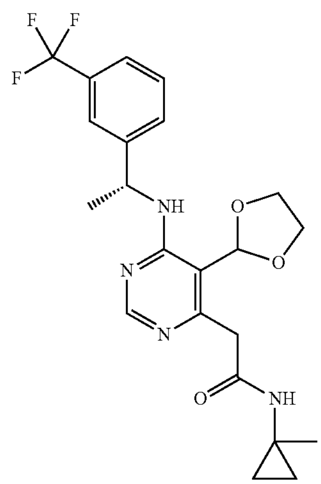 [SMILES: C[C@@H](Nc1ncnc(CC(=O)NC2(C)CC2)c1C1OCCO1)c1cccc(C(F)(F)F)c1] | 0.937 | 451 | VAB |
| A-7cq | 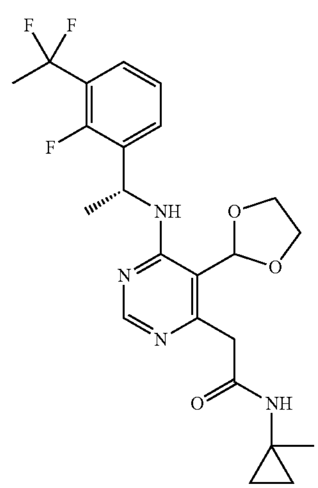 [SMILES: C[C@@H](Nc1ncnc(CC(=O)NC2(C)CC2)c1C1OCCO1)c1cccc(C(C)(F)F)c1F] | 0.938 | 465 | VAB |

TABLE 6-continued
| # | structure | $t_{ret}$ [min] | $[M + H]^+$ | HPLC method |
|---|---|---|---|---|
| A-7cr | 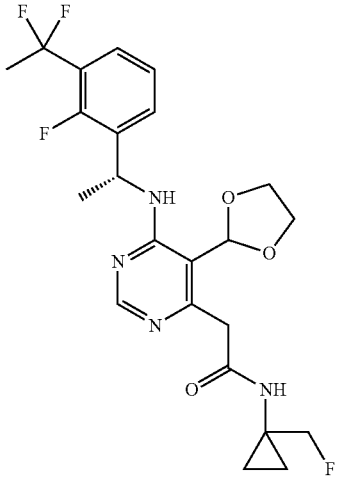 [SMILES: C[C@@H](Nc1ncnc(CC(=O)NC2(CF)CC2)c1C1OCCO1)c1cccc(C(C)(F)F)c1F] | 0.917 | 483.2 | VAB |
| A-7cs | 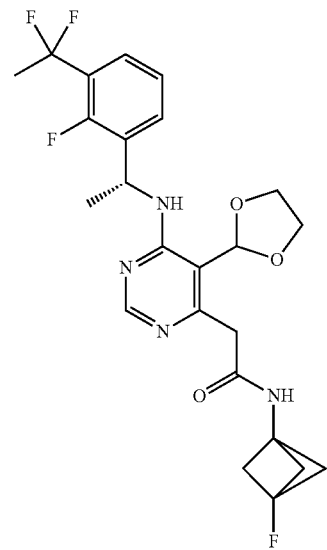 [SMILES: C[C@@H](Nc1ncnc(CC(=O)NC23CC(F)(C2)C3)c1C1OCCO1)c1cccc(C(C)(F)F)c1F] | 0.978 | 495 | VAB |
| A-7ct | 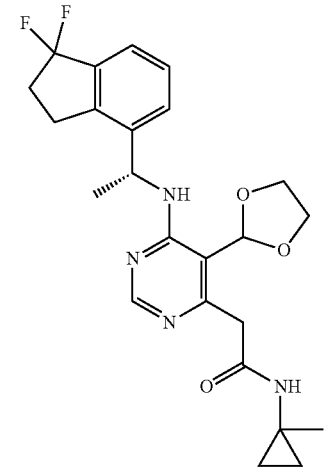 [SMILES: C[C@@H](Nc1ncnc(CC(=O)NC2(C)CC2)c1C1OCCO1)c1cccc2c1CCC2(F)F] | 0.925 | 459.2 | VAB |

TABLE 6-continued
| # | structure | $t_{ret}$ [min] | [M + H]⁺ | HPLC method |
|---|---|---|---|---|
| A-7cu | 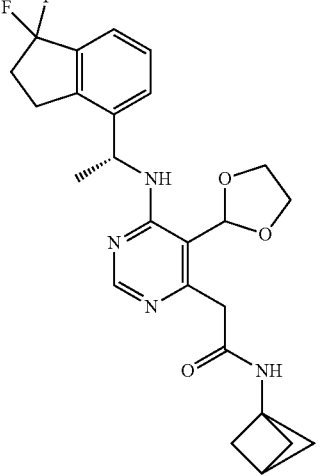 | 0.967 | 471.2 | VAB |
| A-7cv | 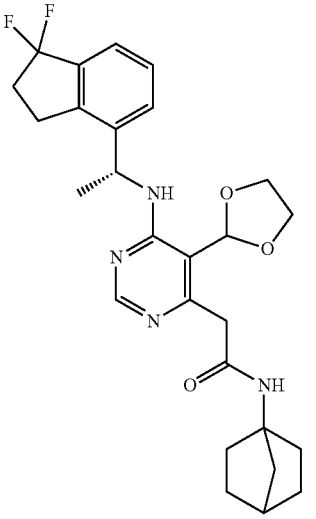 [SMILES: C[C@@H](Nc1ncnc(CC(=O)NC23CCC(CC2)C3)c1C1OCCO1)c1cccc2c1CCC2(F)F] | 1.022 | 499.3 | VAB |
| A-7cw | 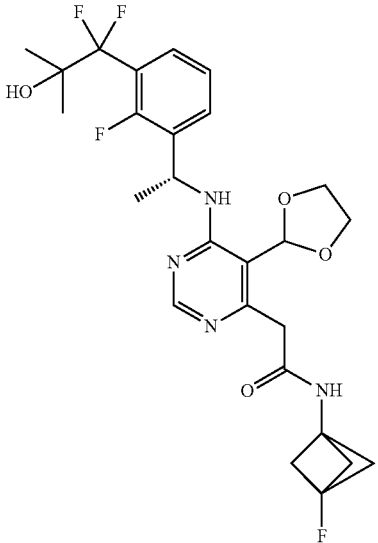 [SMILES: C[C@@H](Nc1ncnc(CC(=O)NC23CC(F)(C2)C3)c1C1OCCO1)c1cccc(C(F)(F)C(C)(C)O)c1F] | 0.915 | 539.3 | VAB |

TABLE 6-continued

| # | structure | $t_{ret}$ [min] | $[M + H]^+$ | HPLC method |
|---|---|---|---|---|
| A-7cx | 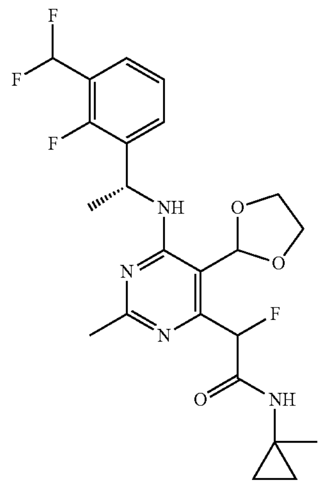 [SMILES: Cc1nc(N[C@H](C)c2cccc(C(F)F)c2F)c(C2OCCO2)c(C(F)C(=O)NC2(C)CC2)n1] | 0.976 | 483.2 | VAB |
| A-7cy | 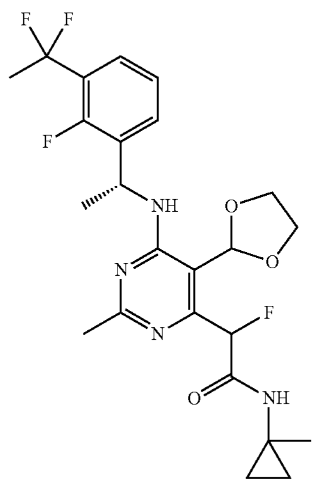 [SMILES: Cc1nc(N[C@H](C)c2cccc(C(C)(F)F)c2F)c(C2OCCO2)c(C(F)C(=O)NC2(C)CC2)n1] | 1.011 | 497.3 | VAB |
| A-7cz | 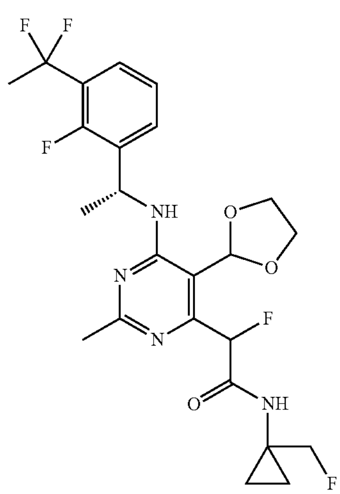 [SMILES: Cc1nc(N[C@H](C)c2cccc(C(C)(F)F)c2F)c(C2OCCO2)c(C(F)C(=O)NC2(CF)CC2)n1] | 1.008 | 515.3 | VAB |

TABLE 6-continued

| # | structure | $t_{ret}$ [min] | $[M + H]^+$ | HPLC method |
|---|---|---|---|---|
| A-7da | 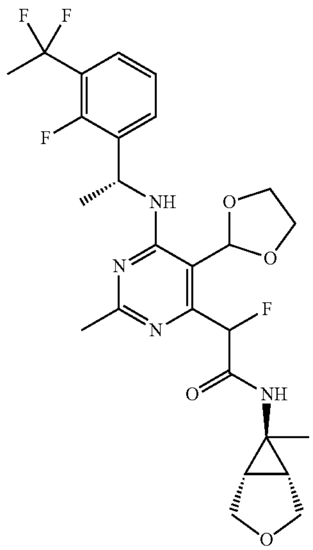 [SMILES: Cc1nc(N[C@H](C)c2cccc(C(C)(F)F)c2F)c(C2OCCO2)c(C(F)C(=O)N[C@@]2(C)[C@@H]3COC[C@@H]32)n1] | 0.980 | 539.3 | VAB |
| A-7db | 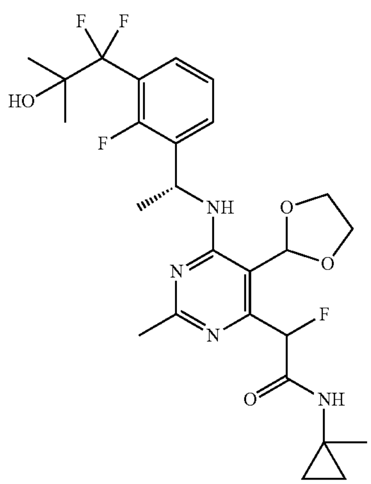 [SMILES: Cc1nc(N[C@H](C)c2cccc(C(F)(F)C(C)(C)O)c2F)c(C2OCCO2)c(C(F)C(=O)NC2(C)CC2)n1] | 0.949 | 541.3 | VAB |
| A-7dc | 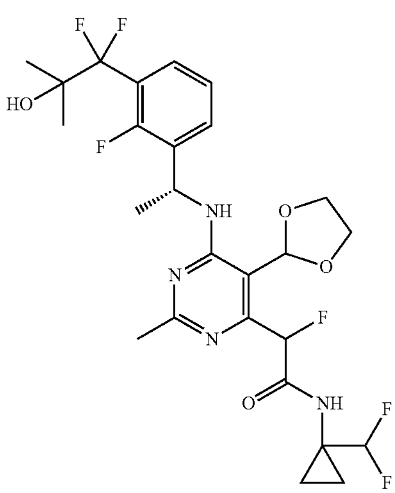 [SMILES: Cc1nc(N[C@H](C)c2cccc(C(F)(F)C(C)(C)O)c2F)c(C2OCCO2)c(C(F)C(=O)NC2(C(F)F)CC2)n1] | 0.961 | 577.3 | VAB |

TABLE 6-continued
| # | structure | $t_{ret}$ [min] | [M + H]⁺ | HPLC method |
|---|---|---|---|---|
| A-7dd | 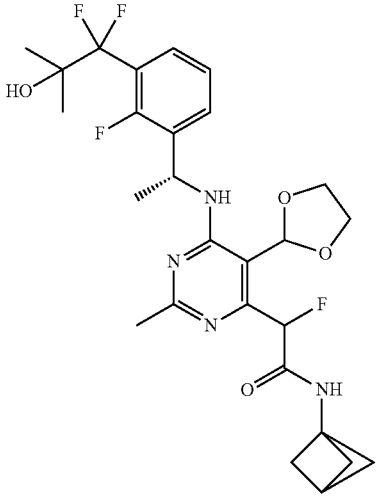 [SMILES: Cc1nc(N[C@H](C)c2cccc(C(F)(F)C(C)(C)O)c2F)c(C2OCCO2)c(C(F)C(=O)NC23CC(C2)C3)n1] | 0.973 | 553.3 | VAB |
| A-7de | 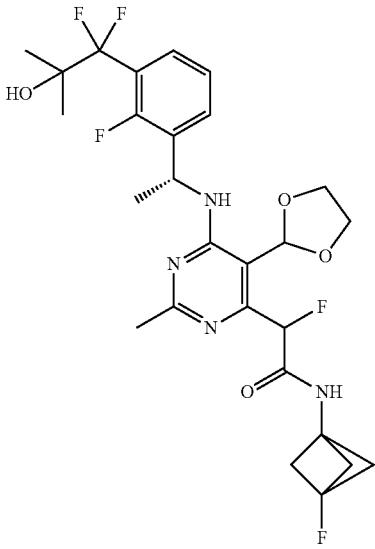 [SMILES: Cc1nc(N[C@H](C)c2cccc(C(F)(F)C(C)(C)O)c2F)c(C2OCCO2)c(C(F)C(=O)NC23CC(F)(C2)C3)n1] | 0.969 | 571.3 | VAB |
| A-7df | 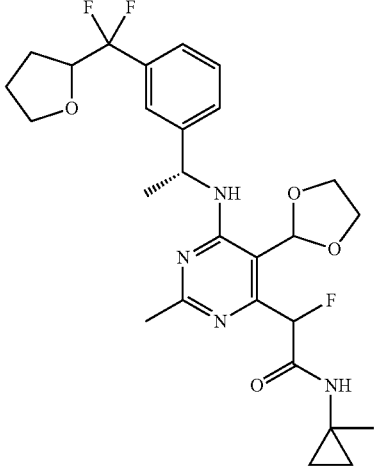 [SMILES: Cc1nc(N[C@H](C)c2cccc(C(F)(F)C3CCCO3)c2)c(C2OCCO2)c(C(F)C(=O)NC2(C)CC2)n1] | 1.016 | 553.3 | VAB |

TABLE 6-continued

| # | structure | t_ret [min] | [M + H]+ | HPLC method |
|---|---|---|---|---|
| A-7dg | 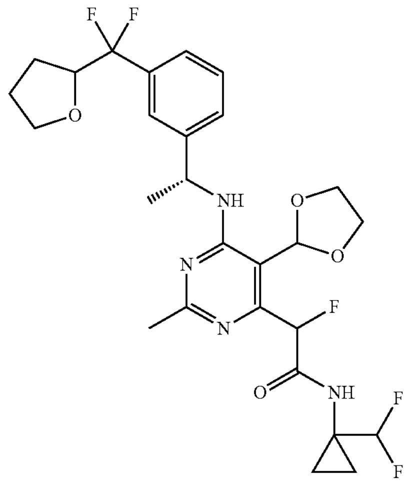 [SMILES: Cc1nc(N[C@H](C)c2cccc(C(F)(F)C3CCCO3)c2)c(C2OCCO2)c(C(F)C(=O)NC2(C(F)F)CC2)n1] | 1.033 | 589.3 | VAB |
| A-7dh | 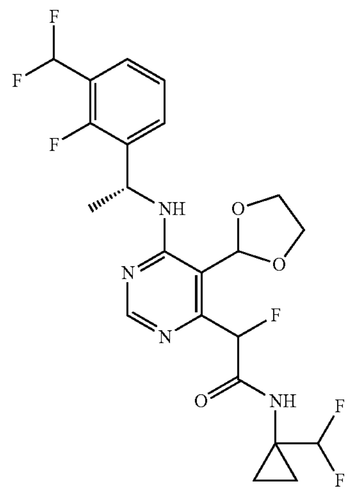 [SMILES: C[C@@H](Nc1ncnc(C(F)C(=O)NC2(C(F)F)CC2)c1C1OCCO1)c1cccc(C(F)F)c1F] | 0.953 | 505.3 | VAB |
| A-7di | 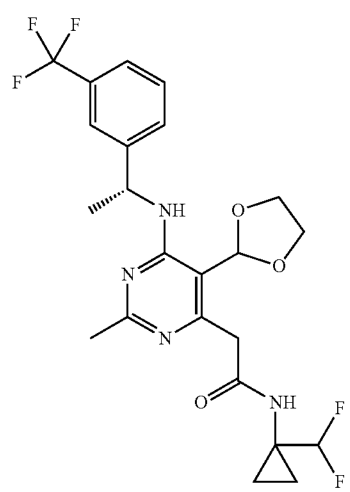 [SMILES: Cc1nc(CC(=O)NC2(C(F)F)CC2)c(C2OCCO2)c(N[C@H](C)c2cccc(C(F)(F)F)c2)n1] | 1.032 | 501.2 | VAB |

TABLE 6-continued
| # | structure | $t_{ret}$ [min] | $[M + H]^+$ | HPLC method |
|---|---|---|---|---|
| A-7dj | 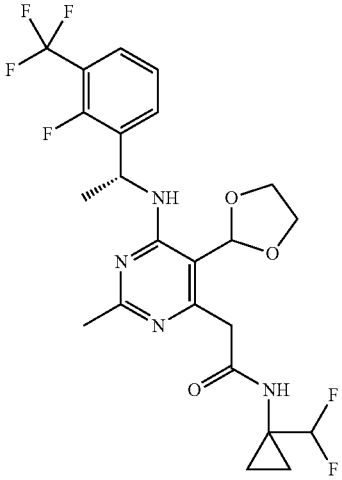 [SMILES: Cc1nc(CC(=O)NC2(C(F)F)CC2)c(C2OCCO2)c(N[C@H](C)c2cccc(C(F)(F)F)c2F)n1] | 1.018 | 519.2 | VAB |
| A-7dk | 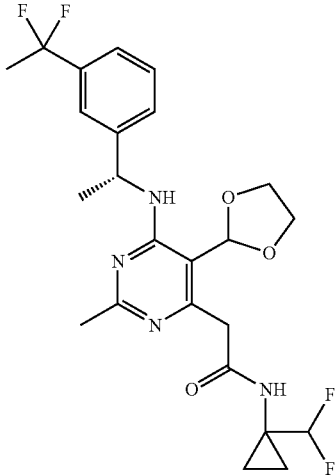 [SMILES: Cc1nc(CC(=O)NC2(C(F)F)CC2)c(C2OCCO2)c(N[C@H](C)c2cccc(C(C)(F)F)c2)n1] | 0.970 | 497.3 | VAB |
| A-7dl | 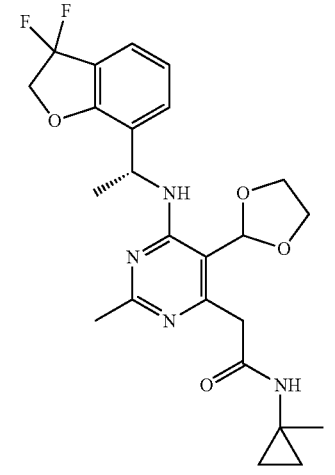 [SMILES: Cc1nc(CC(=O)NC2(C)CC2)c(C2OCCO2)c(N[C@H](C)c2cccc3c2OCC3(F)F)n1] | 0.935 | 475.3 | VAB |

TABLE 6-continued

| # | structure | $t_{ret}$ [min] | [M + H]$^+$ | HPLC method |
|---|---|---|---|---|
| A-7dm | 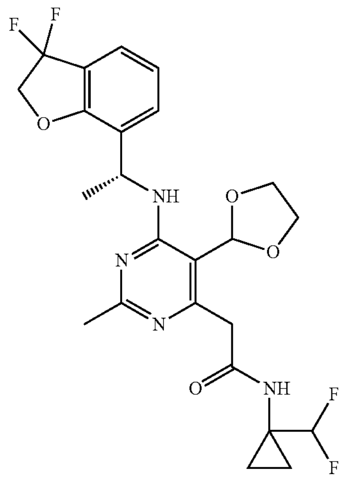 [SMILES: Cc1nc(CC(=O)NC2(C(F)F)CC2)c(C2OCCO2)c(N[C@H](C)c2cccc3c2OCC3(F)F)n1] | 0.962 | 511.1 | VAB |
| A-7dn | 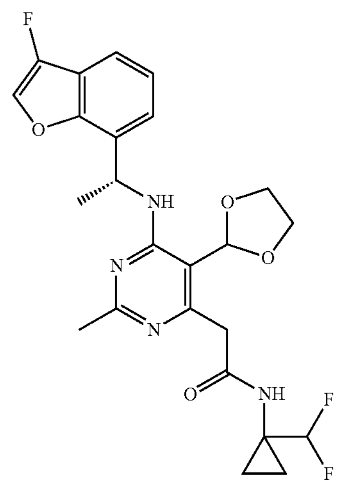 [SMILES: Cc1nc(CC(=O)NC2(C(F)F)CC2)c(C2OCCO2)c(N[C@H](C)c2cccc3c(F)coc23)n1] | 0.973 | 491.1 | VAB |
| A-7do | 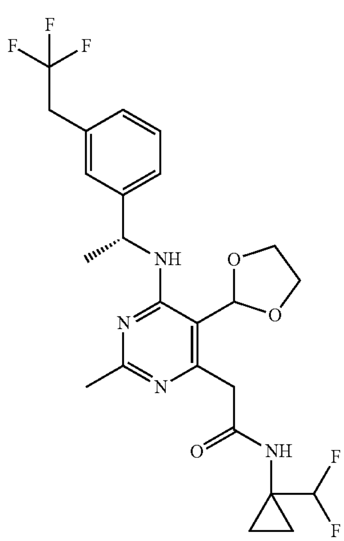 [SMILES: Cc1nc(CC(=O)NC2(C(F)F)CC2)c(C2OCCO2)c(N[C@H](C)c2cccc(CC(F)(F)F)c2)n1] | n.a. | n.a. | — |

Experimental Procedure for the Synthesis of A-7dp

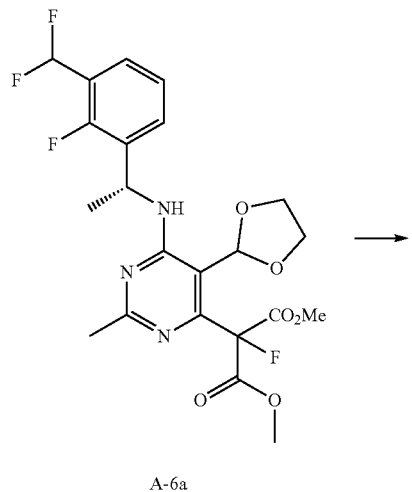

A-6a

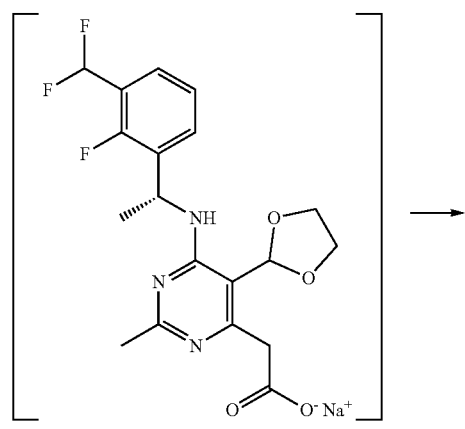

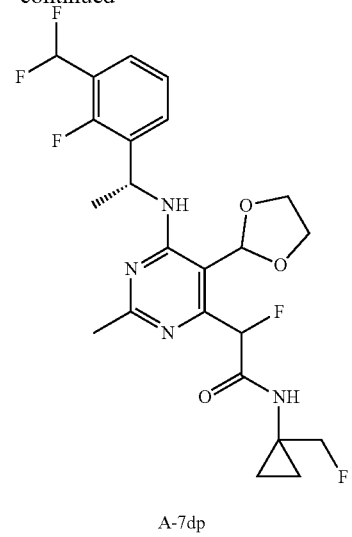

A-7dp

A-6a (16.0 mg, 0.032 mmol, 1.0 equiv.) is dissolved in DMSO (1.5 mL). An aqueous sodium hydroxide solution (20%, 16 μL, 0.096 mmol, 3.0 equiv.) is added and the resulting mixture stirred for 30 min until complete conversion of the starting material is observed. Triethylamine (8.5 μL, 0.061 mmol, 2.0 equiv.), 1-fluoromethyl-cyclopropylamine hydrochloride (4.8 mg, 0.038 mmol, 1.3 equiv.) and HATU (17.3 mg, 0.045 mmol, 1.5 equiv.) are added and the resulting mixture stirred for 20 min until complete conversion is observed. Water is added and the mixture diluted with DCM. The aqueous layer is extracted with DCM, the organic layers are combined and dried with magnesium sulfate. The resulting crude product A-7dp can be used without further purification in the next step.

The following intermediates A-7 (table 7) are available in an analogous manner starting from different pyrimidines A-6 and coupling with various amines C-1 or their corresponding salts. The crude product A-7 is purified by chromatography if necessary.

TABLE 7

| # | structure | $t_{ret}$ [min] | $[M + H]^+$ | HPLC method |
|---|---|---|---|---|
| A-7dp | (structure shown) | 0.966 | 501.2 | VAB |

TABLE 7-continued

| # | structure | t_ret [min] | [M + H]+ | HPLC method |
|---|---|---|---|---|
| A-7dq | 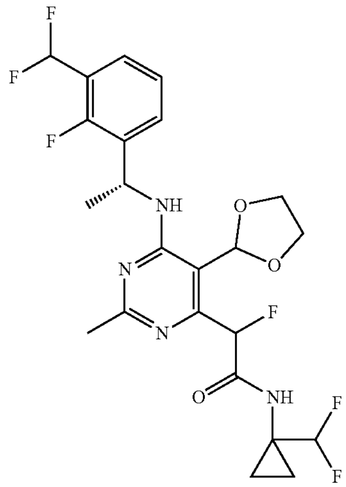 [SMILES: Cc1nc(N[C@H](C)c2cccc(C(F)F)c2F)c(C2OCCO2)c(C(F)C(=O)NC2(C(F)F)CC2)n1] | 0.998 | 519.2 | VAB |
| A-7dr | 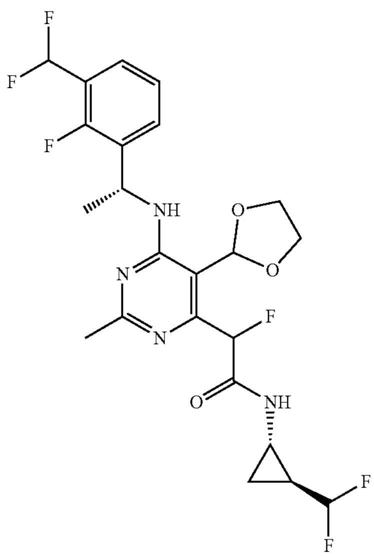 [SMILES: Cc1nc(N[C@H](C)c2cccc(C(F)F)c2F)c(C2OCCO2)c(C(F)C(=O)N[C@H]2C[C@@H]2C(F)F)n1] | 0.977 | 519.2 | VAB |
| A-7ds | 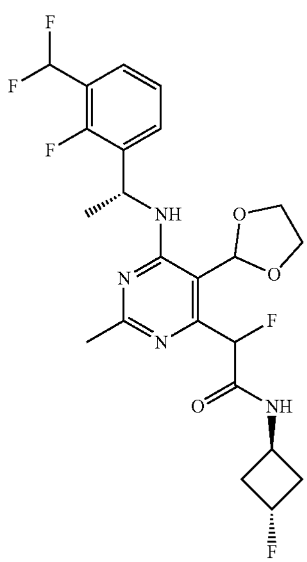 [SMILES: Cc1nc(N[C@H](C)c2cccc(C(F)F)c2F)c(C2OCCO2)c(C(F)C(=O)N[C@H]2C[C@H](F)C2)n1] | 0.979 | 501.4 | VAB |

TABLE 7-continued

| # | structure | t_ret [min] | [M + H]+ | HPLC method |
|---|---|---|---|---|
| A-7dt | 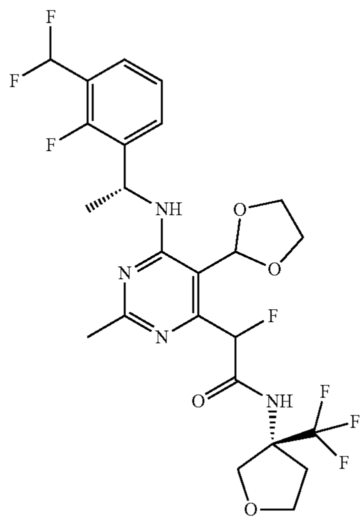 [SMILES: Cc1nc(N[C@H](C)c2cccc(C(F)F)c2F)c(C2OCCO2)c(C(F)C(=O)N[C@]2(C(F)(F)F)CCOC2)n1] | 1.001 | 567.2 | VAB |
| A-7du | 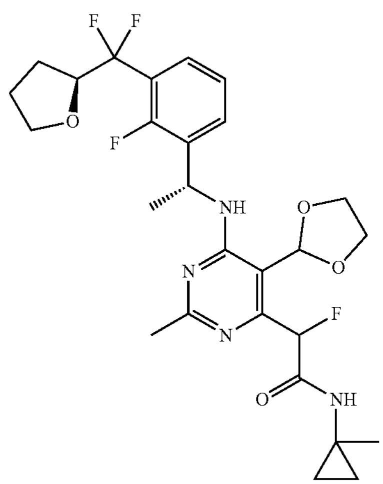 [SMILES: Cc1nc(N[C@H](C)c2cccc(C(F)(F)[C@@H]3CCCO3)c2F)c(C2OCCO2)c(C(F)C(=O)NC2(C)CC2)n1] | 1.014 | 553.3 | VAB |
| A-7dv | 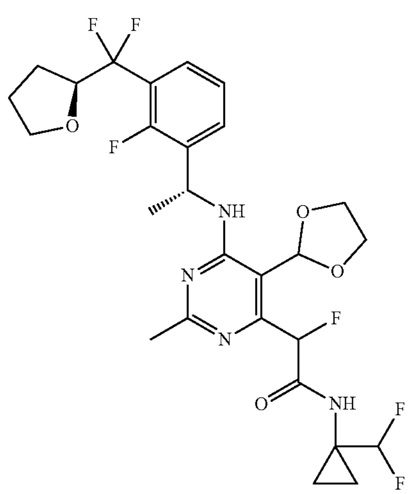 [SMILES: Cc1nc(N[C@H](C)c2cccc(C(F)(F)[C@@H]3CCCO3)c2F)c(C2OCCO2)c(C(F)C(=O)NC2(C(F)F)CC2)n1] | 1.028 | 589.3 | VAB |

Synthesis of Intermediates B-1
Experimental Procedure for the Synthesis of D-2a

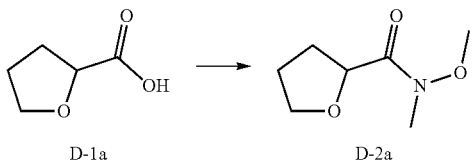

D-1a → D-2a

To a stirred solution of D-1a (20.00 g, 172.24 mmol, 1.0 equiv.) in DCM (200 mL) is added EDCI (49.35 g, 258.37 mmol, 1.5 equiv.), triethylamine (26.14 g, 258.37 mmol, 1.5 equiv.), DMAP (0.21 g, 1.72 mmol, 0.01 equiv.) and N,O-dimethylhydroxylamine hydrochloride (25.20 g, 258.37 mmol, 1.5 equiv.) at 0° C. The reaction mixture is warmed to room temperature and stirred for 16 h. After complete conversion of the starting material 1N HCl is added to the reaction mixture. The aqueous layer is extracted with EtOAc, the combined organic layers are washed with saturated aqueous NaHCO$_3$, dried over Na$_2$SO$_4$ and concentrated under reduced pressure. The crude product is purified by flash column chromatography (5% ethyl acetate in hexane) yielding the desired product D-2a.

The following intermediates D-2 (table 8) are available in an analogous manner starting from different acids D-1. The crude product D-2 is purified by chromatography if necessary.

TABLE 8

| # | structure | $t_{ret}$ [min] | [M + H]$^+$ | HPLC method |
|---|---|---|---|---|
| D-2a | 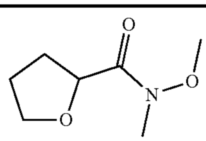 | 1.034 | 160 | GVK_LCMS_18 |
| D-2b | 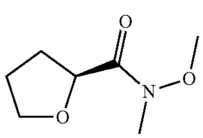 | 1.045 | 160 | GVK_LCMS_18 |
| D-2c | 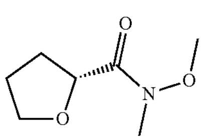 | 1.059 | 160 | GVK_LCMS_18 |

Experimental Procedure for the Synthesis of D-3a

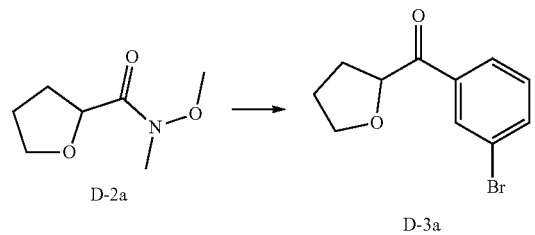

D-2a → D-3a

To a stirred solution of D-2a (150 mg, 0.942 mmol, 1.0 equiv.) in THF (5 mL) is slowly added 3-bromophenylmagnesium bromide (0.5 N, 2.26 mL, 1.130 mmol, 1.2 equiv) at −15° C. The reaction mixture is warmed to room temperature and stirred for 3 h. After complete conversion of the starting material, water is added. The aqueous layer is extracted with EtOAc, the organic layers are combined, dried over Na$_2$SO$_4$ and concentrated under reduced pressure. The crude product is purified by flash column chromatography (eluent: 10% ethyl acetate in hexane) yielding the desired product D-3a.

Experimental Procedure for the Synthesis of D-3b

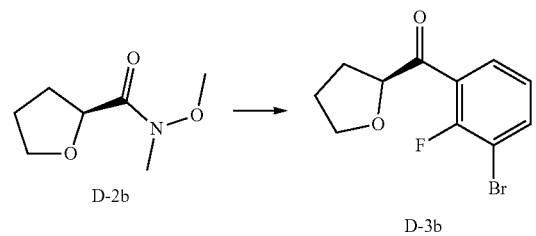

D-2b → D-3b

A stirred solution of 1,3-dibromo-2-fluoro-benzene (15.95 g, 62.82 mmol, 1.0 equiv.) in anhydrous THF (100 mL) is cooled to −78° C. n-Butyllithium (1.6 N, 47.1 mL, 75.36 mmol, 1.2 equiv.) is added dropwise and the resulting mixture is stirred for 30 min at −78° C. D-2b (10.00 g, 62.82 mmol, 1.0 equiv.) dissolved in THF (40 mL) is slowly added. After complete conversion, saturated aqueous ammonium chloride is added. The aqueous layer is extracted with EtOAc, the organic layers are combined, dried over Na$_2$SO$_4$ and concentrated under reduced pressure. The crude product is purified by chromatography on silica gel (gradient elution: 10% to 20% ethyl acetate in petroleum ether) yielding the desired product D-3b.

The following intermediates D-3 (table 9) are available in an analogous manner starting from different amides D-2. The crude product D-3 is purified by chromatography if necessary.

TABLE 9

| # | structure | $t_{ret}$ [min] | [M + H]$^+$ | HPLC method |
|---|---|---|---|---|
| D-3a | 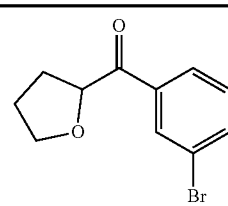 | n.a. | n.a. | — |
| D-3b | 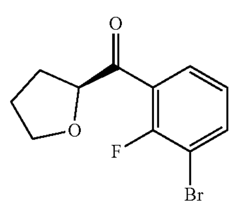 [SMILES: O=C(c1cccc(Br)c1F)[C@@H]1CCCO1] | 1.762 | 273 | GVK_LCMS_34 |
| D-3c | 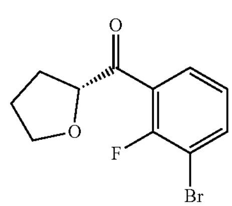 [SMILES: O=C(c1cccc(Br)c1F)[C@H]1CCCO1] | 1.756 | 273 | GVK_LCMS_34 |

Experimental Procedure for the Synthesis of B-1a

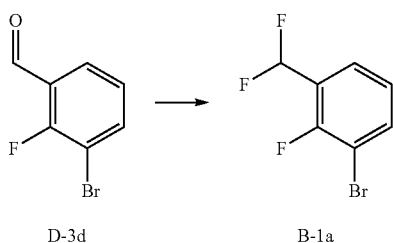 [SMILES: O=Cc1cccc(Br)c1F ; Fc1c(Br)cccc1C(F)F]

D-3d → B-1a

To a stirred solution of D-3d (150 g, 738.89 mmol, 1.0 equiv.) in DCM (1.5 L) is slowly added diethylaminosulfur trifluoride (178.64 g, 1108.33 mmol, 1.5 equiv) at 0° C. The reaction mixture is warmed to room temperature and stirred for 16 h. After complete conversion of the starting material, ice water is added. The aqueous layer is extracted with EtOAc, the organic layers are combined, dried over $Na_2SO_4$ and concentrated under reduced pressure. The crude product B-1a is used without further purification in the next step.

The following intermediates B-1 (table 10) are available in an analogous manner starting from different bromobenzenes D-3. The crude product B-1 is purified by chromatography if necessary.

TABLE 10

| # | structure | $t_{ret}$ [min] | $[M + H]^+$ | HPLC method |
|---|---|---|---|---|
| B-1a | ![structure] | n.a. | n.a. | — |
| B-1b | ![structure] | 1.66 | n.a. | GVK_LCMS_34 |
| B-1c | ![structure] | 1.974 | 278 | GVK_LCMS_31 |
| B-1d | ![structure] | n.a. | n.a. | — |

TABLE 10-continued

| # | structure | $t_{ret}$ [min] | $[M + H]^+$ | HPLC method |
|---|---|---|---|---|
| B-1e | ![structure] | n.a. | n.a. | — |

Experimental Procedure for the Synthesis of D-5a

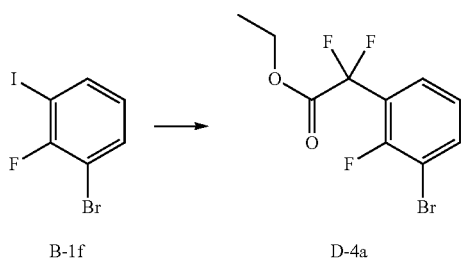 [SMILES: Fc1c(Br)cccc1I ; CCOC(=O)C(F)(F)c1cccc(Br)c1F]

B-1f → D-4a

To a stirred solution of ethyl bromodifluoroacetate (126.50 g, 623 mmol, 2.5 equiv.) in DMSO (225 mL) is added copper powder (39.26 g, 623 mmol, 2.5 equiv) at room temperature. After 1 h B-1f (75.00 g, 249.26 mmol, 1.0 equiv) is added and the resulting mixture heated to 70° C. and stirred for additional 3 h. After complete conversion of the starting material, ice water and EtOAc is added. Insolubles are removed by filtration and the aqueous layer is extracted with EtOAc. The organic layers are combined, dried over $Na_2SO_4$ and concentrated under reduced pressure. The crude product is purified by column chromatography (gradient elution: 0% to 10% ethyl acetate in petroleum ether) yielding the desired product D-4a.

Experimental Procedure for the Synthesis of B-1g

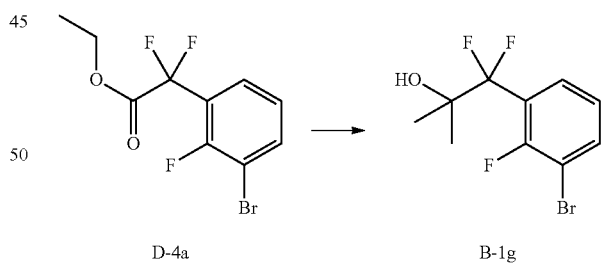

D-4a → B-1g

To a stirred solution of D-4a (100.00 g, 336.62 mmol, 1.0 equiv.) in anhydrous toluene (1 L) is slowly added methylmagnesium bromide (1 N, 1.34 L, 1340 mmol, 4.0 equiv) at 0° C. The resulting mixture is stirred for 1 h at room temperature. After complete conversion of the starting material, saturated aqueous ammonium chloride is added and the aqueous layer is extracted with EtOAc. The organic layers are combined, dried over $Na_2SO_4$ and concentrated under reduced pressure. The crude product is purified by chromatography (25% ethyl acetate in hexane) yielding the desired product B-1 g.

Experimental Procedure for the Synthesis of D-5a

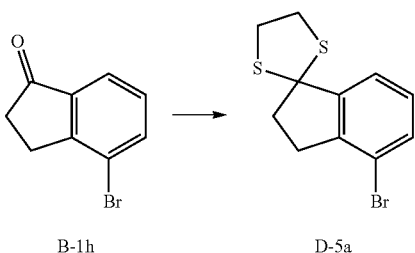 [SMILES: O=C1CCc2c(Br)cccc21 ; Brc1cccc2c1CCC21SCCS1]

B-1h (480.00 g, 2274 mmol, 1.0 equiv.) and ethane-1,2-dithiol (213.78 g, 2274 mmol, 1.0 equiv.) are dissolved in toluene (5 L), TsOH (78.24 g, 454.9 mmol, 0.2 equiv.) is added at room temperature and the resulting mixture heated to reflux for 24 h. After complete conversion of the starting material, a 10% aqueous NaOH solution is added and the aqueous layer is extracted with EtOAc. The organic layers are combined, washed with water and brine, dried over $Na_2SO_4$ and concentrated under reduced pressure. The crude product is purified by chromatography (gradient elution: 0% to 10% ethyl acetate in petroleum ether) yielding the desired product D-5a.

Experimental Procedure for the Synthesis of B-1j

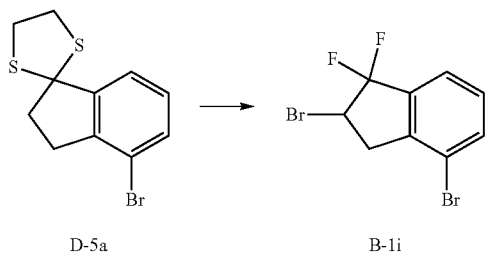 [SMILES: Brc1cccc2c1CCC21SCCS1 ; FC1(F)c2cccc(Br)c2CC1Br]

To a stirred solution of 1,3-dibromo-5,5-dimethylimidazolidine-2,4-dione (793.8 g, 2785 mmol, 4.0 equiv.) in DCM (1.5 L) is added HF-pyridine (70%, 800 mL, 30800 mmol, 44 equiv.) at −70° C. To this mixture D-5a (200.00 g, 696.28 mmol, 1.0 equiv.) dissolved in DCM (0.5 L) is added dropwise. The temperature is kept below −60° C. for 4 h and then the resulting mixture is stirred for additional 16 h at room temperature. After complete conversion of the starting material, a 2 N aqueous NaOH solution and a 30% aqueous $NaHSO_3$ solution are added. The organic layer is washed with water and brine, dried over $Na_2SO_4$ and concentrated under reduced pressure. The crude product is purified by column chromatography on silica gel (gradient elution: 0% to 3% ethyl acetate in petroleum ether) yielding the desired product B-1i.

Experimental Procedure for the Synthesis of B-1j

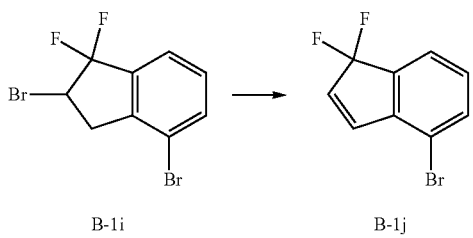 [SMILES: FC1(F)c2cccc(Br)c2CC1Br ; FC1(F)C=Cc2c(Br)cccc21]

B-1i (140.00 g, 448.79 mmol, 1.0 equiv.) is dissolved in DCM (1.5 L) and DBU (102.32 g, 673.19 mmol, 1.5 equiv.) is added at 0° C. The resulting mixture is stirred for 6 h at room temperature. After complete conversion of the starting material, the mixture is diluted with DCM, washed with 0.5 N aqueous HCl, water and brine, dried over $Na_2SO_4$ and concentrated under reduced pressure. The crude product is purified by chromatography (gradient elution: 0% to 10% ethyl acetate in petroleum ether) yielding the desired product B-1j.

Experimental Procedure for the Synthesis of B-1k

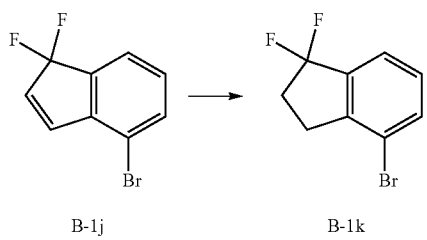 [SMILES: FC1(F)C=Cc2c(Br)cccc21 ; FC1(F)CCc2c(Br)cccc21]

To a stirred solution of B-1j (130.00 g, 562.68 mmol, 1.0 equiv.) and 2-nitrobenzenesulfonyl chloride (124.35 g, 562.68 mmol, 1.0 equiv.) in acetonitrile (1.3 L) are slowly added $K_3PO_4$ (23.86 g, 112.54 mmol, 0.2 equiv) and hydrazine hydrate (56.27 g, 1125.36 mmol, 2.0 equiv) at 0° C. The resulting mixture is stirred for 24 h at room temperature. After complete conversion of the starting material, water is added and the aqueous layer is extracted with EtOAc. The organic layers are combined, washed with water and brine, dried over $Na_2SO_4$ and concentrated under reduced pressure. The crude product is purified by column chromatography on silica gel (gradient elution: 0% to 5% ethyl acetate in petroleum ether) yielding the desired product B-1k.

Synthesis of Intermediates B-2

Experimental Procedure for the Synthesis of B-2a

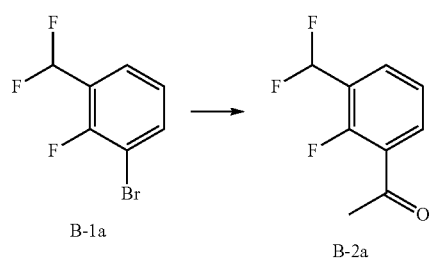

B-1a (125.0 g, 555.54 mmol, 1.0 equiv.) is dissolved in anhydrous 1,4-dioxane (1.2 L). Triethylamine (140.27 mL, 1388.85 mmol, 2.5 equiv.) and tributyl(1-ethoxyvinyl)tin (240.66 g, 666.65 mmol, 1.2 equiv.) are added and the resulting solution is purged with argon for 15 min. Bis(triphenylphosphine)palladium(II)chloride (3.90 g, 5.6 mmol, 0.01 equiv.) is added and the reaction mixture heated to 100° C. in an autoclave for 16 h. After complete conversion of the starting material, the reaction mixture is cooled to room temperature and treated with 1 N HCl and stirred for additional 16 h. The aqueous layer is extracted with EtOAc, the combined organic layers are dried over $Na_2SO_4$, filtered and the solvent is removed under reduced pressure. The crude product B-2a is used without further purification in the next step.

The following intermediates B-2 (table 11) are available in an analogous manner starting from different bromobenzenes B-1. The crude product B-2 is purified by chromatography if necessary.

TABLE 11

| # | structure | $t_{ret}$ [min] | [M + H]$^+$ | HPLC method |
|---|---|---|---|---|
| B-2a | 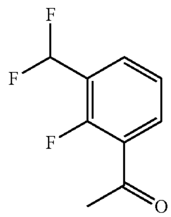 | n.a. | n.a. | — |
| B-2b | 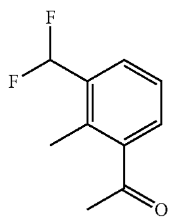 | 1.665 | 185 | GVK_LCMS_18 |
| B-2c | 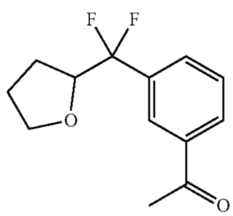 [SMILES: CC(=O)c1cccc(C(F)(F)C2CCCO2)c1] | 2.023 | 241 | GVK_LCMS_31 |
| B-2d | 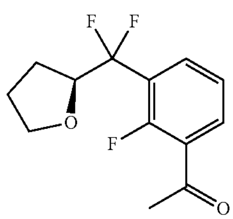 [SMILES: CC(=O)c1cccc(C(F)(F)[C@@H]2CCCO2)c1F] | n.a. | n.a. | — |
| B-2e | 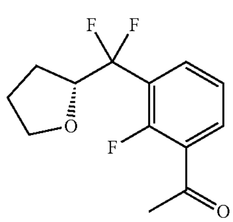 [SMILES: CC(=O)c1cccc(C(F)(F)[C@H]2CCCO2)c1F] | n.a. | n.a. | — |
| B-2f | 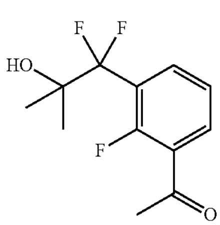 [SMILES: CC(=O)c1cccc(C(F)(F)C(C)(C)O)c1F] | 1.95 | 247 | GVK_LCMS_35 |

TABLE 11-continued

| # | structure | $t_{ret}$ [min] | [M + H]$^+$ | HPLC method |
|---|---|---|---|---|
| B-2g | 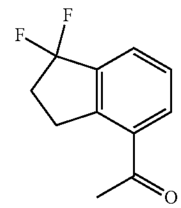 | 2.04 | 197 | GVK_LCMS_31 |
| B-2h | 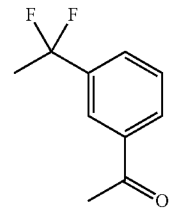 | 1.699 | 185 | GVK_LCMS_18 |

Experimental Procedure for the Synthesis of D-6a

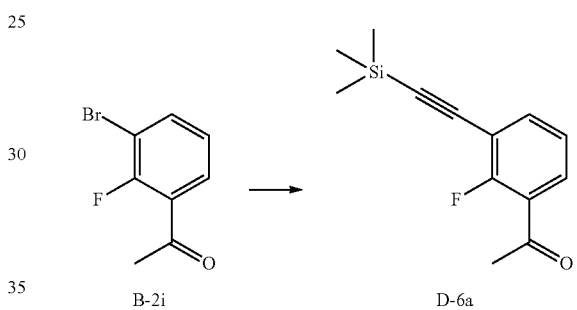

To a stirred solution of B-2i (80.00 g, 368.60 mmol, 1.0 equiv.) in THF (800 mL) are added TMS-acetylene (54.31 g, 552.94 mmol, 1.5 equiv.), triethylamine (111.69 g, 1105.84 mmol, 3.0 equiv.), CuI (4.034 g, 36.86 mmol, 0.1 equiv.) and Pd(PPhs)$_2$Cl$_2$ (25.88 g, 36.87 mmol, 0.1 equiv.) at room temperature. The resulting mixture is heated to reflux for 16 h. After complete conversion of the starting material, ice water and EtOAc are added and the aqueous layer is extracted with EtOAc. The organic layers are combined, dried over Na$_2$SO$_4$ and concentrated under reduced pressure. The crude product is purified by flash column chromatography (gradient elution: 0% to 10% ethyl acetate in hexane) yielding the desired product D-6a.

Experimental Procedure for the Synthesis of B-2j

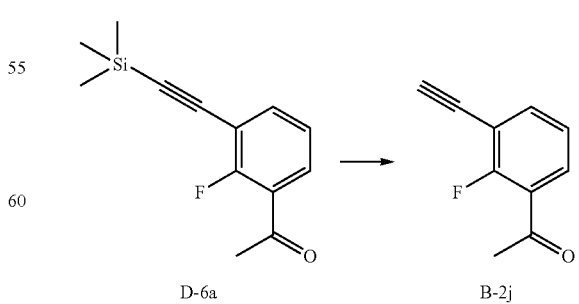

To a stirred solution of D-6a (60.00 g, 256.04 mmol, 1.0 equiv.) in DCM (1.2 L) and methanol (1.2 L) is added potassium carbonate (353.87 g, 2560.38 mmol, 10.0 equiv.) at room temperature. The resulting mixture is stirred for 2 h. After complete conversion of the starting material, ice water is added and the aqueous layer is extracted with DCM. The organic layers are combined, dried over Na$_2$SO$_4$ and concentrated under reduced pressure. The crude product is purified by flash column chromatography (gradient elution: 20% ethyl acetate in hexane) yielding the desired product B-2j.

Experimental Procedure for the Synthesis of B-2k

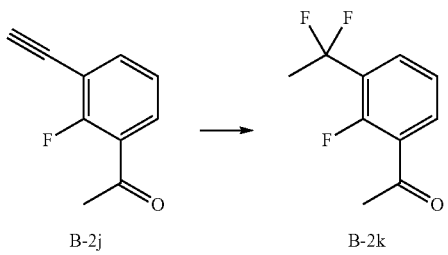

B-2j (98.00 g, 604.34 mmol, 1.0 equiv.) is dissolved in 1,1,1,3,3,3-hexafluoro propanol (500 mL) in a teflon flask. HF-pyridine (70%, 250 mL, 9625 mmol, 16 equiv.) is added and the flask is sealed. The resulting mixture is stirred for 3 d at room temperature. After complete conversion of the starting material, ice water and EtOAc are added and the aqueous layer is extracted with EtOAc. The organic layers are combined, washed with a saturated aqueous NaHCO$_3$ solution and brine, dried over Na$_2$SO$_4$ and concentrated under reduced pressure. The crude product is purified by flash column chromatography (gradient elution: 0% to 20% ethyl acetate in hexane) yielding the desired product B-2k.

Experimental Procedure for the Synthesis of D-8a

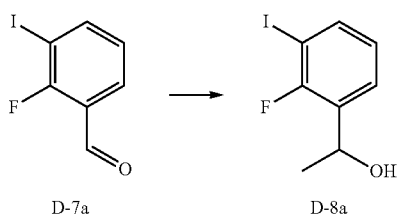

To a stirred solution of D-7a (120.00 g, 479.98 mmol, 1.0 equiv.) in THF (1.2 L) is added methylmagnesiumbromide (1 N, 720 mL, 720.00 mmol, 1.5 equiv) dropwise at −78° C. The resulting mixture is stirred for 3 h at same temperature. After complete conversion of the starting material, a saturated aqueous ammonium chloride solution is added and the aqueous layer is extracted with EtOAc. The organic layers are combined, dried over Na$_2$SO$_4$ and concentrated under reduced pressure. The crude product is purified by chromatography on silica gel (gradient elution: 0% to 10% ethyl acetate in petroleum ether) yielding the desired product D-8a.

Experimental Procedure for the Synthesis of B-21

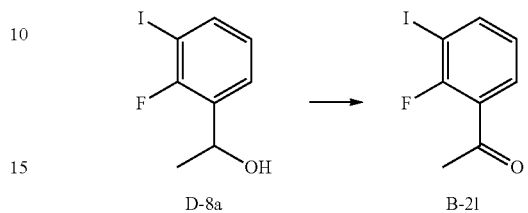

To a stirred solution of D-8a (24.00 g, 90.21 mmol, 1.0 equiv.) in acetonitrile (240 mL) is added tetrapropylammonium perruthenate (3.166 g, 9.01 mmol, 0.1 equiv.) and 4-methylmorpholine N-oxide (15.83 g, 135.30 mmol, 1.5 equiv.) at room temperature. The resulting mixture is stirred for 4 h at same temperature. After complete conversion of the starting material, insolubles are removed by filtration and the filtrate concentrated under reduced pressure. The crude product is purified by chromatography on silica gel (gradient elution: 0% to 5% ethyl acetate in petroleum ether) yielding the desired product B-21.

Experimental Procedure for the Synthesis of D-9a

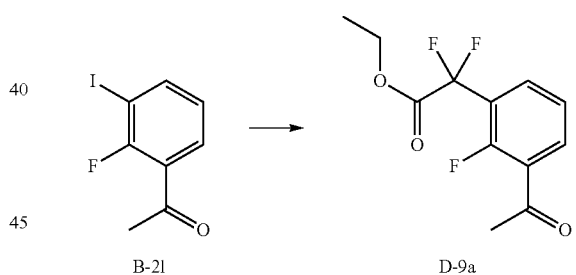

To a stirred solution of B-21 (22.00 g, 83.32 mmol, 1.0 equiv) in DMSO (220 mL) is added ethyl bromodifluoroacetate (50.74 g, 249.95 mmol, 3.0 equiv.) and copper powder (15.75 g, 250.00 mmol, 3.0 equiv) at room temperature. The resulting mixture is heated to 80° C. and stirred for 16 h. After complete conversion of the starting material, ice water and diethyl ether are added. Insolubles are removed by filtration and the aqueous layer is extracted with diethyl ether. The organic layers are combined, dried over Na$_2$SO$_4$ and concentrated under reduced pressure. The crude product is purified by chromatography (gradient elution: 0% to 3% ethyl acetate in petroleum ether) yielding the desired product D-9a.

Experimental Procedure for the Synthesis of B-2m

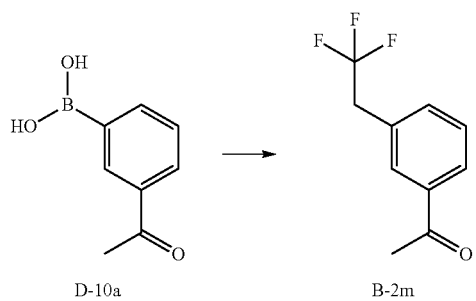

Synthesis of Intermediates B-3
Experimental Procedure for the Synthesis of B-3a

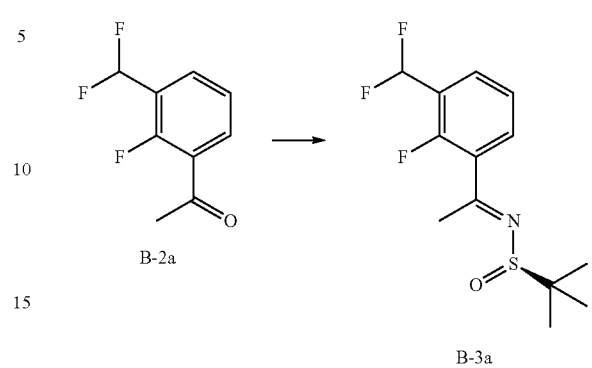

D-10a (20.00 g, 121.98 mmol, 1.0 equiv.) and 2,2,2-trifluoroethyl iodide (51.23 g, 243.95 mmol, 2.0 equiv.) are added to a stirred suspension of tris(dibenzylideneacetone)-dipalladium (7.819 g, 8.54 mmol, 0.1 equiv.), xantphos (7.05 g, 12.20 mmol, 0.1 equiv.) and cesium carbonate (118.93 g, 365.94 mmol, 3.0 equiv.) in THF (200 mL) under an argon atmosphere. The resulting mixture is stirred for one minute and then heated to 80 C for 12 h in a sealed tube. After complete conversion of the starting material, ice water and EtOAc are added and the aqueous layer is extracted with EtOAc. The organic layers are combined, dried over $Na_2SO_4$ and concentrated under reduced pressure. The crude product is purified by flash column chromatography yielding the desired product B-2m.

B-2a (170.00 g, 903.53 mmol; 1.0 equiv.) is dissolved in THF (1.7 L). (R)-(+)-2-methyl-2-propanesulfinamide (164.13 g; 1355.33 mmol; 1.5 equiv.) and titanium tetraethoxide (618.03 g, 2710.66 mmol; 3.0 equiv.) are added at room temperature and the resulting reaction mixture is heated to 80° C. for 16 h. After complete conversion of the starting material, ice water and EtOAc are added and the aqueous layer is extracted with EtOAc. The organic layers are combined, dried over $Na_2SO_4$ and concentrated under reduced pressure. The crude product B-3a is used without further purification in the next step.

The following intermediates B-3 and D-10 (table 12) are available in an analogous manner starting from different acetophenones B-2 and D-9. The crude product is purified by chromatography if necessary.

TABLE 12

| # | structure | $t_{ret}$ [min] | $[M + H]^+$ | HPLC method |
|---|---|---|---|---|
| B-3a | 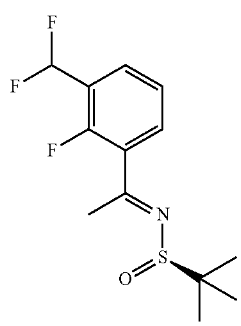 [SMILES: C/C(=N\[S@](=O)C(C)(C)C)c1cccc(C(F)F)c1F] | n.a. | n.a. | — |
| B-3b | 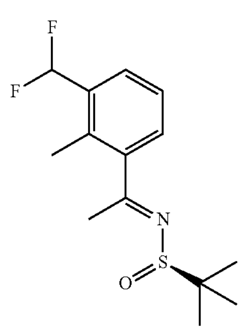 [SMILES: C/C(=N\[S@](=O)C(C)(C)C)c1cccc(C(F)F)c1C] | 1.896 | 288 | GVK_LCMS_22 |

TABLE 12-continued
| # | structure | $t_{ret}$ [min] | [M + H]$^+$ | HPLC method |
|---|---|---|---|---|
| B-3c | 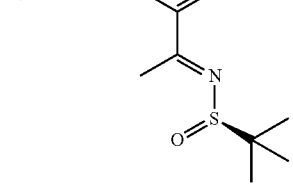 | 1.898 | 344 | GVK_LCMS_18 |
| B-3d | 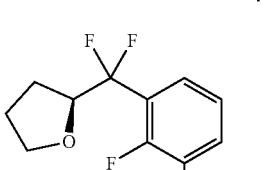 | 1.897 | 362 | GVK_LCMS_34 |
| B-3e | 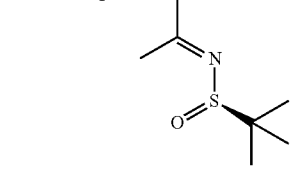 | 1.916 | 362 | GVK_LCMS_34 |
| B-3f | 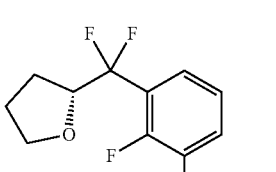 | 1.750 | 350 | GVK_LCMS_18 |
| B-3g | 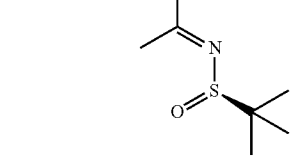 | 1.877 | 300 | GVK_LCMS_18 |

TABLE 12-continued

| # | structure | $t_{ret}$ [min] | [M + H]$^+$ | HPLC method |
|---|---|---|---|---|
| B-3h | 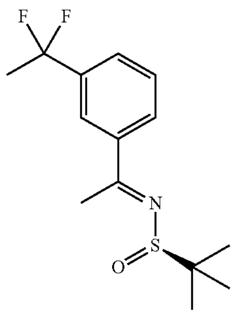 [SMILES: C/C(=N\[S@](=O)C(C)(C)C)c1cccc(C(C)(F)F)c1] | n.a. | n.a. | — |
| B-3i | 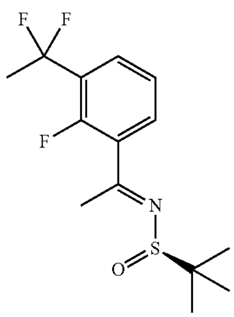 [SMILES: C/C(=N\[S@](=O)C(C)(C)C)c1cccc(C(C)(F)F)c1F] | n.a. | n.a. | — |
| B-3j | 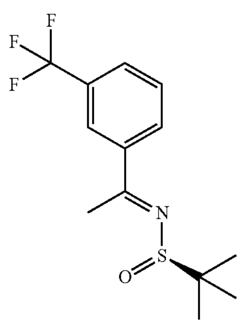 [SMILES: C/C(=N\[S@](=O)C(C)(C)C)c1cccc(C(F)(F)F)c1] | 2.036 | 292 | GVK_LCMS_22 |
| B-3k | 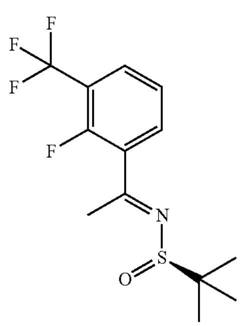 [SMILES: C/C(=N\[S@](=O)C(C)(C)C)c1cccc(C(F)(F)F)c1F] | 2.32 | 310 | GVK_LCMS_34 |
| B-3l | 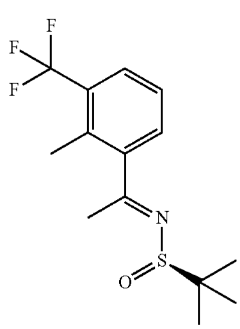 [SMILES: C/C(=N\[S@](=O)C(C)(C)C)c1cccc(C(F)(F)F)c1C] | 1.502 | 306 | GVK_LCMS_21 |

TABLE 12-continued

| # | structure | $t_{ret}$ [min] | $[M + H]^+$ | HPLC method |
|---|---|---|---|---|
| B-3m | ![structure] | n.a. | n.a. | — |
| D-11a | ![structure] | 1.926 | 364 | GVK_LCMS_18 |

Synthesis of Intermediates B-4

Experimental Procedure for the Synthesis of B-4a

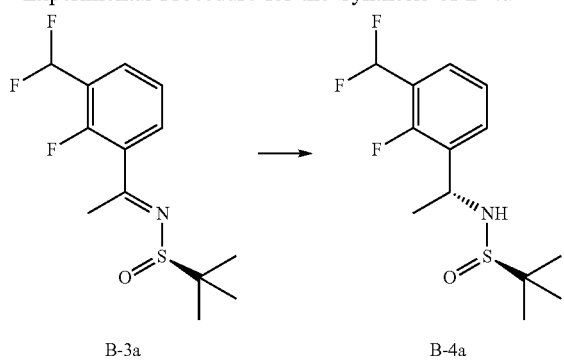

B-3a → B-4a

A solution of B-3a (170.00 g, 583.53 mmol; 1.0 equiv.) is dissolved in THF (1.7 L) and cooled to 0° C. Sodium borohydride (21.59 g; 583.51 mmol; 1.0 equiv.) is added and the resulting reaction mixture stirred at room temperature for 6 h. After complete conversion of the starting material, ice water and EtOAc are added and the aqueous layer is extracted with EtOAc. The organic layers are combined, dried over $Na_2SO_4$ and concentrated under reduced pressure. The crude product is purified by chromatography (gradient elution: 33% ethyl acetate in petroleum ether) yielding the desired product B-4a.

The following intermediates B-4 (table 13) are available in an analogous manner starting from different sulfinamides B-3. The crude product B-4 is purified by chromatography if necessary.

TABLE 13

| # | structure | $t_{ret}$ [min] | $[M + H]^+$ | HPLC method |
|---|---|---|---|---|
| B-4a | ![structure] | 1.763 | 294 | GVK_LCMS_18 |

TABLE 13-continued

| # | structure | t_ret [min] | [M + H]+ | HPLC method |
|---|---|---|---|---|
| B-4b | 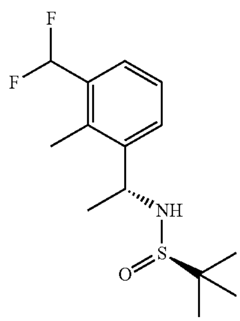 [SMILES: Cc1c(C(F)F)cccc1[C@@H](C)N[S@](=O)C(C)(C)C] | n.a. | n.a. | — |
| B-4c | 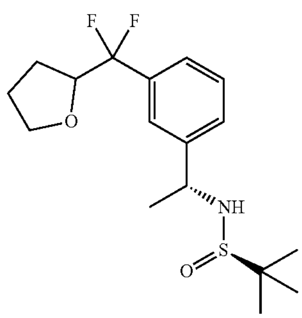 [SMILES: C[C@@H](N[S@](=O)C(C)(C)C)c1cccc(C(F)(F)C2CCCO2)c1] | 1.841 | 346 | GVK_LCMS_18 |
| B-4d | 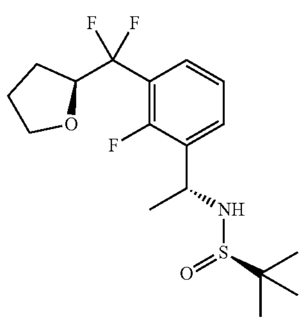 [SMILES: C[C@@H](N[S@](=O)C(C)(C)C)c1cccc(C(F)(F)[C@@H]2CCCO2)c1F] | 1.854 | 364 | GVK_LCMS_18 |
| B-4e | 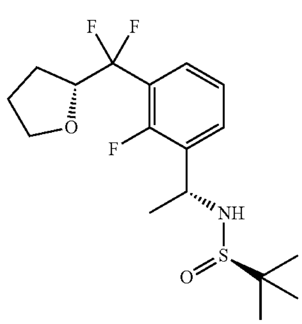 [SMILES: C[C@@H](N[S@](=O)C(C)(C)C)c1cccc(C(F)(F)[C@H]2CCCO2)c1F] | 1.86 | 364 | GVK_LCMS_34 |
| B-4f | 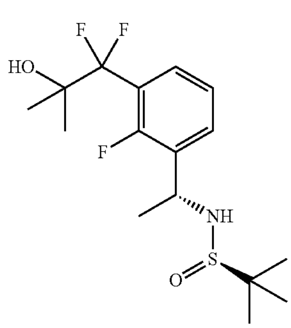 [SMILES: C[C@@H](N[S@](=O)C(C)(C)C)c1cccc(C(F)(F)C(C)(C)O)c1F] | 2.1 | 352 | GVK_LCMS_35 |

TABLE 13-continued

| # | structure | $t_{ret}$ [min] | [M + H]$^+$ | HPLC method |
|---|---|---|---|---|
| B-4g | 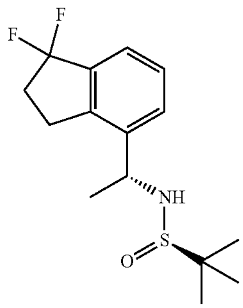 [SMILES: C[C@@H](N[S@](=O)C(C)(C)C)c1cccc2c1CCC2(F)F] | 1.842 | 302 | GVK_LCMS_18 |
| B-4h | 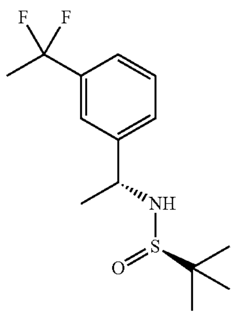 [SMILES: C[C@@H](N[S@](=O)C(C)(C)C)c1cccc(C(C)(F)F)c1] | n.a. | n.a. | — |
| B-4i | 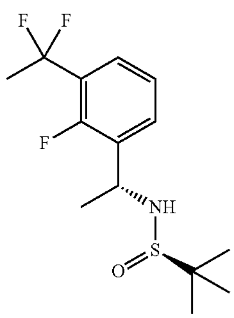 | 1.85 | 364 | GVK_LCMS_34 |
| B-4j | 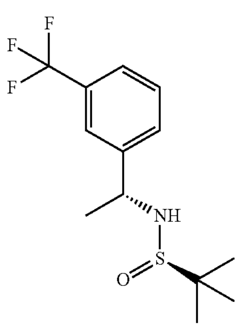 [SMILES: C[C@@H](N[S@](=O)C(C)(C)C)c1cccc(C(F)(F)F)c1] | 1.77 | 294 | GVK_LCMS_34 |
| B-4k | 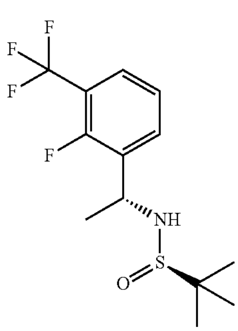 [SMILES: C[C@@H](N[S@](=O)C(C)(C)C)c1cccc(C(F)(F)F)c1F] | 2.27 | 312 | GVK_LCMS_35 |

TABLE 13-continued

| # | structure | $t_{ret}$ [min] | [M + H]+ | HPLC method |
|---|---|---|---|---|
| B-4l | 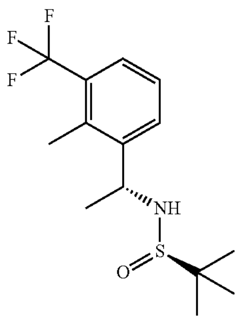 [SMILES: Cc1c([C@@H](C)N[S@](=O)C(C)(C)C)cccc1C(F)(F)F] | 1.48 | 308 | GVK_LCMS_21 |
| B-4m | 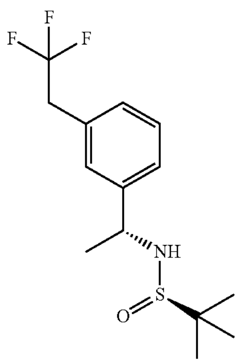 [SMILES: C[C@@H](N[S@](=O)C(C)(C)C)c1cccc(CC(F)(F)F)c1] | 1.99 | 3.08 | GVK_LCMS_41 |

Experimental Procedure for the Synthesis of B-4n

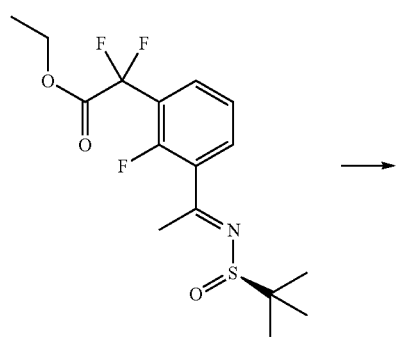

D-11a

A solution of D-11a (26.00 g, 71.55 mmol; 1.0 equiv.) is dissolved in THF (260 mL) and water (5 mL) cooled to −78° C. Sodium borohydride (8.156 g; 214.63 mmol; 3.0 equiv.) is added and the resulting reaction mixture is warmed to room temperature and stirred for 4 h. After complete conversion of the starting material, ice water and EtOAc are added and the aqueous layer is extracted with EtOAc. The organic layers are combined, dried over $Na_2SO_4$ and concentrated under reduced pressure. The crude product is purified by reversed phase chromatography yielding the desired product B-4n.

Experimental Procedure for the Synthesis of B-4o

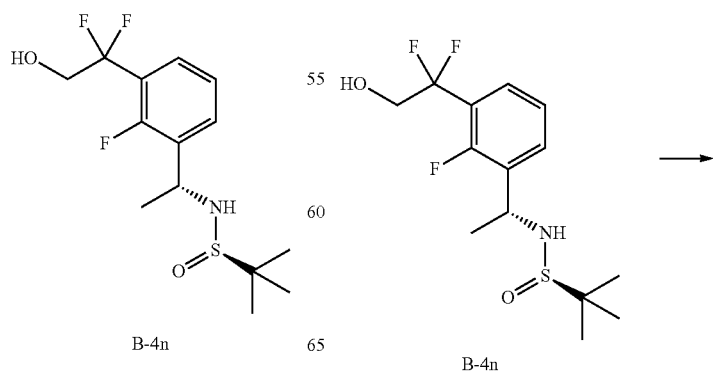

-continued

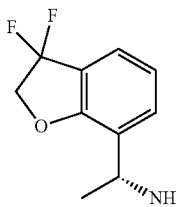

B-4o

To a stirred solution of B-4n (5.00 g, 15.46 mmol, 1.0 equiv.) in THF (50 mL) are added cesium carbonate (15.12 g, 46.38 mmol, 3.0 equiv.) and 18-crown-6 (2.04 g, 7.73 mmol, 0.5 equiv.) at rt. The resulting mixture is heated to 80° C. for 16 h. After complete conversion of the starting material, water and EtOAc are added and the aqueous layer is extracted with EtOAc. The organic layers are combined, dried over Na$_2$SO$_4$ and concentrated under reduced pressure. The crude product is purified by flash column chromatography (80% EtOAc in hexane) and reverse phase chromatography to yield the desired product B-4o.

Experimental Procedure for the Synthesis of B-4p

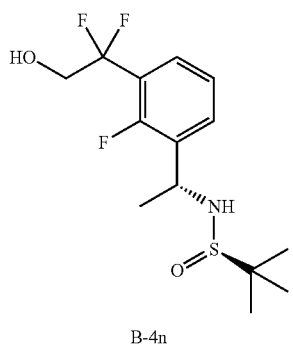

B-4n

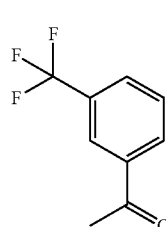

B-4p

To a stirred solution of B-4n (1.00 g, 3.09 mmol, 1.0 equiv.) in THF (10 mL) is added potassium tert-butoxide (0.52 g, 4.64 mmol, 1.5 equiv.) and 18-crown-6 (2.04 g, 7.73 mmol, 0.5 equiv.) at rt. The resulting mixture is warmed to 80° C. for 16 h. After complete conversion of the starting material, water and EtOAc are added and the aqueous layer is extracted with EtOAc. The organic layers are combined, dried over Na$_2$SO$_4$ and concentrated under reduced pressure. The crude product is purified by HPLC to yield the desired product B-4p.

Synthesis of Intermediates B-6

Experimental Procedure for the Synthesis of B-6a

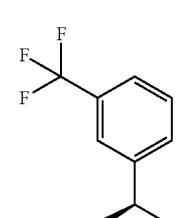

B-2n → B-6a

Acetophenone B-2n (5.00 g, 24.3 mmol, 1.0 equiv.) is dissolved in toluene (15 mL) and 2-methyltetrahydrofurane (5.0 mL). Sodium tert-amylate (281 µL, 50% in toluene, 1.21 mmol, 5 mol %) is added and the reaction mixture is purged with Ar atmosphere. (R)-RUCY-Xyl-BINAP (58.0 mg, 49.0 µmol, 0.2 mol %) is added to the reaction mixture. The reaction mixture is charged with hydrogen atmosphere (3 bar) and stirred at room temperature for 19 h until complete conversion of B-2n is achieved. The reaction is diluted with EtOAc (50 mL) and washed with water (1×50 mL), aqueous HCl (1×10 mL, 1.0 M) and water (1×50 mL). The organic layer is dried over Na$_2$SO$_4$, filtered and concentrated in vacuo to furnish the desired product.

The following intermediates B-6 (table 14) are available in an analogues manner starting from different acetophenones B-2. The crude product is purified by chromatography if necessary.

TABLE 14

| # | structure | $t_{ret}$ [min] | m/z | HPLC method |
|---|---|---|---|---|
| B-6a | ![structure] | 1.283 | [M + H]$^+$: 191.1 | D_LC_SSTD |
| B-6b | ![structure] | 1.254 | [M]$^+$: 204.2 | D_LC_SSTD |

TABLE 14-continued

| # | structure | $t_{ret}$ [min] | m/z | HPLC method |
|---|---|---|---|---|
| B-6c | (3-(difluoromethyl)-2-fluorophenyl with CF added, ethanol) | 1.281 | [M]$^+$: 208.2 | D_LC_SSTD |
| B-6d | (3-(difluoromethyl)-2-methylphenyl ethanol with F) | 1.095 | [M − H]$^−$: 203.1 | D_LC_SSTD |

Synthesis of Intermediates B-5
Experimental Procedure for the Synthesis of B-5a

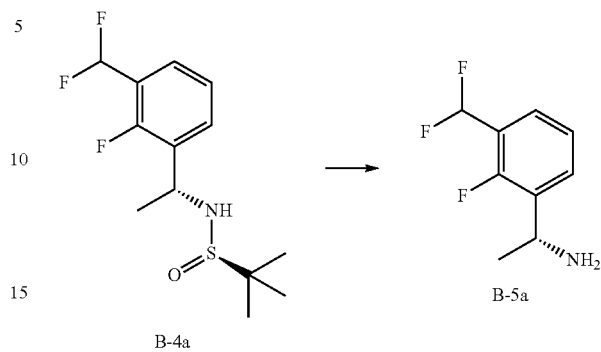

B-4a → B-5a

A solution of B-4a (13.20 g, 45.00 mmol; 1.0 equiv.) in 1,4-dioxane (100 mL) is cooled to 0° C. and treated with 4 N HCl in 1,4-dioxane (50.00 mL, 200.00 mmol, 4.4 equiv.). The reaction mixture is stirred for 3 h. After complete conversion of the starting material, the reaction mixture is concentrated under reduced pressure, the precipitate filtered and washed with diethyl ether to obtain the desired product B-5a as HCl salt.

The following benzyl amines B-5 (table 15) are available in an analogous manner starting from different sulfinamides B-4. The crude product B-5 is purified by chromatography if necessary and isolated as HCl salt.

TABLE 15

| # | structure | $t_{ret}$ [min] | [M + H]$^+$ | HPLC method |
|---|---|---|---|---|
| B-5a | 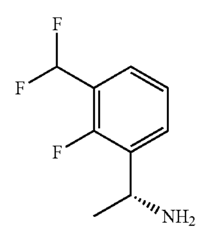 | 1.18 | 190 | GVK_LCMS_34 |
| B-5b | 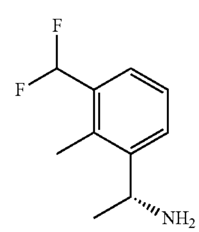 | 1.33 | 186 | GVK_LCMS_22 |
| B-5c | 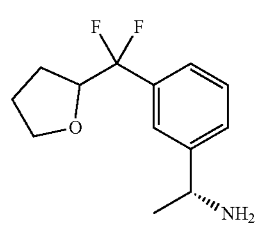 [SMILES: C[C@@H](N)c1cccc(C(F)(F)C2CCCO2)c1] | 1.12 | 242 | GVK_LCMS_31 |

TABLE 15-continued

| # | structure | $t_{ret}$ [min] | [M + H]$^+$ | HPLC method |
|---|---|---|---|---|
| B-5d | 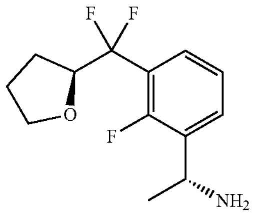 [SMILES: C[C@@H](N)c1cccc(C(F)(F)[C@@H]2CCCO2)c1F] | 1.396 | 260 | GVK_LCMS_31 |
| B-5e | 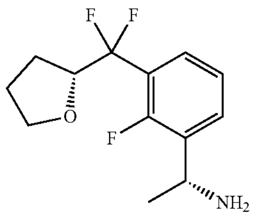 [SMILES: C[C@@H](N)c1cccc(C(F)(F)[C@H]2CCCO2)c1F] | 1.381 | 260 | GVK_LCMS_31 |
| B-5f | 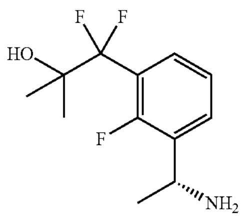 [SMILES: C[C@@H](N)c1cccc(C(F)(F)C(C)(C)O)c1F] | 1.63 | 248 | GVK_LCMS_02 |
| B-5g | 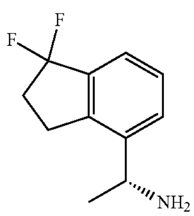 | 1.31 | 198 | GVK_LCMS_31 |
| B-5h | 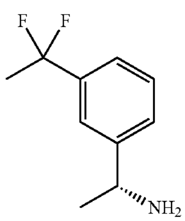 | 1.22 | 186 | GVK_LCMS_31 |
| B-5i | 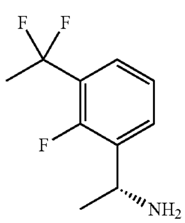 | 1.355 | 204 | GVK_LCMS_31 |
| B-5j | 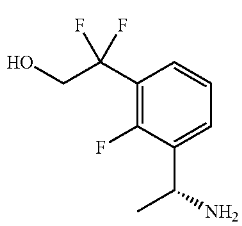 | 1.11 | 220 | GVK_LCMS_31 |

TABLE 15-continued

| # | structure | t_ret [min] | [M + H]+ | HPLC method |
|---|---|---|---|---|
| B-5k | 3-(trifluoromethyl)phenyl-CH(NH₂)CH₃ | 1.370 | 190 | GVK_LCMS_31 |
| B-5l | 2-fluoro-3-(trifluoromethyl)phenyl-CH(NH₂)CH₃ | 1.48 | 208 | GVK_LCMS_35 |
| B-5m | 2-methyl-3-(trifluoromethyl)phenyl-CH(NH₂)CH₃ | 0.963 | 204 | GVK_LCMS_21 |
| B-5n | 3-(2,2,2-trifluoroethyl)phenyl-CH(NH₂)CH₃ | 1.49 | 204 | GVK_LCMS_41 |
| B-5o | 3,3-difluoro-2,3-dihydrobenzofuran-7-yl-CH(NH₂)CH₃ | 1.592 | 200 | GVK_LCMS_19 |
| B-5p | 3-fluorobenzofuran-7-yl-CH(NH₂)CH₃ | 1.609 | 180 | GVK_LCMS_19 |

Experimental Procedure for the Synthesis of B-5k (Alternative)

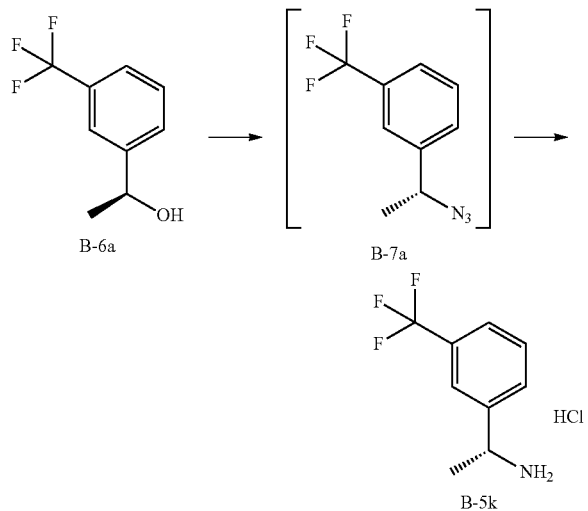

Alcohol B-6a (2.00 g, 9.61 mmol, 1.0 equiv.) is dissolved in anhydrous toluene (20 mL). Diazabicycloundecene (1.73 mL, 11.5 mmol, 1.2 equiv.) and diphenylphosphonic azide (2.28 mL, 10.6 mmol, 1.1 equiv.) are added subsequently. The reaction mixture is stirred at 40° C. for 18 h until complete conversion of B-6a is achieved. The reaction mixture is cooled to room temperature and the organic layer is washed with aqueous $Na_2CO_3$ solution (2×10 mL). Azide B-7a thus obtained is not isolated but directly converted in the next step. Pd/C (200 mg, 10% w/w, 10% Pd) is added to the organic layer. The reaction mixture is charged with a $H_2$ atmosphere (10 bar) and is stirred for 24 h until complete conversion of B-7a is achieved. The reaction is filtered and the volatiles are removed in vacuo. The residue is dissolved in methyl tert-butyl ether (30 mL) and treated with HCl in dioxane (4.8 mL, 4 M). The white precipitate is filter, washed with methyl tert-butyl ether (20 mL) and further dried in vacuo to furnish the desired product B-5k. The crude product is purified by chromatography if necessary.

The following intermediates B-5 (table 16) are available in an analogues manner starting from different alcohols B-6 via azides B-7.

TABLE 16

| # | structure | $t_{ret}$ [min] | $[M + H]^+$ | HPLC method |
|---|---|---|---|---|
| B-7a | | n.a. | n.a. | n.a. |
| B-7b | | n.a. | n.a. | n.a. |
| B-7c | 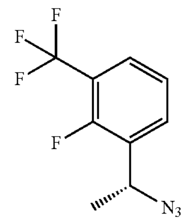 | n.a. | n.a. | n.a. |
| B-7d | 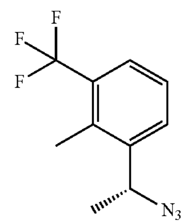 | n.a. | n.a. | n.a. |
| B-5k | 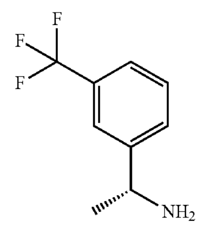 | 1.290 | 190.0 | D_LC_BSTD |
| B-5i | 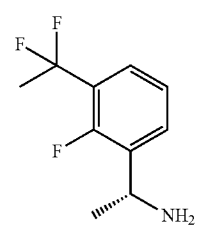 | 1.294 | 204.0 | D_LC_BSTD |
| B-5l | 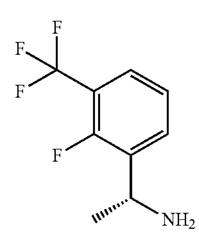 | 1.311 | 208.0 | D_LC_BSTD |
| B-5m | 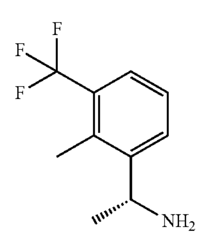 | 0.829 | 204.2 | D_LC_SSTD |

Synthesis of Intermediates C-1
Experimental Procedure for the Synthesis of D-13a

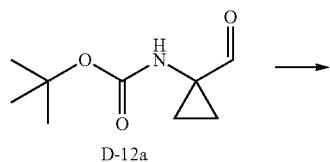

D-12a

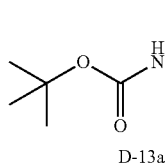

D-13a

To a stirred solution of D-12a (6.50 g, 35.093 mmol, 1.0 equiv.) in DCM (100 mL) is added diethylaminosulfur trifluoride (8.48 g, 52.67 mmol, 1.5 equiv) dropwise at 0° C. The reaction mixture is slowly warmed to room temperature and stirred for 16 h. After complete conversion of the starting material, a saturated aqueous NaHCO₃ solution is added. The aqueous layer is extracted with DCM, the organic layers are combined, dried over Na₂SO₄ and concentrated under reduced pressure. The crude product is purified by chromatography on silica gel (gradient elution: 0% to 12% ethyl acetate in petroleum ether) yielding the desired product D-13a.

Experimental Procedure for the Synthesis of C-1a

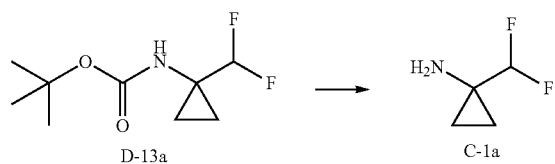

To a stirred solution of D-13a (2.40 g, 11.582 mmol, 1.0 equiv.) in 1,4-dioxane (5.0 mL) is added 4 N HCl in 1,4-dioxane (10 mL, 40.00 mmol, 3.5 equiv) at 0° C. The reaction mixture is warmed to room temperature and stirred for 16 h. After complete conversion of the starting material the reaction mixture is concentrated under reduced pressure. N-Pentane is added to the crude product. The solid material is filtered and washed with n-pentane to yield the desired product C-1a as HCl salt.

Experimental Procedure for the Synthesis of D-15a:

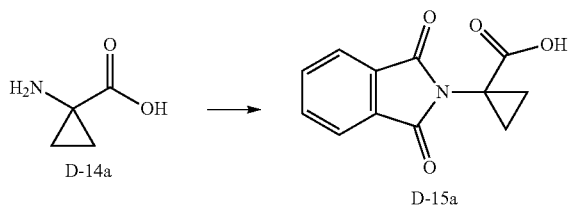 [SMILES: NC1(C(=O)O)CC1 ; O=C1c2ccccc2C(=O)N1C1(C(=O)O)CC1]

Amino acid D-14a (2.00 g, 19.7 mmol, 1.0 equiv.) and phthalic anhydride (2.92 g, 19.7 mmol, 1.0 equiv.) are suspended in acetic acid (20 mL). The reaction mixture is set to reflux and the obtained solution is stirred at this temperature for 3 h. The reaction mixture is cooled to 0° C. while the product D-15a crystallizes. Water (20 mL) is added and the reaction mixture is stirred at this temperature for 1 h. The precipitate is filtered, washed with water and further dried in vacuo to furnish the desired product. The crude product is further purified by chromatography if necessary ($t_{ret}$=1.03 min; [M−H]⁺=230.0; HPLC method D_LC_SSTD).

Experimental Procedure for the Synthesis of D-16a:

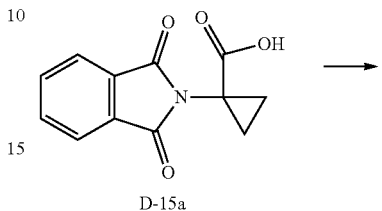

D-15a

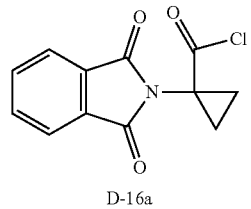

D-16a

Acid D-15a (2.00 g, 8.6 mmol, 1.0 equiv.) is suspended in toluene (10 mL) and N,N-dimethylformamide (0.1 mL). Thionyl chloride (1.08 g, 9.1 mmol, 1.05 equiv.) is added at room temperature, then the reaction mixture is set to reflux and the obtained solution is stirred at this temperature for 3 h until complete conversion of D-15a is achieved (quench with benzylamine). The reaction mixture is cooled to room temperature while the product D-16a crystallizes. Heptane (10 mL) is added and the reaction mixture is cooled further to 5° C. and stirred at this temperature for 1 h. The precipitate is filtered, washed with water and further dried in vacuo to furnish the desired product. The crude product is further purified by chromatography if necessary ($t_{ret}$=1.27 min; [M+H]⁺=246/247/248; HPLC method D_LC_SSTD as benzylamide after quench with benzylamine; ¹H NMR (400 MHz, CDCl₃) b ppm 1.70-1.85 (m, 2H), 2.10-2.31 (m, 2H), 7.64-8.11 (m, 4H).

Experimental Procedure for the Synthesis of D-17a:

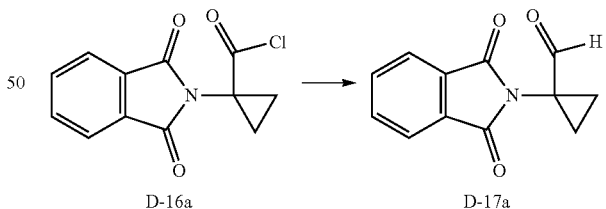

Acyl chloride D-16a (2.00 g, 8.0 mmol, 1.0 equiv.) and 10% Pd/C (dry, 100 mg, 5% w/w) are suspended in tetrahydrofurane (12 mL) and 2,6-lutidine (1.03 g, 9.6 mmol, 1.2 equiv.). The reaction mixture is hydrogenated at 3 bar and 30° C. After 20 h additional catalyst is added (25 mg) and the hydrogenation is continued for additional 24 h. After this time the reaction mixture is filtered and the filtrate is evaporated. The residual is partitioned between toluene and an aqueous solution of NaHCO₃. The organic phase is separated and washed again with the NaHCO₃ solution and finally with a citric acid solution. The organic layer is dried (Na₂SO₄) and concentrated under reduced pressure. The crude product is further purified by chromatography if necessary ($t_{ret}$=1.26 min; [M+H]⁺=216; HPLC method D_LC_BSTD).

Experimental Procedure for the Synthesis of D-18a:

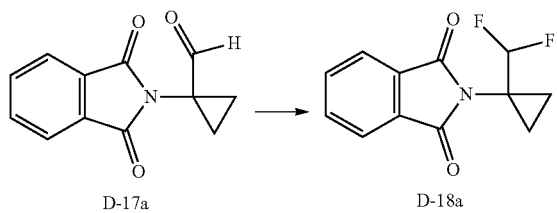 [SMILES: O=CC1(N2C(=O)c3ccccc3C2=O)CC1 ; O=C1c2ccccc2C(=O)N1C1(C(F)F)CC1]

D-17a    D-18a

Aldehyde D-17a (2.00 g, 9.3 mmol, 1.0 equiv.) is dissolved in dichloromethane (12 mL) and a 50% toluene solution of bis(2-methoxyethyl)aminosulfur trifluoride (9.90 g, 22.3 mmol, 2.4 equiv.) is added slowly at room temperature. After two days of stirring the reaction mixture is cautiously treated with an aqueous solution of NaHCO₃ and with additional dichloromethane (15 mL). The organic layer is dried (Na₂SO₄) and concentrated under reduced pressure. The crude product D-18a is further purified by chromatography or crystallization if necessary ($t_{ret}$=1.24 min; [M+H]⁺=238; HPLC method D_LC_SSTD). (Potential alternative fluorinating agents to be used for the conversion of D-17a are for example (diethylamino)difluorosulfonium tetrafluoroborate and sulfur tetrafluoride)

Experimental Procedure for the Synthesis of C-1a:

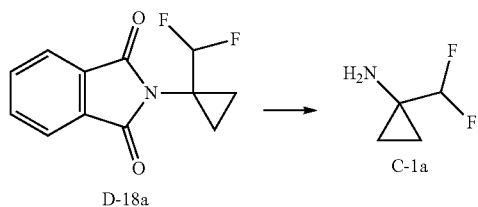 [SMILES: O=C1c2ccccc2C(=O)N1C1(C(F)F)CC1 ; NC1(C(F)F)CC1]

D-18a    C-1a

Imide D-18a (15.0 g, 63.2 mmol, 1.0 equiv.) is suspended in N-(2-hydroxyethyl)ethylendiamine (45 mL) and the mixture heated to 80° C. After 2 h at this temperature the reaction mixture is cooled to 40° C. and methanol (30 mL) is added. The mixture is heated again to 80° C. and product C-1a is distilled off at 60-70° C. and atmospheric pressure as a methanol solution. The addition of methanol and the distillation step is repeated twice. The product C-1a can be directly used in the next step as a methanol solution (¹H NMR (400 MHz, DMSO-d₆) δ (ppm)=0.44-0.81 (m, 4H), 5.64 (t, J=57.1 Hz, 1H). Methanol protons at b (ppm)=3.18 (d, 3H), 4.08 (q, 1H) not reported). Experimental procedure for the synthesis of D-20a

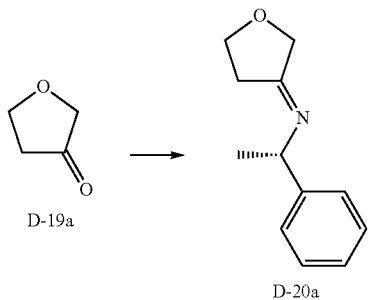

D-19a

D-20a

To a stirred solution of D-19a (5.00 g, 58.08 mmol, 1.0 equiv.) in DCM (50 mL) are added (S)-(−)-1-phenylethylamine (6.21 g, 58.08 mmol, 1.0 equiv) and magnesium sulfate (13.94 g, 116.16 mmol, 2.0 equiv.). The reaction mixture is stirred at room temperature for 16 h. After complete conversion of the starting material, insolubles are removed by filtration and the filtrate concentrated under reduced pressure. The crude product D-20a is used without further purification in the next step.

Experimental Procedure for the Synthesis of D-21a and D-21b

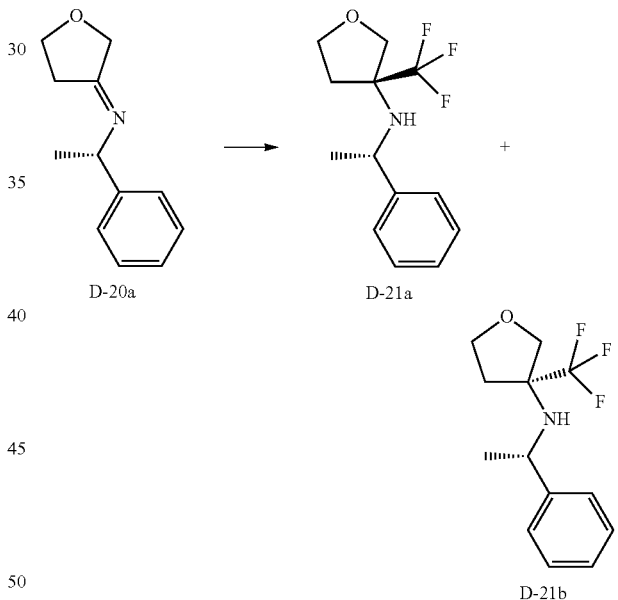

D-20a    D-21a

D-21b

To a stirred solution of D-20a (8.00 g, 42.27 mmol, 1.0 equiv.) in acetonitrile (80 mL) and DMF (8 mL) are added potassium hydrogen fluoride (2.64 g, 33.85 mmol, 0.8 equiv) and trifluoroacetic acid (5.30 g, 46.49 mmol, 1.1 equiv) at 0° C. The reaction mixture is stirred for 10 min, then trimethyl-trifluoromethyl-silane (9.02 g, 63.43 mmol, 1.5 equiv.) is added and the resulting mixture warmed to room temperature and stirred for additional 16 h. After complete conversion of the starting material, water and ethyl acetate are added, the aqueous layer extracted with ethyl acetate and the combined organic layers washed with brine and dried over Na₂SO₄ and concentrated under reduced pressure. The crude product is purified by SFC yielding the desired products D-21a and D-21b.

Experimental Procedure for the Synthesis of C-1b

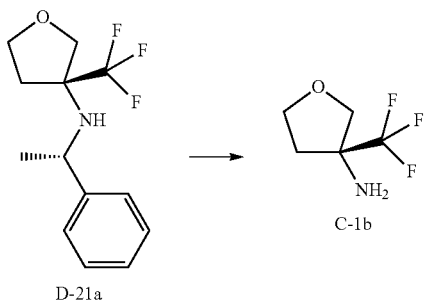 [SMILES: C[C@H](N[C@]1(C(F)(F)F)CCOC1)c1ccccc1 ; N[C@]1(C(F)(F)F)CCOC1]

D-21a (2.00 g, 7.714 mmol, 1.0 equiv.) is dissolved in 3 N HCl in methanol (6.00 mL, 18.00 mmol, 2.3 equiv.) and stirred for 5 min at room temperature. The solvent is removed under reduced pressure and the resulting solid material dissolved in methanol (20 mL). Palladium on alumina (10 wt-%, 200.00 mg, 0.188 mmol, 0.025 equiv.) is added and the resulting mixture is stirred for 16 h at room temperature. After complete conversion, insolubles are removed by filtration and the filtrate is concentrated under reduced pressure. Diethyl ether is added to the crude product. The solid material is filtered and washed with diethyl ether to yield the desired product C-1b as HCl salt.

The following amines C-1 (table 17) are available in an analogous manner starting from different intermediates D-21. The crude product C-1 is purified by chromatography if necessary and isolated as HCl salt.

TABLE 17

| # | structure | $t_{ret}$ [min] | $[M + H]^+$ | HPLC method |
|---|---|---|---|---|
| C-1b | 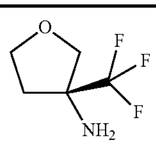 | n.a. | n.a. | — |
| C-1c | | n.a. | n.a. | — |

Experimental Procedure for the Synthesis of D-23a

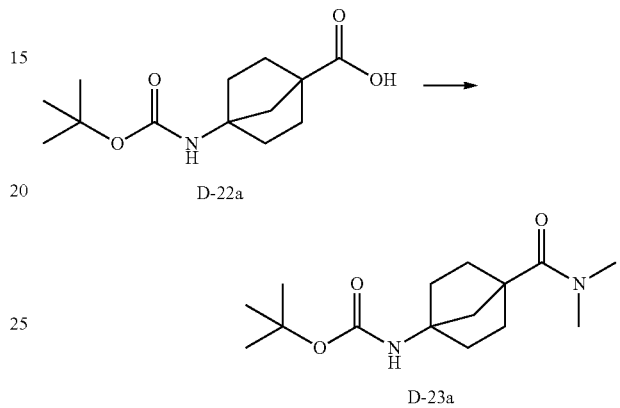

To a stirred solution of D-22a (330 mg, 1.293 mmol, 1.0 equiv.) in THF (1.0 mL) are added triethylamine (99%, 544 µL, 3.875 mmol, 3.0 equiv) and TBTU (518.8 g, 1.616 mmol, 1.3 equiv.). The reaction mixture is stirred at room temperature for 15 min, then dimethylamine hydrochloride (110.7 mg, 1.358 mmol, 1.1 equiv.) is added. The resulting mixture is stirred for additional 2 h. After complete conversion of the starting material, water and DCM are added and the aqueous layer is extracted with DCM. The organic layers are combined, dried over $MgSO_4$ and concentrated under reduced pressure. The crude product D-23a is used without further purification in the next step.

The following amides D-23 (table 18) are available in an analogous manner starting from different acids D-22. The crude product D-23 is purified by chromatography if necessary.

TABLE 18

| # | structure | $t_{ret}$ [min] | $[M + H]^+$ | HPLC method |
|---|---|---|---|---|
| D-23a | 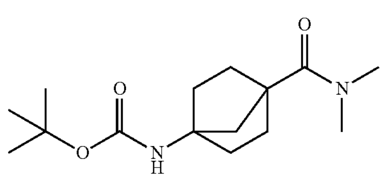 [SMILES: CN(C)C(=O)C12CCC(NC(=O)OC(C)(C)C)(CC1)C2] | 0.816 | 283 | VAB |
| D-23b | 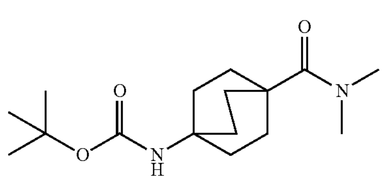 [SMILES: CN(C)C(=O)C12CCC(NC(=O)OC(C)(C)C)(CC1)CC2] | 0.853 | 297 | VAB |

Experimental Procedure for the Synthesis of C-1d

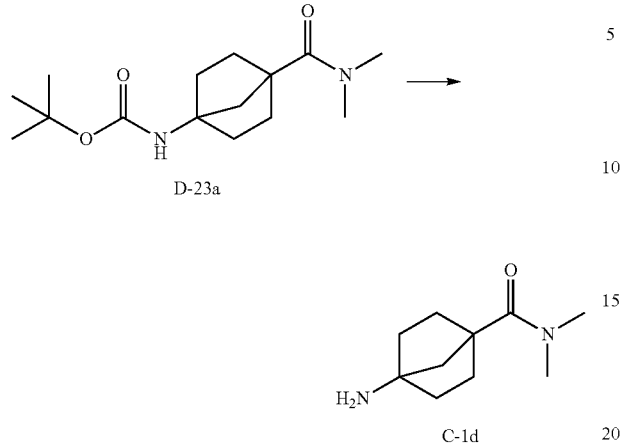

D-23a (360 mg, 1.275 mmol, 1.0 equiv.) is dissolved in DCM (5.0 mL) and treated with 4 N HCl in 1,4-dioxane (2.55 mL, 10.200 mmol, 8.0 equiv.). The reaction mixture is stirred for 18 h. After complete conversion of the starting material, the solvents are partially removed under reduced pressure. The solid material is filtered and dried to yield the desired product C-1d as HCl salt.

The following amides C-1 (table 19) are available in an analogous manner starting from different intermediates D-23. The crude product C-1 is purified by chromatography if necessary and isolated as HCl salt.

TABLE 19

| # | structure | $t_{ret}$ [min] | $[M + H]^+$ | HPLC method |
|---|---|---|---|---|
| C-1d | ![structure] | n.a. | n.a. | — |
| C-1e | ![structure] | n.a. | n.a. | — |

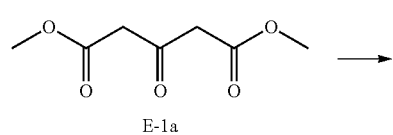

Synthesis of Intermediates E-3

Experimental Procedure for the Synthesis of E-3a:

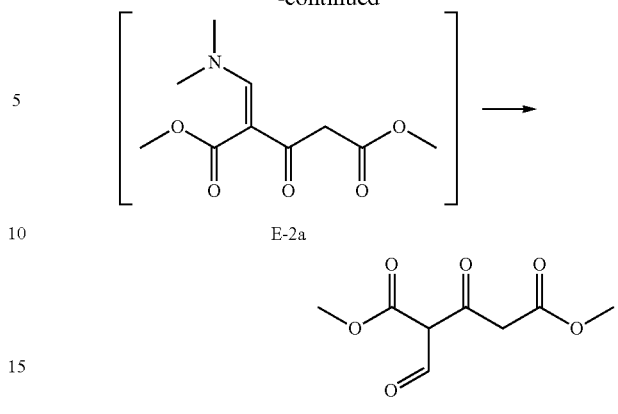

At 0° C. dimethyl 3-oxopentanedioate E-1a (10.0 g, 57.4 mmol, 1.0 equiv.) is combined with N,N-dimethylformamide dimethyl acetale (7.60 mL, 57.4 mmol, 1.0 equiv.) in 2-methyltetrahydrofurane (75 mL). After stirring 3 h at 0-4° C. the reaction mixture is warmed to room temperature and aqueous hydrochloric acid (4 N, 26 mL) is slowly added (intermediate E-2a is not isolated). After stirring 3 h at room temperature the organic layer is separated, washed with water and then brine and concentrated under reduced pressure. The crude product E-3a is further purified by distillation or chromatography if necessary ($t_{ret}$=0.99/1.04 min; $[M+H]^+$=203; HPLC method D_LC_SSTD).

Synthesis of Intermediates E-4

Experimental Procedure for the Synthesis of E-4a:

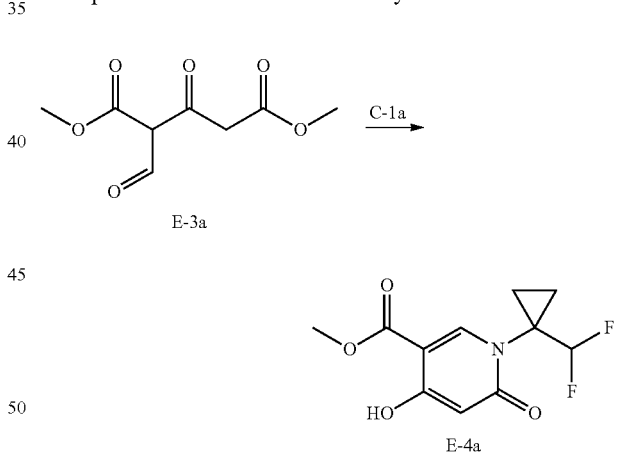

Dimethyl 2-formyl-3-oxopentanedioate E-3a (4.34 g, 21.5 mmol, 1.15 equiv.) and a methanol solution of the amine C-1a (2.00 g 18.7 mmol, 1.0 equiv. in 14.5 mL methanol) are combined in methanol (5.5 mL) at room temperature. After stirring overnight at this temperature NaOMe (3.8 mL, 21.5 mmol, 1.15 equiv. 30% w/w in methanol) is added, rinsing with additional methanol (2 mL). After stirring 2 h at room temperature water (24 mL) is slowly added followed by addition of conc. hydrochloric acid (4.7 mL). The precipitate is filtered, washed with water and further dried in vacuo to furnish the desired product. The crude product is purified by chromatography if necessary ($t_{ret}$=1.06 min; $[M-H]^+$=258; HPLC method D_LC_SSTD).

Synthesis of Intermediates E-5

Experimental Procedure for the Synthesis of E-5a:

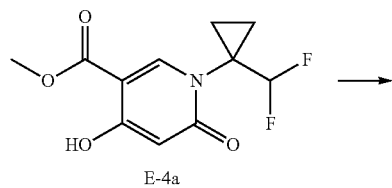

E-4a

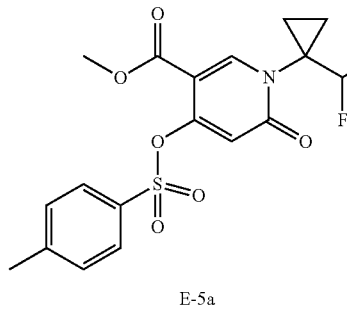

E-5a

4-Hydroxypyridinone E-4a (2.00 g, 7.7 mmol, 1.0 equiv.) is suspended in acetonitrile (16 mL). Triethylamine (1.61 mL, 11.6 mmol, 1.5 equiv.) is added at room temperature followed by p-toluenesulfonyl chloride (1.47 g, 7.7 mmol, 1.0 equiv.) in portions, rinsing with acetonitrile (4 mL). The reaction mixture is stirred at room temperature for 2 h until complete conversion is achieved then is concentrated at the rotavapor and treated with water (20 mL). After stirring 1 h at room temperature the precipitate is filtered, washed with water and further dried in vacuo to furnish the desired product. The crude product is purified by chromatography if necessary ($t_{ret}$=1.34 min; [M−H]⁺=414; HPLC method D_LC_SSTD).

Synthesis of Intermediates E-6

Experimental Procedure for the Synthesis of E-6a:

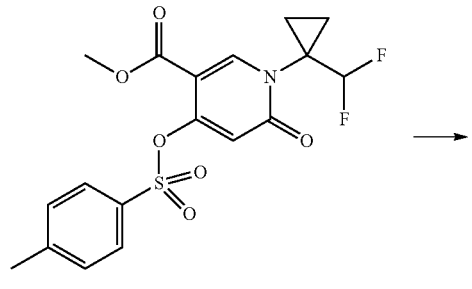

E-5a

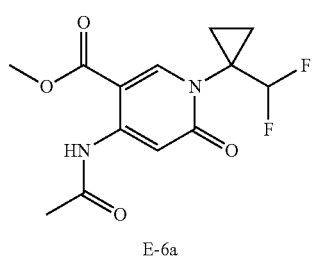

E-6a

Tosylate E-5a (4.00 g, 9.78 mmol, 1.0 equiv.), acetamide (686 mg, 11.6 mmol, 1.0 equiv.), $K_3PO_4$ (2.26 g, 10.6 mmol, 1.1 equiv.), palladium(π-cinnamyl) chloride dimer (75.2 mg, 145 μmol, 1.5 mol %) and Xantphos (168 mg, 290 μmol, 3.0 mol %) are suspended in dioxane (20 mL). The reaction mixture is purged with Ar atmosphere and stirred at reflux for 2 h until complete conversion is achieved. At 50° C. conc. HCl (36%, 83 μL, 968 mmol, 0.1 equiv.) and water (40 mL) is added. The reaction is further cooled and stirred at room temperature for 2 h. The precipitate is filtered, washed with water and further dried in vacuo to furnish the desired product. The crude product E-6a is purified by chromatography if necessary ($t_{ret}$=1.123 min; [M+H]⁺=301.0; HPLC method D_LC_SSTD).

Synthesis of Intermediates E-7

Experimental Procedure for the Synthesis of E-7a:

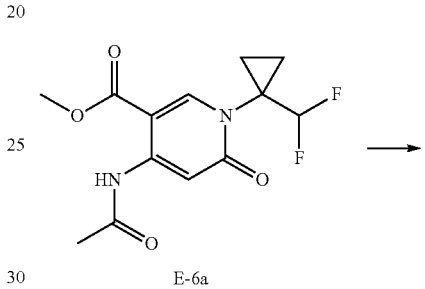

E-6a

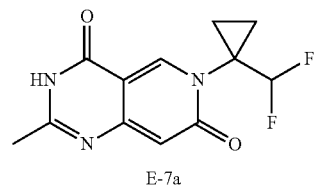

E-7a

Acetamide E-6a (2.50 g, 8.33 mmol, 1.0 equiv.) is suspended in methanolic $NH_3$ (7M, 20 mL) and stirred at room temperature for 5 days until complete conversion of E-6a is achieved. The solvent is removed in vacuo and the solid residue is dissolved in methanol (10 mL). Aqueous NaOH solution (1 M, 10 mL) is added to the reaction mixture and the reaction is stirred at 50° C. for 20 min. The reaction mixture is filtered, the residual solids are washed with methanol (5 mL) and the filtrate is neutralized using aqueous HCl (1 M, ca. 10 mL). The precipitate is filtered, washed with water and acetonitrile and further dried in vacuo to furnish the desired product. The crude product E-7a is purified by chromatography if necessary ($t_{ret}$=0.885 min; [M+H]⁺=268.0; HPLC method D_LC_SSTD). Synthesis of compounds (O) according to the invention

Experimental Procedure for the Synthesis of I-1

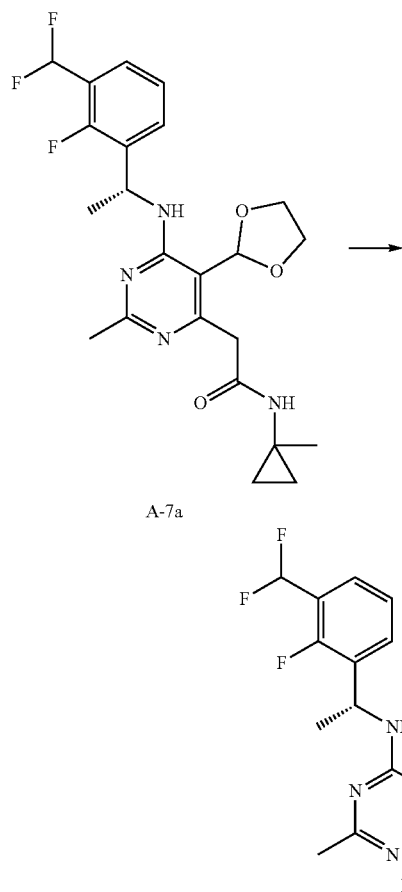

A-7a (272.0 mg, 0.586 mmol, 1.0 equiv.) is dissolved in 2-propanol (0.5 mL). An aqueous 5 N HCl solution (586 μL, 2.928 mmol, 5.0 equiv.) is added and the resulting mixture stirred for 1 hour at 50° C. until complete conversion of the starting material is observed. The reaction mixture is basified with aqueous ammonia, filtered and the filtrate purified by basic reversed phase chromatography (gradient elution: 20% to 60% acetonitrile in water) to furnish the desired product.

Experimental Procedure for the Synthesis of I-97

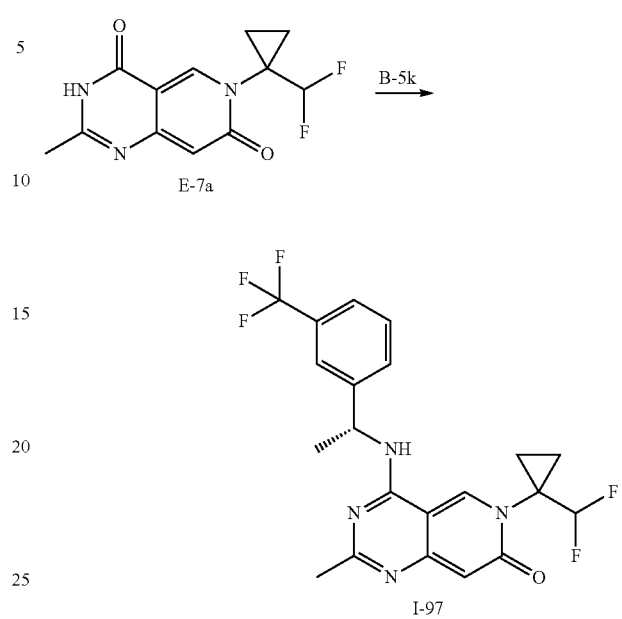

E-7a (1.00 g, 3.74 mmol, 1.0 equiv.) is suspended in MeCN (20 mL). $K_3PO_4$ (2.00 g, 9.42 mmol, 2.5 equiv.) and hexachlorocyclotriphosphazene (1.30 g, 3.74 mmol, 1.0 equiv.) is added and the reaction mixture is stirred at room temperature for 1 h. The phenethylamine hydrochloride B-5k (930 mg, 4.12 mmol, 1.1 equiv.) is added and the reaction mixture is stirred for further 1 h. Aqueous $NH_3$ solution (25%, 2.0 mL) and after 1 h a sat. $K_2CO_3$ solution (20 mL) are added. The biphasic reaction mixture is stirred at room temperature for 16 h and the organic layer is concentrated in vacuo. The crude product I-97 is purified by chromatography if necessary.

The following compounds I (table 20) are available in an analogous manner starting from different acetals A-7 or starting from different building blocks E-7 and B-5. The crude products are purified by chromatography if necessary.

TABLE 20

| # | structure | $t_{ret}$ [min], [M + H]$^+$ | HPLC method | $IC_{50}$ [nM] |
|---|---|---|---|---|
| I-1 | (structure) | 1.16 403 | LCMSBAS1 | 5 |

TABLE 20-continued

| # | structure | $t_{ret}$ [min], [M + H]$^+$ | HPLC method | IC$_{50}$ [nM] |
|---|---|---|---|---|
| I-2 | 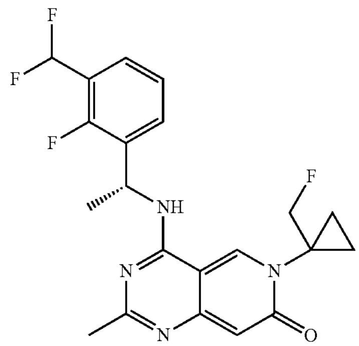 [SMILES: Cc1nc(N[C@H](C)c2cccc(C(F)F)c2F)c2cn(C3(CF)CC3)c(=O)cc2n1] | 1.16 421 | LCMSBAS1 | 4 |
| I-3 | 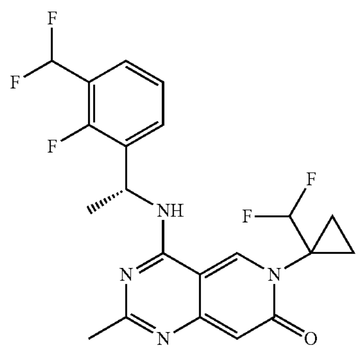 [SMILES: Cc1nc(N[C@H](C)c2cccc(C(F)F)c2F)c2cn(C3(C(F)F)CC3)c(=O)cc2n1] | 1.20 439 | LCMSBAS1 | 5 |
| I-4 | 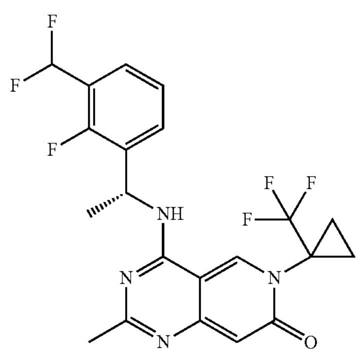 [SMILES: Cc1nc(N[C@H](C)c2cccc(C(F)F)c2F)c2cn(C3(C(F)(F)F)CC3)c(=O)cc2n1] | 1.22 457 | LCMSBAS1 | 8 |
| I-5 | 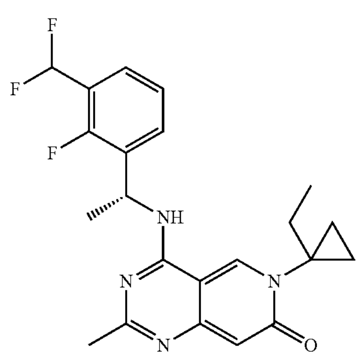 [SMILES: CCC1(n2cc3c(N[C@H](C)c4cccc(C(F)F)c4F)nc(C)nc3cc2=O)CC1] | 1.20 417 | LCMSBAS1 | 12 |

TABLE 20-continued

| # | structure | $t_{ret}$ [min], $[M + H]^+$ | HPLC method | $IC_{50}$ [nM] |
|---|---|---|---|---|
| I-6 | 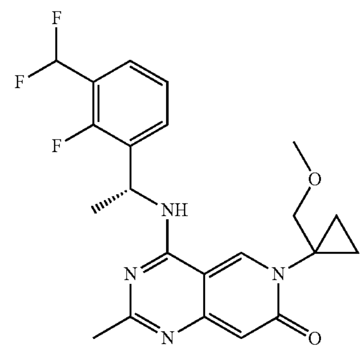 [SMILES: COCC1(n2cc3c(N[C@H](C)c4cccc(C(F)F)c4F)nc(C)nc3cc2=O)CC1] | 1.15 433 | LCMSBAS1 | 6 |
| I-7 | 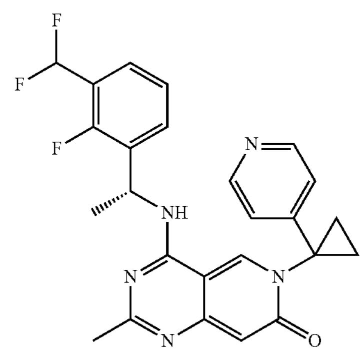 [SMILES: Cc1nc(N[C@H](C)c2cccc(C(F)F)c2F)c2cn(C3(c4ccncc4)CC3)c(=O)cc2n1] | 1.13 466 | LCMSBAS1 | 8 |
| I-8 | 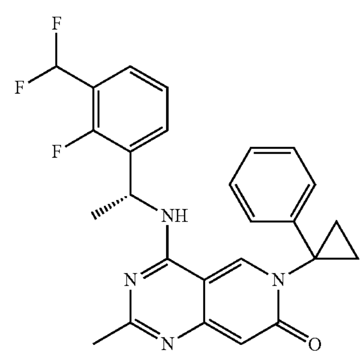 [SMILES: Cc1nc(N[C@H](C)c2cccc(C(F)F)c2F)c2cn(C3(c4ccccc4)CC3)c(=O)cc2n1] | 1.27 465 | LCMSBAS1 | 16 |
| I-9 | 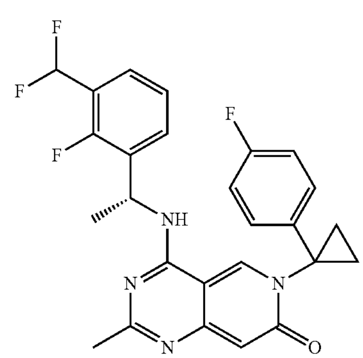 [SMILES: Cc1nc(N[C@H](C)c2cccc(C(F)F)c2F)c2cn(C3(c4ccc(F)cc4)CC3)c(=O)cc2n1] | 1.28 483 | LCMSBAS1 | 30 |

TABLE 20-continued

| # | structure | t_ret [min], [M + H]+ | HPLC method | IC50 [nM] |
|---|---|---|---|---|
| I-10 | 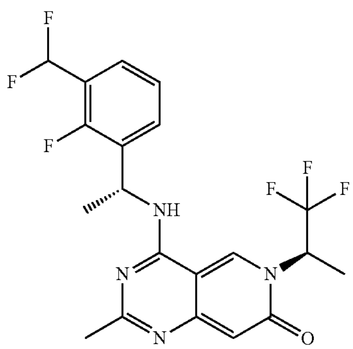 [SMILES: Cc1nc(N[C@H](C)c2cccc(C(F)F)c2F)c2cn([C@H](C)C(F)(F)F)c(=O)cc2n1] | 1.25 445 | LCMSBAS1 | 11 |
| I-11 | 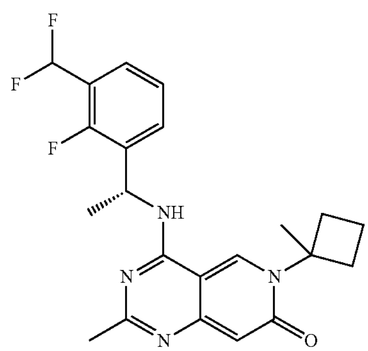 [SMILES: Cc1nc(N[C@H](C)c2cccc(C(F)F)c2F)c2cn(C3(C)CCC3)c(=O)cc2n1] | 1.22 417 | LCMSBAS1 | 5 |
| I-12 | 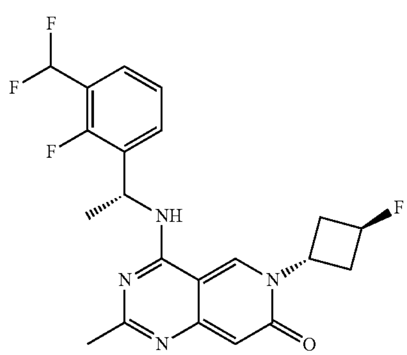 [SMILES: Cc1nc(N[C@H](C)c2cccc(C(F)F)c2F)c2cn([C@H]3C[C@H](F)C3)c(=O)cc2n1] | 1.16 421 | LCMSBAS1 | 7 |
| I-13 | 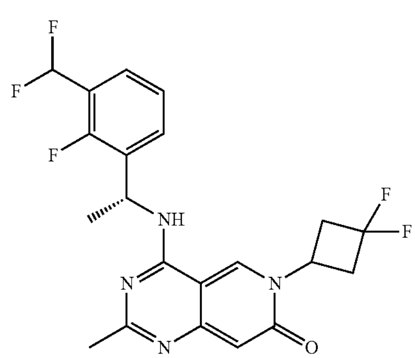 [SMILES: Cc1nc(N[C@H](C)c2cccc(C(F)F)c2F)c2cn(C3CC(F)(F)C3)c(=O)cc2n1] | 1.20 439 | LCMSBAS1 | 11 |

TABLE 20-continued

| # | structure | t_ret [min], [M + H]+ | HPLC method | IC_50 [nM] |
|---|-----------|----------------------|-------------|------------|
| I-14 | 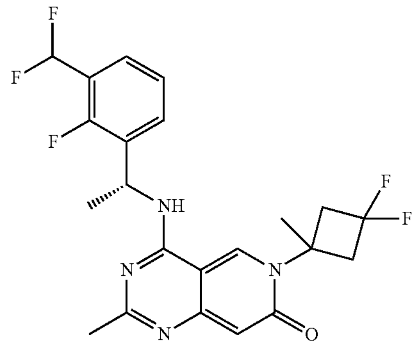 [SMILES: Cc1nc(N[C@H](C)c2cccc(C(F)F)c2F)c2cn(C3(C)CC(F)(F)C3)c(=O)cc2n1] | 1.24 453 | LCMSBAS1 | 21 |
| I-15 | 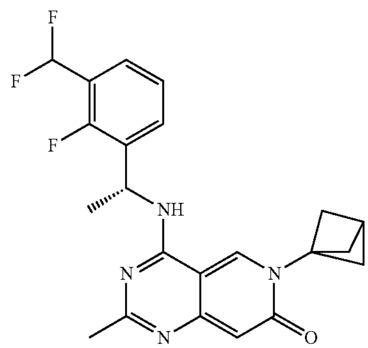 [SMILES: Cc1nc(N[C@H](C)c2cccc(C(F)F)c2F)c2cn(C34CC(C3)C4)c(=O)cc2n1] | 1.21 415 | LCMSBAS1 | 8 |
| I-16 | 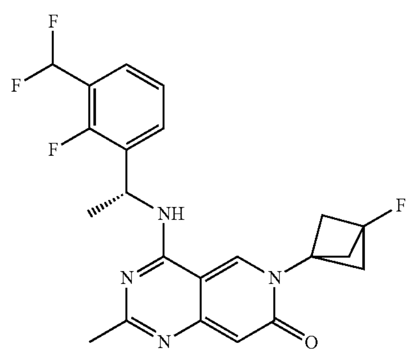 [SMILES: Cc1nc(N[C@H](C)c2cccc(C(F)F)c2F)c2cn(C34CC(F)(C3)C4)c(=O)cc2n1] | 1.22 433 | LCMSBAS1 | 12 |
| I-17 | 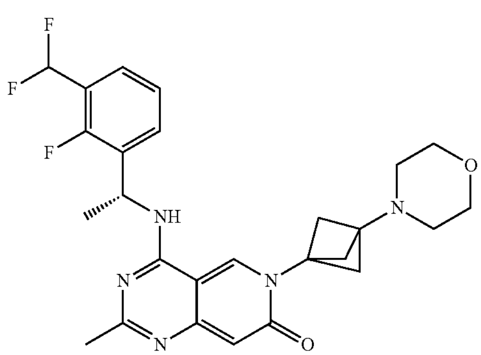 [SMILES: Cc1nc(N[C@H](C)c2cccc(C(F)F)c2F)c2cn(C34CC(N5CCOCC5)(C3)C4)c(=O)cc2n1] | 1.13 500 | LCMSBAS1 | 5 |

TABLE 20-continued

| # | structure | t_ret [min], [M + H]+ | HPLC method | IC_50 [nM] |
|---|---|---|---|---|
| I-18 | 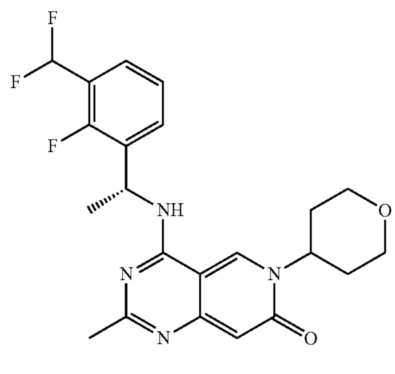 [SMILES: Cc1nc(N[C@H](C)c2cccc(C(F)F)c2F)c2cn(C3CCOCC3)c(=O)cc2n1] | 1.06 433 | LCMSBAS1 | 5 |
| I-19 | 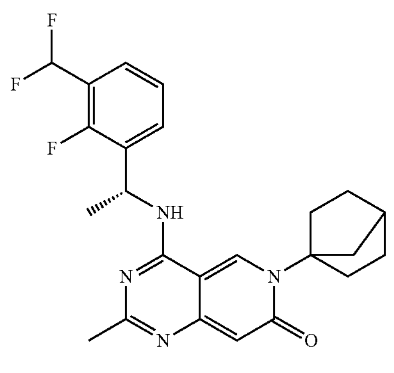 [SMILES: Cc1nc(N[C@H](C)c2cccc(C(F)F)c2F)c2cn(C34CCC(CC3)C4)c(=O)cc2n1] | 1.28 443 | LCMSBAS1 | 2 |
| I-20 | 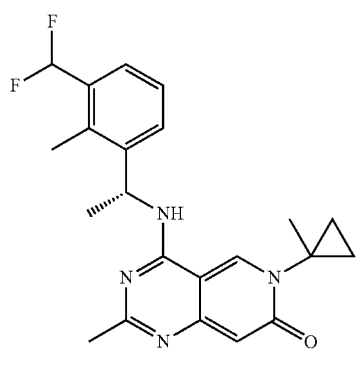 [SMILES: Cc1nc(N[C@H](C)c2cccc(C(F)F)c2C)c2cn(C3(C)CC3)c(=O)cc2n1] | 1.18 399 | LCMSBAS1 | 3 |
| I-21 | 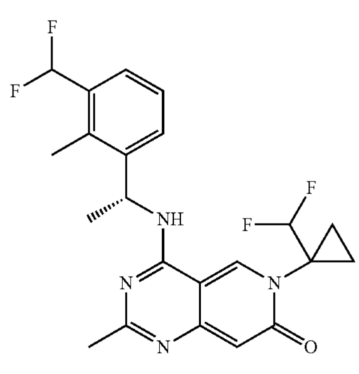 [SMILES: Cc1nc(N[C@H](C)c2cccc(C(F)F)c2C)c2cn(C3(C(F)F)CC3)c(=O)cc2n1] | 1.22 435 | LCMSBAS1 | 3 |

TABLE 20-continued

| # | structure | $t_{ret}$ [min], $[M+H]^+$ | HPLC method | IC$_{50}$ [nM] |
|---|---|---|---|---|
| I-22 | 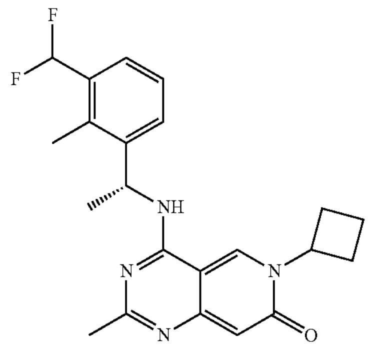 [SMILES: Cc1nc(N[C@H](C)c2cccc(C(F)F)c2C)c2cn(C3CCC3)c(=O)cc2n1] | 1.19  399 | LCMSBAS1 | 6 |
| I-23 | 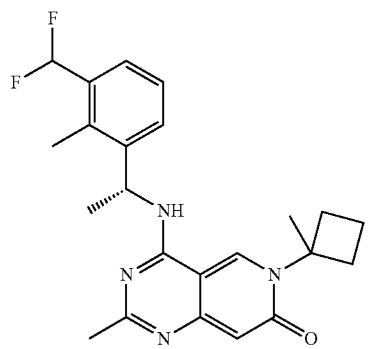 [SMILES: Cc1nc(N[C@H](C)c2cccc(C(F)F)c2C)c2cn(C3(C)CCC3)c(=O)cc2n1] | 1.23  413 | LCMSBAS1 | 4 |
| I-24 | 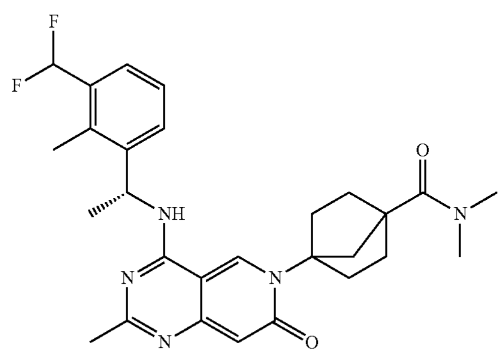 [SMILES: Cc1nc(N[C@H](C)c2cccc(C(F)F)c2C)c2cn(C34CCC(C(=O)N(C)C)(CC3)C4)c(=O)cc2n1] | 1.20  510 | LCMSBAS1 | 10 |
| I-25 | 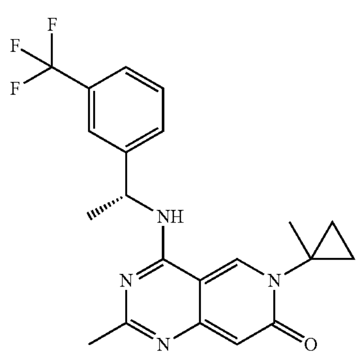 [SMILES: Cc1nc(N[C@H](C)c2cccc(C(F)(F)F)c2)c2cn(C3(C)CC3)c(=O)cc2n1] | 1.22  403 | LCMSBAS1 | 13 |

TABLE 20-continued

| # | structure | $t_{ret}$ [min], $[M + H]^+$ | HPLC method | $IC_{50}$ [nM] |
|---|---|---|---|---|
| I-26 | 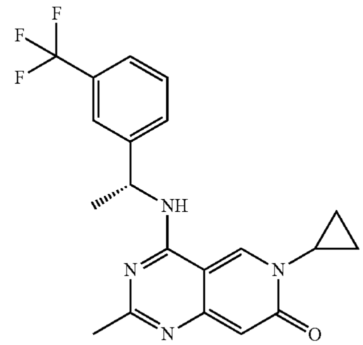 [SMILES: Cc1nc(N[C@H](C)c2cccc(C(F)(F)F)c2)c2cn(C3CC3)c(=O)cc2n1] | 1.13 389 | LCMSBAS1 | 37 |
| I-27 | 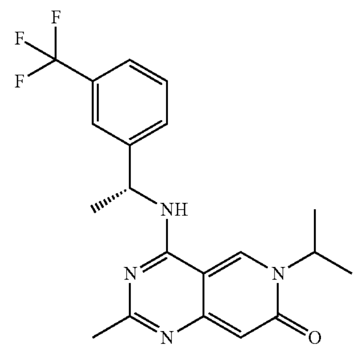 [SMILES: Cc1nc(N[C@H](C)c2cccc(C(F)(F)F)c2)c2cn(C(C)C)c(=O)cc2n1] | 1.17 391 | LCMSBAS1 | 38 |
| I-28 | 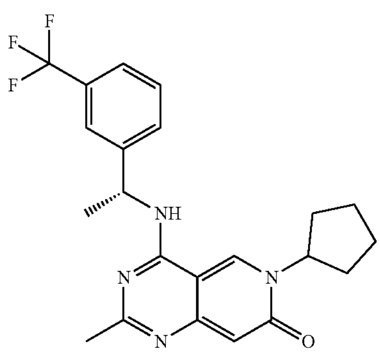 [SMILES: Cc1nc(N[C@H](C)c2cccc(C(F)(F)F)c2)c2cn(C3CCCC3)c(=O)cc2n1] | 1.23 417 | LCMSBAS1 | 27 |
| I-29 | 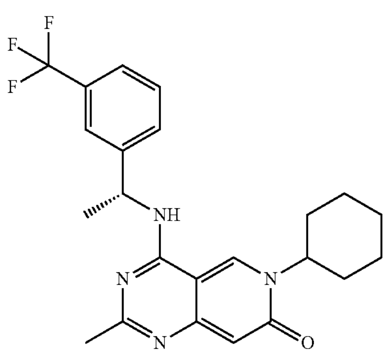 [SMILES: Cc1nc(N[C@H](C)c2cccc(C(F)(F)F)c2)c2cn(C3CCCCC3)c(=O)cc2n1] | 1.27 431 | LCMSBAS1 | 24 |

TABLE 20-continued

| # | structure | $t_{ret}$ [min], $[M + H]^+$ | HPLC method | $IC_{50}$ [nM] |
|---|---|---|---|---|
| I-30 | 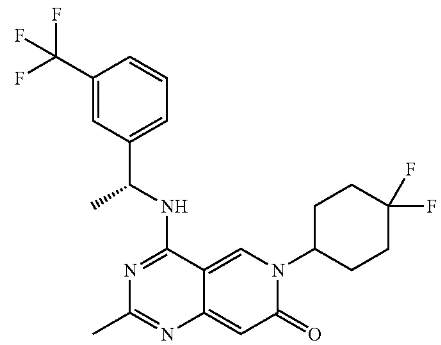 [SMILES: Cc1nc(N[C@H](C)c2cccc(C(F)(F)F)c2)c2cn(C3CCC(F)(F)CC3)c(=O)cc2n1] | 1.27 467 | LCMSBAS1 | 39 |
| I-31 | 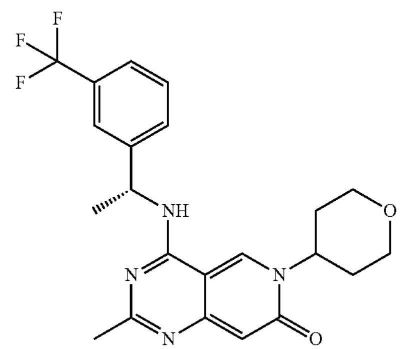 [SMILES: Cc1nc(N[C@H](C)c2cccc(C(F)(F)F)c2)c2cn(C3CCOCC3)c(=O)cc2n1] | 1.13 433 | LCMSBAS1 | 11 |
| I-32 | 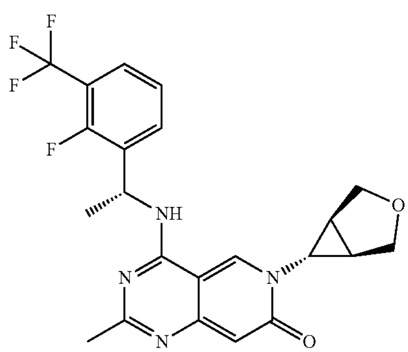 [SMILES: Cc1nc(N[C@H](C)c2cccc(C(F)(F)F)c2F)c2cn([C@H]3[C@@H]4COC[C@@H]43)c(=O)cc2n1] | 1.13 449 | LCMSBAS1 | 12 |
| I-33 | 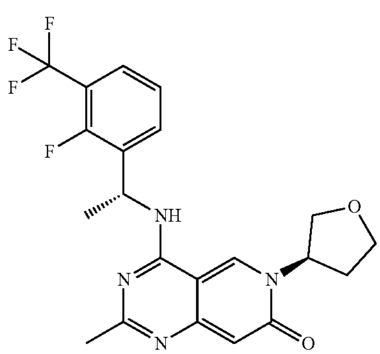 [SMILES: Cc1nc(N[C@H](C)c2cccc(C(F)(F)F)c2F)c2cn([C@@H]3CCOC3)c(=O)cc2n1] | 1.14 437 | LCMSBAS1 | 38 |

TABLE 20-continued

| # | structure | t_ret [min], [M + H]+ | HPLC method | IC_50 [nM] |
|---|---|---|---|---|
| I-34 | 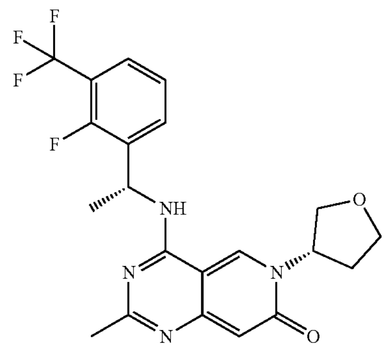 [SMILES: Cc1nc(N[C@H](C)c2cccc(C(F)(F)F)c2F)c2cn([C@H]3CCOC3)c(=O)cc2n1] | 1.14 437 | LCMSBAS1 | 39 |
| I-35 | 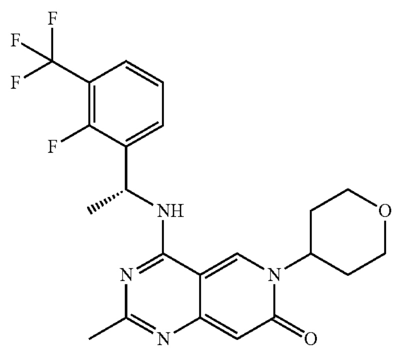 [SMILES: Cc1nc(N[C@H](C)c2cccc(C(F)(F)F)c2F)c2cn(C3CCOCC3)c(=O)cc2n1] | 1.14 451 | LCMSBAS1 | 9 |
| I-36 | 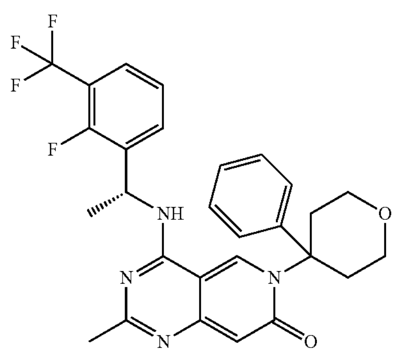 [SMILES: Cc1nc(N[C@H](C)c2cccc(C(F)(F)F)c2F)c2cn(C3(c4ccccc4)CCOCC3)c(=O)cc2n1] | 1.26 527 | LCMSBAS1 | 40 |
| I-37 | 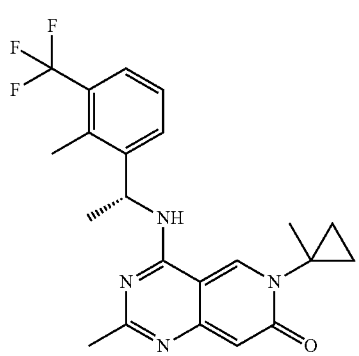 [SMILES: Cc1nc(N[C@H](C)c2cccc(C(F)(F)F)c2C)c2cn(C3(C)CC3)c(=O)cc2n1] | 1.27 417 | LCMSBAS1 | 5 |

TABLE 20-continued

| # | structure | t_ret [min], [M + H]+ | HPLC method | IC_50 [nM] |
|---|---|---|---|---|
| I-38 | 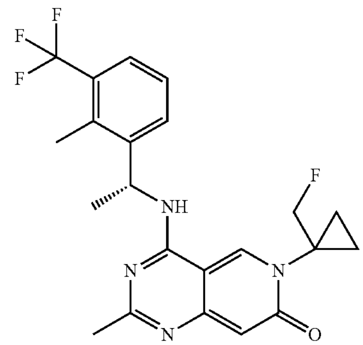 [SMILES: Cc1nc(N[C@H](C)c2cccc(C(F)(F)F)c2C)c2cn(C3(CF)CC3)c(=O)cc2n1] | 1.29 435 | LCMSBAS1 | 4 |
| I-39 | 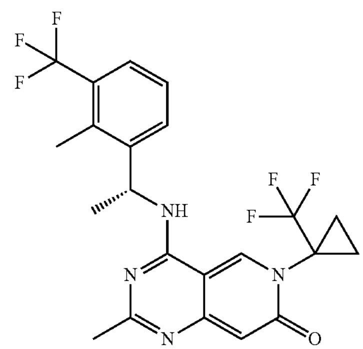 [SMILES: Cc1nc(N[C@H](C)c2cccc(C(F)(F)F)c2C)c2cn(C3(C(F)(F)F)CC3)c(=O)cc2n1] | 1.35 471 | LCMSBAS1 | 18 |
| I-40 | 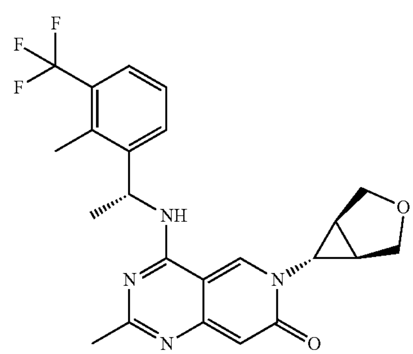 [SMILES: Cc1nc(N[C@H](C)c2cccc(C(F)(F)F)c2C)c2cn([C@H]3[C@@H]4COC[C@@H]43)c(=O)cc2n1] | 1.17 445 | LCMSBAS1 | 9 |
| I-41 | 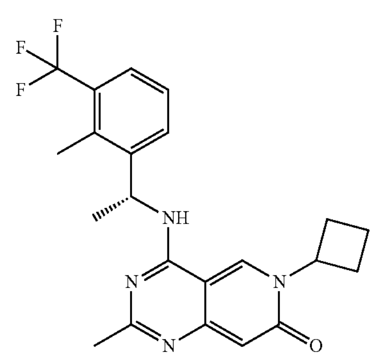 [SMILES: Cc1nc(N[C@H](C)c2cccc(C(F)(F)F)c2C)c2cn(C3CCC3)c(=O)cc2n1] | 1.30 417 | LCMSBAS1 | 14 |

TABLE 20-continued

| # | structure | $t_{ret}$ [min], $[M+H]^+$ | HPLC method | $IC_{50}$ [nM] |
|---|---|---|---|---|
| I-42 | 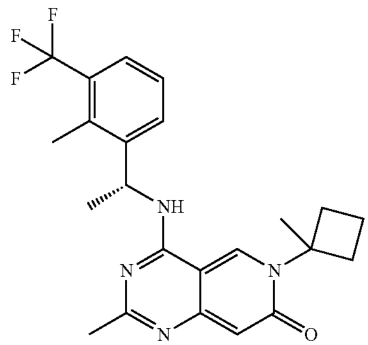 [SMILES: Cc1nc(N[C@H](C)c2cccc(C(F)(F)F)c2C)c2cn(C3(C)CCC3)c(=O)cc2n1] | 1.33<br>431 | LCMSBAS1 | 9 |
| I-43 | 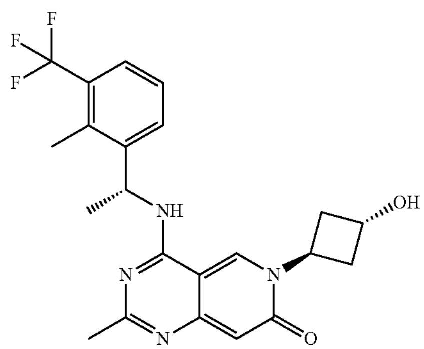 [SMILES: Cc1nc(N[C@H](C)c2cccc(C(F)(F)F)c2C)c2cn([C@H]3C[C@H](O)C3)c(=O)cc2n1] | 1.19<br>433 | LCMSBAS1 | 5 |
| I-44 | 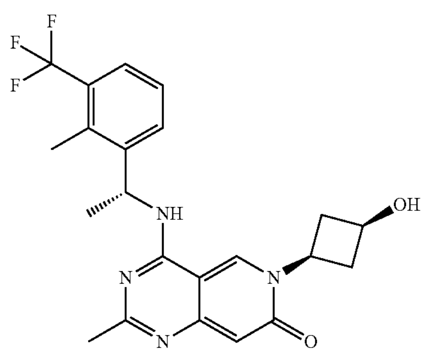 [SMILES: Cc1nc(N[C@H](C)c2cccc(C(F)(F)F)c2C)c2cn([C@H]3C[C@@H](O)C3)c(=O)cc2n1] | 1.18<br>433 | LCMSBAS1 | 12 |
| I-45 | 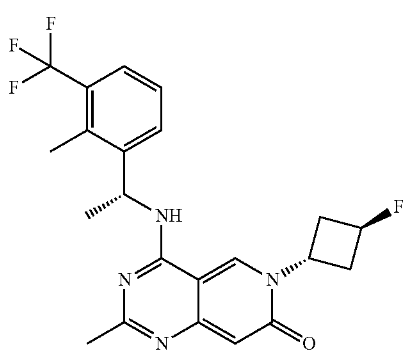 [SMILES: Cc1nc(N[C@H](C)c2cccc(C(F)(F)F)c2C)c2cn([C@H]3C[C@H](F)C3)c(=O)cc2n1] | 1.28<br>435 | LCMSBAS1 | 11 |

TABLE 20-continued

| # | structure | $t_{ret}$ [min], $[M + H]^+$ | HPLC method | $IC_{50}$ [nM] |
| --- | --- | --- | --- | --- |
| I-46 | 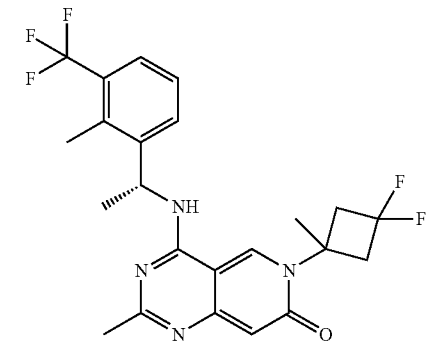 [SMILES: Cc1nc(N[C@H](C)c2cccc(C(F)(F)F)c2C)c2cn(C3(C)CC(F)(F)C3)c(=O)cc2n1] | 1.35<br>467 | LCMSBAS1 | 31 |
| I-47 | 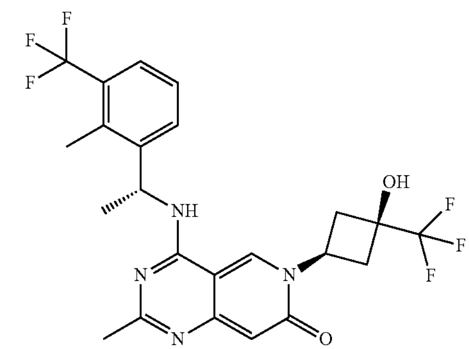 [SMILES: Cc1nc(N[C@H](C)c2cccc(C(F)(F)F)c2C)c2cn([C@H]3C[C@](O)(C(F)(F)F)C3)c(=O)cc2n1] | 1.31<br>501 | LCMSBAS1 | 33 |
| I-48 | 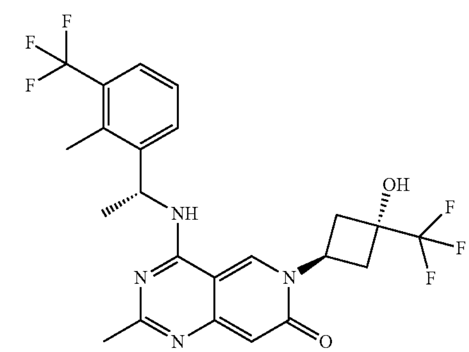 [SMILES: Cc1nc(N[C@H](C)c2cccc(C(F)(F)F)c2C)c2cn([C@H]3C[C@@](O)(C(F)(F)F)C3)c(=O)cc2n1] | 1.27<br>501 | LCMSBAS1 | 27 |
| I-49 | 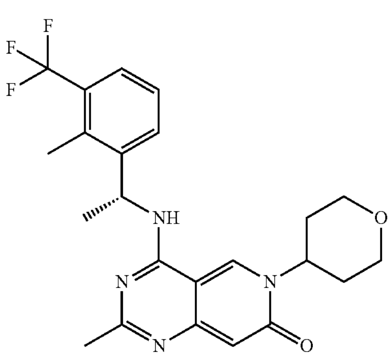 [SMILES: Cc1nc(N[C@H](C)c2cccc(C(F)(F)F)c2C)c2cn(C3CCOCC3)c(=O)cc2n1] | 1.19<br>447 | LCMSBAS1 | 6 |

TABLE 20-continued

| # | structure | t_ret [min], [M + H]+ | HPLC method | IC50 [nM] |
|---|---|---|---|---|
| I-50 | 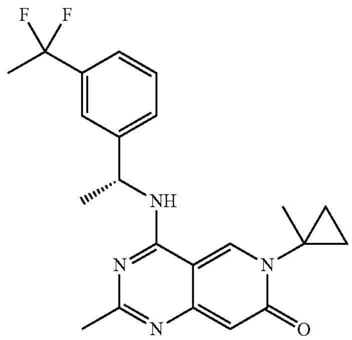 [SMILES: Cc1nc(N[C@H](C)c2cccc(C(C)(F)F)c2)c2cn(C3(C)CC3)c(=O)cc2n1] | 1.19 399 | LCMSBAS1 | 9 |
| I-51 | 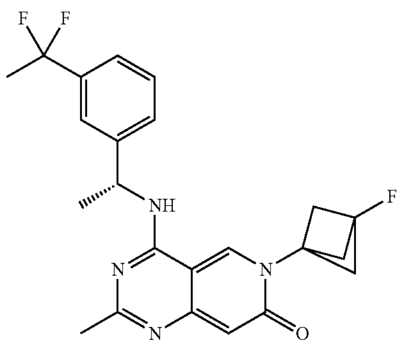 [SMILES: Cc1nc(N[C@H](C)c2cccc(C(C)(F)F)c2)c2cn(C34CC(F)(C3)C4)c(=O)cc2n1] | 1.25 429 | LCMSBAS1 | 31 |
| I-52 | 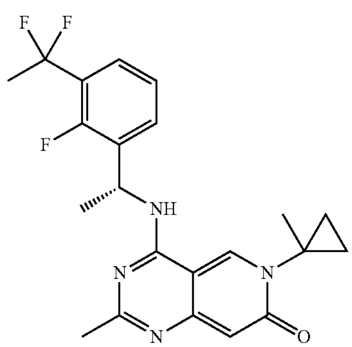 [SMILES: Cc1nc(N[C@H](C)c2cccc(C(C)(F)F)c2F)c2cn(C3(C)CC3)c(=O)cc2n1] | 1.21 417 | LCMSBAS1 | 4 |
| I-53 | 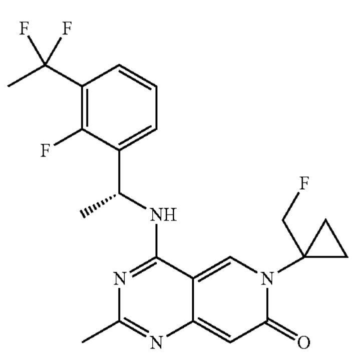 [SMILES: Cc1nc(N[C@H](C)c2cccc(C(C)(F)F)c2F)c2cn(C3(CF)CC3)c(=O)cc2n1] | 1.21 435 | LCMSBAS1 | 4 |

TABLE 20-continued

| # | structure | t_ret [min], [M + H]+ | HPLC method | IC_50 [nM] |
|---|---|---|---|---|
| I-54 | 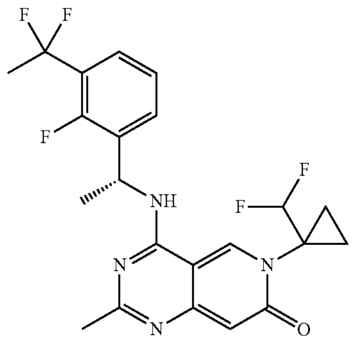 [SMILES: Cc1nc(N[C@H](C)c2cccc(C(C)(F)F)c2F)c2cn(C3(C(F)F)CC3)c(=O)cc2n1] | 1.24 453 | LCMSBAS1 | 5 |
| I-55 | 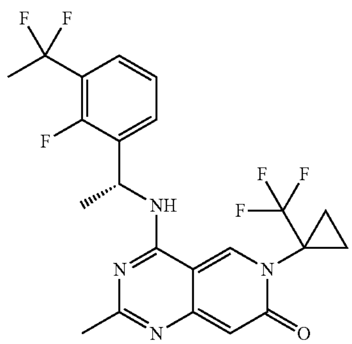 [SMILES: Cc1nc(N[C@H](C)c2cccc(C(C)(F)F)c2F)c2cn(C3(C(F)(F)F)CC3)c(=O)cc2n1] | 1.28 471 | LCMSBAS1 | 13 |
| I-56 | 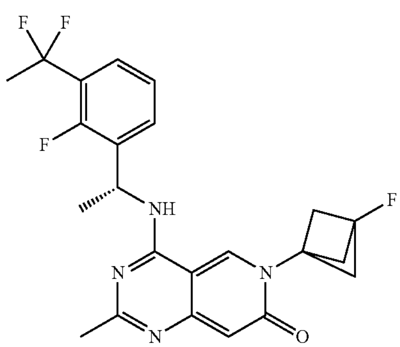 [SMILES: Cc1nc(N[C@H](C)c2cccc(C(C)(F)F)c2F)c2cn(C34CC(F)(C3)C4)c(=O)cc2n1] | 1.27 447 | LCMSBAS1 | 15 |
| I-57 | 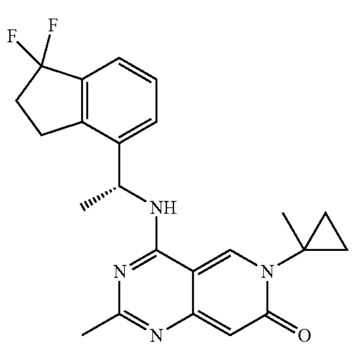 | 1.21 411 | LCMSBAS1 | 2 |

TABLE 20-continued
| # | structure | $t_{ret}$ [min], $[M + H]^+$ | HPLC method | $IC_{50}$ [nM] |
|---|---|---|---|---|
| I-58 | 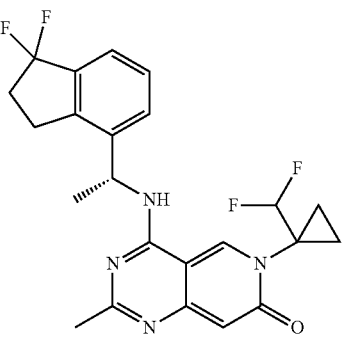 [SMILES: Cc1nc(N[C@H](C)c2cccc3c2CCC3(F)F)c2cn(C3(C(F)F)CC3)c(=O)cc2n1] | 1.24 447 | LCMSBAS1 | 2 |
| I-59 | 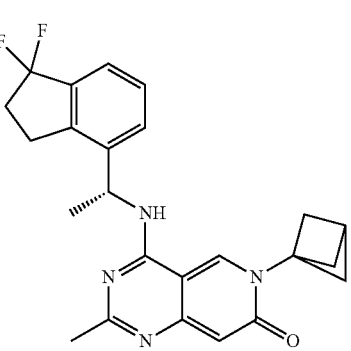 | 1.25 423 | LCMSBAS1 | 3 |
| I-60 | 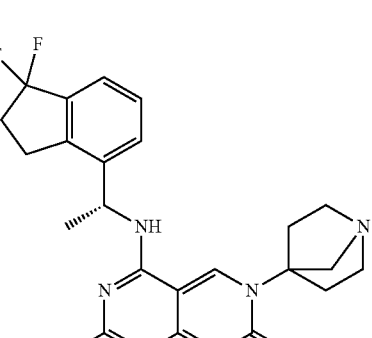 | 1.14 452 | LCMSBAS1 | 2 |
| I-61 | 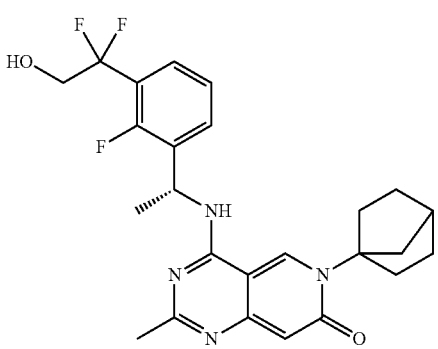 [SMILES: Cc1nc(N[C@H](C)c2cccc(C(F)(F)CO)c2F)c2cn(C34CCC(CC3)C4)c(=O)cc2n1] | 1.15 473 | LCMSBAS1 | 1 |

TABLE 20-continued

| # | structure | $t_{ret}$ [min], [M + H]$^+$ | HPLC method | IC$_{50}$ [nM] |
|---|---|---|---|---|
| I-62 | 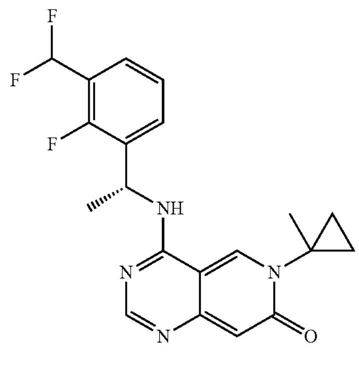 [SMILES: C[C@@H](Nc1ncnc2cc(=O)n(C3(C)CC3)cc12)c1cccc(C(F)F)c1F] | 1.10 389 | LCMSBAS1 | 7 |
| I-63 | 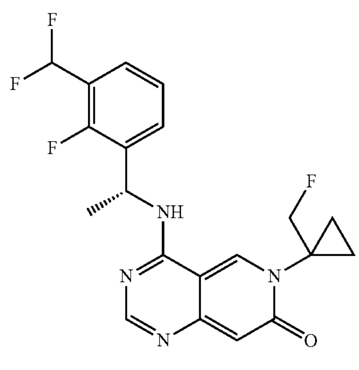 [SMILES: C[C@@H](Nc1ncnc2cc(=O)n(C3(CF)CC3)cc12)c1cccc(C(F)F)c1F] | 1.10 407 | LCMSBAS1 | 7 |
| I-64 | 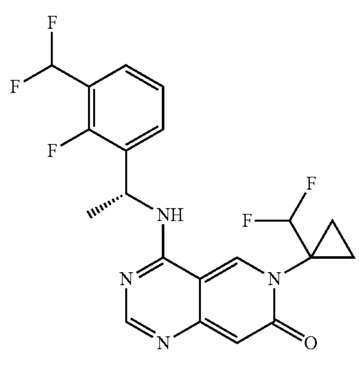 [SMILES: C[C@@H](Nc1ncnc2cc(=O)n(C3(C(F)F)CC3)cc12)c1cccc(C(F)F)c1F] | 1.14 425 | LCMSBAS1 | 8 |
| I-65 | 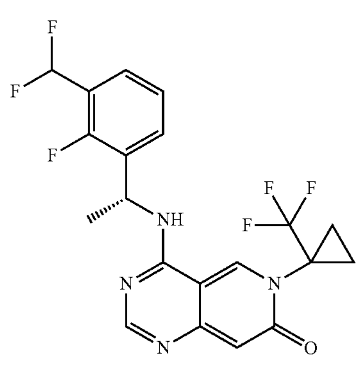 [SMILES: C[C@@H](Nc1ncnc2cc(=O)n(C3(C(F)(F)F)CC3)cc12)c1cccc(C(F)F)c1F] | 1.16 443 | LCMSBAS1 | 10 |

TABLE 20-continued

| # | structure | $t_{ret}$ [min], [M + H]$^+$ | HPLC method | IC$_{50}$ [nM] |
|---|---|---|---|---|
| I-66 | 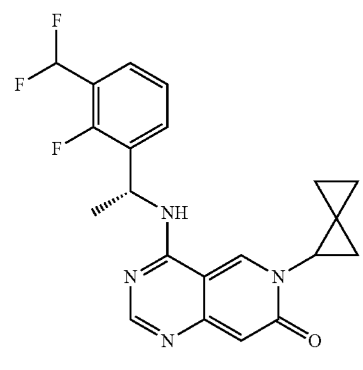 [SMILES: C[C@@H](Nc1ncnc2cc(=O)n(C3CC34CC4)cc12)c1cccc(C(F)F)c1F] | 1.14<br>401 | LCMSBAS1 | 15 |
| I-67 | 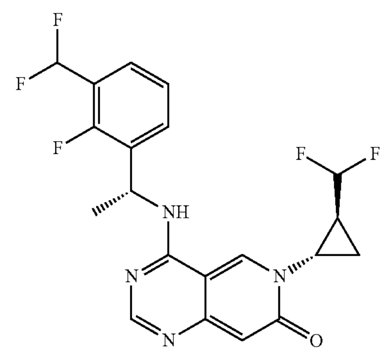 [SMILES: C[C@@H](Nc1ncnc2cc(=O)n([C@H]3C[C@@H]3C(F)F)cc12)c1cccc(C(F)F)c1F] | 1.12<br>425 | LCMSBAS1 | |
| I-68 | 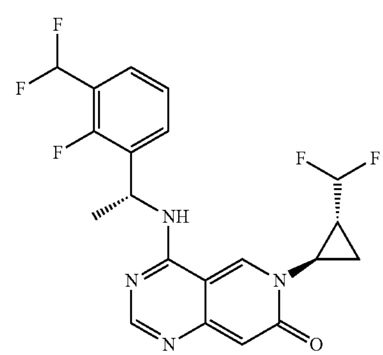 [SMILES: C[C@@H](Nc1ncnc2cc(=O)n([C@@H]3C[C@H]3C(F)F)cc12)c1cccc(C(F)F)c1F] | 1.12<br>427 | LCMSBAS1 | |
| I-69 | 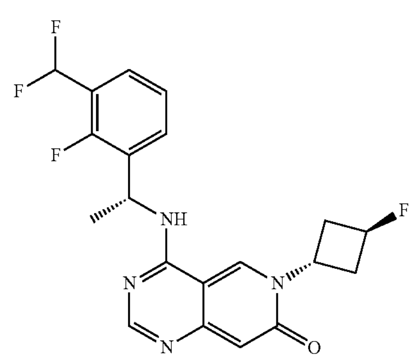 [SMILES: C[C@@H](Nc1ncnc2cc(=O)n([C@H]3C[C@H](F)C3)cc12)c1cccc(C(F)F)c1F] | 1.10<br>407 | LCMSBAS1 | 6 |

TABLE 20-continued

| # | structure | $t_{ret}$ [min], [M + H]$^+$ | HPLC method | IC$_{50}$ [nM] |
|---|---|---|---|---|
| I-70 | 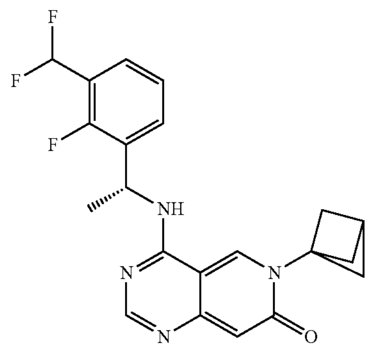 [SMILES: C[C@@H](Nc1ncnc2cc(=O)n(C34CC(C3)C4)cc12)c1cccc(C(F)F)c1F] | 1.15 401 | LCMSBAS1 | 7 |
| I-71 | 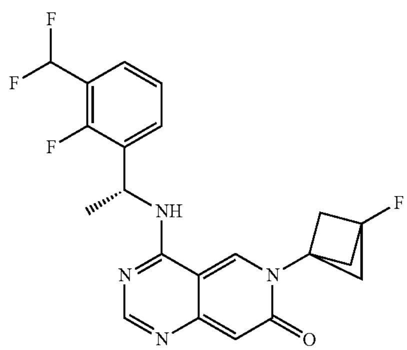 [SMILES: C[C@@H](Nc1ncnc2cc(=O)n(C34CC(F)(C3)C4)cc12)c1cccc(C(F)F)c1F] | 1.16 419 | LCMSBAS1 | 7 |
| I-72 | 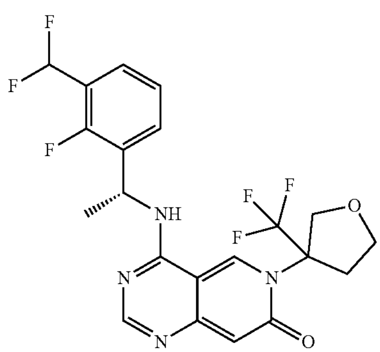 [SMILES: C[C@@H](Nc1ncnc2cc(=O)n(C3(C(F)(F)F)CCOC3)cc12)c1cccc(C(F)F)c1F] | 1.16 473 | LCMSBAS1 | 11 |
| I-73 | 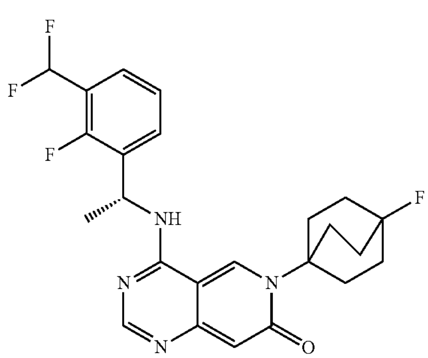 [SMILES: C[C@@H](Nc1ncnc2cc(=O)n(C34CCC(F)(CC3)CC4)cc12)c1cccc(C(F)F)c1F] | 1.22 461 | LCMSBAS1 | 3 |

TABLE 20-continued

| # | structure | t_ret [min], [M + H]+ | HPLC method | IC_50 [nM] |
|---|---|---|---|---|
| I-74 | 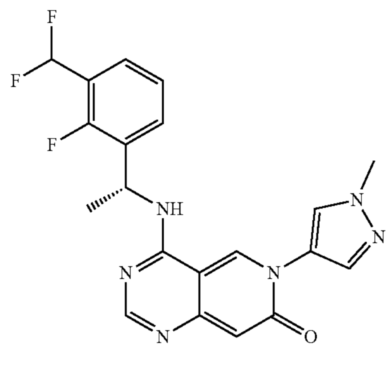 [SMILES: C[C@@H](Nc1ncnc2cc(=O)n(-c3cnn(C)c3)cc12)c1cccc(C(F)F)c1F] | 1.04 415 | LCMSBAS1 | |
| I-75 | 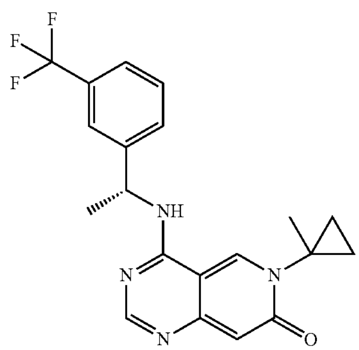 [SMILES: C[C@@H](Nc1ncnc2cc(=O)n(C3(C)CC3)cc12)c1cccc(C(F)(F)F)c1] | 1.16 389 | LCMSBAS1 | 15 |
| I-76 | 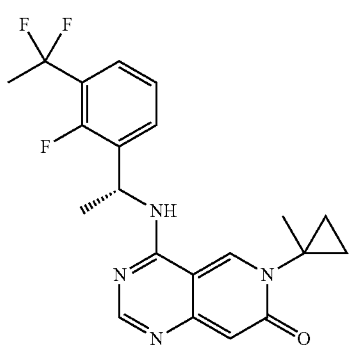 [SMILES: C[C@@H](Nc1ncnc2cc(=O)n(C3(C)CC3)cc12)c1cccc(C(C)(F)F)c1F] | 1.15 403 | LCMSBAS1 | 7 |
| I-77 | 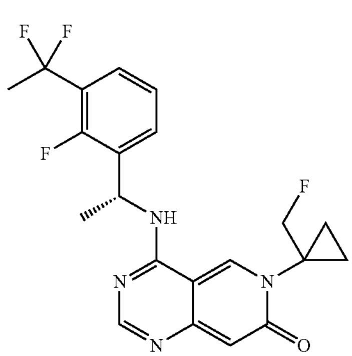 [SMILES: C[C@@H](Nc1ncnc2cc(=O)n(C3(CF)CC3)cc12)c1cccc(C(C)(F)F)c1F] | 1.15 421 | LCMSBAS1 | 6 |

TABLE 20-continued

| # | structure | t_ret [min], [M + H]+ | HPLC method | IC$_{50}$ [nM] |
|---|---|---|---|---|
| I-78 | 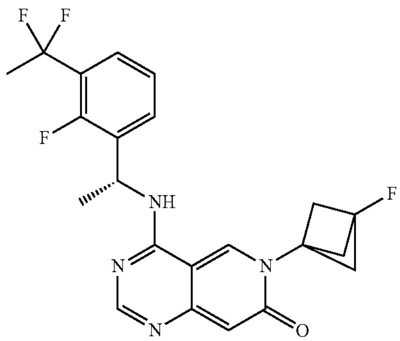 [SMILES: C[C@@H](Nc1ncnc2cc(=O)n(C34CC(F)(C3)C4)cc12)c1cccc(C(C)(F)F)c1F] | 1.21 433 | LCMSBAS1 | 9 |
| I-79 | 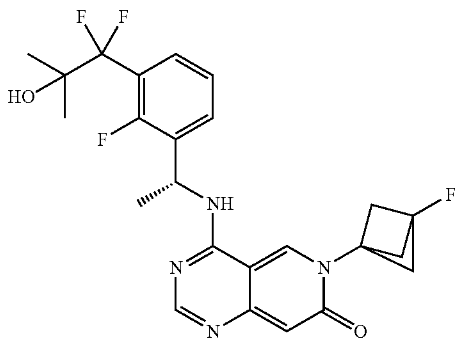 [SMILES: C[C@@H](Nc1ncnc2cc(=O)n(C34CC(F)(C3)C4)cc12)c1cccc(C(F)(F)C(C)(C)O)c1F] | 0.840 477.2 | VAB | |
| I-80 | 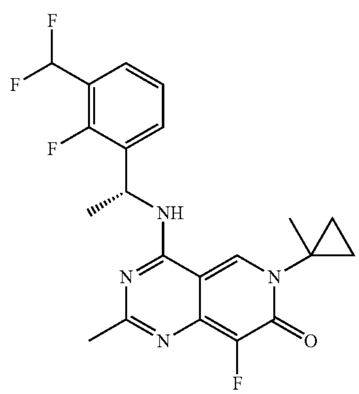 [SMILES: Cc1nc(N[C@H](C)c2cccc(C(F)F)c2F)c2cn(C3(C)CC3)c(=O)c(F)c2n1] | 1.18 421 | LCMSBAS1 | 9 |
| I-81 | 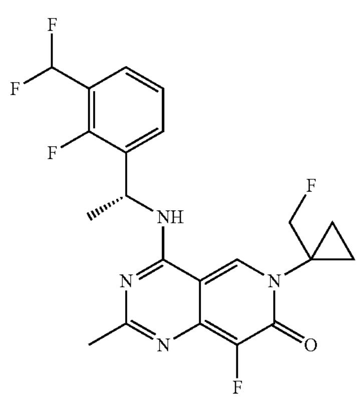 [SMILES: Cc1nc(N[C@H](C)c2cccc(C(F)F)c2F)c2cn(C3(CF)CC3)c(=O)c(F)c2n1] | 1.18 439 | LCMSBAS1 | 6 |

TABLE 20-continued

| # | structure | $t_{ret}$ [min], $[M+H]^+$ | HPLC method | $IC_{50}$ [nM] |
|---|---|---|---|---|
| I-82 | 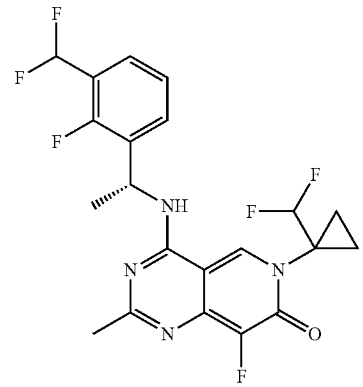 [SMILES: Cc1nc(N[C@H](C)c2cccc(C(F)F)c2F)c2cn(C3(C(F)F)CC3)c(=O)c(F)c2n1] | 1.21 457 | LCMSBAS1 | 5 |
| I-83 | 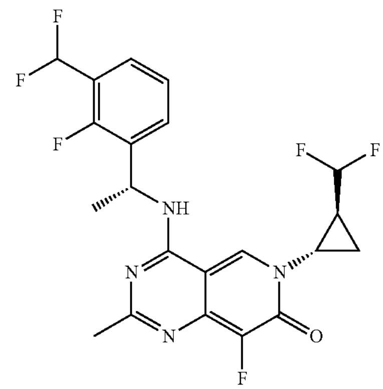 [SMILES: Cc1nc(N[C@H](C)c2cccc(C(F)F)c2F)c2cn([C@H]3C[C@@H]3C(F)F)c(=O)c(F)c2n1] | 1.20 457 | LCMSBAS1 | 15 |
| I-84 | 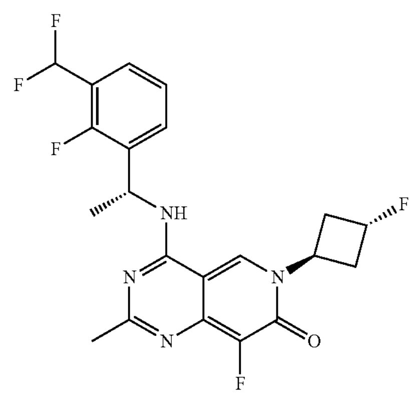 [SMILES: Cc1nc(N[C@H](C)c2cccc(C(F)F)c2F)c2cn([C@H]3C[C@H](F)C3)c(=O)c(F)c2n1] | 1.17 439 | LCMSBAS1 | 8 |
| I-85 | 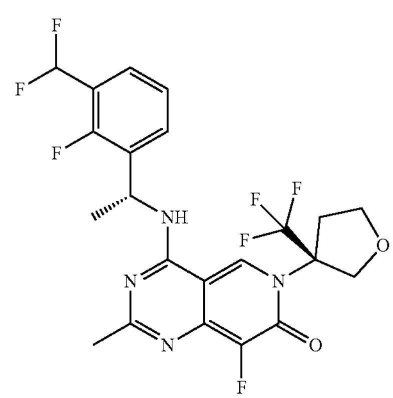 [SMILES: Cc1nc(N[C@H](C)c2cccc(C(F)F)c2F)c2cn([C@]3(C(F)(F)F)CCOC3)c(=O)c(F)c2n1] | 1.22 505 | LCMSBAS1 | 9 |

TABLE 20-continued

| # | structure | $t_{ret}$ [min], $[M + H]^+$ | HPLC method | $IC_{50}$ [nM] |
|---|---|---|---|---|
| I-86 | 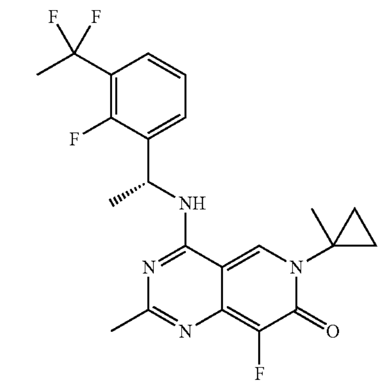 [SMILES: Cc1nc(N[C@H](C)c2cccc(C(C)(F)F)c2F)c2cn(C3(C)CC3)c(=O)c(F)c2n1] | 0.41<br>435 | LCMSBAS1 | 6 |
| I-87 | 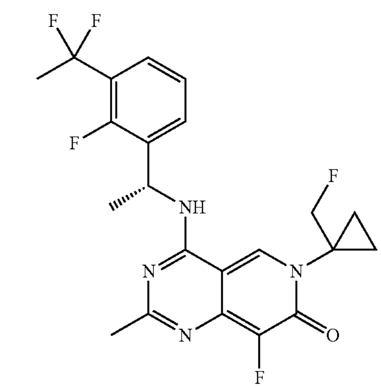 [SMILES: Cc1nc(N[C@H](C)c2cccc(C(C)(F)F)c2F)c2cn(C3(CF)CC3)c(=O)c(F)c2n1] | 1.23<br>453 | LCMSBAS1 | 4 |
| I-88 | 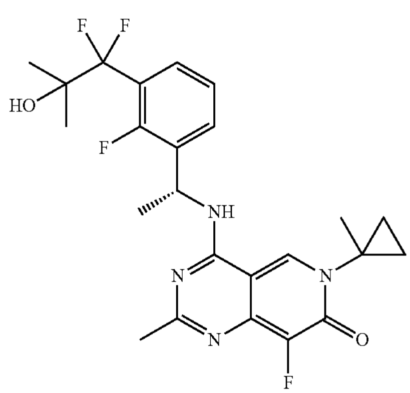 [SMILES: Cc1nc(N[C@H](C)c2cccc(C(F)(F)C(C)(C)O)c2F)c2cn(C3(C)CC3)c(=O)c(F)c2n1] | 1.06<br>479 | LCMSBAS1 | 2 |
| I-89 | 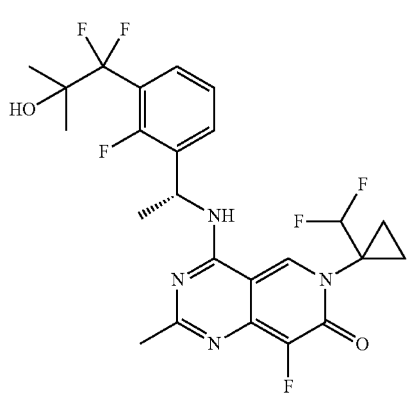 [SMILES: Cc1nc(N[C@H](C)c2cccc(C(F)(F)C(C)(C)O)c2F)c2cn(C3(C(F)F)CC3)c(=O)c(F)c2n1] | 1.16<br>515 | LCMSBAS1 | 2 |

TABLE 20-continued

| # | structure | $t_{ret}$ [min], $[M+H]^+$ | HPLC method | $IC_{50}$ [nM] |
|---|---|---|---|---|
| I-90 | 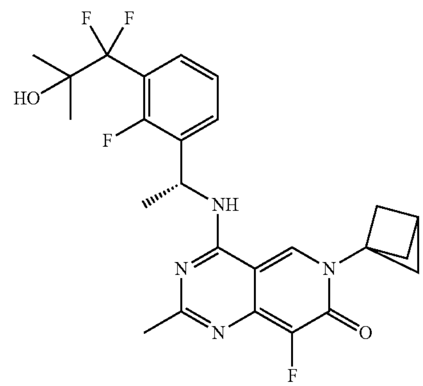 [SMILES: Cc1nc(N[C@H](C)c2cccc(C(F)(F)C(C)(C)O)c2F)c2cn(C34CC(C3)C4)c(=O)c(F)c2n1] | 1.12 491 | LCMSBAS1 | 4 |
| I-91 | 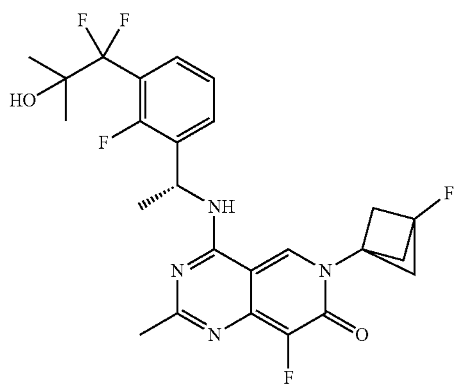 [SMILES: Cc1nc(N[C@H](C)c2cccc(C(F)(F)C(C)(C)O)c2F)c2cn(C34CC(F)(C3)C4)c(=O)c(F)c2n1] | 1.13 509 | LCMSBAS1 | 4 |
| I-92 | 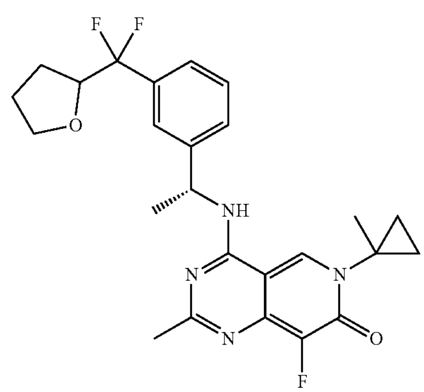 [SMILES: Cc1nc(N[C@H](C)c2cccc(C(F)(F)C3CCCO3)c2)c2cn(C3(C)CC3)c(=O)c(F)c2n1] | 1.22 473 | LCMSBAS1 | 4 |
| I-93 | 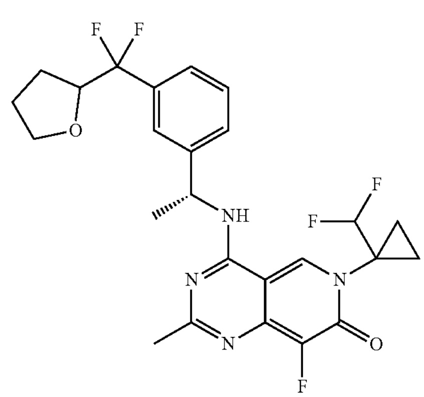 [SMILES: Cc1nc(N[C@H](C)c2cccc(C(F)(F)C3CCCO3)c2)c2cn(C3(C(F)F)CC3)c(=O)c(F)c2n1] | 1.27 509 | LCMSBAS1 | 3 |

TABLE 20-continued

| # | structure | t_ret [min], [M + H]+ | HPLC method | IC50 [nM] |
|---|---|---|---|---|
| I-94 | 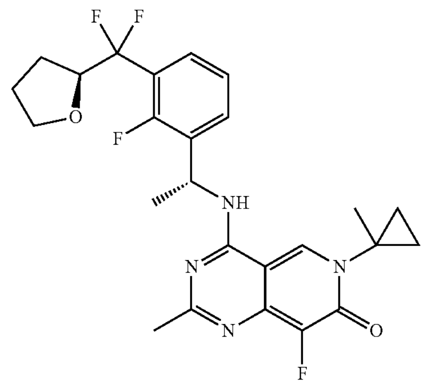 [SMILES: Cc1nc(N[C@H](C)c2cccc(C(F)(F)[C@@H]3CCCO3)c2F)c2cn(C3(C)CC3)c(=O)c(F)c2n1] | 1.19 491 | LCMSBAS1 | 5 |
| I-95 | 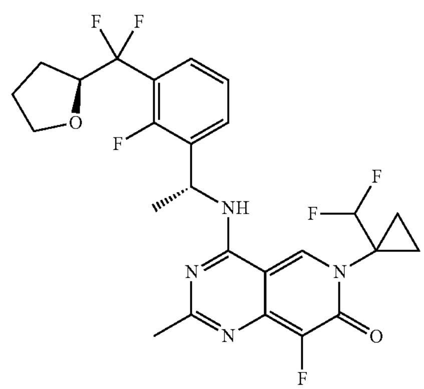 [SMILES: Cc1nc(N[C@H](C)c2cccc(C(F)(F)[C@@H]3CCCO3)c2F)c2cn(C3(C(F)F)CC3)c(=O)c(F)c2n1] | 1.22 527 | LCMSBAS1 | 5 |
| I-96 | 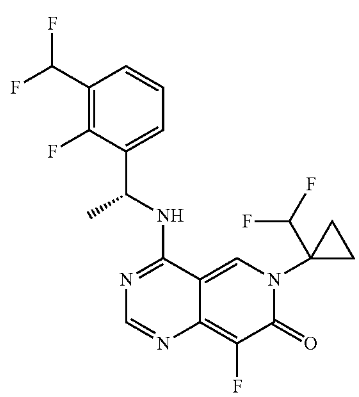 [SMILES: C[C@@H](Nc1ncnc2c(F)c(=O)n(C3(C(F)F)CC3)cc12)c1cccc(C(F)F)c1F] | 1.15 443 | LCMSBAS1 | 7 |
| I-97 | 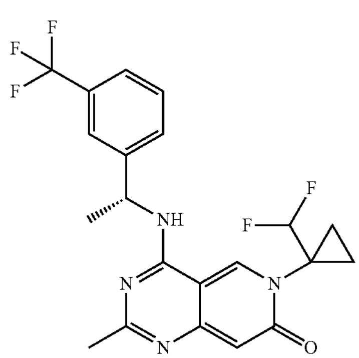 [SMILES: Cc1nc(N[C@H](C)c2cccc(C(F)(F)F)c2)c2cn(C3(C(F)F)CC3)c(=O)cc2n1] | 0.924 439.3 | VAB | 14 |

TABLE 20-continued

| # | structure | t_ret [min], [M + H]+ | HPLC method | IC50 [nM] |
|---|---|---|---|---|
| I-98 | 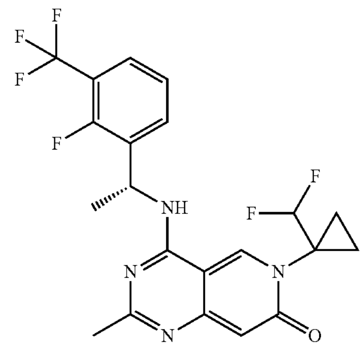 [SMILES: Cc1nc(N[C@H](C)c2cccc(C(F)(F)F)c2F)c2cn(C3(C(F)F)CC3)c(=O)cc2n1] | 0.955 457.3 | VAB | 8 |
| I-99 | 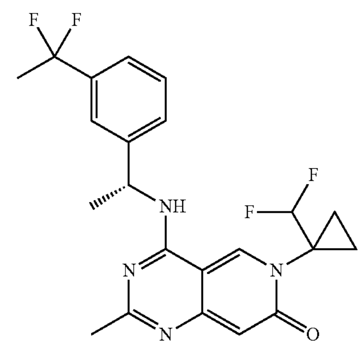 [SMILES: Cc1nc(N[C@H](C)c2cccc(C(C)(F)F)c2)c2cn(C3(C(F)F)CC3)c(=O)cc2n1] | 0.903 435.2 | VAB | 7 |
| I-100 | 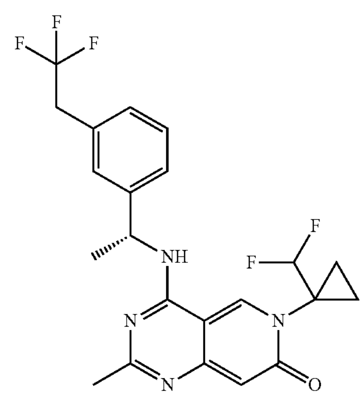 [SMILES: Cc1nc(N[C@H](C)c2cccc(CC(F)(F)F)c2)c2cn(C3(C(F)F)CC3)c(=O)cc2n1] | 0.912 453.2 | VAB | 30 |
| I-101 | 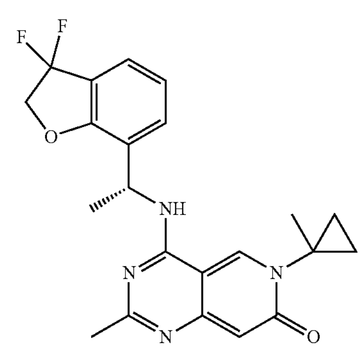 [SMILES: Cc1nc(N[C@H](C)c2cccc3c2OCC3(F)F)c2cn(C3(C)CC3)c(=O)cc2n1] | 0.864 413.1 | VAB | 4 |

TABLE 20-continued
| # | structure | $t_{ret}$ [min], $[M + H]^+$ | HPLC method | $IC_{50}$ [nM] |
|---|---|---|---|---|
| I-102 | 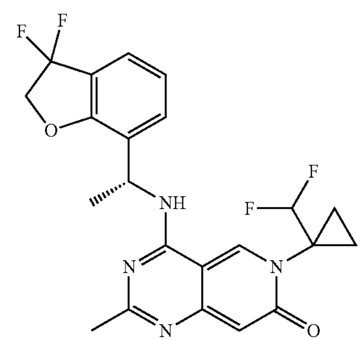 [SMILES: Cc1nc(N[C@H](C)c2cccc3c2OCC3(F)F)c2cn(C3(C(F)F)CC3)c(=O)cc2n1] | 0.884 449.1 | VAB | 4 |
| I-103 | 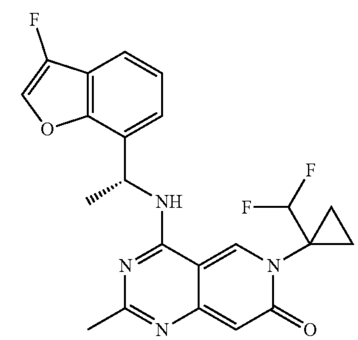 [SMILES: Cc1nc(N[C@H](C)c2cccc3c(F)coc23)c2cn(C3(C(F)F)CC3)c(=O)cc2n1] | 0.901 429.2 | VAB | 5 |
Experimental Procedure for the Synthesis of I-104 and I-105
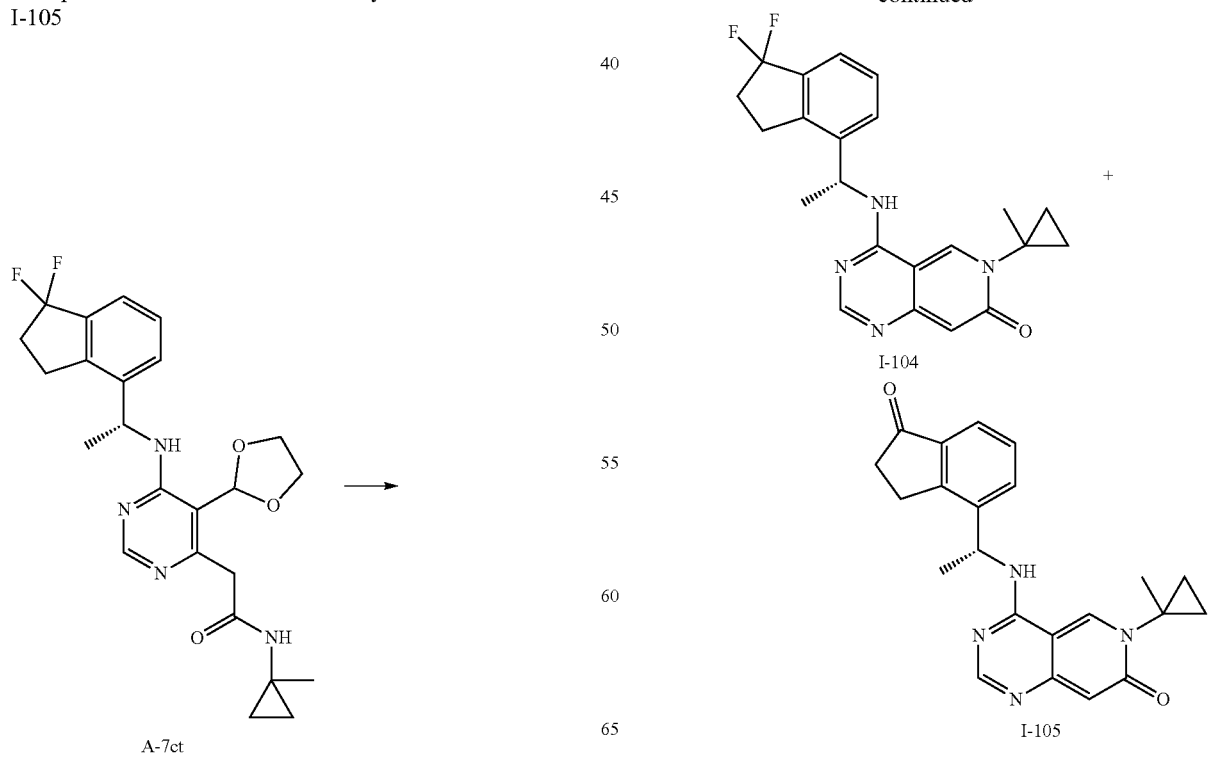

A-7ct (90 mg, 0.196 mmol, 1.0 equiv.) is dissolved in 2-propanol (0.5 mL). An aqueous 2 N HCl solution (500 µL, 1.000 mmol, 5.1 equiv.) is added and the resulting mixture stirred for 3 h at 50° C. until complete conversion of the starting material is observed. The reaction mixture is basified with aqueous ammonia, filtered and the filtrate purified by basic reversed phase chromatography (gradient elution: 15% to 85% acetonitrile in water) to furnish the desired products.

The following compounds I (table 21) are available in an analogous manner starting from different pyrimidines A-7. The crude products are purified by chromatography if necessary.

TABLE 21

| # | structure | t_ret [min] [M + H]+ | HPLC method | IC_50 [nM] |
|---|---|---|---|---|
| I-104 | 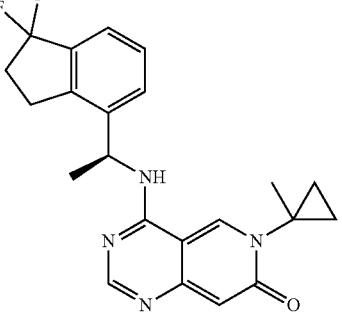 | 1.15 397 | LCMSBAS1 | 4 |
| I-105 | 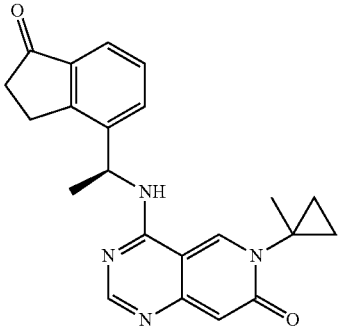 [SMILES: C[C@H](Nc1ncnc2cc(=O)n(C3(C)CC3)cc12)c1cccc2c1CCC2=O] | 0.94 375 | LCMSBAS1 | 25 |
| I-106 | 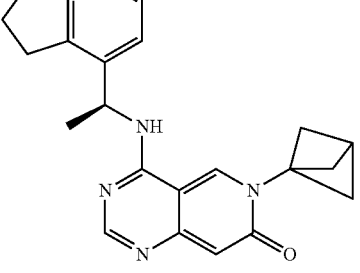 | 1.20 409 | LCMSBAS1 | 4 |
| I-107 | 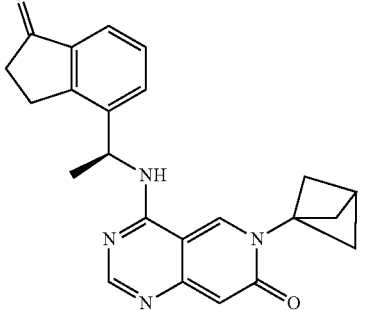 | 1.00 387 | LCMSBAS1 | 17 |

TABLE 21-continued
| # | structure | t_ret [min] [M + H]+ | HPLC method | IC50 [nM] |
|---|---|---|---|---|
| I-108 | 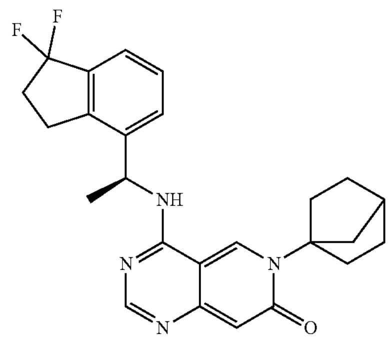 [SMILES: C[C@H](Nc1ncnc2cc(=O)n(C34CCC(CC3)C4)cc12)c1cccc2c1CCC2(F)F] | 1.27 435 | LCMSBAS1 | 4 |
| I-109 | 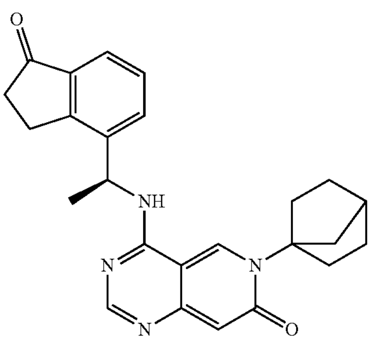 [SMILES: C[C@H](Nc1ncnc2cc(=O)n(C34CCC(CC3)C4)cc12)c1cccc2c1CCC2=O] | 1.09 415 | LCMSBAS1 | 6 |
Experimental Procedure for the Synthesis of I-110
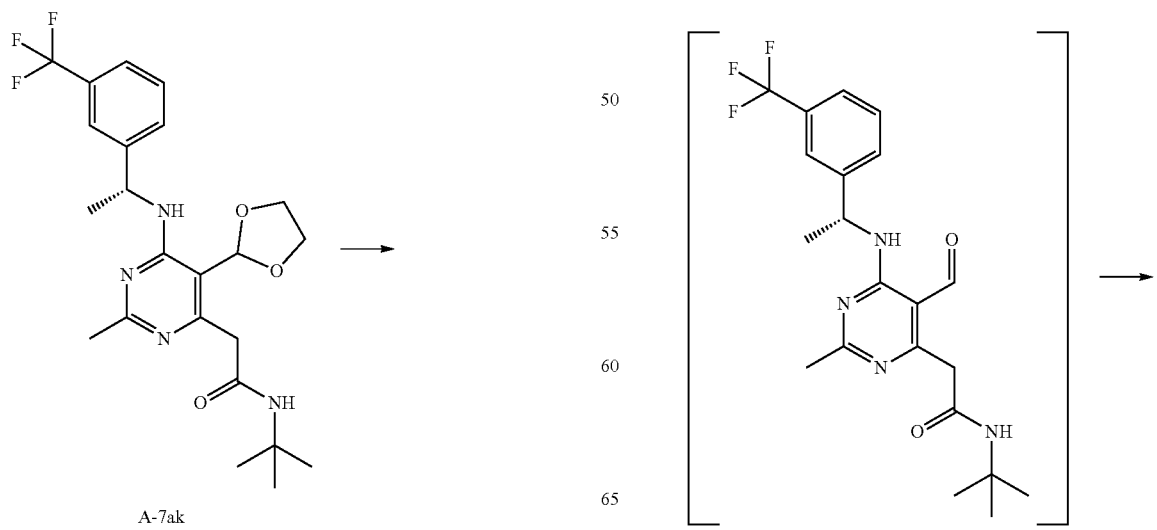

-continued

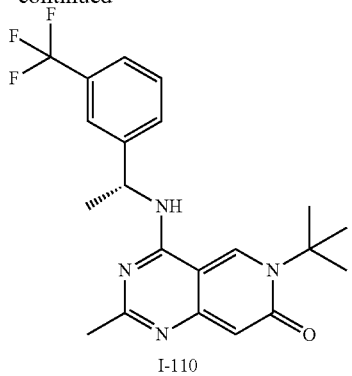

I-110

A-7ak (56.0 mg, 0.120 mmol, 1.0 equiv.) is dissolved in 2-propanol (0.5 mL). An aqueous 2 N HCl solution (500 μL, 1.000 mmol, 8.3 equiv.) is added and the resulting mixture stirred for 1 h at 50° C. until complete conversion of the starting material is observed. An aqueous 2 M NaOH (500 μL, 1.000 mmol, 8.3 equiv.) is added and the resulting mixture stirred for an additional hour at room temperature until complete conversion of the intermediate is observed. The reaction mixture is filtered and the filtrate purified by basic reversed phase chromatography (gradient elution: 30% to 70% acetonitrile in water) to furnish the desired product.

The following compounds I (table 22) are available in an analogous manner starting from different pyrimidines A-7. For the preparation of some compounds also other bases like aqueous ammonia have been used instead of aqueous NaOH. The crude products are purified by chromatography if necessary.

TABLE 22

| # | structure | $t_{ret}$ [min] $[M + H]^+$ | HPLC method | $IC_{50}$ [nM] |
|---|-----------|------------------------------|-------------|----------------|
| I-110 | 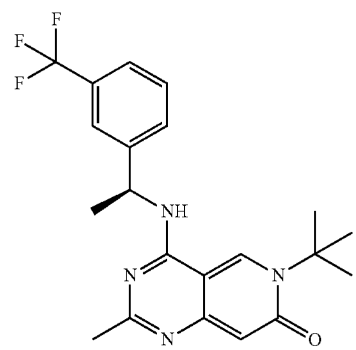 [SMILES: Cc1nc(N[C@@H](C)c2cccc(C(F)(F)F)c2)c2cn(C(C)(C)C)c(=O)cc2n1] | 1.22 405 | LCMSBAS1 | 25 |
| I-111 | 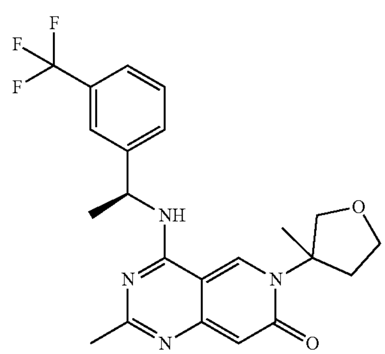 [SMILES: Cc1nc(N[C@@H](C)c2cccc(C(F)(F)F)c2)c2cn(C3(C)CCOC3)c(=O)cc2n1] | 1.14 433 | LCMSBAS1 | 9 |
| I-112 | 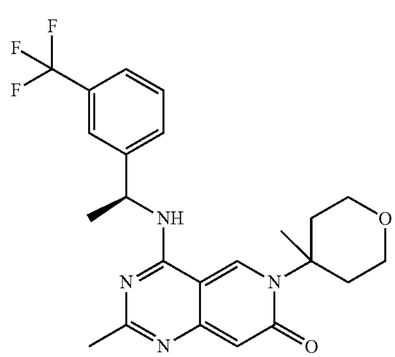 [SMILES: Cc1nc(N[C@@H](C)c2cccc(C(F)(F)F)c2)c2cn(C3(C)CCOCC3)c(=O)cc2n1] | 1.17 447 | LCMSBAS1 | 13 |

TABLE 22-continued

| # | structure | t_ret [min] [M + H]+ | HPLC method | IC_50 [nM] |
|---|---|---|---|---|
| I-113 | 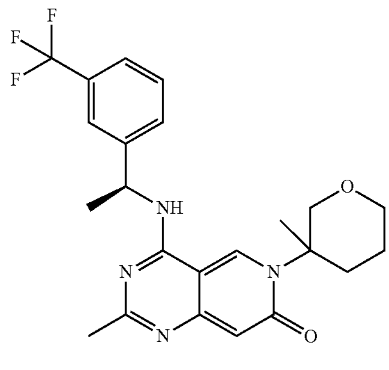 [SMILES: Cc1nc(N[C@@H](C)c2cccc(C(F)(F)F)c2)c2cn(C3(C)CCCOC3)c(=O)cc2n1] | 1.21 447 | LCMSBAS1 | 39 |
| I-114 | 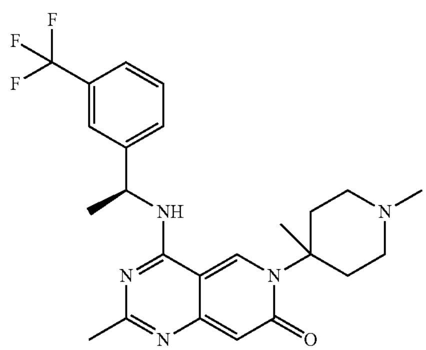 [SMILES: Cc1nc(N[C@@H](C)c2cccc(C(F)(F)F)c2)c2cn(C3(C)CCN(C)CC3)c(=O)cc2n1] | 1.21 460 | LCMSBAS1 | 26 |
| I-115 | 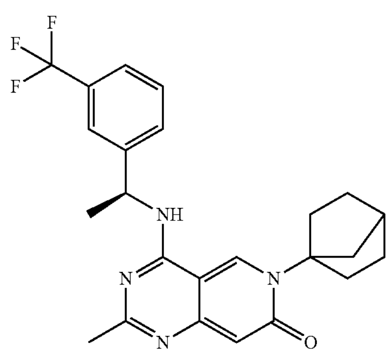 [SMILES: Cc1nc(N[C@@H](C)c2cccc(C(F)(F)F)c2)c2cn(C34CCC(CC3)C4)c(=O)cc2n1] | 1.30 443 | LCMSBAS1 | 10 |
| I-116 | 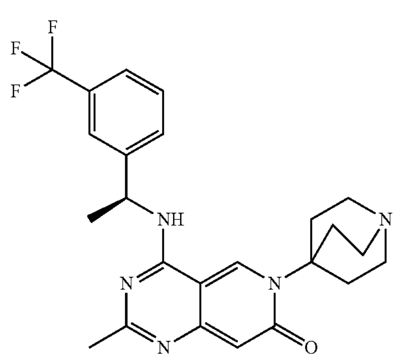 [SMILES: Cc1nc(N[C@@H](C)c2cccc(C(F)(F)F)c2)c2cn(C34CCN(CC3)CC4)c(=O)cc2n1] | 1.18 458 | LCMSBAS1 | 4 |

TABLE 22-continued

| # | structure | t_ret [min] [M + H]+ | HPLC method | IC_50 [nM] |
|---|---|---|---|---|
| I-117 | 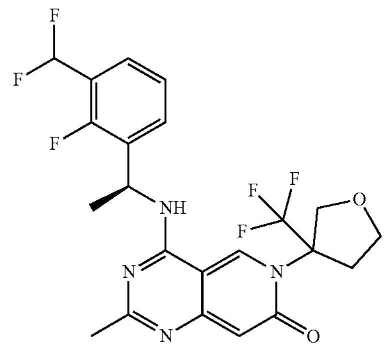 [SMILES: Cc1nc(N[C@@H](C)c2cccc(C(F)F)c2F)c2cn(C3(C(F)(F)F)CCOC3)c(=O)cc2n1] | 1.22 487 | LCMSBAS1 | 9 |
| I-118 | 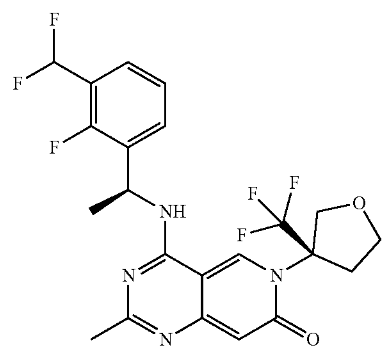 [SMILES: Cc1nc(N[C@@H](C)c2cccc(C(F)F)c2F)c2cn([C@@]3(C(F)(F)F)CCOC3)c(=O)cc2n1] | 1.22 487 | LCMSBAS1 | 20 |
| I-119 | 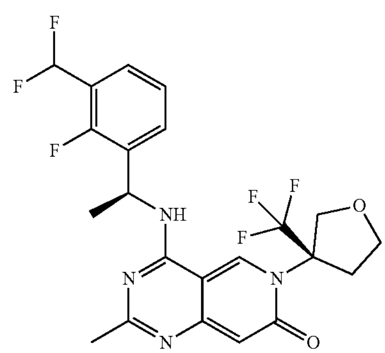 [SMILES: Cc1nc(N[C@@H](C)c2cccc(C(F)F)c2F)c2cn([C@@]3(C(F)(F)F)CCOC3)c(=O)cc2n1] | 1.22 487 | LCMSBAS1 | 5 |
| I-120 | 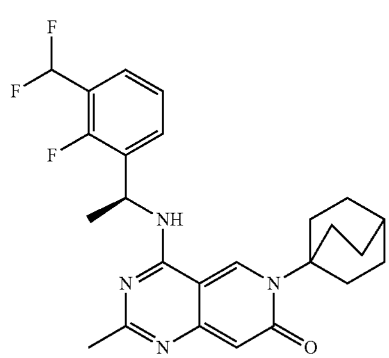 [SMILES: Cc1nc(N[C@@H](C)c2cccc(C(F)F)c2F)c2cn(C34CCC(CC3)CC4)c(=O)cc2n1] | 1.33 457 | LCMSBAS1 | 6 |

TABLE 22-continued

| # | structure | t_ret [min] [M + H]+ | HPLC method | IC_50 [nM] |
|---|---|---|---|---|
| I-121 | 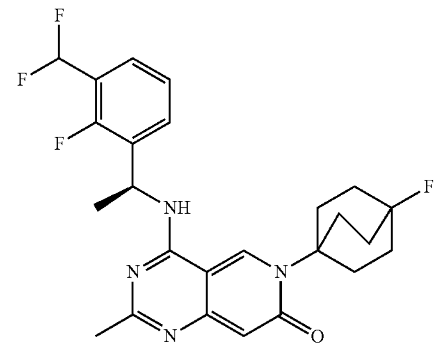 [SMILES: Cc1nc(N[C@@H](C)c2cccc(C(F)F)c2F)c2cn(C34CCC(F)(CC3)CC4)c(=O)cc2n1] | 1.28 475 | LCMSBAS1 | 5 |
| I-122 | 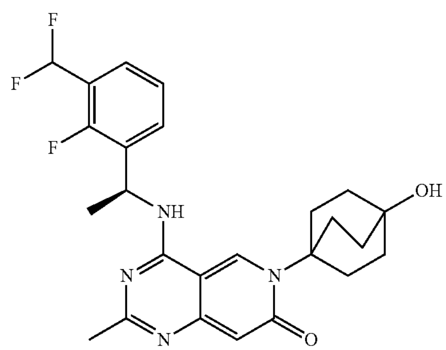 [SMILES: Cc1nc(N[C@@H](C)c2cccc(C(F)F)c2F)c2cn(C34CCC(O)(CC3)CC4)c(=O)cc2n1] | 1.14 473 | LCMSBAS1 | 3 |
| I-123 | 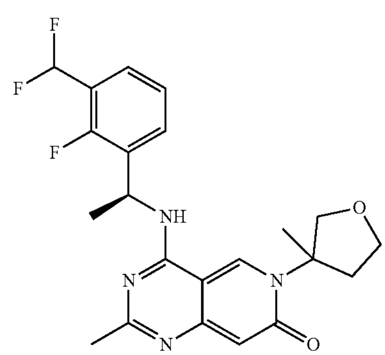 | 1.16 429 | LCMSBAS1 | 3 |
| I-124 | 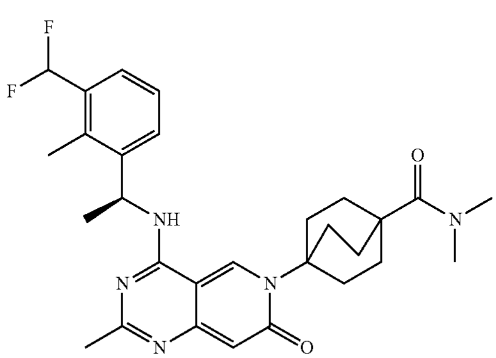 [SMILES: Cc1nc(N[C@@H](C)c2cccc(C(F)F)c2C)c2cn(C34CCC(C(=O)N(C)C)(CC3)CC4)c(=O)cc2n1] | 1.21 524 | LCMSBAS1 | 2 |

TABLE 22-continued
| # | structure | $t_{ret}$ [min] [M + H]$^+$ | HPLC method | IC$_{50}$ [nM] |
|---|---|---|---|---|
| I-125 | 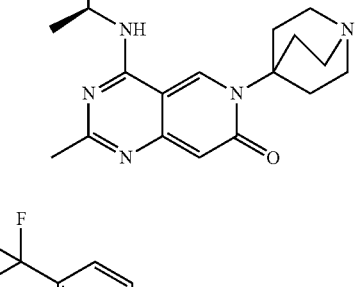 | 1.37 486 | LCMSBAS1 | 2 |
| I-126 | 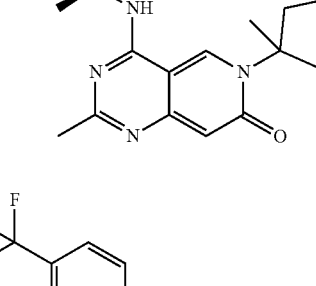 | 1.25 447 | LCMSBAS1 | 5 |
| I-127 | 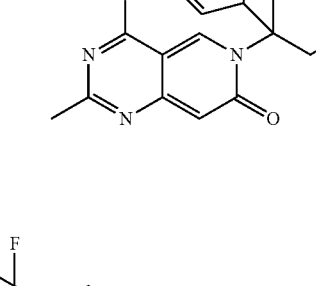 | 1.31 523 | LCMSBAS1 | 23 |
| I-128 | 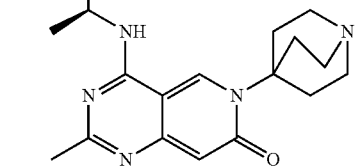 | 1.24 472 | LCMSBAS1 | 2 |

TABLE 22-continued
| # | structure | $t_{ret}$ [min] $[M + H]^+$ | HPLC method | $IC_{50}$ [nM] |
|---|---|---|---|---|
| I-129 | 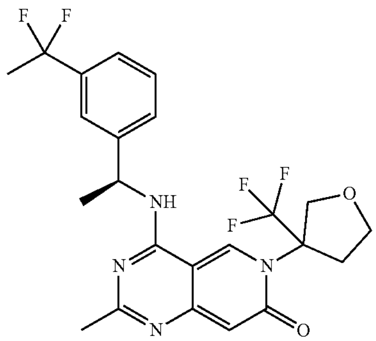 [SMILES: Cc1nc(N[C@@H](C)c2cccc(C(C)(F)F)c2)c2cn(C3(C(F)(F)F)CCOC3)c(=O)cc2n1] | 1.24 483 | LCMSBAS1 | 18 |
| I-130 | 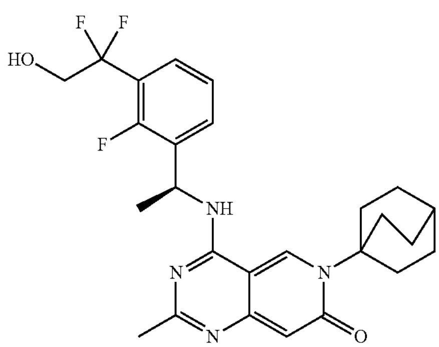 [SMILES: Cc1nc(N[C@@H](C)c2cccc(C(F)(F)CO)c2F)c2cn(C34CCC(CC3)CC4)c(=O)cc2n1] | 1.20 487 | LCMSBAS1 | 1 |
Experimental Procedure for the Synthesis of I-131
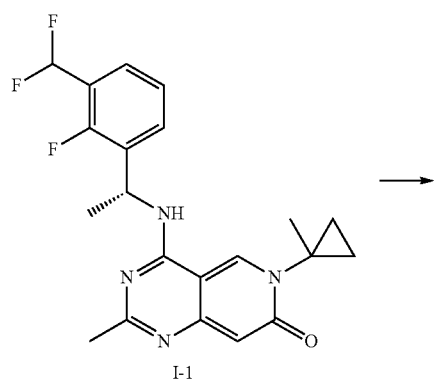
I-1
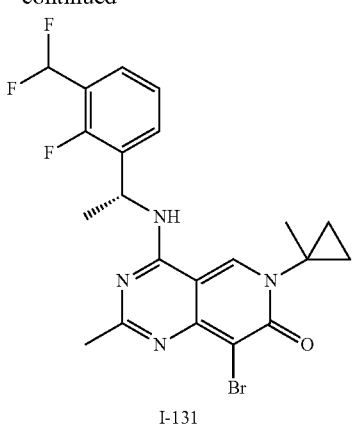
I-131

I-1 (179.0 mg, 0.445 mmol, 1.0 equiv.) is dissolved in acetonitrile (1.5 mL). A solution of NBS (80.8 mg, 0.454 mmol, 1.0 equiv.) in acetonitrile (0.5 mL) is added dropwise and the resulting mixture stirred for 1 h at room temperature until complete conversion of the starting material is observed. The reaction mixture is diluted with DCM and washed with water. Organic layers are combined, dried (MgSO$_4$) and concentrated under reduced pressure to provide the desired product I-131.

The following compounds I (table 23) are available in an analogous manner starting from different compounds I. The crude products are purified by chromatography if necessary.

TABLE 23

| # | structure | $t_{ret}$ [min]<br>[M + H]$^+$ | HPLC method |
|---|---|---|---|
| I-131 | 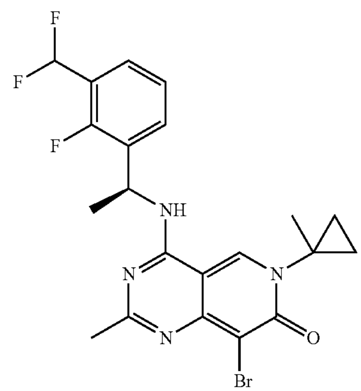 [SMILES: Cc1nc(N[C@@H](C)c2cccc(C(F)F)c2F)c2cn(C3(C)CC3)c(=O)c(Br)c2n1] | 1.24<br>481 | LCMSBAS1 |
| I-132 | 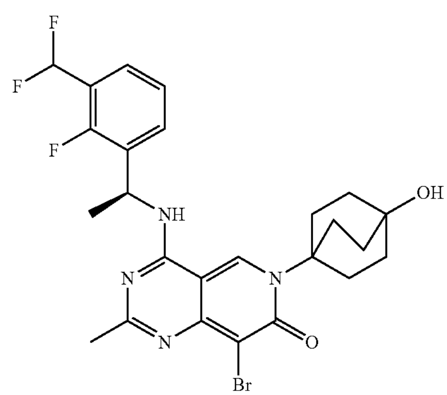 [SMILES: Cc1nc(N[C@@H](C)c2cccc(C(F)F)c2F)c2cn(C34CCC(O)(CC3)CC4)c(=O)c(Br)c2n1] | 0.92<br>551/553 | VAB |
| I-133 | 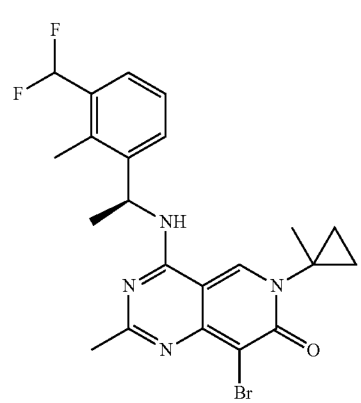 [SMILES: Cc1nc(N[C@@H](C)c2cccc(C(F)F)c2C)c2cn(C3(C)CC3)c(=O)c(Br)c2n1] | 0.94<br>477/479 | VAB |

TABLE 23-continued

| # | structure | t_ret [min] [M + H]+ | HPLC method |
|---|---|---|---|
| I-134 | 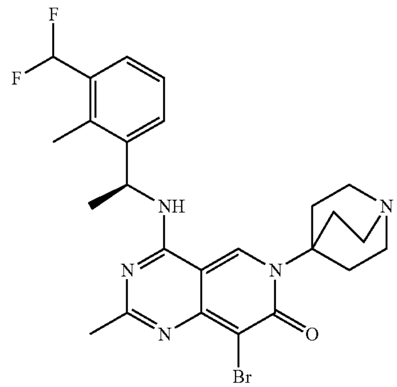 [SMILES: Cc1nc(N[C@@H](C)c2cccc(C(F)F)c2C)c2cn(C34CCN(CC3)CC4)c(=O)c(Br)c2n1] | 0.90 532/534 | VAB |
| I-135 | 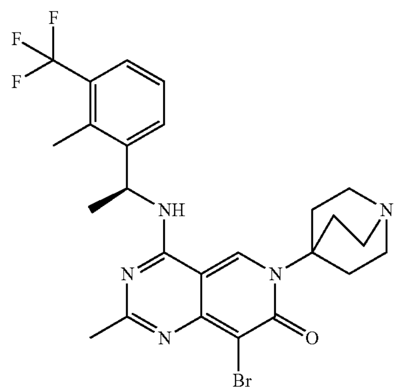 [SMILES: Cc1nc(N[C@@H](C)c2cccc(C(F)(F)F)c2C)c2cn(C34CCN(CC3)CC4)c(=O)c(Br)c2n1] | 0.96 550/552 | VAB |
| I-136 | 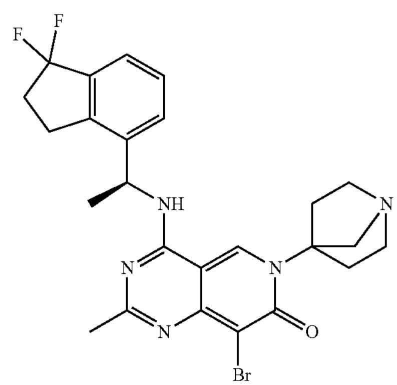 [SMILES: Cc1nc(N[C@@H](C)c2cccc3c2CCC3(F)F)c2cn(C34CCN(CC3)C4)c(=O)c(Br)c2n1] | 0.89 530/532 | VAB |
| I-137 | 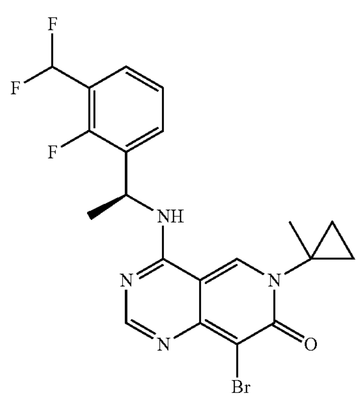 [SMILES: C[C@H](Nc1ncnc2c(Br)c(=O)n(C3(C)CC3)cc12)c1cccc(C(F)F)c1F] | 0.856 467.1/469 | VAB |

TABLE 23-continued

| # | structure | $t_{ret}$ [min] $[M + H]^+$ | HPLC method |
|---|---|---|---|
| I-138 | 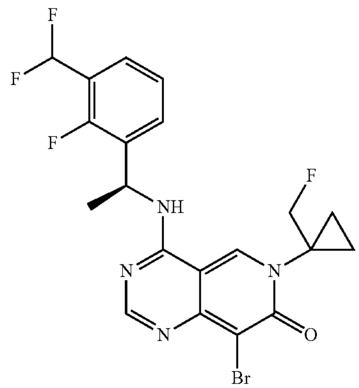 [SMILES: C[C@H](Nc1ncnc2c(Br)c(=O)n(C3(CF)CC3)cc12)c1cccc(C(F)F)c1F] | 0.858<br>485/487 | VAB |
| I-139 | 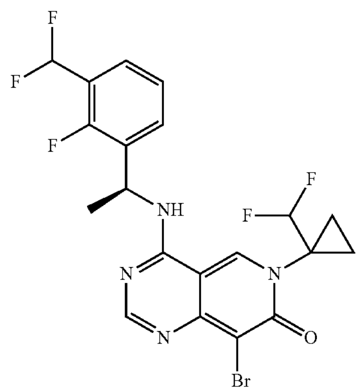 [SMILES: C[C@H](Nc1ncnc2c(Br)c(=O)n(C3(C(F)F)CC3)cc12)c1cccc(C(F)F)c1F] | 0.887<br>503/505.1 | VAB |
| I-140 | 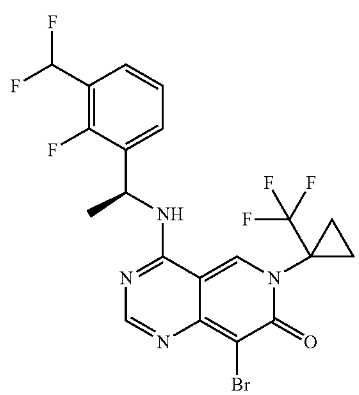 [SMILES: C[C@H](Nc1ncnc2c(Br)c(=O)n(C3(C(F)(F)F)CC3)cc12)c1cccc(C(F)F)c1F] | 0.913<br>521/513 | VAB |
| I-141 | 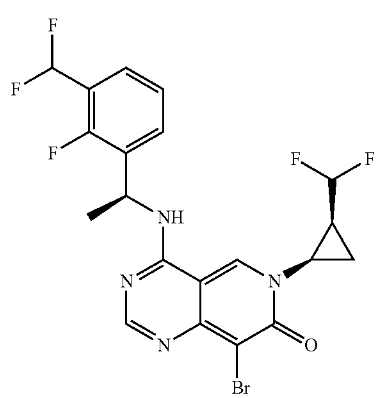 [SMILES: C[C@H](Nc1ncnc2c(Br)c(=O)n([C@@H]3C[C@@H]3C(F)F)cc12)c1cccc(C(F)F)c1F] | 0.872<br>503/505 | VAB |

TABLE 23-continued

| # | structure | t_ret [min] [M + H]+ | HPLC method |
|---|---|---|---|
| I-142 | 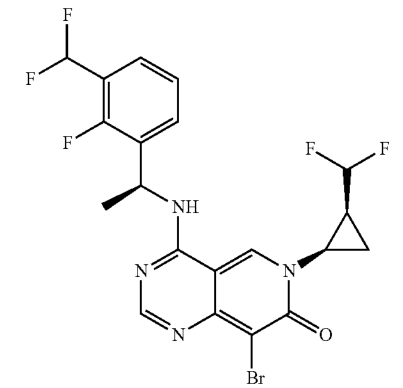 [SMILES: C[C@H](Nc1ncnc2c(Br)c(=O)n([C@@H]3C[C@@H]3C(F)F)cc12)c1cccc(C(F)F)c1F] | 0.872 503/505 | VAB |
| I-143 | 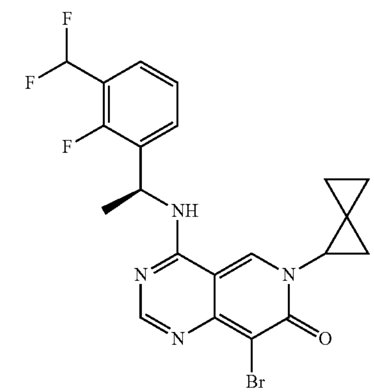 [SMILES: C[C@H](Nc1ncnc2c(Br)c(=O)n(C3CC34CC4)cc12)c1cccc(C(F)F)c1F] | 0.890 479/481 | VAB |
| I-144 | 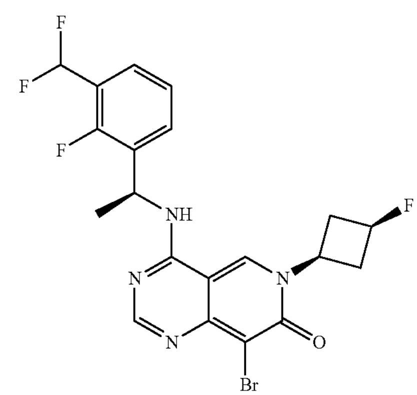 [SMILES: C[C@H](Nc1ncnc2c(Br)c(=O)n([C@H]3C[C@@H](F)C3)cc12)c1cccc(C(F)F)c1F] | 0.805 485/487 | VAB |
| I-145 | 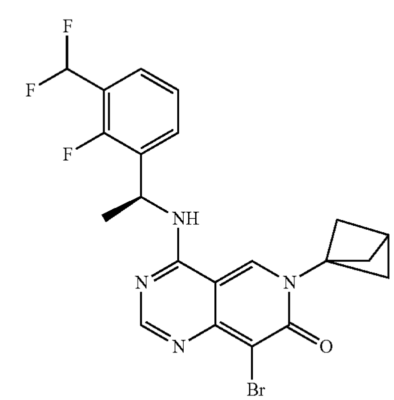 [SMILES: C[C@H](Nc1ncnc2c(Br)c(=O)n(C34CC(C3)C4)cc12)c1cccc(C(F)F)c1F] | 0.900 479/481 | VAB |

TABLE 23-continued

| # | structure | t_ret [min] [M + H]+ | HPLC method |
|---|-----------|----------------------|-------------|
| I-146 | 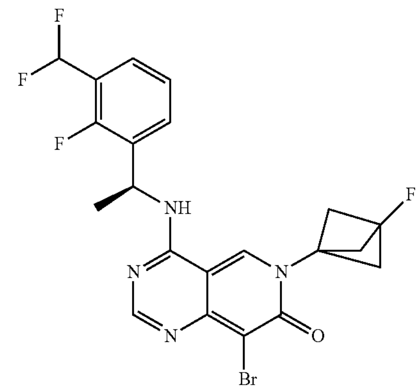 [SMILES: C[C@H](Nc1ncnc2c(Br)c(=O)n(C34CC(F)(C3)C4)cc12)c1cccc(C(F)F)c1F] | 0.914 497/499 | VAB |
| I-147 | 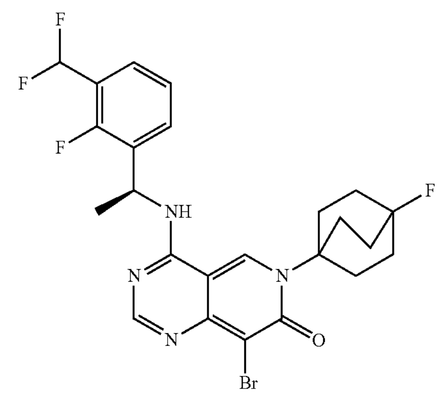 [SMILES: C[C@H](Nc1ncnc2c(Br)c(=O)n(C34CCC(F)(CC3)CC4)cc12)c1cccc(C(F)F)c1F] | 0.950 539/541 | VAB |
| I-148 | 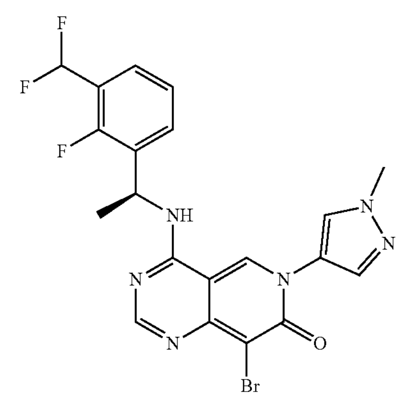 [SMILES: C[C@H](Nc1ncnc2c(Br)c(=O)n(-c3cnn(C)c3)cc12)c1cccc(C(F)F)c1F] | 0.849 493/495 | VAB |
| I-149 | 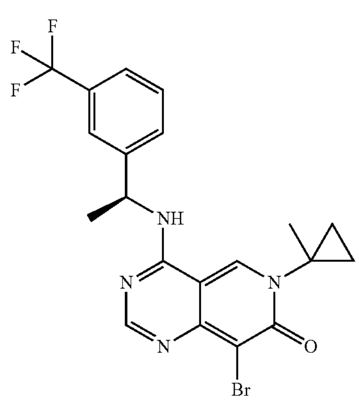 [SMILES: C[C@H](Nc1ncnc2c(Br)c(=O)n(C3(C)CC3)cc12)c1cccc(C(F)(F)F)c1] | 1.21 467 | LCMSBAS1 |

TABLE 23-continued
| # | structure | t_ret [min] [M + H]+ | HPLC method |
|---|---|---|---|
| I-150 | 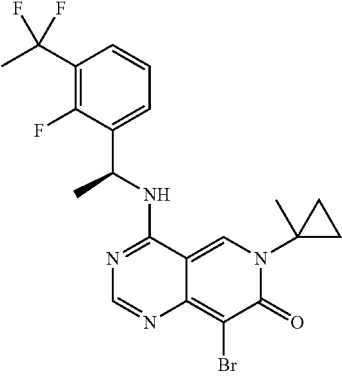 [SMILES: C[C@H](Nc1ncnc2c(Br)c(=O)n(C3(C)CC3)cc12)c1cccc(C(C)(F)F)c1F] | 0.897 481/483 | VAB |
| I-151 | 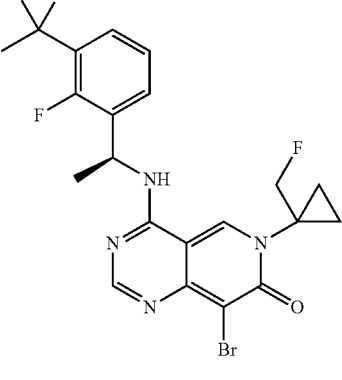 | 0.912 499/501 | VAB |
| I-152 | 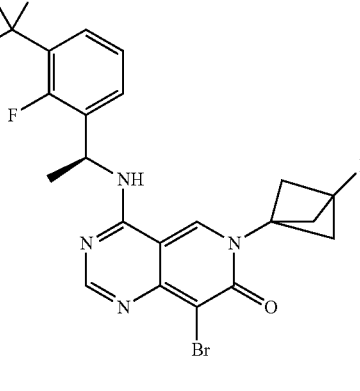 | 0.940 511/513 | VAB |

TABLE 23-continued
| # | structure | $t_{ret}$ [min] [M + H]$^+$ | HPLC method |
|---|---|---|---|
| I-153 | 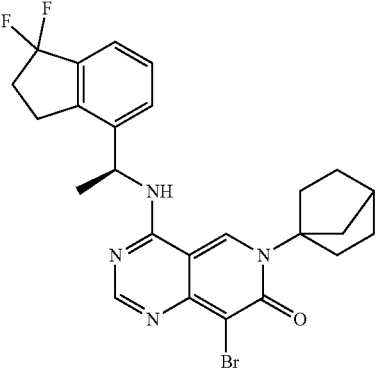 [SMILES: C[C@H](Nc1ncnc2c(Br)c(=O)n(C34CCC(CC3)C4)cc12)c1cccc2c1CCC2(F)F] | 0.976 515/517 | VAB |
| I-154 | 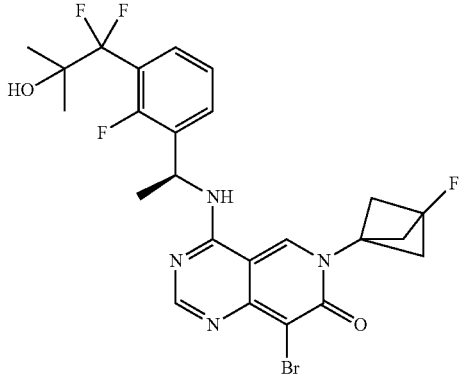 [SMILES: C[C@H](Nc1ncnc2c(Br)c(=O)n(C34CC(F)(C3)C4)cc12)c1cccc(C(F)(F)C(C)(C)O)c1F] | 0.886 555/557 | VAB |
Experimental Procedure for the Synthesis of I-155
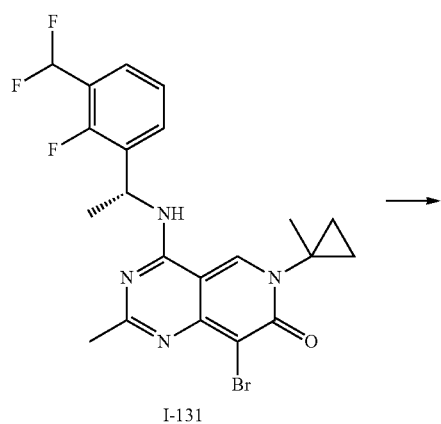
I-131
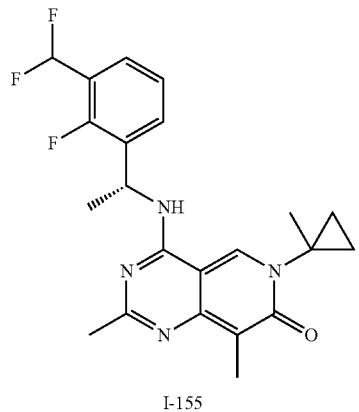
I-155

I-131 (23.0 mg, 0.048 mmol, 1.0 equiv.) is dissolved in dioxane (0.75 mL) and water (0.25 mL). Cesium carbonate (90%, 26.0 mg, 0.072 mmol, 1.5 equiv.), bis(diphenylphosphino)ferrocene]dichloropalladium(II) (complex with DCM) (3.9 mg, 0.005 mmol, 0.1 equiv.) and trimethylboroxine (99%, 7.5 µL, 0.054 mmol, 1.1 equiv.) are added. The flask is flushed with argon and the reaction mixture stirred for 16 h at 100° C. until full conversion of the starting material is observed. The reaction mixture is diluted with DCM and washed with aqueous NaHCO$_3$. Organic layers are combined, dried (MgSO$_4$) and concentrated under reduced pressure. Purification by basic reversed phase chromatography (gradient elution: 25% to 85% acetonitrile in water) furnishes the desired product.

The following compounds I (table 24) are available in an analogous manner starting from different compounds I. The crude products are purified by chromatography if necessary.

TABLE 24

| # | structure | t$_{ret}$ [min] [M + H]$^+$ | HPLC method | IC$_{50}$ [nM] |
|---|---|---|---|---|
| I-155 | 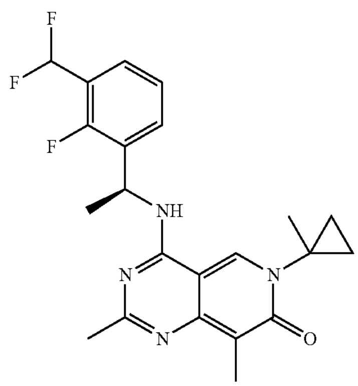 [SMILES: Cc1nc(N[C@@H](C)c2cccc(C(F)F)c2F)c2cn(C3(C)CC3)c(=O)c(C)c2n1] | 1.25 417 | LCMSBAS1 | 5 |
| I-156 | 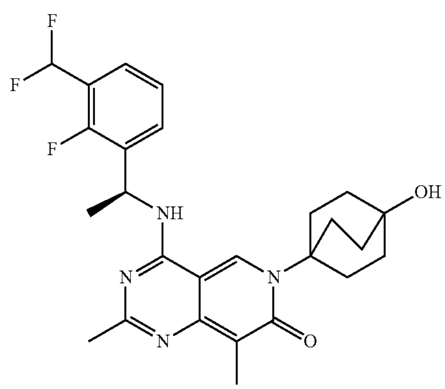 [SMILES: Cc1nc(N[C@@H](C)c2cccc(C(F)F)c2F)c2cn(C34CCC(O)(CC3)CC4)c(=O)c(C)c2n1] | 1.22 487 | LCMSBAS1 | 4 |
| I-157 | 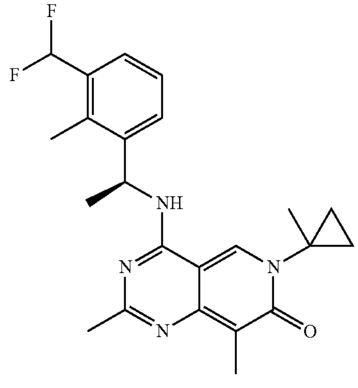 [SMILES: Cc1nc(N[C@@H](C)c2cccc(C(F)F)c2C)c2cn(C3(C)CC3)c(=O)c(C)c2n1] | 1.28 413 | LCMSBAS1 | 5 |

TABLE 24-continued

| # | structure | t_ret [min] [M + H]+ | HPLC method | IC_50 [nM] |
|---|---|---|---|---|
| I-158 | 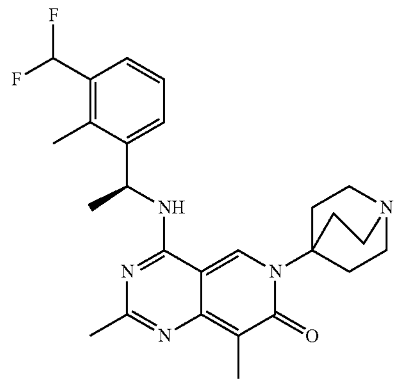 [SMILES: Cc1nc(N[C@@H](C)c2cccc(C(F)F)c2C)c2cn(C34CCN(CC3)CC4)c(=O)c(C)c2n1] | 1.23 468 | LCMSBAS1 | 2 |
| I-159 | 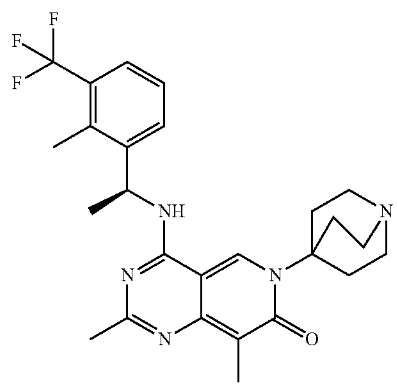 [SMILES: Cc1nc(N[C@@H](C)c2cccc(C(F)(F)F)c2C)c2cn(C34CCN(CC3)CC4)c(=O)c(C)c2n1] | 1.37 488 | LCMSBAS1 | 3 |
| I-160 | 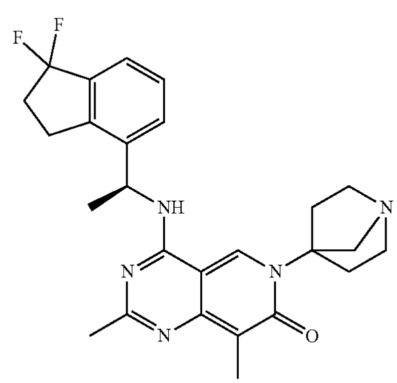 [SMILES: Cc1nc(N[C@@H](C)c2cccc3c2CCC3(F)F)c2cn(C34CCN(CC3)C4)c(=O)c(C)c2n1] | 1.21 466 | LCMSBAS1 | 2 |
| I-161 | 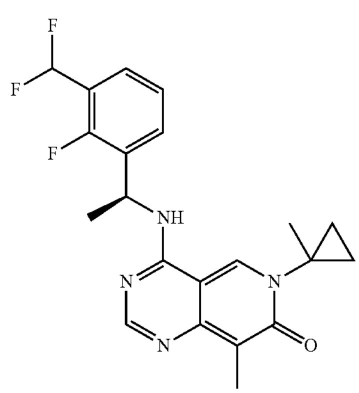 [SMILES: Cc1c(=O)n(C2(C)CC2)cc2c(N[C@@H](C)c3cccc(C(F)F)c3F)ncnc12] | 1.16 403 | LCMSBAS1 | 12 |

TABLE 24-continued

| # | structure | t_ret [min] [M + H]+ | HPLC method | IC50 [nM] |
|---|---|---|---|---|
| I-162 | 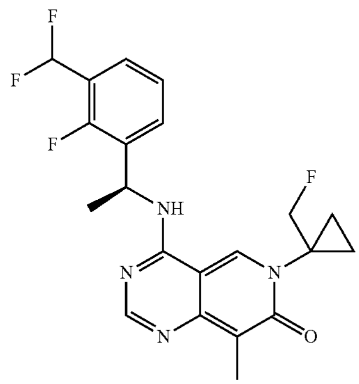 [SMILES: Cc1c(=O)n(C2(CF)CC2)cc2c(N[C@@H](C)c3cccc(C(F)F)c3F)ncnc12] | 1.16 421 | LCMSBAS1 | 7 |
| I-163 | 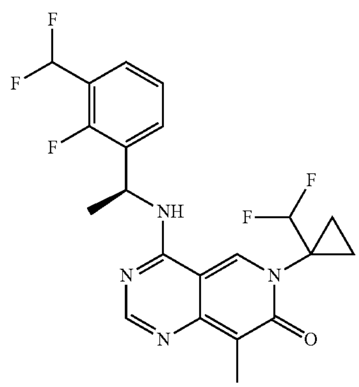 [SMILES: Cc1c(=O)n(C2(C(F)F)CC2)cc2c(N[C@@H](C)c3cccc(C(F)F)c3F)ncnc12] | 1.20 439 | LCMSBAS1 | 15 |
| I-164 | 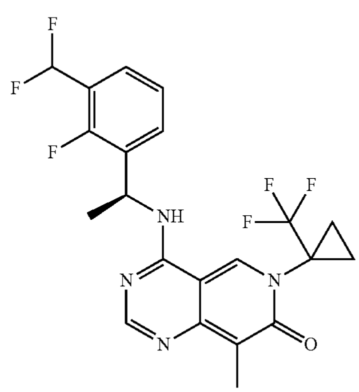 [SMILES: Cc1c(=O)n(C2(C(F)(F)F)CC2)cc2c(N[C@@H](C)c3cccc(C(F)F)c3F)ncnc12] | 1.23 457 | LCMSBAS1 | 13 |
| I-165 | 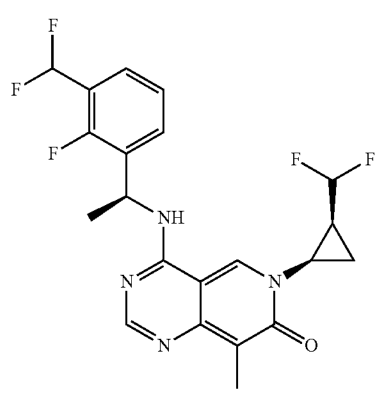 [SMILES: Cc1c(=O)n([C@@H]2C[C@@H]2C(F)F)cc2c(N[C@@H](C)c3cccc(C(F)F)c3F)ncnc12] | 1.17 439 | LCMSBAS1 | 17 |

TABLE 24-continued

| # | structure | t_ret [min] [M + H]+ | HPLC method | IC50 [nM] |
|---|---|---|---|---|
| I-166 | 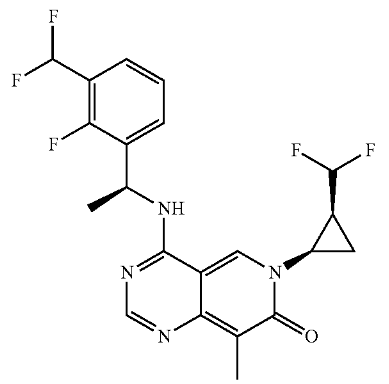 [SMILES: Cc1c(=O)n([C@@H]2C[C@@H]2C(F)F)cc2c(N[C@@H](C)c3cccc(C(F)F)c3F)ncnc12] | 1.18 439 | LCMSBAS1 | 26 |
| I-167 | 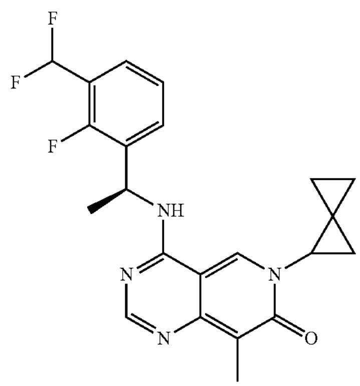 [SMILES: Cc1c(=O)n(C2CC23CC3)cc2c(N[C@@H](C)c3cccc(C(F)F)c3F)ncnc12] | 1.20 415 | LCMSBAS1 | 36 |
| I-168 | 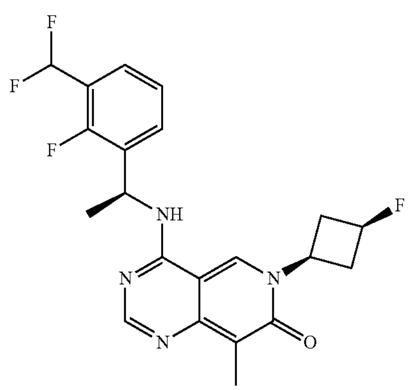 [SMILES: Cc1c(=O)n([C@H]2C[C@@H](F)C2)cc2c(N[C@@H](C)c3cccc(C(F)F)c3F)ncnc12] | 1.16 421 | LCMSBAS1 | 9 |
| I-169 | 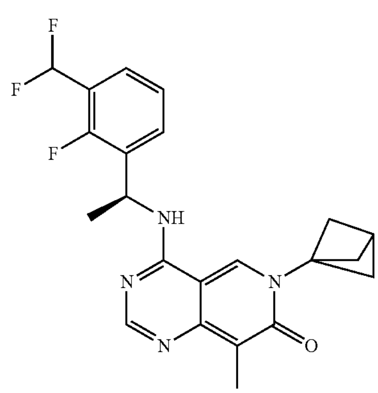 [SMILES: Cc1c(=O)n(C23CC(C2)C3)cc2c(N[C@@H](C)c3cccc(C(F)F)c3F)ncnc12] | 1.21 415 | LCMSBAS1 | 12 |

TABLE 24-continued

| # | structure | t_ret [min] [M + H]+ | HPLC method | IC50 [nM] |
|---|---|---|---|---|
| I-170 | 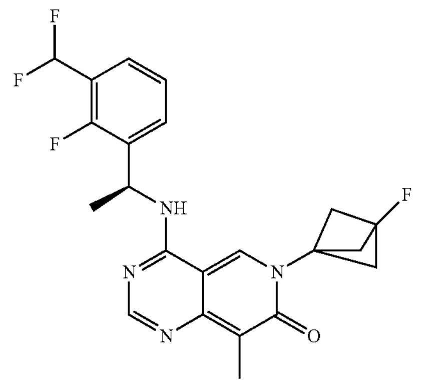 [SMILES: Cc1c(=O)n(C23CC(F)(C2)C3)cc2c(N[C@@H](C)c3cccc(C(F)F)c3F)ncnc12] | 1.22 433 | LCMSBAS1 | 12 |
| I-171 | 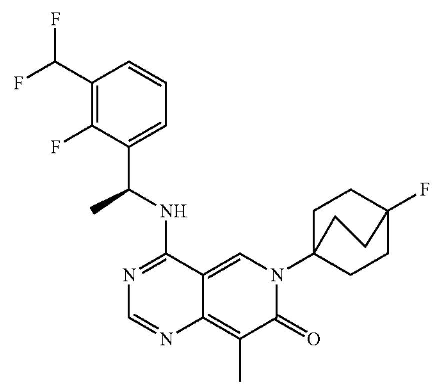 [SMILES: Cc1c(=O)n(C23CCC(F)(CC2)CC3)cc2c(N[C@@H](C)c3cccc(C(F)F)c3F)ncnc12] | 1.31 475 | LCMSBAS1 | 6 |
| I-172 | 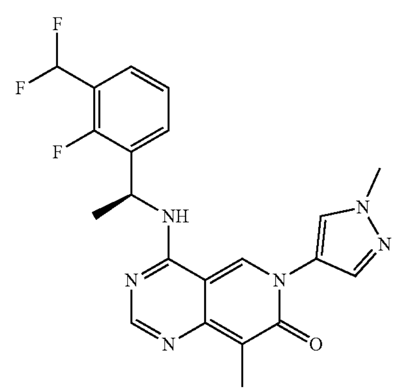 [SMILES: Cc1c(=O)n(-c2cnn(C)c2)cc2c(N[C@@H](C)c3cccc(C(F)F)c3F)ncnc12] | 1.11 429 | LCMSBAS1 | 14 |
| I-173 | 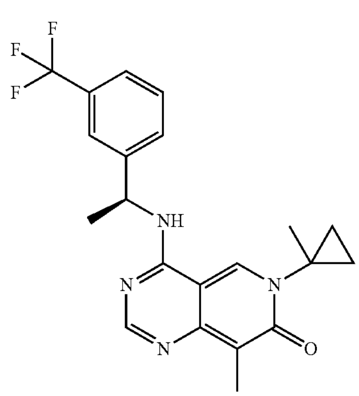 [SMILES: Cc1c(=O)n(C2(C)CC2)cc2c(N[C@@H](C)c3cccc(C(F)(F)F)c3)ncnc12] | 1.22 403 | LCMSBAS1 | 18 |

TABLE 24-continued

| # | structure | t_ret [min] [M + H]+ | HPLC method | IC_50 [nM] |
|---|---|---|---|---|
| I-174 | 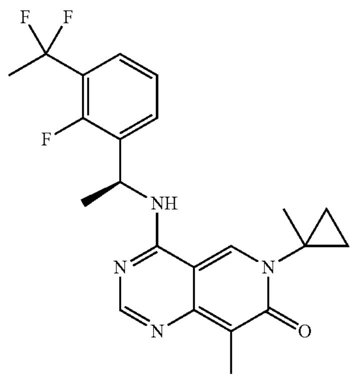 [SMILES: Cc1c(=O)n(C2(C)CC2)cc2c(N[C@@H](C)c3cccc(C(C)(F)F)c3F)ncnc12] | 1.21 417 | LCMSBAS1 | 9 |
| I-175 | 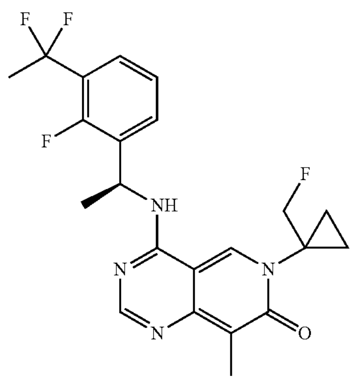 [SMILES: Cc1c(=O)n(C2(CF)CC2)cc2c(N[C@@H](C)c3cccc(C(C)(F)F)c3F)ncnc12] | 1.21 435 | LCMSBAS1 | 13 |
| I-176 | 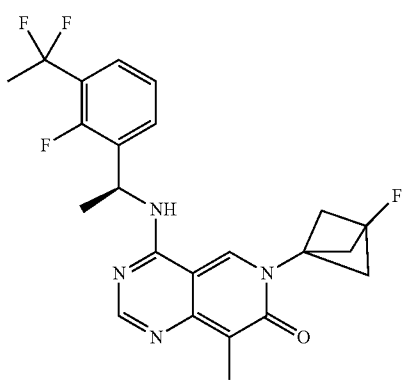 [SMILES: Cc1c(=O)n(C23CC(F)(C2)C3)cc2c(N[C@@H](C)c3cccc(C(C)(F)F)c3F)ncnc12] | 1.28 447 | LCMSBAS1 | 10 |
| I-177 | 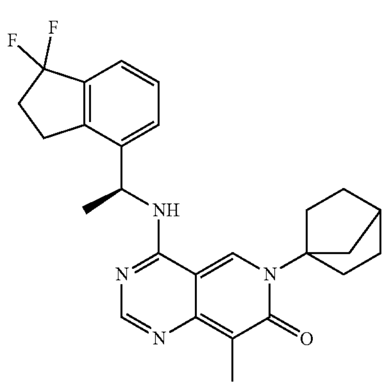 [SMILES: Cc1c(=O)n(C23CCC(CC2)C3)cc2c(N[C@@H](C)c3cccc4c3CCC4(F)F)ncnc12] | 1.34 451 | LCMSBAS1 | 2 |

TABLE 24-continued

| # | structure | $t_{ret}$ [min] $[M+H]^+$ | HPLC method | $IC_{50}$ [nM] |
|---|---|---|---|---|
| I-178 | 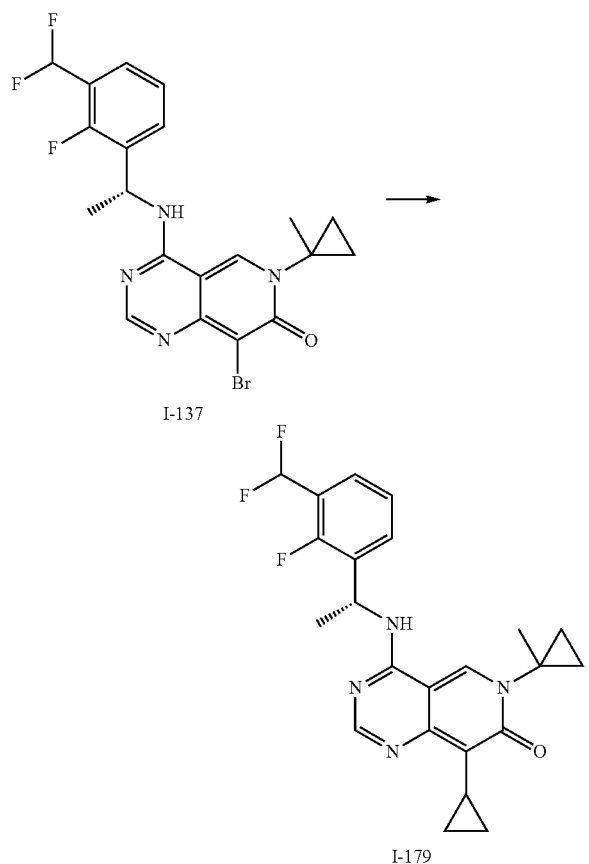 | 1.18 491 | LCMSBAS1 | 5 |

Experimental Procedure for the Synthesis of I-179

I-137 (50.0 mg, 0.107 mmol, 1.0 equiv.) is dissolved in dioxane (0.8 mL) and water (0.2 mL). Potassium carbonate (90%, 33.0 mg, 0.214 mmol, 2.0 equiv.), bis(diphenylphosphino)ferrocene]dichloropalladium(II) (complex with DCM) (9.0 mg, 0.011 mmol, 0.1 equiv.) and cyclopropylboronic acid (14.0 mg, 0.161 mmol, 1.5 equiv.) are added. The flask is flushed with argon and the reaction mixture is stirred for 4 h at 100° C. until full conversion of the starting material is observed. The reaction mixture is diluted with DCM and washed with aqueous $NaHCO_3$. Organic layers are combined, dried ($MgSO_4$) and concentrated under reduced pressure. Purification by basic reversed phase chromatography (gradient elution: 25% to 85% acetonitrile in water) furnishes the desired product (HPLC method: LCMS-BAS1, $t_{ret.}$=1.27 min; $[M+H]^+$=429; $IC_{50}$=11 nM).

The following Examples describe the biological activity of the compounds according to the invention, without restricting the invention to these Examples.

Compounds of formula (I) are characterized by their many possible applications in the therapeutic field.

KRAS::SOS1 AlphaScreen Binding Assay

This assay can be used to examine the potency with which compounds inhibit the protein-protein interaction between SOS1 and KRAS G12D. This demonstrates the molecular mode of action of compounds. Low $IC_{50}$ values are indicative of high potency of the SOS1 inhibitor compound in this assay setting:

Reagents:
GST-tagged SOS1 (564_1049_GST_TEV_ECO) produced in-house
GST-TEV-SOS1 (564-1049) is purchased from Viva Biotech Ltd.
6×His-Tev-K-RasG12D(1-169)Avi is purchased from Xtal BioStructures, Inc. (Lot #X129-110)
GDP (Sigma Cat No G7127)
AlphaLISA Glutathione Acceptor Beads (PerkinElmer, Cat No AL109)
AlphaScreen Streptavidin Donor Beads (PerkinElmer Cat No 6760002)
Assay plates: Proxiplate-384 PLUS, white (PerkinElmer, Cat No 6008289)

Assay Buffer:
1×PBS
0.1% BSA
100 μM EDTA or without EDTA ($IC_{50}$S in the tables are measured without EDTA unless they are marked with an asterisk)
0.05% Tween 20

KRAS::SOS1 GDP mix:
10 nM (final assay concentration) KRAS G12D, 10 μM (final assay concentration) GDP and 5 nM (final assay concentration) GST-SOS1 are mixed in assay buffer prior to use and kept at room temperature.

Bead Mix:
AlphaLSA Glutathione Acceptor Beads and AlphaScreen Streptavidin Donor Beads are mixed in assay buffer at a concentration of 10 µg/mL (final assay concentration) each prior to use and kept at room temperature.

Assay Protocol:

Compounds are diluted to a final start concentration of 100 µM and are tested in duplicate. Assay-ready plates (ARPs) are generated using an Access Labcyte Workstation with a Labcyte Echo 550 or 555 acoustic dispenser. For compound a start concentration of 100 µM, 150 nL of compound solution is transferred per well in 11 concentrations in duplicate with serial 1:5 dilutions.

The assay is run using a fully automated robotic system in a darkened room below 100 Lux. 10 µL of KRAS::SOS1 GDP mix is added into columns 1-24 to the 150 nL of compound solution (final dilution in the assay 1:100, final DMSO concentration 1%).

After a 30 minute incubation time 5 µL of bead mix is added into columns 1-23. Plates are kept at room temperature in a darkened incubator. After a further 60 minute incubation, the signal is measured using a PerkinElmer Envision HTS Multilabel Reader using the AlphaScreen specifications from PerkinElmer. Each plate contains the following controls:

diluted DMSO+KRAS::SOS1 GDP mix+bead mix
diluted DMSO+KRAS::SOS1 GDP mix

Result Calculation:

$IC_{50}$ values are calculated and analyzed using a 4 parametric logistic model.

Tables of example compounds disclosed herein contain $IC_{50}$ values determined using the above assay.

Cell Proliferation Assays

Cell proliferation assays are used to examine the potency with which compounds inhibit the SOS1-mediated proliferation, growth and apoptosis of cancer cell lines in vitro. This demonstrates the molecular mode of action of compounds. Low $IC_{50}$ values are indicative of high potency of the SOS1 inhibitor compounds in this assay setting. In particular, it is observed that SOS1 inhibitor compounds demonstrate a potent inhibitory effect on the proliferation of KRAS mutant human cancer cell lines and not on BRAF V600E mutant cancer cell lines or non-addicted KRAS wild-type human cancer cell lines. This confirms the molecular mode of action of the SOS1 inhibitor compounds as selectively targeting cancer cells dependent on RAS-family protein function.

Cell proliferation assays are performed in three-dimensional (3D) anchorage-independent soft-agar conditions with the following human cell lines:

NCI-H358: human non-small cell lung cancer (NSCLC) with a KRAS G12C mutation;

PC-9: human non-small cell lung cancer (NSCLC) with wild-type KRAS and an EGFR del 19 mutation;

NCI-H1792: human non-small cell lung cancer (NSCLC) with a KRAS G12C mutation;

SW900: human non-small cell lung cancer (NSCLC) with a KRAS G12V mutation;

A-549: human non-small cell lung cancer (NSCLC) with a KRAS G12S mutation;

NCI-H2122: human non-small cell lung cancer (NSCLC) with a KRAS G12C mutation;

NCI-H520: human non-small cell lung cancer (NSCLC) with wild-type KRAS; MIA PaCa-2: human pancreatic cancer cell (PAC) with a KRAS G12C mutation;

DLD-1: human colon cancer with a KRAS G13D mutation;

A-375: human melanoma cancer with wildtype KRAS but a BRAFV600E mutation, which is used as a cell line being non-responsive following treatment with a SOS1 inhibitor compound;

All cell lines but PC-9 can be purchased from the American Type Culture Collection (ATCC). PC-9 can be purchased from the European Collection of Authenticated Cell Cultures (ECACC).

Materials Used:

96-well Ultra low binding plates from Corning (CLS2474-24EA);

4% Agarose Gel 1× liquid 40 mL from Gibco (18300-012);

RPMI-1640 Medium (ATCC© 30-2001™);

Leibovitz's L-15 (Gibco, Cat #11415);

F-12K (ATCC, Catalog No. 30-2004);

DMEM (Lonza BE12-604F); Fetal Bovine Serum (FBS) from HyClone (SH30071.03); Alamar Blue from Invitrogen (DAL1100CSTM1)

Cell Culture:

NCI-H358 cells (ATCC HTB-182), DLD-1 cells (ATCC CCL-221), NCI-H520 cells (ATCC HTB-182), PC-9 cells (ECACC 90071810), NCI-H1792 cells (ATCC CRL-5895) and NCI-H2122 cells (ATCC CRL-5985) are grown in cell culture flasks (175 cm$^2$) using RPMI medium. SW900 cells (ATCC HTB-59) are grown in Leibovitz's L-15 medium, A-549 cells (ATCC CCL-185) are grown in F12K medium, MIA PaCa-2 cells (ATCC CRL-1420) and A-375 (ATCC-CRL-1619) are grown in DMEM medium. Cell culture medium for all listed cell lines is supplemented with 10% FBS. Cultures are incubated at 37° C. and 5% $CO_2$ in a humidified atmosphere, with medium change or subcultivation performed 2-3 times a week. SW900 cells are cultured without addition of $CO_2$.

Assay Conditions:

The assay set-up is composed of the following:

A bottom layer consisting of 90 µL medium including 1.2% agarose

A cell-layer consisting of 60 µL medium including 0.3% agarose

A top-layer consisting of 30 µL medium including the test compounds (without agarose)

For preparation of the bottom layer, 4% agarose (microwave-heated) is mixed with culture medium (incl. 2% FBS for all cell lines but SW900, for SW900 10% FCS was used to achieve cellular growth) to a final dilution of 1.2% agarose in medium. Each well is filled with 90 µL of the bottom layer suspension and cooled to room temperature for 1 h. For the cell-layer, cells are trypsinized, counted and plated in 60 µL culture medium (2% FBS) including 0.3% agarose (1500 cells per well). After cooling to room temperature for 1 h, plates are incubated overnight at 37° C. and 5% $CO_2$ in a humidified atmosphere. The next day the compounds (30 µL of serial dilutions) are added in triplicates. The concentration of the test compounds covers a range between 10 micromolar and 0.13 nanomolar minimum. Compounds (Stock: 10 mM in 100% DMSO) are diluted in medium. Cells are incubated at 37° C. and 5% $CO_2$ in a humidified atmosphere for 14 days.

Detection:

20 µL/well of AlamarBlue suspension is added per well and incubated 4-24 hours in the incubator. Fluorescence intensity is determined using a fluorescence reader (2030 VICTOR X5, Perkin Elmer). The excitation wavelength is 544/15 nm, emission 590 nm. In monotherapy data is fitted by iterative calculation using a sigmoidal curve analysis program (GraphPAD Prism) with variable hill slope to ascertain $IC_{50}$ values.

ERK Phosphorylation Assay

ERK phosphorylation assays are used to examine the potency with which compounds inhibit the SOS1-mediated signal transduction in a KRAS mutant human cancer cell line in vitro. This demonstrates the molecular mode of action of compounds by interfering with the RAS-family protein signal transduction cascade. Low $IC_{50}$ values are indicative of high potency of the SOS1 inhibitor compounds in this assay setting. It is observed that SOS1 inhibitor compounds demonstrate an inhibitory effect on ERK phosphorylation in a KRAS mutant human cancer cell line, thus confirming the molecular mode of action of the SOS1 inhibitor compounds on RAS-family protein signal transduction.

ERK phosphorylation assays are performed using the following human cell lines:

DLD-1 (ATCC CCL-221): human colon cancer with a KRAS G13D mutation;

Materials Used:
RPMI-1640 Medium (ATCC®30-2001™)
Fetal Bovine Serum (FBS) from HyClone (SH30071.03)
Non-essential amino acids from Thermo Fischer Scientific (Ser. No. 11/140,035)
Pyruvate from Thermo Fischer Scientific (Ser. No. 11/360,039)
Glutamax from Thermo Fischer Scientific (35050061)
384 plates from Greiner Bio-One (781182)
Proxiplate™ 384 from PerkinElmer Inc. (6008280)
AlphaLISA SureFire Ultra p-ERK1/2 (Thr202/Tyr204) Assay Kit (ALSU-PERK-A500)
EGF from Sigma (E4127)
Acceptor Mix: Protein A Acceptor Beads from PerkinElmer (6760137M)
Donor Mix: AlphaScreen Streptavidin-coated Donor Beads from PerkinElmer (6760002)
Trametinib
Staurosporine from Sigma Aldrich (S6942)

Assay Setup:

DLD-1 cells (ATCC CCL-221) are seeded at 50,000 cells per well in/60 µL of RPMI with 10% FBS, non-essential amino acids, pyruvate and glutamax in Greiner TC 384 plates. The cells are incubated for 1 h at room temperature and then incubated overnight in an incubator at 37° C. and 5% $CO_2$ in a humidified atmosphere. 60 nL compound solution (10 mM DMSO stock solution) is then added using a Labcyte Echo 550 device. After a 1 h incubation in the aforementioned incubator, 3 µL Epidermal Growth Factor (EGF, final concentration 50 ng/mL) is added. 10 minutes later the medium is removed, and the cells lysed by addition of 20 µL of 1.6-fold lysis buffer from the AlphaLSA SureFire Ultra pERK/2 (Thr202/Tyr204) Assay Kit with added protease inhibitors, 100 nM trametinib+100 nM staurosporine. After 20 minutes of incubation at room temperature with shaking, 6 µL of each lysate sample is transferred to a 384-well Proxiplate and analyzed for pERK (Thr202/Tyr204) with the AlphaLISA SureFire Ultra pERK1/2 (Thr202/Tyr204) Assay Kit. 3 µL Acceptor Mix and 3 µL Donor Mix are added under subdued light and incubated for 2 h at room temperature in the dark, before the signal is measured on a Perkin Elmer Envision plate reader using 384 AlphaScreen settings for Proxiplates. Data are fitted by iterative calculation with variable hill slope. The sigmoidal curve slope is fitted using a default fitting curve to ascertain $IC_{50}$ values.

Table 25 shows data obtained with the disclosed assay for a selection of compounds (I) according to the invention.

TABLE 25

| # | pERK [nM] |
|---|---|
| I-21 | 113 |
| I-23 | 111 |
| I-37 | 61 |
| I-38 | 33 |
| I-39 | 62 |
| I-45 | 47 |
| I-49 | 81 |
| I-52 | 96 |
| I-53 | 74 |
| I-57 | 63 |
| I-58 | 89 |
| I-59 | 113 |
| I-61 | 95 |
| I-73 | 88 |
| I-87 | 100 |
| I-97 | 81 |
| I-101 | 79 |
| I-102 | 67 |
| I-103 | 70 |
| I-104 | 87 |
| I-106 | 113 |
| I-108 | 77 |
| I-119 | 70 |
| I-121 | 93 |
| I-123 | 118 |
| I-124 | 85 |
| I-126 | 51 |
| I-130 | 38 |
| I-156 | 57 |
| I-157 | 104 |
| I-171 | 93 |
| I-176 | 120 |
| I-177 | 91 |

Metabolic (Microsomal) Stability Assay:

The metabolic degradation of the test compound is assayed at 37° C. with pooled liver microsomes (mouse (MLM), rat (RLM) or human (HLM)). The final incubation volume of 74 µL per time point contains TRIS buffer (pH 7.5; 0.1 M), magnesium chloride (6.5 mM), microsomal protein (0.5 mg/mL for mouse/rat, 1 mg/mL for human specimens) and the test compound at a final concentration of 1 µM. Following a short preincubation period at 37° C., the reactions are initiated by addition of 8 µL beta-nicotinamide adenine dinucleotide phosphate, reduced form (NADPH, 10 mM) and terminated by transferring an aliquot into solvent after different time points. Additionally, the NADPH-independent degradation is monitored in incubations without NADPH, terminated at the last time point by addition of acetonitrile. The quenched incubations are pelleted by centrifugation (1811 g, 5 min). An aliquot of the supernatant is assayed by LC-MS/MS for the amount of parent compound. In vitro intrinsic clearance ($CL_{int,in\ vitro}$) is calculated from the time course of the disappearance of the test drug during the microsomal incubation. Each plot is fitted to the first-order elimination rate constant as $C(t)=C_0 \ast \exp(-ke \ast t)$, where $C(t)$ and $C_0$ are the concentration of unchanged test drug at incubation time t and that at preincubation and ke is the disappearance rate constant of the unchanged drug. Subsequently, $CL_{int,in\ vitro}$ (µL $min^{-1}$·amount protein) values are converted to $CL_{int,in\ vitro}$ (mL $min^{-1}$·$kg^{-1}$) for the whole body. $CL_{int,in\ vitro}$ data are scaled up using physiological parameters. For better across species comparison the predicted clearance is expressed as percent of the liver blood flow [% QH] in the individual species. In general, high stability (corresponding to low % QH) of the compounds across species is desired.

Table 26 shows metabolic stability data obtained with the disclosed assay for a selection of compounds (I) according to the invention.

TABLE 26

| # | MLM [% QH] | RLM [% QH] | HLM [% QH] |
|---|---|---|---|
| I-3 | 51 | <23 | <24 |
| I-4 | 46 | <23 | <24 |
| I-10 | 41 | 40 | <24 |
| I-13 | <24 | 52 | <24 |
| I-14 | 26 | 56 | 27 |
| I-25 | <24 | <23 | <24 |
| I-27 | 88 | <23 | <24 |
| I-47 | <24 | 29 | 24 |
| I-50 | <24 | <23 | <24 |
| I-51 | <24 | 49 | <24 |
| I-54 | 55 | <23 | <24 |
| I-69 | <24 | 40 | <24 |
| I-71 | <24 | <23 | <24 |
| I-78 | <24 | <23 | <24 |
| I-80 | 50 | <23 | <24 |
| I-81 | 64 | <23 | <24 |
| I-83 | <24 | 42 | <24 |
| I-84 | <24 | 29 | <24 |
| I-85 | 55 | <23 | 24 |
| I-86 | 33 | <23 | <24 |
| I-88 | <24 | <23 | 24 |
| I-90 | <24 | <23 | <24 |
| I-96 | 30 | <23 | <24 |
| I-97 | <24 | <23 | <24 |
| I-98 | <24 | <23 | <24 |
| I-101 | 59 | <23 | 36 |
| I-128 | <24 | <23 | 29 |
| I-161 | 44 | <23 | 31 |
| I-165 | 54 | <23 | <24 |
| I-166 | 48 | 38 | 24 |
| I-169 | 64 | 44 | <24 |
| I-170 | 51 | 37 | <24 |
| I-172 | 53 | <23 | <24 |

Time Dependent Inhibition of CYP3A4 assay (TDI3A4):

The time dependent inhibition towards CYP3A4 is assayed in human liver microsomes (0.02 mg/mL) with midazolam (15 µM) as a substrate. The test compounds are preincubated in presence of NADPH with human liver microsomes (0.2 mg/mL) at a concentration of 25 uM for 0 min and 30 min. After preincubation, the incubate is diluted 1:10 and the substrate midazolam is added for the main incubation (15 min). The main incubation is quenched with acetonitrile and the formation of hydroxy-midazolam is quantified via LC/MS-MS. The formation of hydroxy-midazolam from the 30 min preincubation relative to the formation from the 0 min preincubation is used as a readout. Values of less than 100% mean that the substrate midazolam is metabolized to a lower extend upon 30 min preincubation compared to 0 min preincubation. In general low effects upon 30 min preincubation are desired (corresponding to values close to 100%)

Table 27 shows data obtained with the disclosed assay for a selection of compounds (I) according to the invention.

TABLE 27

| # | TDI 3A4 [%] |
|---|---|
| I-20 | 93 |
| I-22 | 87 |
| I-25 | 90 |
| I-49 | 92 |
| I-50 | 82 |
| I-53 | 84 |
| I-54 | 84 |
| I-57 | 87 |

TABLE 27-continued

| # | TDI 3A4 [%] |
|---|---|
| I-75 | 86 |
| I-80 | 86 |
| I-81 | 85 |
| I-87 | 81 |
| I-89 | 83 |
| I-98 | 85 |
| I-123 | 87 |
| I-125 | 93 |
| I-126 | 88 |
| I-127 | 97 |
| I-128 | 98 |
| I-163 | 82 |
| I-166 | 87 |
| I-169 | 84 |
| I-170 | 82 |
| I-173 | 84 |

Determination of Off-Target Liabilities

There are certain targets (44) which are considered to be all strongly associated with in vivo adverse drug reactions as referenced in the publication *Reducing safety-related drug attrition: the use of in vitro pharmacological profiling*, Nature Review Drug Discovery 11, 909-922 (December 2012). This paper was a collaborative effort between several large pharmaceutical company safety pharmacology groups with the aim of establishing a core panel of in vitro pharmacology assays. Eurofins Cerep (France) commercially offers measurement on its SafetyScreen44™ Panel (comprising these off-targets) for a rational first step in preliminary safety assessments. Compounds (I) according to the invention may be assayed against this panel to investigate off-target liability.

Therapeutic Use

Due to their biological properties the compounds of the invention, their tautomers, racemates, enantiomers, diastereomers, mixtures thereof and the salts of all the above-mentioned forms may be suitable for treating diseases characterised by excessive or abnormal cell proliferation such as cancer.

For example, the following cancers, tumors and other proliferative diseases may be treated with compounds of the invention, without being restricted thereto:

Cancers/tumors/carcinomas of the head and neck: e.g. tumors/carcinomas/cancers of the nasal cavity, paranasal sinuses, nasopharynx, oral cavity (including lip, gum, alveolar ridge, retromolar trigone, floor of mouth, tongue, hard palate, buccal mucosa), oropharynx (including base of tongue, tonsil, tonsillar pilar, soft palate, tonsillar fossa, pharyngeal wall), middle ear, larynx (including supraglottis, glottis, subglottis, vocal cords), hypopharynx, salivary glands (including minor salivary glands);

cancers/tumors/carcinomas of the lung: e.g. non-small cell lung cancer (NSCLC) (squamous cell carcinoma, spindle cell carcinoma, adenocarcinoma, large cell carcinoma, clear cell carcinoma, bronchioalveolar), small cell lung cancer (SCLC) (oat cell cancer, intermediate cell cancer, combined oat cell cancer);

neoplasms of the mediastinum: e.g. neurogenic tumors (including neurofibroma, neurilemoma, malignant schwannoma, neurosarcoma, ganglioneuroblastoma, ganglioneuroma, neuroblastoma, pheochromocytoma, paraganglioma), germ cell tumors (including seminoma, teratoma, non-seminoma), thymic tumors (including thymoma, thymolipoma, thymic carcinoma, thymic carcinoid), mesenchymal tumors (including fibroma, fibrosarcoma, lipoma, liposarcoma, myxoma, mesothelioma, leiomyoma, leiomyosarcoma, rhabdomyosarcoma, xanthogranuloma, mesenchymoma, hemangioma, hemangioendothelioma, hemangiopericytoma, lymphangioma, lymphangiopericytoma, lymphangiomyoma);

cancers/tumors/carcinomas of the gastrointestinal (GI) tract: e.g. tumors/carcinomas/cancers of the esophagus, stomach (gastric cancer), pancreas, liver and biliary tree (including hepatocellular carcinoma (HCC), e.g. childhood HCC, fibrolamellar HCC, combined HCC, spindle cell HCC, clear cell HCC, giant cell HCC, carcinosarcoma HCC, sclerosing HCC; hepatoblastoma; cholangiocarcinoma; cholangiocellular carcinoma; hepatic cystadenocarcinoma; angiosarcoma, hemangioendothelioma, leiomyosarcoma, malignant schwannoma, fibrosarcoma, Klatskin tumor), gall bladder, extrahepatic bile ducts, small intestine (including duodenum, jejunum, ileum), large intestine (including cecum, colon, rectum, anus; colorectal cancer, gastrointestinal stroma tumor (GIST)), genitourinary system (including kidney, e.g. renal pelvis, renal cell carcinoma (RCC), nephroblastoma (Wilms' tumor), hypernephroma, Grawitz tumor; ureter; urinary bladder, e.g. urachal cancer, urothelial cancer; urethra, e.g. distal, bulbomembranous, prostatic; prostate (androgen dependent, androgen independent, castration resistant, hormone independent, hormone refractory), penis);

cancers/tumors/carcinomas of the testis: e.g. seminomas, non-seminomas,

Gynecologic cancers/tumors/carcinomas: e.g. tumors/carcinomas/cancers of the ovary, fallopian tube, peritoneum, cervix, vulva, vagina, uterine body (including endometrium, fundus);

cancers/tumors/carcinomas of the breast: e.g. mammary carcinoma (infiltrating ductal, colloid, lobular invasive, tubular, adenocystic, papillary, medullary, mucinous), hormone receptor positive breast cancer (estrogen receptor positive breast cancer, progesterone receptor positive breast cancer), Her2 positive breast cancer, triple negative breast cancer, Paget's disease of the breast;

cancers/tumors/carcinomas of the endocrine system: e.g. tumors/carcinomas/cancers of the endocrine glands, thyroid gland (thyroid carcinomas/tumors; papillary, follicular, anaplastic, medullary), parathyroid gland (parathyroid carcinoma/tumor), adrenal cortex (adrenal cortical carcinoma/tumors), pituitary gland (including prolactinoma, craniopharyngioma), thymus, adrenal glands, pineal gland, carotid body, islet cell tumors, paraganglion, pancreatic endocrine tumors (PET; non-functional PET, PPoma, gastrinoma, insulinoma, VIPoma, glucagonoma, somatostatinoma, GRFoma, ACTHoma), carcinoid tumors;

sarcomas of the soft tissues: e.g. fibrosarcoma, fibrous histiocytoma, liposarcoma, leiomyosarcoma, rhabdomyosarcoma, angiosarcoma, lymphangiosarcoma, Kaposi's sarcoma, glomus tumor, hemangiopericytoma, synovial sarcoma, giant cell tumor of tendon sheath, solitary fibrous tumor of pleura and peritoneum, diffuse mesothelioma, malignant peripheral nerve sheath tumor (MPNST), granular cell tumor, clear cell sarcoma, melanocytic schwannoma, plexosarcoma, neuroblastoma, ganglioneuroblastoma, neuroepithelioma, extraskeletal Ewing's sarcoma, paraganglioma, extraskeletal chondrosarcoma, extraskeletal osteosarcoma, mesenchymoma, alveolar soft part sarcoma, epithelioid sarcoma, extrarenal rhabdoid tumor, desmoplastic small cell tumor;

sarcomas of the bone: e.g. myeloma, reticulum cell sarcoma, chondrosarcoma (including central, peripheral, clear cell, mesenchymal chondrosarcoma), osteosarcoma (including parosteal, periosteal, high-grade surface, small cell, radiation-induced osteosarcoma, Paget's sarcoma), Ewing's tumor, malignant giant cell tumor, adamantinoma, (fibrous) histiocytoma, fibrosarcoma, chordoma, small round cell sarcoma, hemangioendothelioma, hemangiopericytoma, osteochondroma, osteoid osteoma, osteoblastoma, eosinophilic granuloma, chondroblastoma;

mesothelioma: e.g. pleural mesothelioma, peritoneal mesothelioma; cancers of the skin: e.g. basal cell carcinoma, squamous cell carcinoma, Merkel's cell carcinoma, melanoma (including cutaneous, superficial spreading, lentigo maligna, acral lentiginous, nodular, intraocular melanoma), actinic keratosis, eyelid cancer;

neoplasms of the central nervous system and brain: e.g. astrocytoma (cerebral, cerebellar, diffuse, fibrillary, anaplastic, pilocytic, protoplasmic, gemistocytary), glioblastoma, gliomas, oligodendrogliomas, oligoastrocytomas, ependymomas, ependymoblastomas, choroid plexus tumors, medulloblastomas, meningiomas, schwannomas, hemangioblastomas, hemangiomas, hemangiopericytomas, neuromas, ganglioneuromas, neuroblastomas, retinoblastomas, neurinomas (e.g. acoustic), spinal axis tumors;

lymphomas and leukemias: e.g. B-cell non-Hodgkin lymphomas (NHL) (including small lymphocytic lymphoma (SLL), lymphoplasmacytoid lymphoma (LPL), mantle cell lymphoma (MCL), follicular lymphoma (FL), diffuse large cell lymphoma (DLCL), Burkitt's lymphoma (BL)), T-cell non-Hodgkin lymphomas (including anaplastic large cell lymphoma (ALCL), adult T-cell leukemia/lymphoma (ATLL), cutaneous T-cell lymphoma (CTCL), peripheral T-cell lymphoma (PTCL)), lymphoblastic T-cell lymphoma (T-LBL), adult T-cell lymphoma, lymphoblastic B-cell lymphoma (B-LBL), immunocytoma, chronic B-cell lymphocytic leukemia (B-CLL), chronic T-cell lymphocytic leukemia (T-CLL) B-cell small lymphocytic lymphoma (B-SLL), cutaneous T-cell lymphoma (CTLC), primary central nervous system lymphoma (PCNSL), immunoblastoma, Hodgkin's disease (HD) (including nodular lymphocyte predominance HD (NLPHD), nodular sclerosis HD (NSHD), mixed-cellularity HD (MCHD), lymphocyte-rich classic HD, lymphocyte-depleted HD (LDHD)), large granular lymphocyte leukemia (LGL), chronic myelogenous leukemia (CML), acute myelogenous/myeloid leukemia (AML), acute lymphatic/lymphoblastic leukemia (ALL), acute promyelocytic leukemia (APL), chronic lymphocytic/lymphatic leukemia (CLL), prolymphocytic leukemia (PLL), hairy cell leukemia, chronic myelogenous/myeloid leukemia (CML), myeloma, plasmacytoma, multiple myeloma (MM), plasmacytoma, myelodysplastic syndromes (MDS), chronic myelomonocytic leukemia (CMML);

cancers of unknown primary site (CUP);

All cancers/tumors/carcinomas mentioned above which are characterized by their specific location/origin in the body are meant to include both the primary tumors and the metastatic tumors derived therefrom.

All cancers/tumors/carcinomas mentioned above may be further differentiated by their histopathological classification:

Epithelial cancers, e.g. squamous cell carcinoma (SCC) (carcinoma in situ, superficially invasive, verrucous carcinoma, pseudosarcoma, anaplastic, transitional cell, lymphoepithelial), adenocarcinoma (AC) (well-differentiated, mucinous, papillary, pleomorphic giant cell, ductal, small cell, signet-ring cell, spindle cell, clear cell, oat cell, colloid, adenosquamous, mucoepidermoid, adenoid cystic), mucinous cystadenocarcinoma, acinar cell carcinoma, large cell carcinoma, small cell carcinoma, neuroendocrine tumors (small cell carcinoma, paraganglioma, carcinoid); oncocytic carcinoma;

Nonepithilial cancers, e.g. sarcomas (fibrosarcoma, chondrosarcoma, rhabdomyosarcoma, leiomyosarcoma, hemangiosarcoma, giant cell sarcoma, lymphosarcoma, fibrous histiocytoma, liposarcoma, angiosarcoma, lymphangiosarcoma, neurofibrosarcoma), lymphoma, melanoma, germ cell tumors, hematological neoplasms, mixed and undifferentiatedcarcinomas;

The compounds of the invention may be used in therapeutic regimens in the context of first line, second line, or any further line treatments.

The compounds of the invention may be used for the prevention, short-term or long-term treatment of the above-mentioned diseases, optionally also in combination with radiotherapy and/or surgery.

Of course, the above also includes the use of the compounds of the invention in various methods of treating the above diseases by administering a therapeutically effective dose to a patient in need thereof, as well as the use of these compounds for the manufacture of medicaments for the treatment of such diseases, as well as pharmaceutical compositions including such compounds of the invention, as well as the preparation and/or manufacture of medicaments including such compounds of the invention, and the like.

Combinations with Other Active Substances

The compounds of the invention may be used on their own or in combination with one or several other pharmacologically active substances such as state-of-the-art or standard-of-care compounds, such as e.g. cell proliferation inhibitors, anti-angiogenic substances, steroids or immune modulators/checkpoint inhibitors, and the like.

Pharmacologically active substances which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors and/or of their corresponding receptors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF) and/or their corresponding receptors), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib, bevacizumab and trastuzumab); antimetabolites (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); antitumour antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. *Vinca* alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP activator, Mcl-1, MDM2/MDMX), MEK inhibitors, ERK inhibitors, FLT3 inhibitors, BRD4 inhibitors, IGF-1R inhibitors, TRAILR2 agonists, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYPI7 inhibitors, radiopharmaceuticals, proteasome inhibitors, immunotherapeutic agents such as immune checkpoint inhibitors (e.g. CTLA4, PD1, PD-L1, PD-L2, LAG3, and TIM3 binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), t-cell engagers (e.g. bi-specific T-cell engagers (BiTEs®) like e.g. CD3×BCMA, CD3×CD33, CD3×CD19), PSMA x CD3), tumor vaccines and various chemotherapeutic agents such as amifostin, anagrelid, clodronat, filgrastin, interferon, interferon alpha, leucovorin, procarbazine, levamisole, mesna, mitotane, pamidronate and porfimer.

When two or more substances or principles are to be used as part of a combined treatment regimen, they can be administered via the same route of administration or via different routes of administration, at essentially the same time (i.e. simultaneously, concurrently) or at different times (e.g. sequentially, successively, alternately, consecutively, or according to any other sort of alternating regime).

When the substances or principles are to be administered simultaneously via the same route of administration, they may be administered as different pharmaceutical formulations or compositions or as part of a combined pharmaceutical formulation or composition. Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmacological or therapeutic effect.

Of course, the above includes the preparation and methods of preparing, the compounds of the invention for the combined use with the above combination partners. Also included are the preparation, and methods of preparing, the above-mentioned combination partners for the combined use with the compounds of the invention.

Furthermore, the invention also encompasses kits comprising at least one compound of the invention and one or more other components selected from the group consisting of other drugs used for the treatment of the diseases and disorders as described above, and devices as described below.

Formulations

Suitable preparations for administering the compounds of the invention will be apparent to those with ordinary skill in the art and include for example tablets, pills, capsules, suppositories, lozenges, troches, solutions—particularly solutions for injection (s.c., i.v., i.m.) and infusion (injectables)—elixirs, syrups, sachets, emulsions, inhalatives or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) of the invention with known excipients, for example inert diluents, carriers, disintegrants, adjuvants, surfactants, binders and/or lubricants. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage range of the compounds of formula (I) applicable per day is usually from 1 mg to 2000 mg, preferably from 150 to 1000 mg.

The dosage for intravenous use is from 1 mg to 1000 mg with different infusion rates, preferably between 5 mg and 500 mg with different infusion rates.

However, it may sometimes be necessary to depart from the amounts specified, depending on the body weight, age, the route of administration, severity of the disease, the individual response to the drug, the nature of its formulation and the time or interval over which the drug is administered (continuous or intermittent treatment with one or multiple doses per day). Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

A)

| Tablets | per tablet |
|---|---|
| active substance according to formula (I) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B)

| Tablets | per tablet |
|---|---|
| active substance according to formula (I) ) | 80 mg |
| lactose | 55 mg |
| corn starch | 190 mg |
| microcrystalline cellulose | 35 mg |
| polyvinylpyrrolidone | 15 mg |
| sodiumcarboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

C)

| Tablets | per tablet |
|---|---|
| active substance according to formula (I) | 25 mg |
| lactose | 50 mg |
| microcrystalline cellulose | 24 mg |
| magnesium stearate | 1 mg |
| | 100 mg |

The active substance, lactose and cellulose are mixed together. The mixture is screened, then either moistened with water, kneaded, wet-granulated and dried or dry-granulated or directly final blend with the magnesium stearate and compressed to tablets of suitable shape and size. When wet-granulated, additional lactose or cellulose and magnesium stearate is added and the mixture is compressed to produce tablets of suitable shape and size.

D)

| Ampoule solution | |
|---|---|
| active substance according to formulae (I) | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound selected from the group consisting of

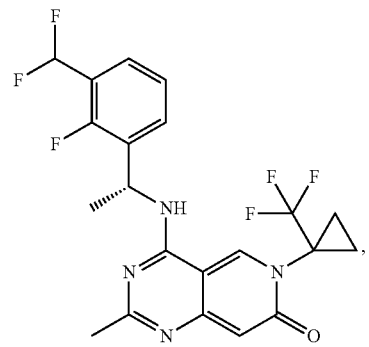

I-4

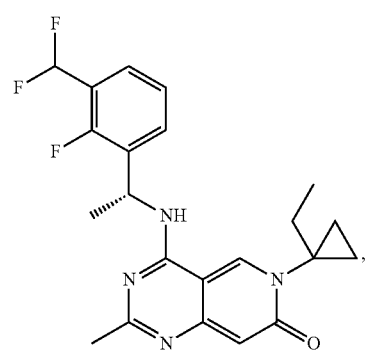

I-5

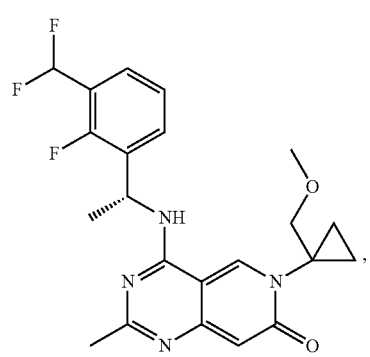

I-6

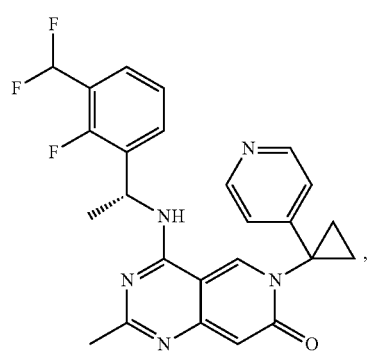

I-7

-continued
I-8
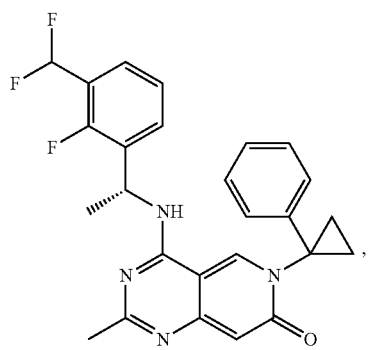
I-9
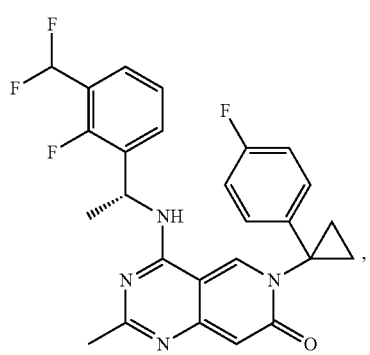
I-10
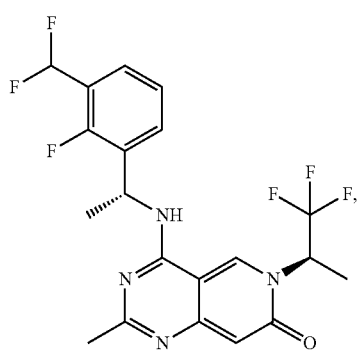
I-11
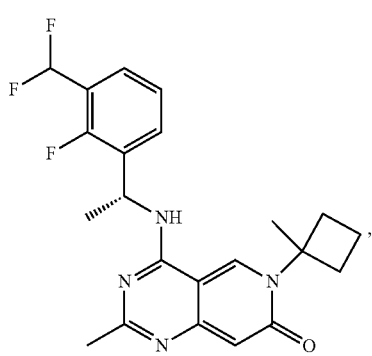
-continued
I-12
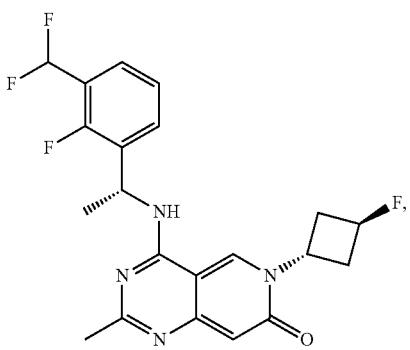
I-14
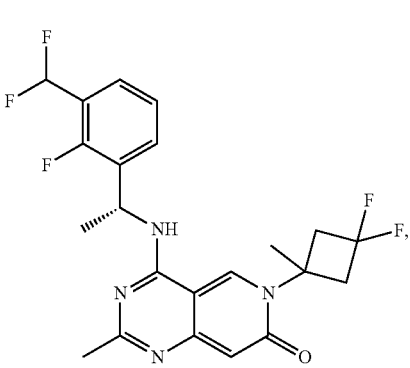
I-15
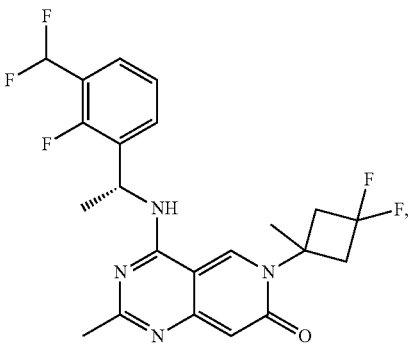
I-16
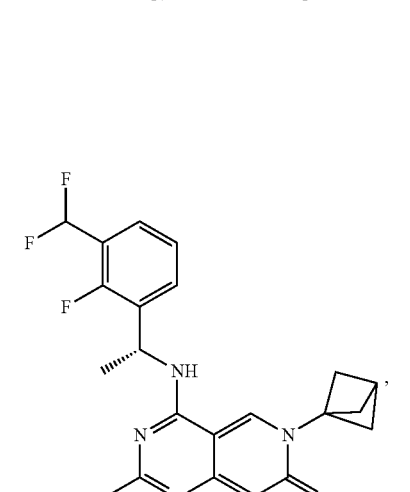

I-17
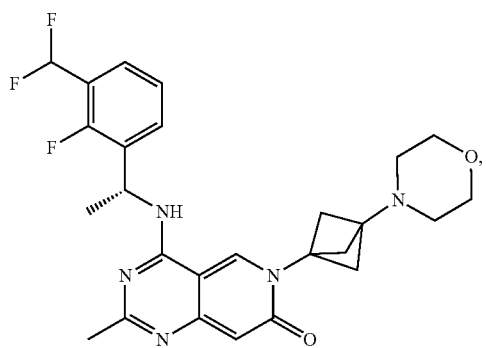
I-18
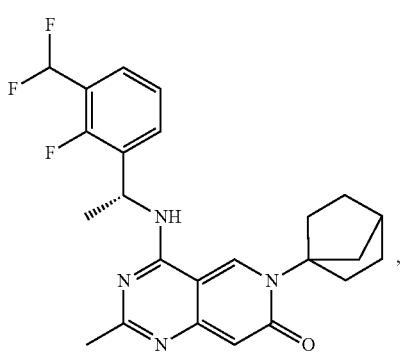
I-19
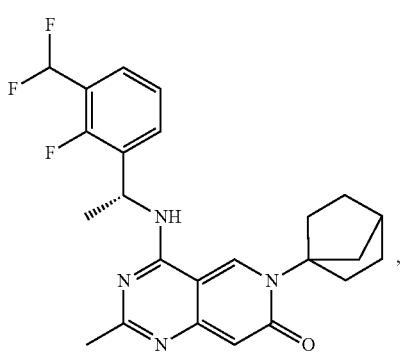
I-22
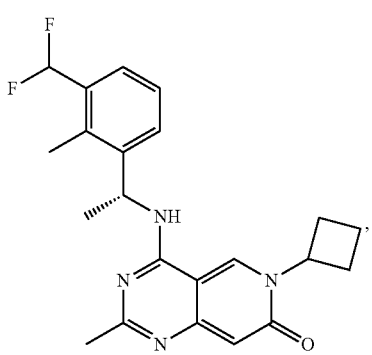
I-23
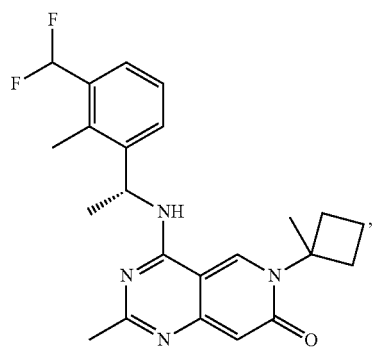
I-24
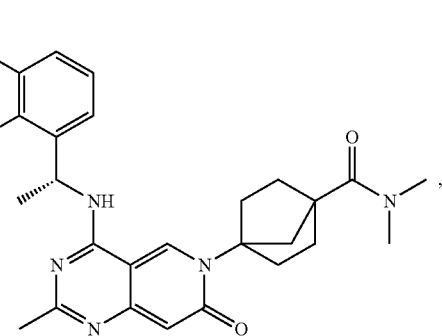
I-25
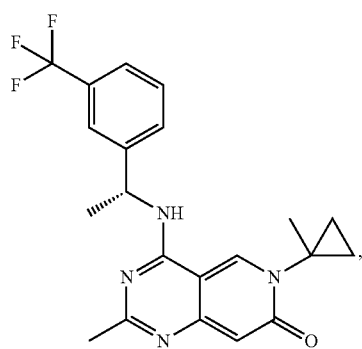
I-26
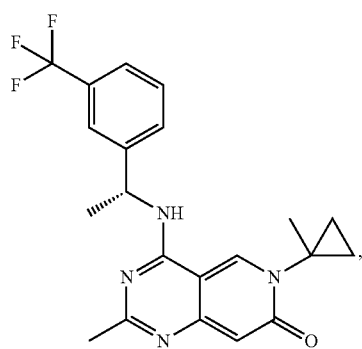

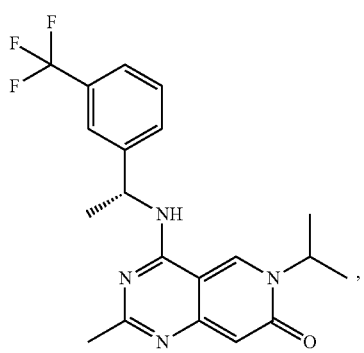
I-27
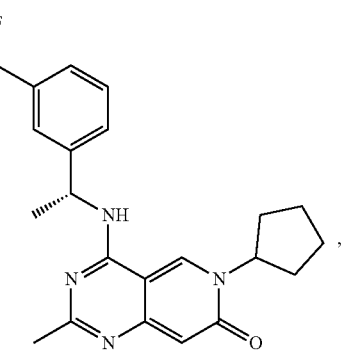
I-28
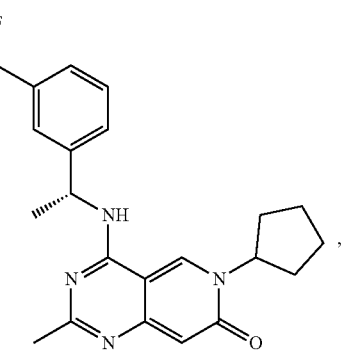
I-29
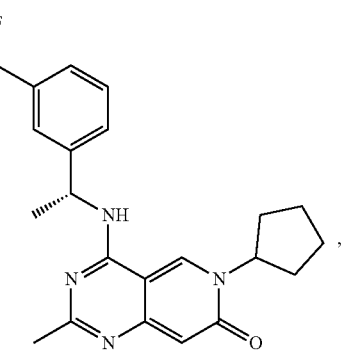
I-30
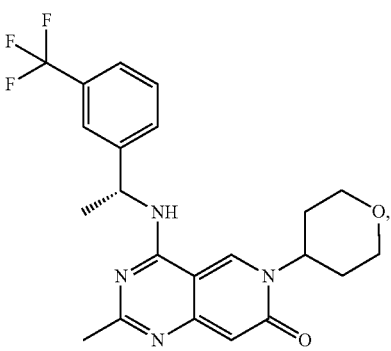
I-31
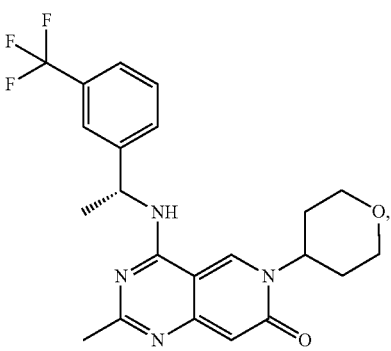
I-32
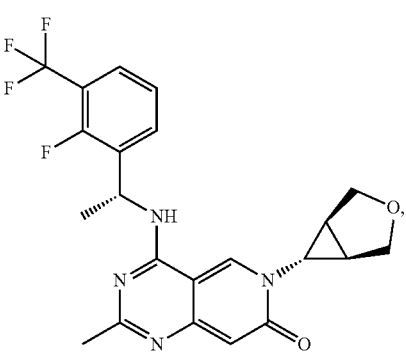
I-33
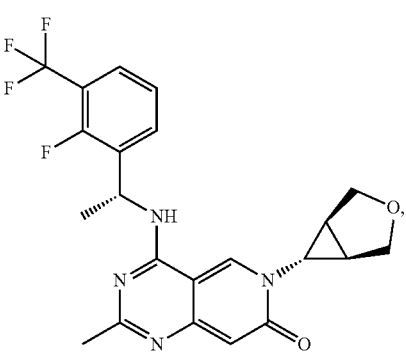
I-34

I-35
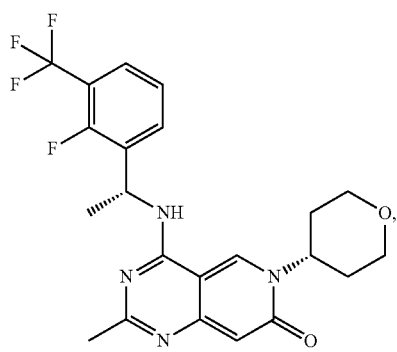
I-36
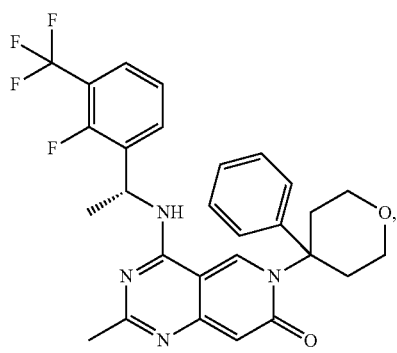
I-37
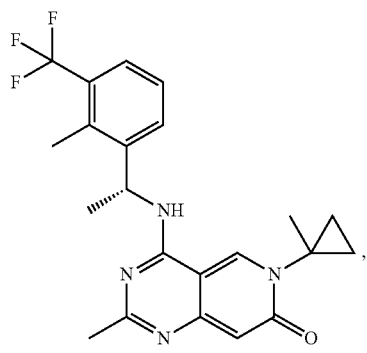
I-39
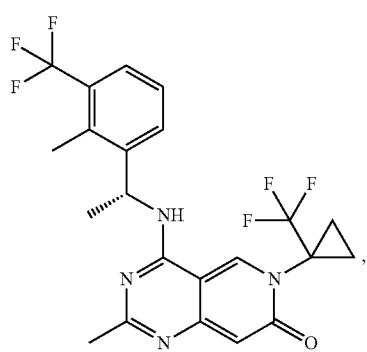
I-40
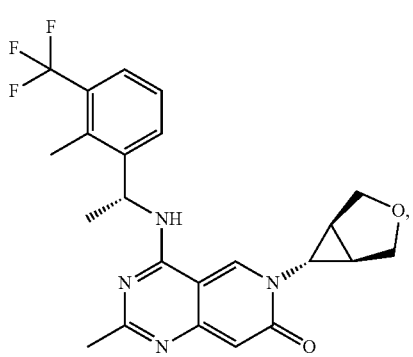
I-41
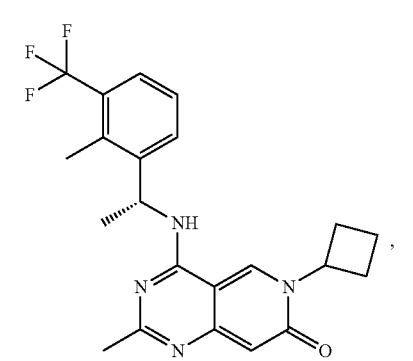
I-42
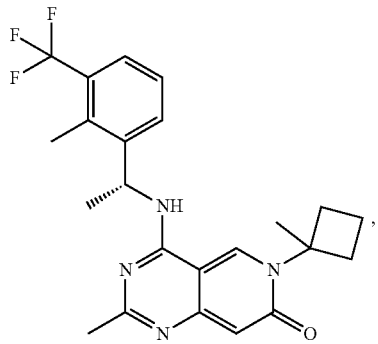
I-43
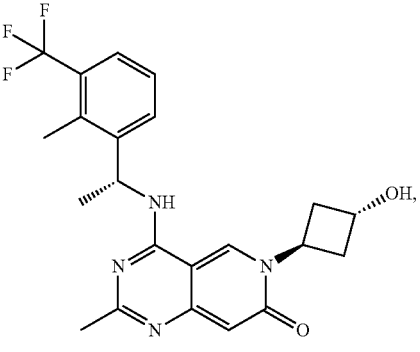

I-44
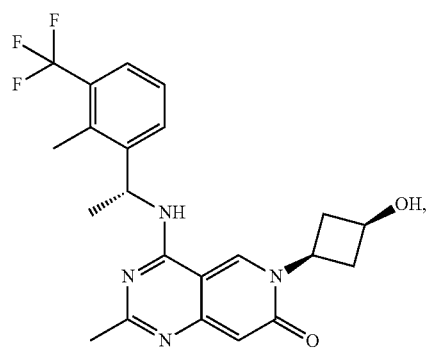
I-46
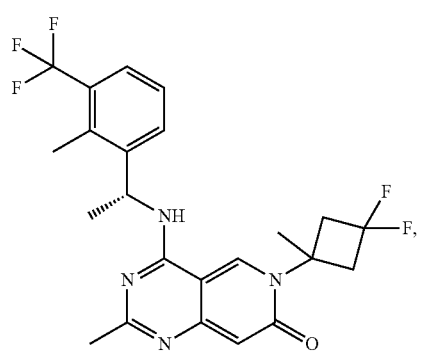
I-47
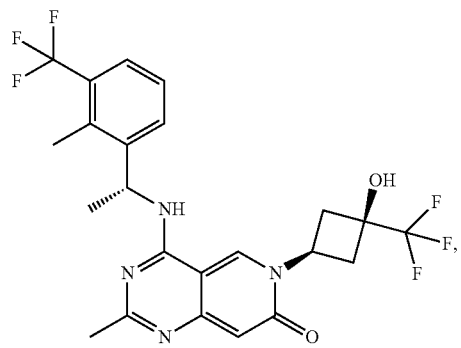
I-48
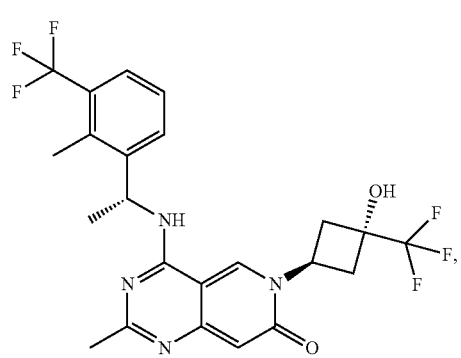
I-50
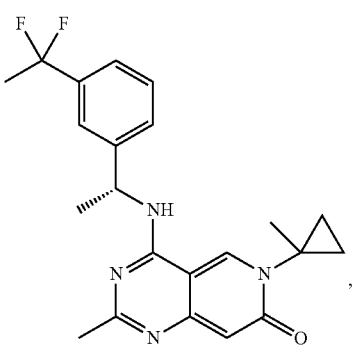
I-51
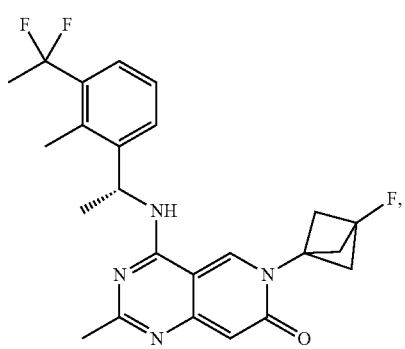
I-56
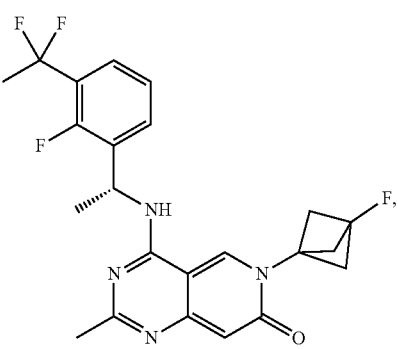
I-57
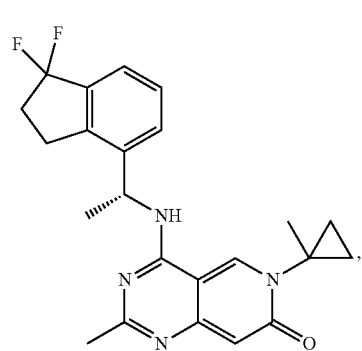

-continued
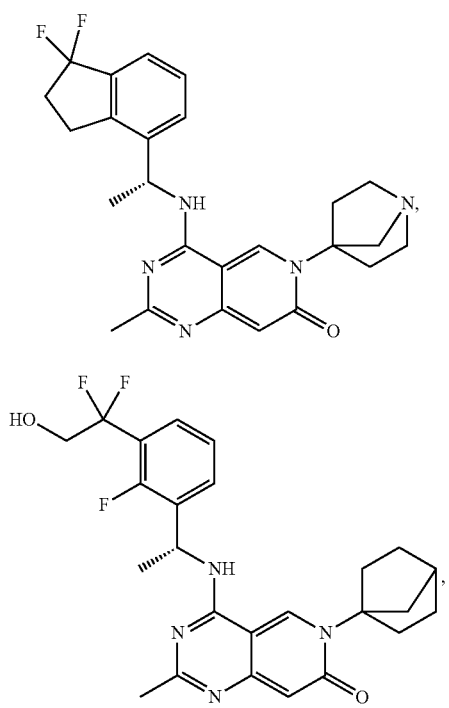
I-60
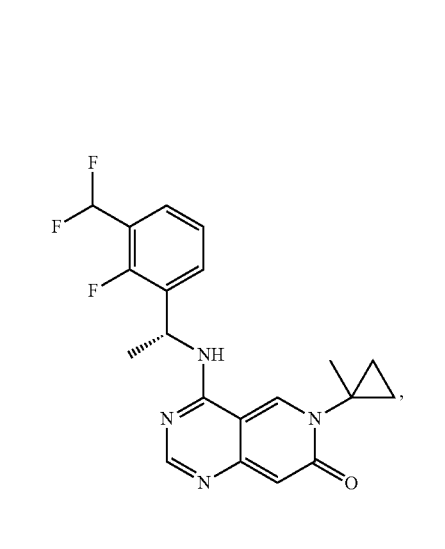
I-61
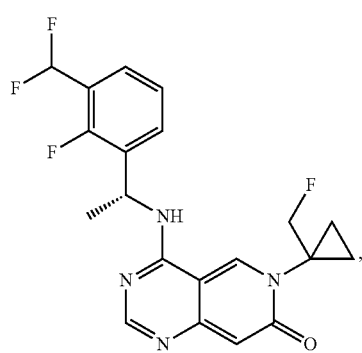
I-62
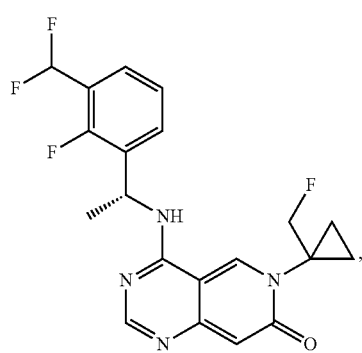
I-63
-continued
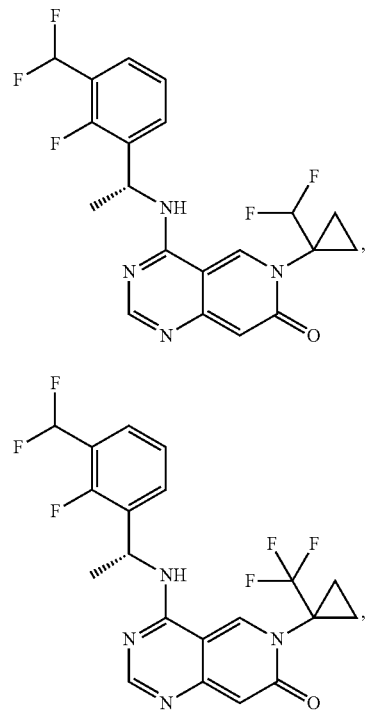
I-64
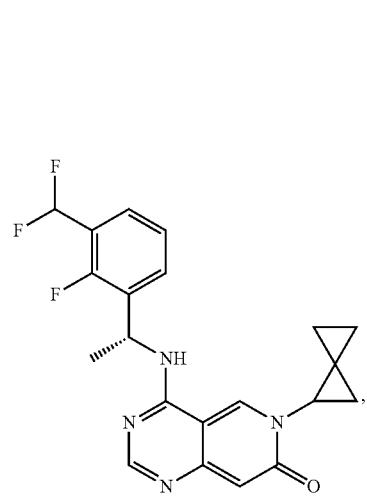
I-65
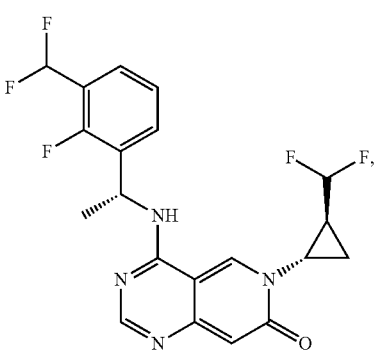
I-66
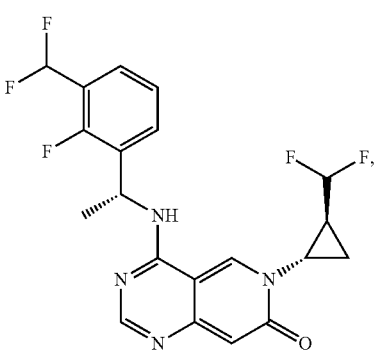
I-67

I-68
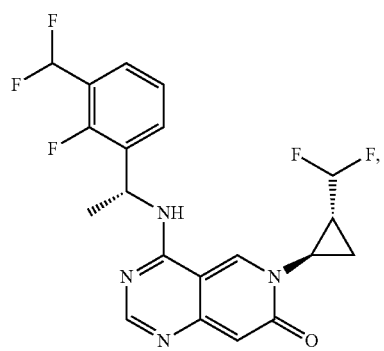
I-69
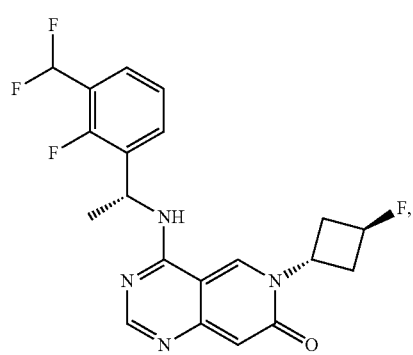
I-70
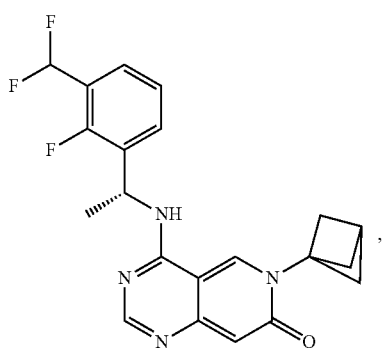
I-71
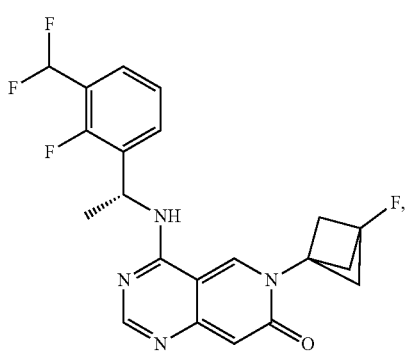
I-72
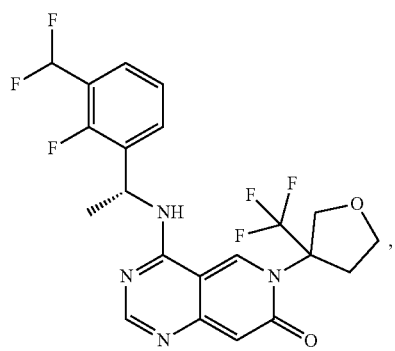
I-74
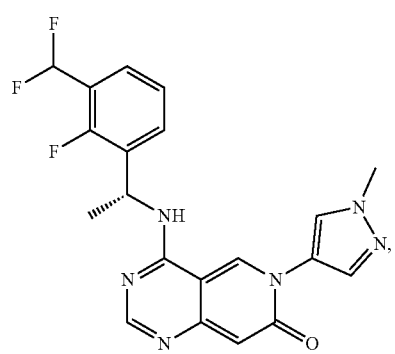
I-75
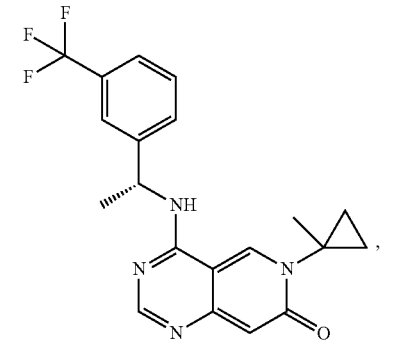
I-76
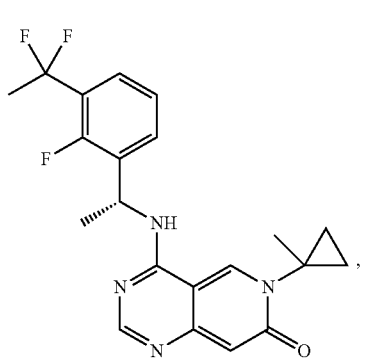

I-78
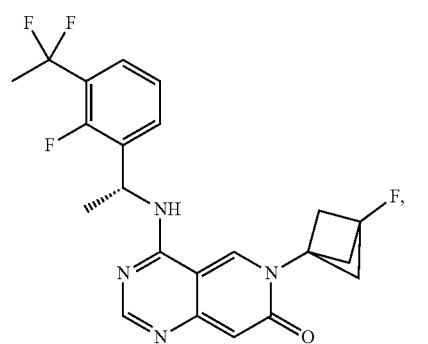
I-79
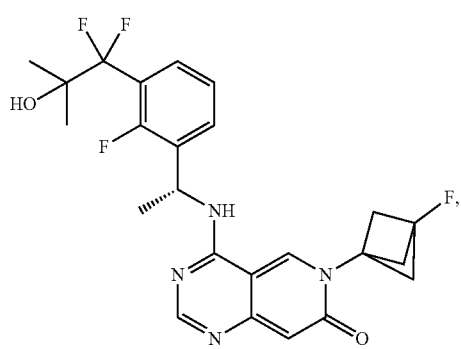
I-80
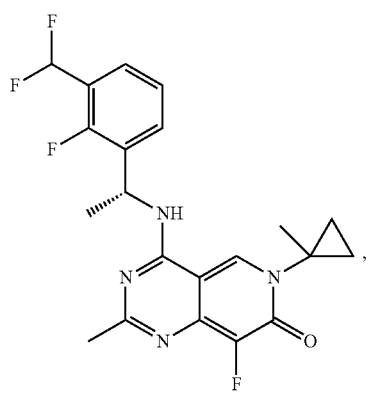
I-81
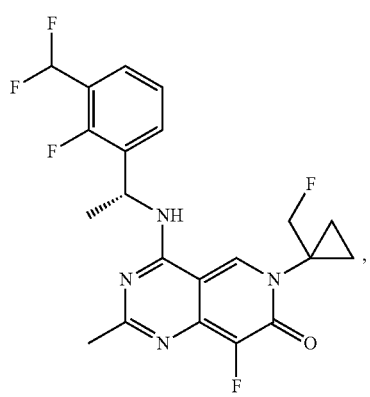
I-83
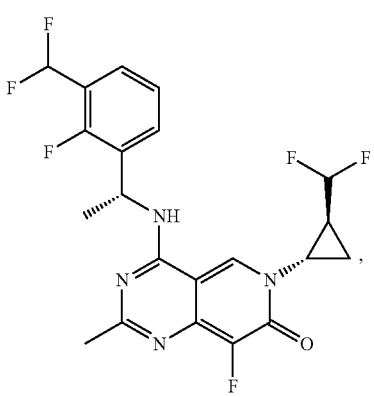
I-84
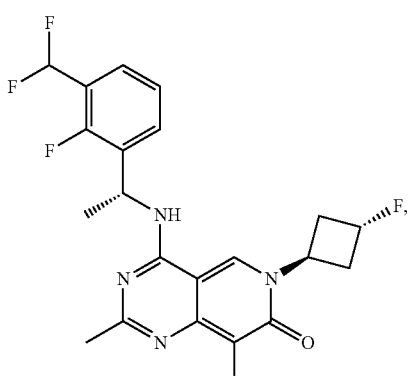
I-85
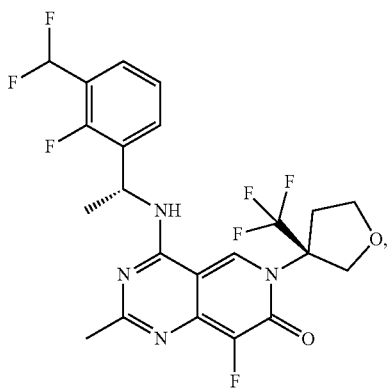
I-86
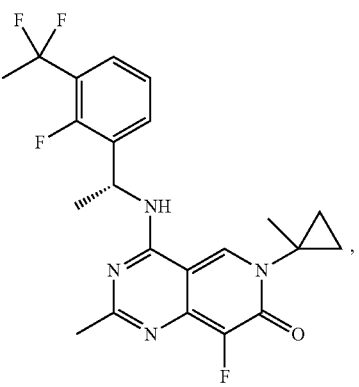

339
-continued
340
-continued
I-87
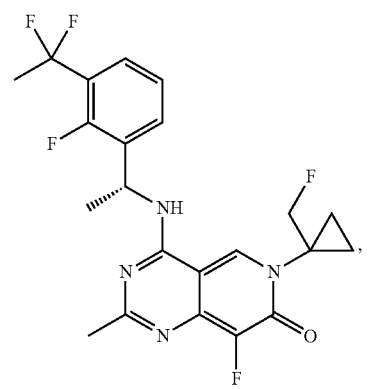
I-91
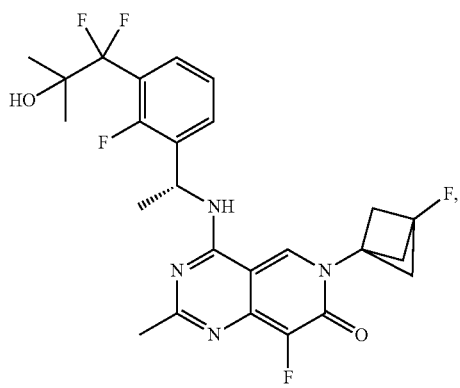
I-88
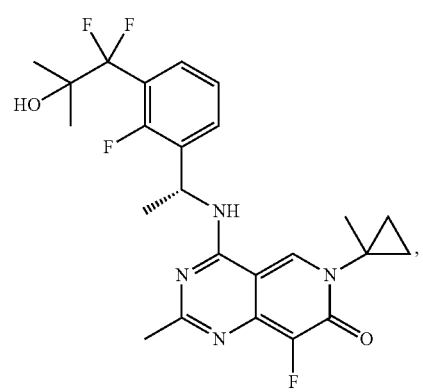
I-92
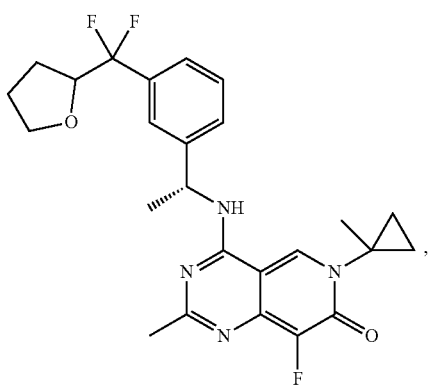
I-89
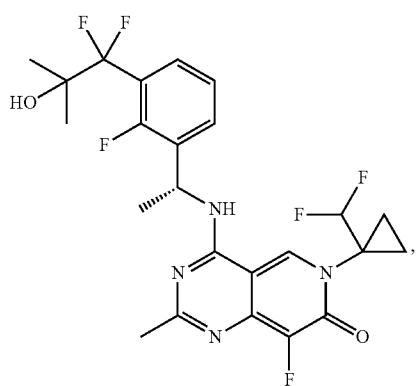
I-93
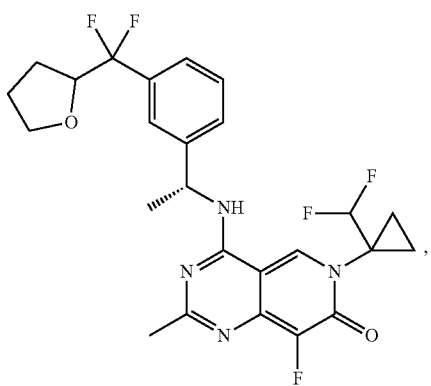
I-90
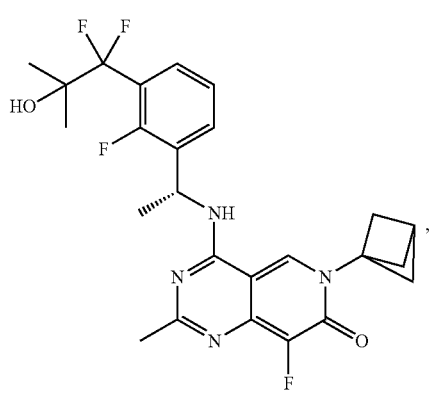
I-94

-continued
I-95
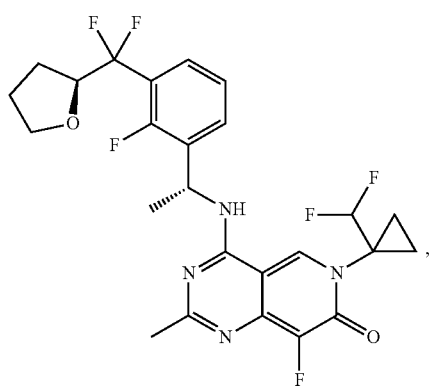
I-97
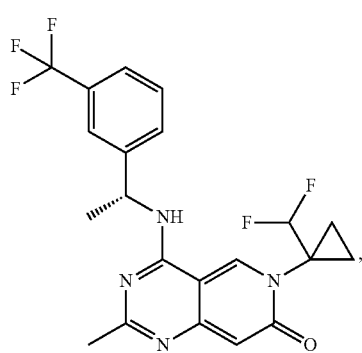
I-98
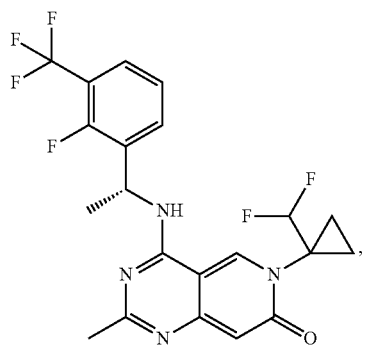
I-99
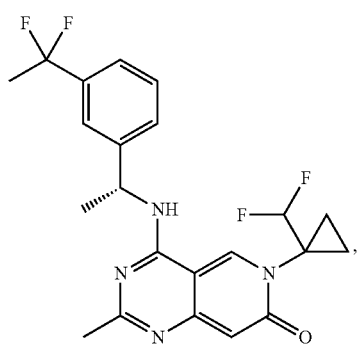
-continued
I-102
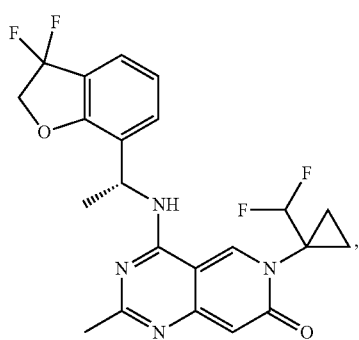
I-103
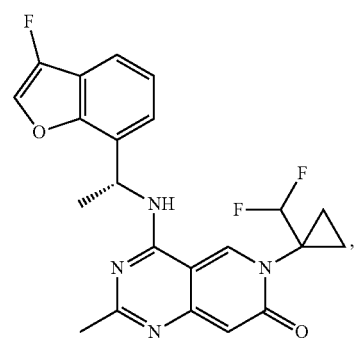
I-104
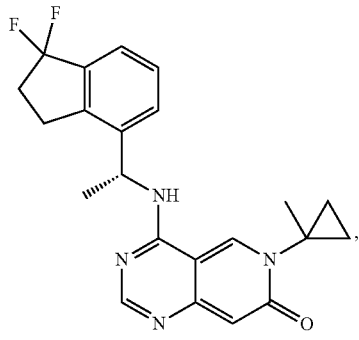
I-105
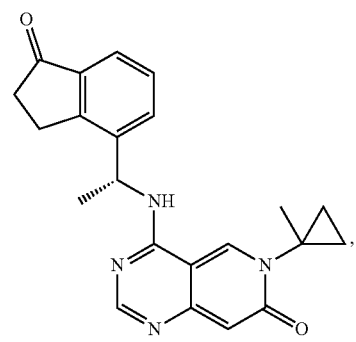

I-106
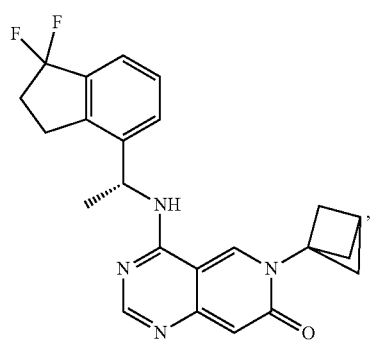
I-107
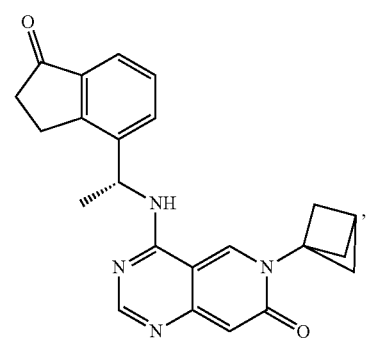
I-108
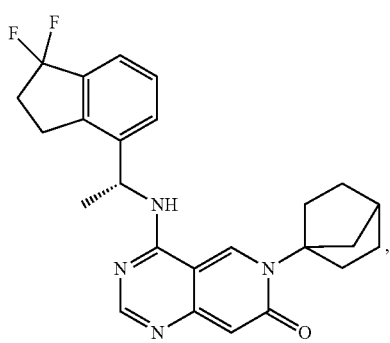
I-109
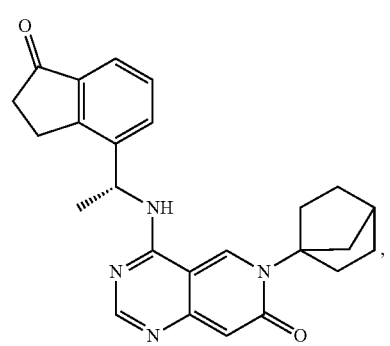
I-110
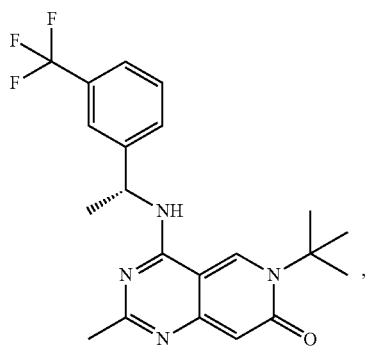
I-111
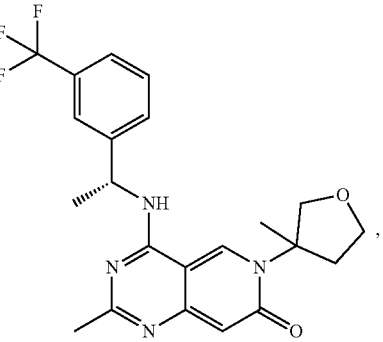
I-112
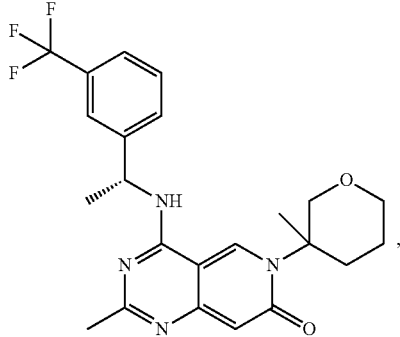
I-113

I-114
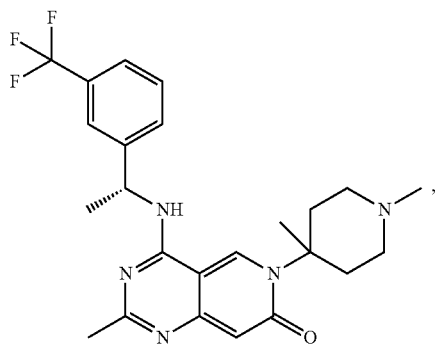
I-115
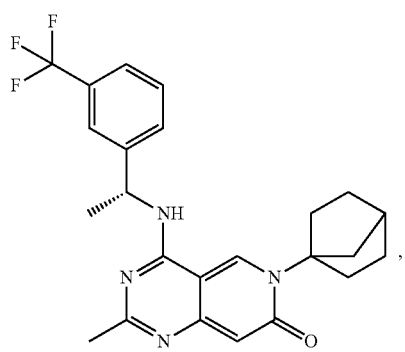
I-116
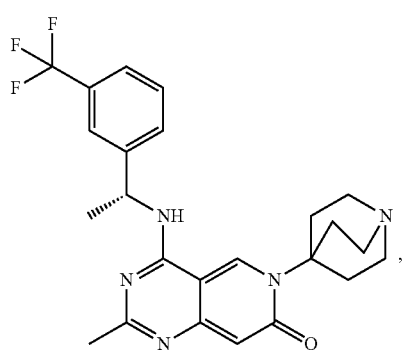
I-117
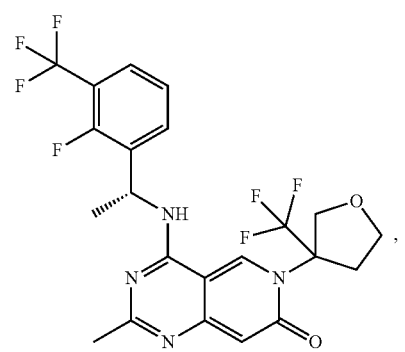
I-118
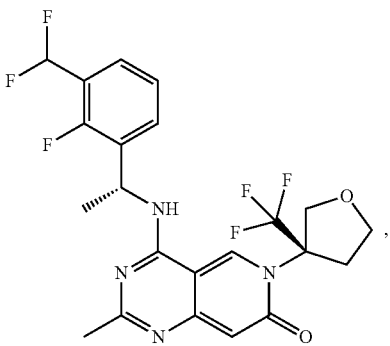
I-119
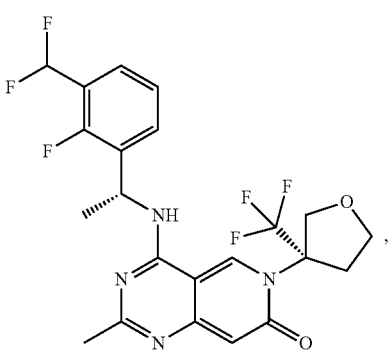
I-120
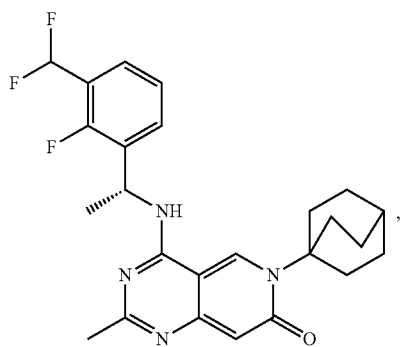
I-121
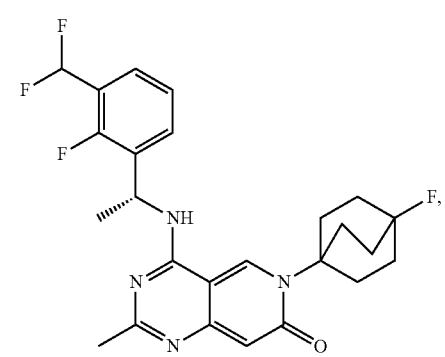

I-122
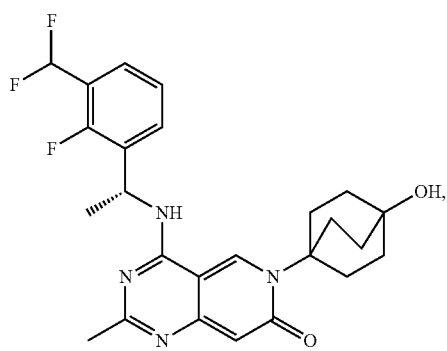
I-124
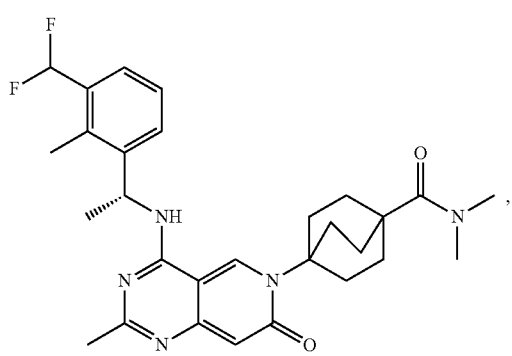
I-125
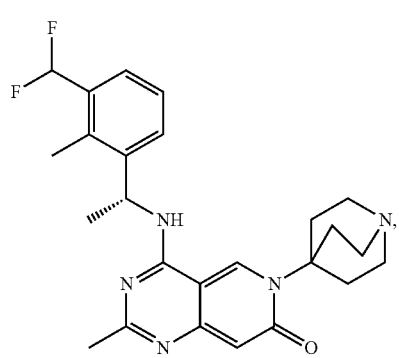
I-127
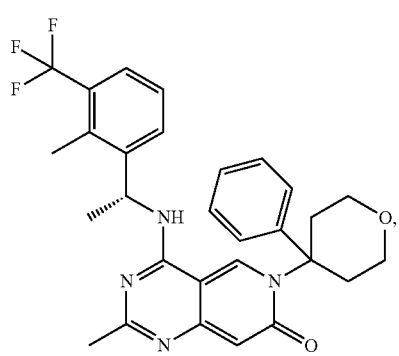
I-128
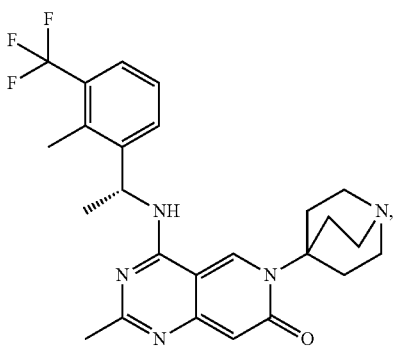
I-129
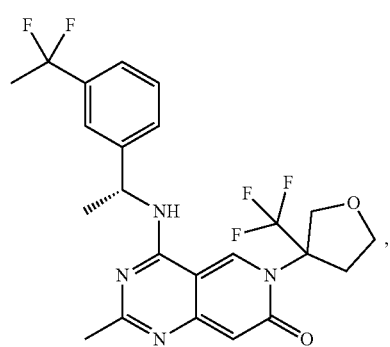
I-130
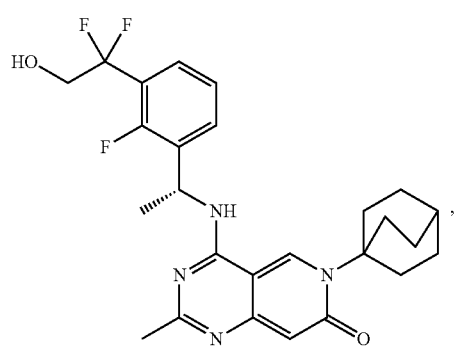
I-131
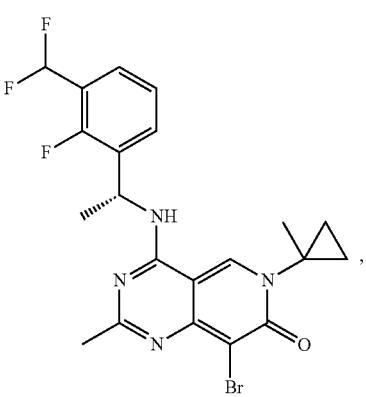

-continued
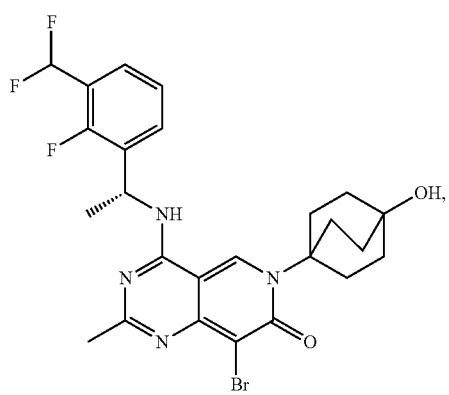
I-132
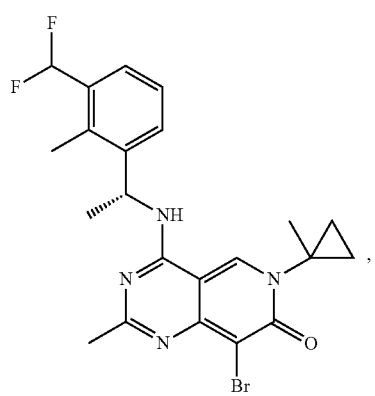
I-133
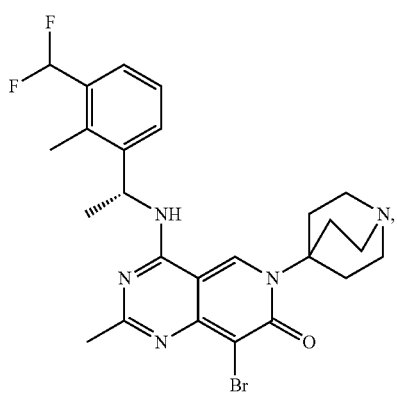
I-134
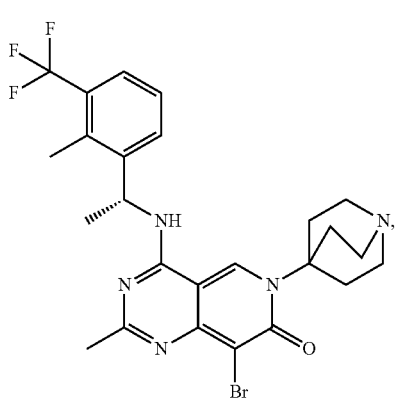
I-135
-continued
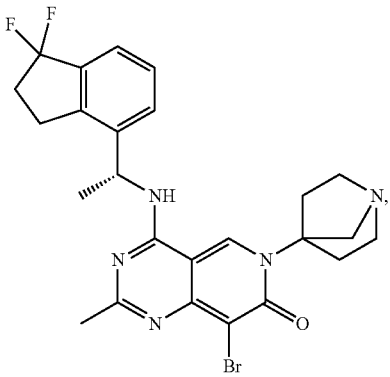
I-136
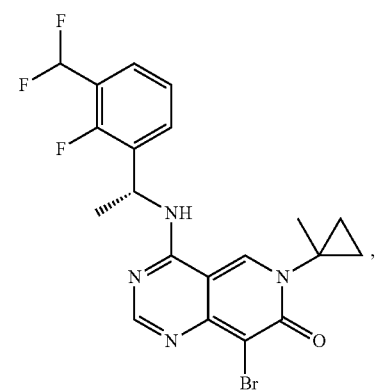
I-137
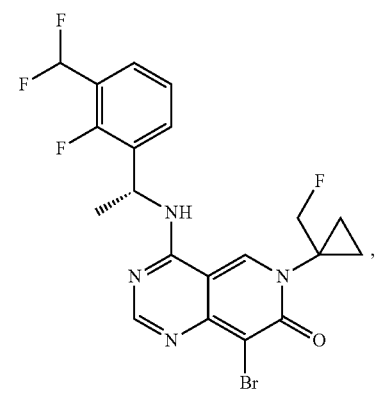
I-138
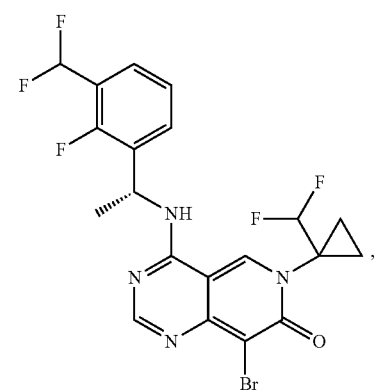
I-139

I-140
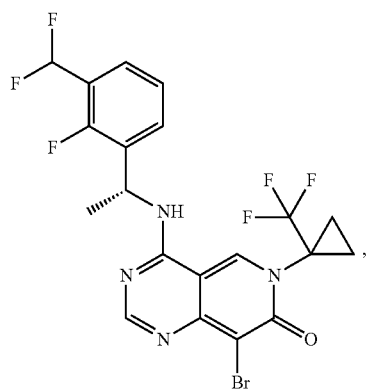
I-141
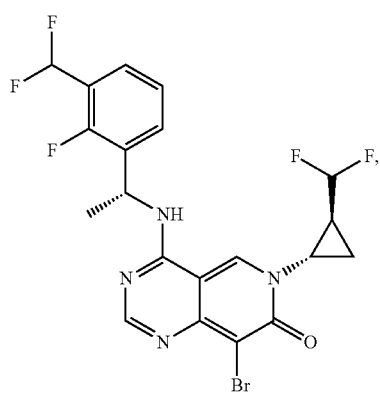
I-142
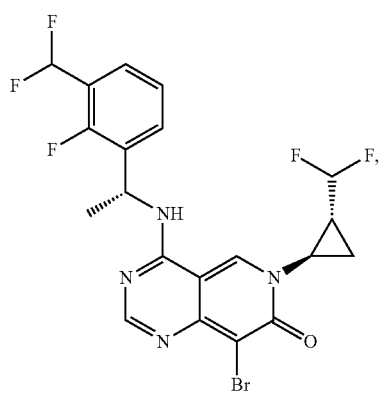
I-143
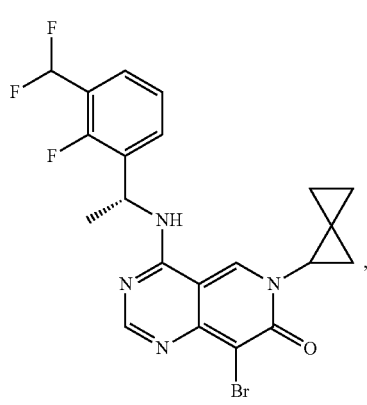
I-144
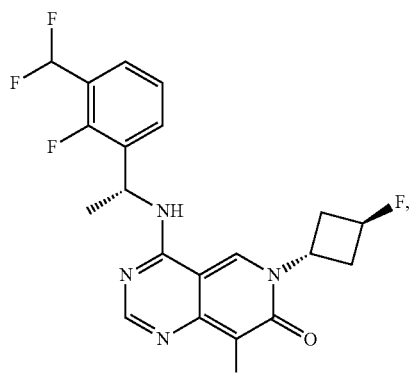
I-145
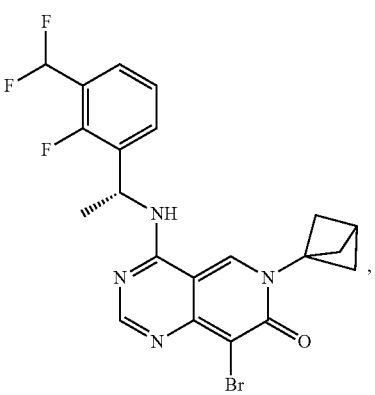
I-146
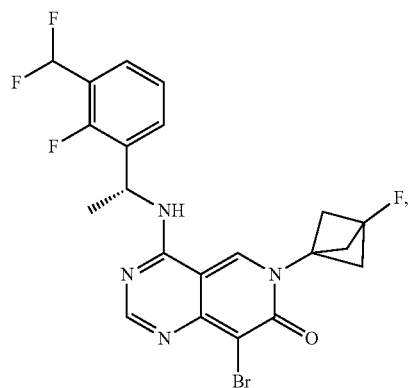
I-147
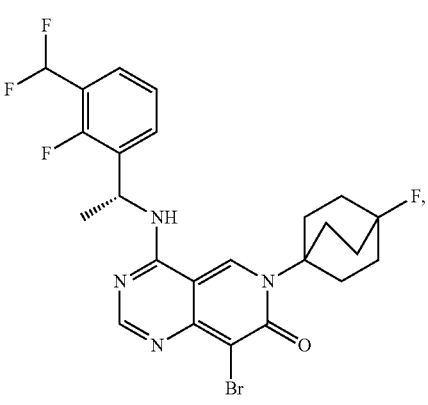

I-148
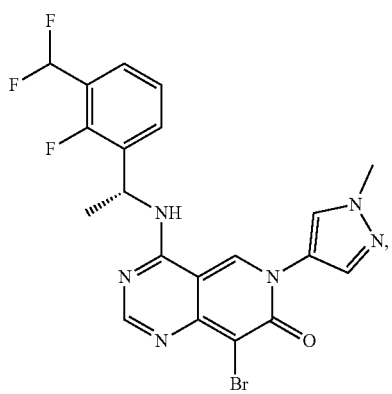
I-149
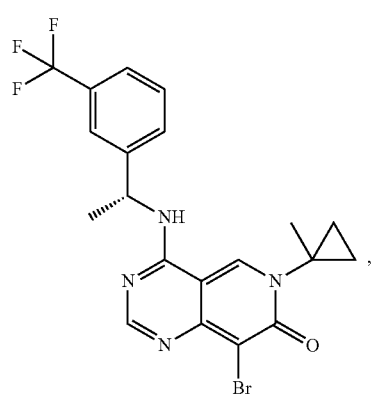
I-150
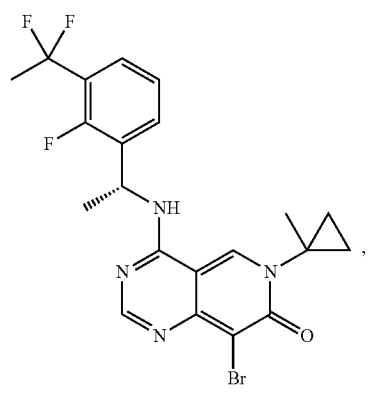
I-151
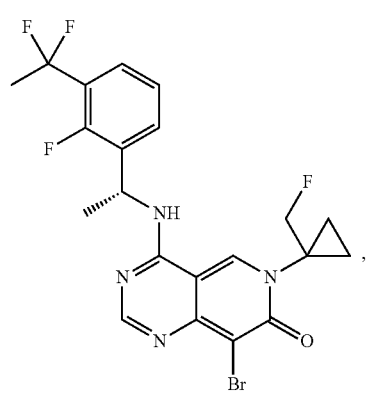
I-152
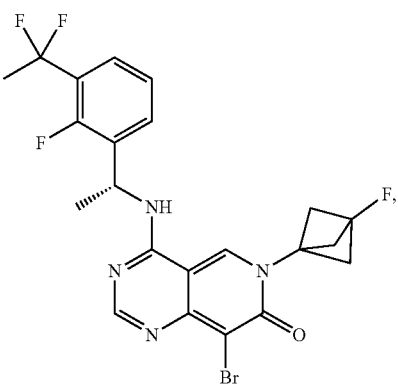
I-153
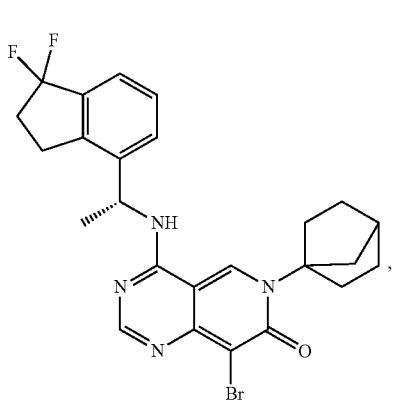
I-154
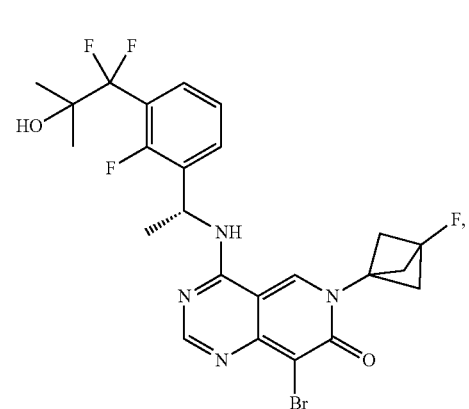
I-155
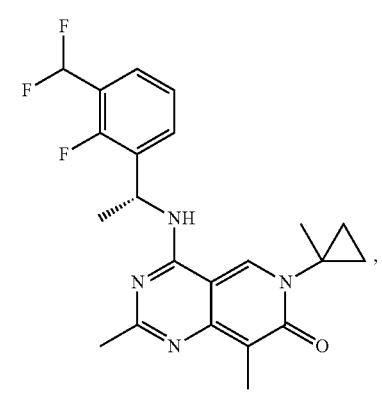

355
-continued
I-156
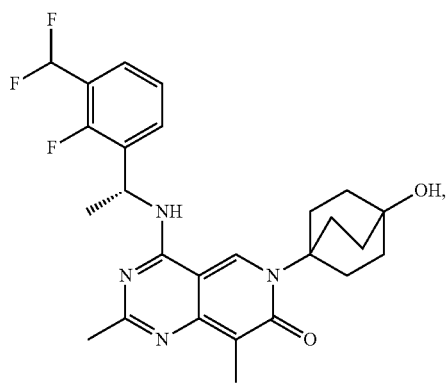
I-158
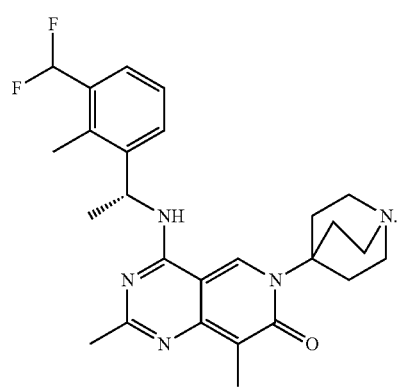
I-159
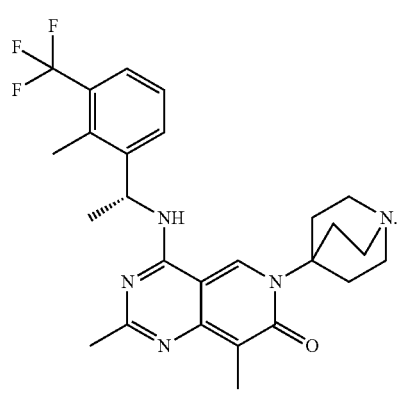
I-160
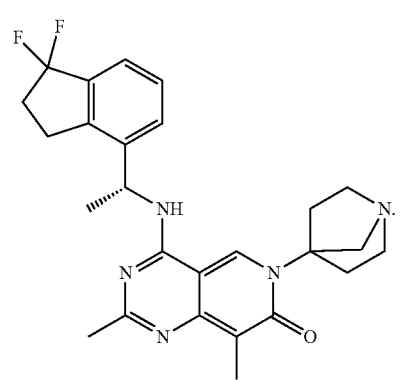
356
-continued
I-161
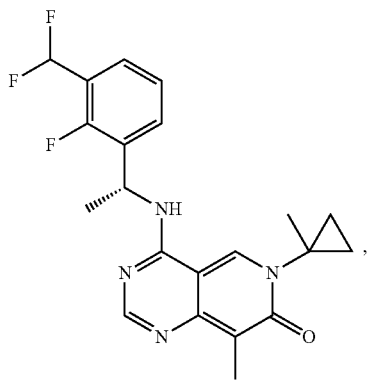
I-162
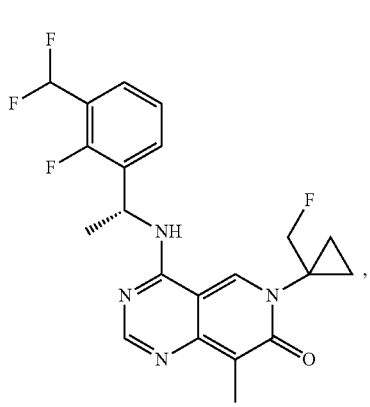
I-163
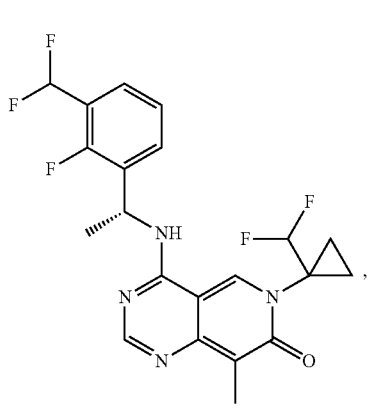
I-164
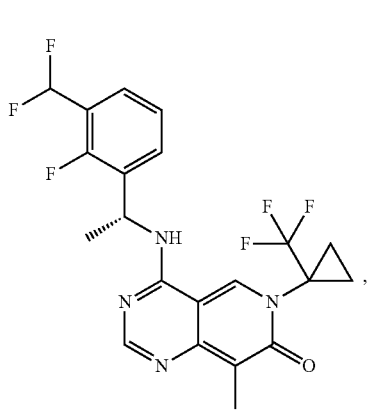

I-165 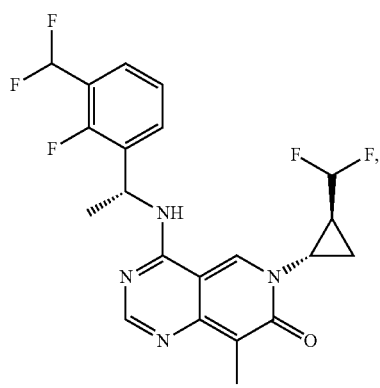
I-166 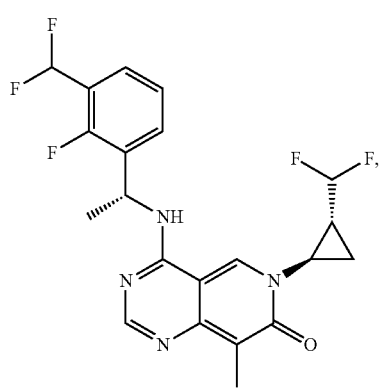
I-167 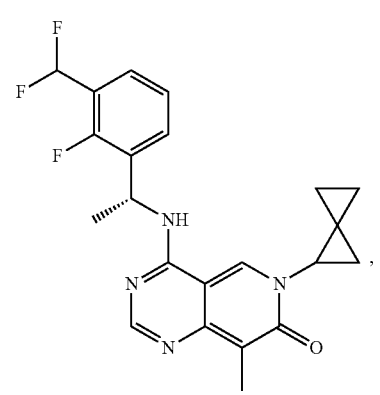
I-168 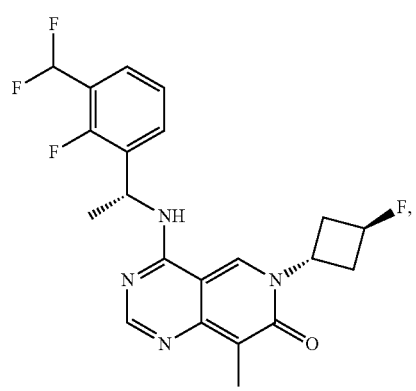
I-169 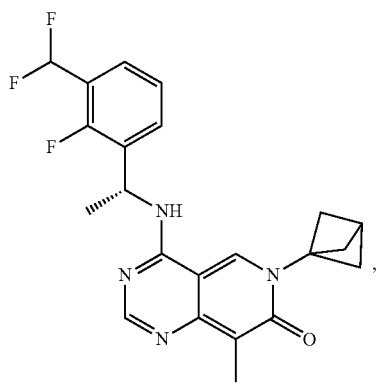
I-170 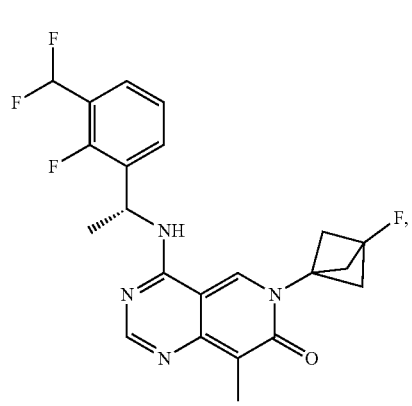
I-171 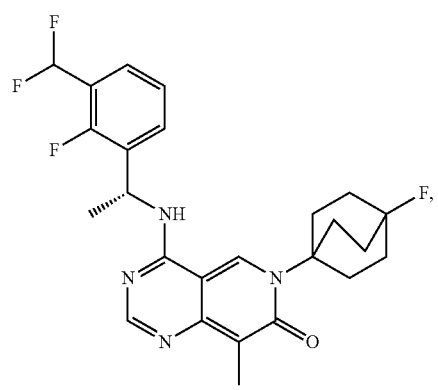
I-172 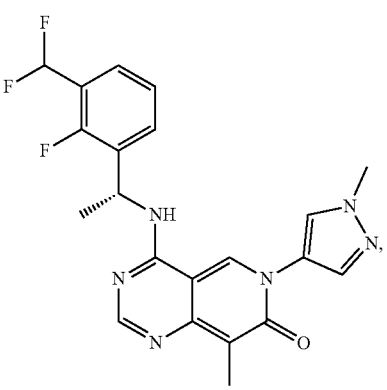

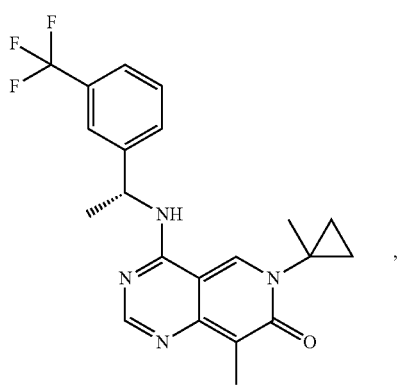
I-173
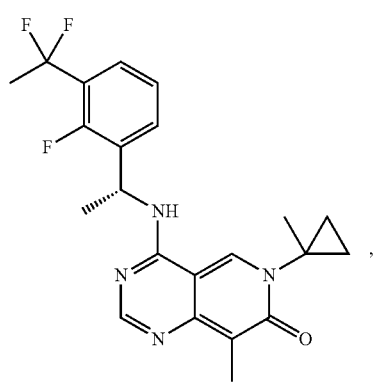
I-174
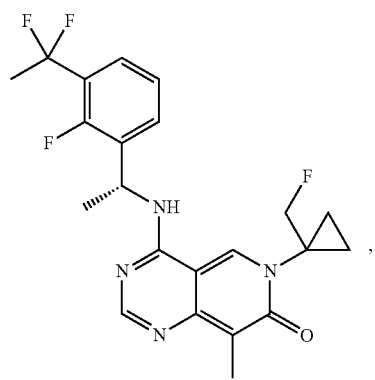
I-175
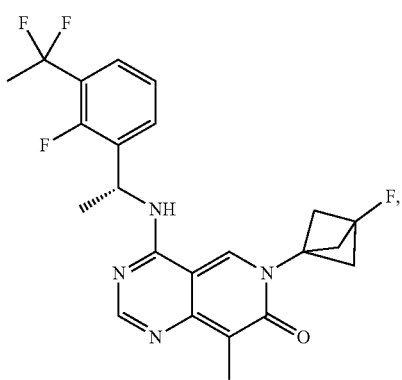
I-176
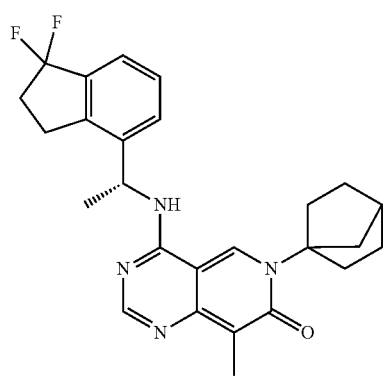
I-177
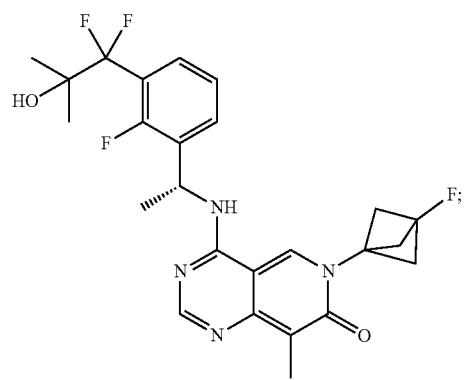
I-178
or a pharmaceutically acceptable salt thereof.
2. A compound having the following structure:
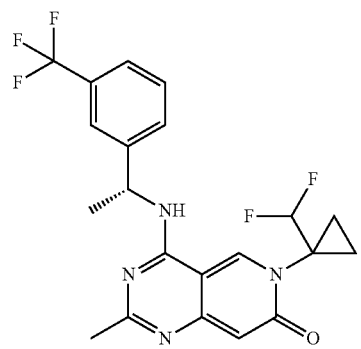
I-97
or a pharmaceutically acceptable salt thereof.

3. A compound having the following structure:

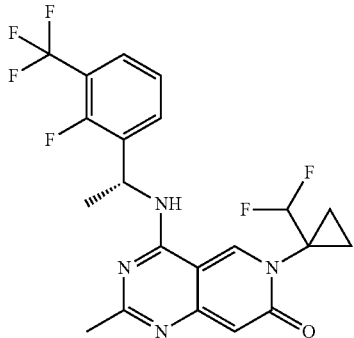

I-98 or a pharmaceutically acceptable salt thereof.

4. A compound having the following structure:

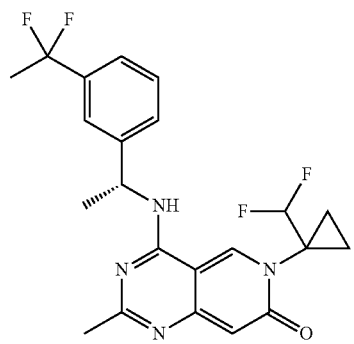

I-99 or a pharmaceutically acceptable salt thereof.

5. A compound having the following structure:

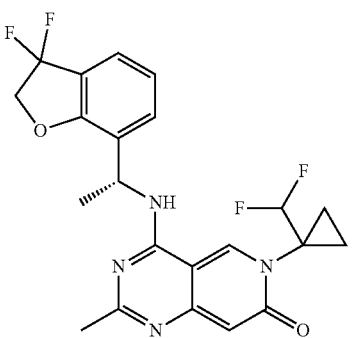

I-102 or a pharmaceutically acceptable salt thereof.

6. A compound having the following structure:

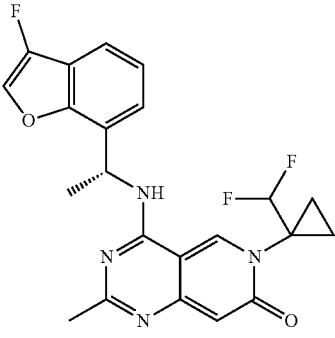

I-103 or a pharmaceutically acceptable salt thereof.

7. A compound having the following structure:

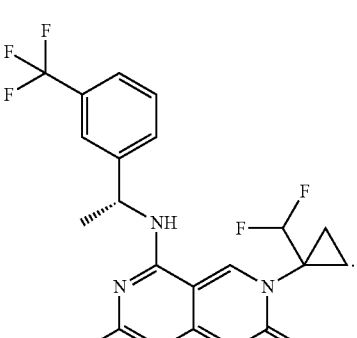

I-97

8. A compound having the following structure:

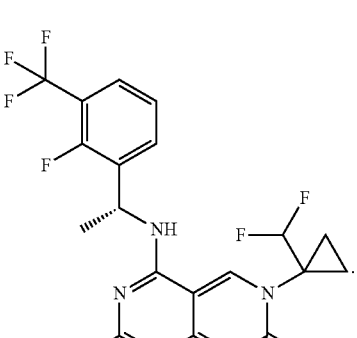

I-98

9. A compound having the following structure:

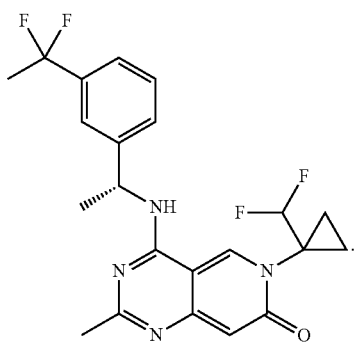

10. A compound having the following structure:

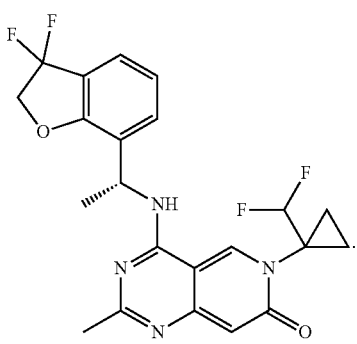
I-102

11. A compound having the following structure:

I-99

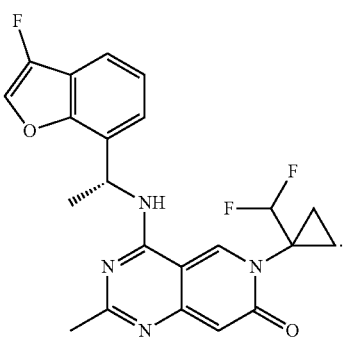
I-103

12. A pharmaceutical composition comprising a compound according to claim 1—or a pharmaceutically acceptable salt thereof—and one or more pharmaceutically acceptable excipient(s).

13. A pharmaceutical preparation comprising a compound according to claim 1—or a pharmaceutically acceptable salt thereof—and at least one other pharmacologically active substance.

14. A pharmaceutical preparation according to claim 13 comprising one other pharmacologically active substance.

* * * * *